US012790399B2

(12) United States Patent
Walter et al.

(10) Patent No.: US 12,790,399 B2
(45) Date of Patent: Nov. 10, 2026

(54) ANTI-CD123 ANTIBODIES WHICH BIND AN EXTRACELLULAR DOMAIN OF CD123

(71) Applicant: Fred Hutchinson Cancer Center, Seattle, WA (US)

(72) Inventors: Roland B. Walter, Seattle, WA (US); George S. Laszlo, Seattle, WA (US); Johnnie J. Orozco, Seattle, WA (US); Yukang Lin, Issaquah, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 962 days.

(21) Appl. No.: 18/052,189

(22) Filed: Nov. 2, 2022

(65) Prior Publication Data

US 2023/0295316 A1 Sep. 21, 2023

Related U.S. Application Data

(60) Provisional application No. 63/274,623, filed on Nov. 2, 2021.

(51) Int. Cl.

*C07K 16/28* (2006.01)
*A61K 51/04* (2006.01)
*A61K 51/10* (2006.01)

(52) U.S. Cl.

CPC ...... *C07K 16/2866* (2013.01); *A61K 51/0482* (2013.01); *A61K 51/1033* (2013.01); *C07K 2317/31* (2013.01)

(58) Field of Classification Search

None
See application file for complete search history.

(56) References Cited

PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*

* cited by examiner

*Primary Examiner* — Christine J Saoud
*Assistant Examiner* — Jon M Lockard
(74) *Attorney, Agent, or Firm* — Christensen O'Connor Johnson Kindness PLLC

(57) ABSTRACT

Humanized, chimeric, murine, and human antibody or antigen binding derivatives thereof that bind to an extracellular domain of interleukin-3 (IL-3) receptor α-chain (CD123) anti-CD123 monoclonal antibodies are provided. Nucleic acids encoding the antibody or antigen binding derivative thereof that binds to an extracellular domain of interleukin-3 (IL-3) receptor α-chain (CD123) and expression vectors comprising the nucleic acid are also provided. Bispecific affinity reagents comprising a first binding domain that specifically binds to an extracellular domain of interleukin-3 (IL-3) receptor α-chain (CD123); and a second binding domain that specifically binds to a therapeutic payload and uses thereof are provided. Embodiments of the invention include isolated antibodies and derivatives and fragments thereof, pharmaceutical formulations comprising one or more of the humanized, chimeric, or human anti-CD123 monoclonal antibodies; and cell lines that produce these monoclonal antibodies.

5 Claims, 35 Drawing Sheets

Specification includes a Sequence Listing.

| | Human CD123 | | | Nonhuman Primate CD123 | | |
|---|---|---|---|---|---|---|
| Ligand | $k_a$ ($M^{-1}$ $s^{-1}$) | $k_d$ ($s^{-1}$) | $K_D$ | $k_a$ ($M^{-1}$ $s^{-1}$) | $k_d$ ($s^{-1}$) | $K_D$ |
| 10C4 | $2.54 \times 10^5$ | $1.02 \times 10^{-4}$ | 401 pM | $1.43 \times 10^5$ | $2.30 \times 10^{-3}$ | 16.1 nM |
| Chi-10C4 (IgG1) | $9.16 \times 10^4$ | $5.24 \times 10^{-5}$ | 572 pM | $7.6 \times 10^4$* | $4.4 \times 10^{-3}$* | 58 nM* |
| Chi-10C4 (IgG4) | $7.91 \times 10^4$ | $1.10 \times 10^{-4}$ | 1.39 nM | | Not tested | |
| HuV1-10C4 (IgG1) | $9.12 \times 10^4$ | $5.56 \times 10^{-4}$ | 6.09 nM | $1.4 \times 10^5$* | $1.9 \times 10^{-2}$* | 136 nM* |
| HuV1-10C4 (IgG4) | $8.32 \times 10^4$ | $5.44 \times 10^{-4}$ | 6.53 nM | | Not tested | |
| HuV2-10C4 (IgG1) | $6.75 \times 10^4$ | $1.63 \times 10^{-2}$ | 242 nM | | Low response* | |
| HuV2-10C4 (IgG4) | $9.06 \times 10^4$ | $2.04 \times 10^{-2}$ | 225 nM | | Not tested | |

*Estimate from a single 100 nM curve screen

*FIG. 14*

| | Calculated concentration at 1/2 OD | |
|---|---|---|
| 10C4 | 1.116 | Immunoreactivity |
| Chi-10C4 (IgG1) | 1.117 | 100% |
| HuV1-10C4 (IgG1) | 1.177 | 105% |
| HuV2-10C4 (IgG1) | 2.331 | 209% |

| | Calculated concentration at 1/2 OD | |
|---|---|---|
| 10C4 | 1.043 | Immunoreactivity |
| Chi-10C4 (IgG4) | 1.206 | 116% |
| HuV1-10C4 (IgG4) | 1.411 | 135% |
| HuV2-10C4 (IgG4) | 2.211 | 212% |

| | | Human CD123 | | | | Nonhuman Primate CD123 | | |
|---|---|---|---|---|---|---|---|---|
| Ligand | | $k_a$ ($M^{-1}$ $s^{-1}$) | $k_d$ ($s^{-1}$) | $K_D$ | | $k_a$ ($M^{-1}$ $s^{-1}$) | $k_d$ ($s^{-1}$) | $K_D$ |
| | | | | | | | | |
| 1B5 (IgG1) | | $6.43 \times 10^5$ | $3.16 \times 10^{-3}$ | 4.92 nM | | *Binding response too low at 200 nM | | |
| 1B5 (IgG4) | | $6.39 \times 10^5$ | $3.01 \times 10^{-3}$ | 4.71 nM | | | Not tested | |
| | | | | | | | | |
| 1D9 (IgG1) | | $6.55 \times 10^4$ | $3.68 \times 10^{-5}$ | 563 pM | | $3.38 \times 10^4$* | $1.09 \times 10^{-3}$* | 32.2 nM* |
| 1D9 (IgG4) | | $7.06 \times 10^4$ | $4.19 \times 10^{-5}$ | 594 pM | | $3.85 \times 10^4$ | $1.12 \times 10^{-3}$ | 29.1 nM |
| | | | | | | | | |
| 1E3 (IgG1) | | $9.44 \times 10^4$ | $6.15 \times 10^{-5}$ | 652 pM | | *Binding response too low at 100 nM | | |
| 1E3 (IgG4) | | $8.86 \times 10^4$ | $7.02 \times 10^{-5}$ | 792 pM | | | Not tested | |
| | | | | | | | | |

*Estimate from a single conc curve screen

*FIG. 22*

ANTI-CD123 ANTIBODIES WHICH BIND AN EXTRACELLULAR DOMAIN OF CD123

CROSS-REFERENCE TO RELATED APPLICATION

This application claims the benefit of U.S. Provisional Application No. 63/274,623, filed Nov. 2, 2021, the disclosure of which is incorporated herein by reference in its entirety.

STATEMENT REGARDING SEQUENCE LISTING

The Sequence Listing XML associated with this application is provided in XML format and is hereby incorporated by reference into the specification. The name of the XML file containing the sequence listing is 1896-P62US_Seq_List_20230321.xml. The XML file is 318,184 bytes; was created on Mar. 21, 2023; and is being submitted electronically via Patent Center with the filing of the specification.

BACKGROUND

Approximately 25,000 people develop acute myeloid or lymphoblastic leukemia (AML or ALL) in the United States every year. Acute leukemias remain difficult to cure despite intensive multi-agent chemotherapy, several new drugs, and allogeneic hematopoietic cell transplantation (HCT). Even with these interventions, few patients remain alive 2-5 years after diagnosis. Leukemia cells are exquisitely sensitive to ionizing radiation. This effect is dose-dependent, which is clinically exploitable as demonstrated many years ago by the effectiveness of total body irradiation (TBI) in the setting of allogeneic HCT. For example, a randomized trial showed significantly lower relapse rates with higher vs. lower TBI doses when given before allogeneic HCT for AML in first remission. Because of higher non-relapse mortality related to toxicities to lung, liver, and mucous membranes, however, this benefit did not translate into better survival. This observation provides a direct, strong impetus to employ radiolabeled mAbs (radioimmunotherapy ("RIT")) to direct radiation toward acute leukemia cells. As an important advantage over other mAb-based therapies, RIT does not require a functional immune system to exert anti-tumor effects. Most RIT efforts to date have focused on augmenting transplant conditioning regimens with mAbs targeting CD45 (for AML and ALL) or CD33 (for AML). Both antigens are expressed on acute leukemia cells in most patients but are also displayed on many normal blood cells. This is particularly true for CD45 (a.k.a. leukocyte common antigen), which is expressed on almost all hematopoietic cells except platelets and erythrocytes and some of their progenitors. Proof of principle for using RIT to treat acute leukemias was demonstrated with β-emitters such as iodine-131 ($^{131}I$). When coupled to anti-CD45 mAbs, they delivered 2-to-3-fold higher radiation doses to spleen and bone marrow (BM) than any critical normal organ together with high-dose chemotherapy/TBI or reduced-intensity conditioning in such patients. An $^{131}I$-labeled anti-CD45 mAb (Iomab-B [apamistamab-I131]) is currently tested in a phase 3 trial (SIERRA) for this purpose in AML (NCT02665065). However, broad display of these antigens on normal blood cells curtails the anti-tumor efficacy of this approach as it limits how much radiation can be safely delivered to leukemic cells without hematopoietic stem cell rescue.

Accordingly, despite the advances in development of targeted treatments of leukemias and other cancers, a need remains for potent and effective interventions that minimize off-target toxicities. The present disclosure addresses these and other needs.

SUMMARY

This disclosure relates, inter alia, to antibody or antigen binding derivatives thereof that binds to an extracellular domain of interleukin-3 (IL-3) receptor α-chain (CD123). In some embodiments the antibodies or antibody derivatives of the disclosure include polyclonal antibodies, monoclonal antibodies, multispecific antibodies (e.g., bispecific antibodies), human antibodies, murine antibodies, and chimeric antibodies, e.g., humanized antibodies. In some embodiments the antibody or antigen binding derivatives thereof that binds to an extracellular domain of interleukin-3 (IL-3) receptor α-chain (CD123) comprises a light chain variable ($V_L$) domain and a heavy chain variable ($V_H$) domain, wherein: a) the $V_L$ domain comprises a VL-CDR1 having a sequence set forth in SEQ ID NO: 3, a VL-CDR2 having a sequence set forth in SEQ ID NO: 4, and a VL-CDR3 having a sequence set forth in SEQ ID NO: 5; and the $V_H$ domain comprises a VH-CDR1 having a sequence set forth in SEQ ID NO: 8, a VH-CDR2 having a sequence set forth in SEQ ID NO: 9, and a VH-CDR3 having a sequence set forth in SEQ ID NO: 10;

b) the $V_L$ domain comprises a VL-CDR1 having a sequence set forth in SEQ ID NO: 13, a VL-CDR2 having a sequence set forth in SEQ ID NO: 14, and a VL-CDR3 having a sequence set forth in SEQ ID NO: 15; and the $V_H$ domain comprises a VH-CDR1 having a sequence set forth in SEQ ID NO: 18, a VH-CDR2 having a sequence set forth in SEQ ID NO: 19, and a VH-CDR3 having a sequence set forth in SEQ ID NO: 20;

c) the $V_L$ domain comprises a VL-CDR1 having a sequence set forth in SEQ ID NO: 23, a VL-CDR2 having a sequence set forth in SEQ ID NO: 24, and a VL-CDR3 having a sequence set forth in SEQ ID NO: 25; and the $V_H$ domain comprises a VH-CDR1 having a sequence set forth in SEQ ID NO: 28, a VH-CDR2 having a sequence set forth in SEQ ID NO: 29, and a VH-CDR3 having a sequence set forth in SEQ ID NO: 30;

d) the $V_L$ domain comprises a VL-CDR1 having a sequence set forth in SEQ ID NO: 33, a VL-CDR2 having a sequence set forth in SEQ ID NO: 34, and a VL-CDR3 having a sequence set forth in SEQ ID NO: 35; and the $V_H$ domain comprises a VH-CDR1 having a sequence set forth in SEQ ID NO: 38, a VH-CDR2 having a sequence set forth in SEQ ID NO: 39, and a VH-CDR3 having a sequence set forth in SEQ ID NO: 40;

e) the $V_L$ domain comprises a VL-CDR1 having a sequence set forth in SEQ ID NO: 43, a VL-CDR2 having a sequence set forth in SEQ ID NO: 44, and a VL-CDR3 having a sequence set forth in SEQ ID NO: 45; and the $V_H$ domain comprises a VH-CDR1 having a sequence set forth in SEQ ID NO: 48, a VH-CDR2 having a sequence set forth in SEQ ID NO: 49, and a VH-CDR3 having a sequence set forth in SEQ ID NO: 50;

f) the $V_L$ domain comprises a VL-CDR1 having a sequence set forth in SEQ ID NO: 53, a VL-CDR2 having a sequence set forth in SEQ ID NO: 54, and a VL-CDR3 having a sequence set forth in SEQ ID NO: 55; and the $V_H$ domain comprises a VH-CDR1 having a sequence set forth in SEQ ID NO: 58, a VH-CDR2 having a sequence set forth in SEQ ID NO: 59, and a VH-CDR3 having a sequence set forth in SEQ ID NO: 60;

g) the $V_L$ domain comprises a VL-CDR1 having a sequence set forth in SEQ ID NO: 63, a VL-CDR2 having a sequence set forth in SEQ ID NO: 64, and a VL-CDR3 having a sequence set forth in SEQ ID NO: 65; and the $V_H$ domain comprises a VH-CDR1 having a sequence set forth in SEQ ID NO: 68, a VH-CDR2 having a sequence set forth in SEQ ID NO: 69, and a VH-CDR3 having a sequence set forth in SEQ ID NO: 70;

h) the $V_L$ domain comprises a VL-CDR1 having a sequence set forth in SEQ ID NO: 73, a VL-CDR2 having a sequence set forth in SEQ ID NO: 74, and a VL-CDR3 having a sequence set forth in SEQ ID NO: 75; and the $V_H$ domain comprises a VH-CDR1 having a sequence set forth in SEQ ID NO: 78, a VH-CDR2 having a sequence set forth in SEQ ID NO: 79, and a VH-CDR3 having a sequence set forth in SEQ ID NO: 80;

i) the $V_L$ domain comprises a VL-CDR1 having a sequence set forth in SEQ ID NO: 83, a VL-CDR2 having a sequence set forth in SEQ ID NO: 84, and a VL-CDR3 having a sequence set forth in SEQ ID NO: 85; and the $V_H$ domain comprises a VH-CDR1 having a sequence set forth in SEQ ID NO: 88, a VH-CDR2 having a sequence set forth in SEQ ID NO: 89, and a VH-CDR3 having a sequence set forth in SEQ ID NO: 90;

j) the $V_L$ domain comprises a VL-CDR1 having a sequence set forth in SEQ ID NO: 93, a VL-CDR2 having a sequence set forth in SEQ ID NO: 94, and a VL-CDR3 having a sequence set forth in SEQ ID NO: 95; and the $V_H$ domain comprises a VH-CDR1 having a sequence set forth in SEQ ID NO: 98, a VH-CDR2 having a sequence set forth in SEQ ID NO: 99, and a VH-CDR3 having a sequence set forth in SEQ ID NO: 100;

k) the $V_L$ domain comprises a VL-CDR1 having a sequence set forth in SEQ ID NO: 103, a VL-CDR2 having a sequence set forth in SEQ ID NO: 104, and a VL-CDR3 having a sequence set forth in SEQ ID NO: 105; and the $V_H$ domain comprises a VH-CDR1 having a sequence set forth in SEQ ID NO: 108, a VH-CDR2 having a sequence set forth in SEQ ID NO: 109, and a VH-CDR3 having a sequence set forth in SEQ ID NO: 110;

l) the $V_L$ domain comprises a VL-CDR1 having a sequence set forth in SEQ ID NO: 113, a VL-CDR2 having a sequence set forth in SEQ ID NO: 114, and a VL-CDR3 having a sequence set forth in SEQ ID NO: 115; and the $V_H$ domain comprises a VH-CDR1 having a sequence set forth in SEQ ID NO: 118, a VH-CDR2 having a sequence set forth in SEQ ID NO: 119, and a VH-CDR3 having a sequence set forth in SEQ ID NO: 120;

m) the $V_L$ domain comprises a VL-CDR1 having a sequence set forth in SEQ ID NO: 123, a VL-CDR2 having a sequence set forth in SEQ ID NO: 124, and a VL-CDR3 having a sequence set forth in SEQ ID NO: 125; and the $V_H$ domain comprises a VH-CDR1 having a sequence set forth in SEQ ID NO: 128, a VH-CDR2 having a sequence set forth in SEQ ID NO: 129, and a VH-CDR3 having a sequence set forth in SEQ ID NO: 130;

n) the $V_L$ domain comprises a VL-CDR1 having a sequence set forth in SEQ ID NO: 133, a VL-CDR2 having a sequence set forth in SEQ ID NO: 134, and a VL-CDR3 having a sequence set forth in SEQ ID NO: 135; and the $V_H$ domain comprises a VH-CDR1 having a sequence set forth in SEQ ID NO: 138, a VH-CDR2 having a sequence set forth in SEQ ID NO: 139, and a VH-CDR3 having a sequence set forth in SEQ ID NO: 140;

o) the $V_L$ domain comprises a VL-CDR1 having a sequence set forth in SEQ ID NO: 143, a VL-CDR2 having a sequence set forth in SEQ ID NO: 144, and a VL-CDR3 having a sequence set forth in SEQ ID NO: 145; and the $V_H$ domain comprises a VH-CDR1 having a sequence set forth in SEQ ID NO: 148, a VH-CDR2 having a sequence set forth in SEQ ID NO: 149, and a VH-CDR3 having a sequence set forth in SEQ ID NO: 150;

(p) the $V_L$ domain comprises a VL-CDR1 having a sequence set forth in SEQ ID NO: 172, a VL-CDR2 having a sequence set forth in SEQ ID NO: 173, and a VL-CDR3 having a sequence set forth in SEQ ID NO: 174; and the $V_H$ domain comprises a VH-CDR1 having a sequence set forth in SEQ ID NO: 176, a VH-CDR2 having a sequence set forth in SEQ ID NO: 177, and a VH-CDR3 having a sequence set forth in SEQ ID NO: 178; or (q) the $V_L$ domain comprises a VL-CDR1 having a sequence set forth in SEQ ID NO: 176, a VL-CDR2 having a sequence set forth in SEQ ID NO: 177, and a VL-CDR3 having a sequence set forth in SEQ ID NO: 178; and the $V_H$ domain comprises a VH-CDR1 having a sequence set forth in SEQ ID NO: 184, a VH-CDR2 having a sequence set forth in SEQ ID NO: 185, and a VH-CDR3 having a sequence set forth in SEQ ID NO: 186.

In some embodiments the antibodies or antibody derivatives thereof that binds to an extracellular domain of interleukin-3 (IL-3) receptor α-chain (CD123) include minibodies, diabodies, a single-chain antibody derivative (scFV) as described herein. In some embodiments the antibodies or antibody derivatives thereof that binds to an extracellular domain of interleukin-3 (IL-3) receptor α-chain (CD123) are chimeric antibodies, humanized antibodies, or human antibodies.

In some embodiments the present disclosure provides nucleic acids encoding the antibody or antigen binding derivative thereof that binds to an extracellular domain of interleukin-3 (IL-3) receptor α-chain (CD123) as described herein. In some embodiments the present disclosure provides expression vectors comprising the nucleic acids as described herein. In some embodiments the present disclosure provides host cells comprising the expression vectors described herein. In some embodiments the host cell is an immune cell. In some embodiments the host cell is a Chimeric Antigen Receptor T (CAR-T) cell or a CAR-NK cell. Chimeric antigen receptors (CARs, also known as chimeric T cell receptors) are synthetic constructs that are designed to be expressed in host T cells or NK cells and to induce an immune response against a specific target antigen and cells expressing that antigen. The CAR typically comprises an antibody fragment, such as a scFv or Fab fragment, incorporated in a fusion protein that also comprises additional components, such as a CD3-ζ or CD28 transmembrane domain and selective T-cell activating moieties, including the endodomains of CD3-5, CD28, OX40, 4-1BB, Lck and/or ICOS. Various combinations of such elements have been used. In some aspects the present disclosure provides, e.g., a composition comprising one or more cells that express a CAR molecule that binds CD123. In some embodiments the CAR molecule is an antibody or antigen binding derivative thereof that binds to an extracellular domain of interleukin-3 (IL-3) receptor α-chain (CD123) as described herein. In some embodiments the antibody or antigen binding derivative thereof is a scFv or a scTCR as described herein.

The present disclosure also provides bispecific affinity reagents that include binding moieties that interact with a particular target. In many embodiments, such binding moieties are or comprise an antibody or antigen binding derivative thereof that binds to an extracellular domain of interleukin-3 (IL-3) receptor α-chain (CD123) as described herein. In some embodiments, bispecific affinity reagents of the present disclosure comprise a first binding domain that specifically binds to an extracellular domain of interleukin-3 (IL-3) receptor α-chain (CD123); and a second binding domain that specifically binds to a radioactive ligand.

The present disclosure also provides methods of treating a neoplastic condition in a subject characterized by elevated expression of interleukin-3 (IL-3) receptor α-chain (CD123), comprising administering to the subject a therapeutically effective amount of a composition comprising the bispecific affinity reagents as described herein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

(FIG. 9A) Average radiance values (mean±SEM) derived from in vivo fluorescence imaging. Kaplan-Meier survival estimates. 8 animals per group. One early death was thought to be a sequelae of radiation exposure rather than leukemia (lack of weight returning to baseline after radiation exposure) (FIG. 9B). All other deaths were attributed to progressive leukemia. For $CD123^+$ cells: P=0.0014 for Ctrl vs. 10C4-B10, P=0.031 for 10C4-B10 vs. 20 μCi; P=0.0112 for 10C4-B10 vs. 40 μCi.

FIG. 14. Summary of surface plasmon resonance (Biacore T-100) analyses performed to rigorously/precisely determine univalent binding affinities of the parent murine anti-human CD123 antibody 10C4 as well as recombinant chimeric and humanized versions of 10C4, using both human IgG1 and human IgG4 frameworks, to human CD123 and nonhuman primate CD123.

FIG. 22. Summary of surface plasmon resonance (Biacore T-100) analyses performed to rigorously/precisely determine univalent binding affinities of recombinant fully human anti-human CD123 antibodies to human CD123 and nonhuman primate CD123, using both human IgG1 and human IgG4 frameworks.

DETAILED DESCRIPTION

Figure 1:
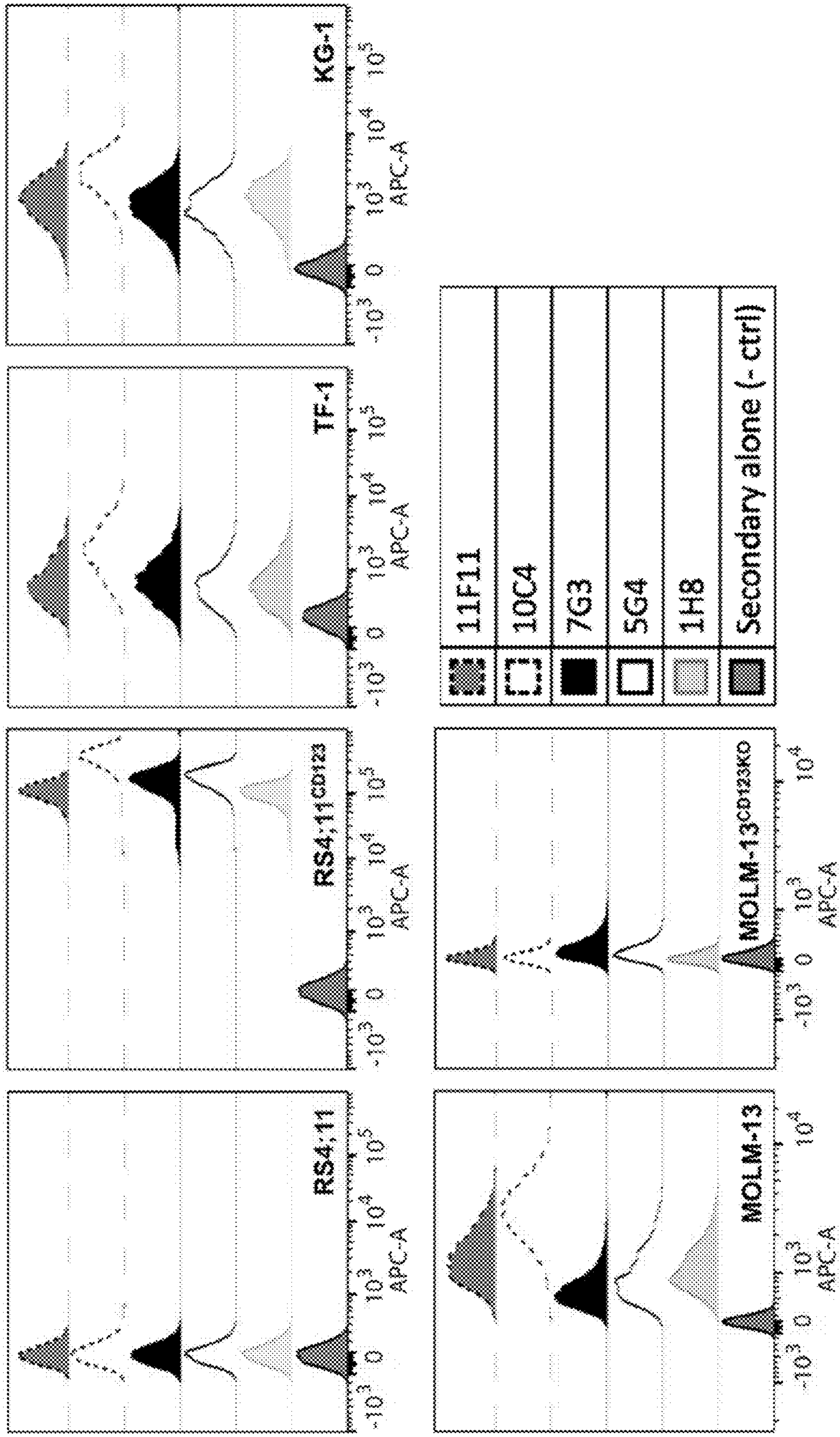
FIG. 1. Parental human RS4; 11 cells (endogenously lacking CD123), RS4; 11 cells transduced with human CD123, CD123-expressing human AML cells lines (TF-1, KG-1, MOLM-13), and MOLM-13 cells with CRISPR/Cas9-mediated knockout of the CD123 locus ($CD123^{KO}$) were left untreated or treated with murine anti-human CD123 mAbs (10C4, 5G6, 11F11, 1H8; used at 2 μg/mL) or a commercial anti-CD123 mAbs (7G3, used at 2 μg/mL) and a labeled secondary antibody before flow cytometric analysis.

The disclosure is based on the inventors' development of affinity reagents that are highly specific for leukemic and other transformed cells. The inventors explored whether a better radioimmunotherapy (RIT) approach is to target interleukin-3 (IL-3) receptor α-chain (CD123). To be most effective and successful even without stem cell support, mAbs with highly potent payloads, such as radioisotopes, need to target an antigen that is selective for leukemia cells. An ideal target for this purpose is found on few (if any) normal cells and is overexpressed on leukemia cells vs. normal cells. Of greatest interest would be a target that is not only expressed on leukemic blasts but overexpressed on leukemic stem cells relative to normal hematopoietic stem cells. Such a target is CD123. Compared to CD45 and CD33, CD123 is displayed on a much more discrete subset of normal cells. Expressed on some hematopoietic progenitors, CD123 is rapidly lost during erythroid and megakaryocytic differentiation and decreased during monocytic differentiation. On mature cells, CD123 is primarily found on basophils and plasmacytoid dendritic cells. Importantly, primitive hematopoietic stem/progenitor cells express little or no CD123, and xenotransplantation studies have shown most normal blood stem cells are unaffected by therapeutics targeting CD123. On the other hand, CD123 is widely displayed on blast cells of patients with AML (45-95%), B-ALL (85-95%), and T-ALL (45%). What makes CD123 particularly attractive is its overexpression on leukemic stem/progenitor cells relative to normal hematopoietic stem/progenitor cells. Contributing to its attractiveness as a target are studies reporting a correlation between higher CD123+ leukemic stem/progenitor cell numbers and worse outcome with AML chemotherapy. This expression pattern renders CD123 an ideal target for cancer (stem) cell-specific treatment of acute leukemia, expected to cause less on-target toxicities to normal tissues than CD45 or CD33. Consistent with this notion are preclinical studies showing limited effects of CD123-directed chimeric antigen receptor (CAR) T cells on normal hematopoietic stem/progenitor cells in vivo whereas CD33 CAR T cells exert extensive toxicities to these cells. Like CD33, CD123 is expressed on leukemia cells at several thousand copies per cell, making it amenable to therapeutic targeting with α-emitter-based RIT. Accordingly, this highly specific expression pattern makes CD123 a highly selective target for cancer (stem) cell-specific therapy of acute leukemia, both for large burden disease as well as measurable ('minimal') residual disease (MRD) cases.

As described in more detail below, the inventors developed a series of antibody-based reagents, both murine and human, that are highly specific for human CD123. Select antibodies were engineered to carry radioisotope (astatine-211 ($^{211}$At)) payloads and used to establish proof of concept for remarkably efficient anti-CD123 directed radioimmunotherapy methods in mice. Subsequently, novel dimeric and monomeric bispecific fusion constructs were developed for pre-targeted radioimmunotherapy (PRIT). In particular, the monomeric bi-specific reagent was shown to have substantially reduced internalization upon binding to CD123 expressed on the cell surface relative to the dimeric reagent, providing a robust binding target for a radiolabeled secondary reagent. While there are efforts targeting CD123 with immunotoxins, mAb-drug conjugates, bispecific antibodies, and CAR-modified T cells, these are the first demonstrations of CD123-directed RIT and PRIT. This work provides new treatment option for patients with acute leukemia and other CD123-expressing neoplastic disorders, such as myelodysplastic syndrome (MDS), plastic plasmacytoid dendritic cell neoplasms (BPDCN), classic hairy cell leukemia, Hodgkin lymphoma, and systemic mastocytosis, many of which currently still lack satisfactory treatments.

Antibody-Based Compositions

In accordance with the foregoing, in one aspect the disclosure provides an antibody or antigen binding derivative thereof that binds to an extracellular domain of interleukin-3 (IL-3) receptor α-chain (CD123). CD123 is a type I cytokine receptor and is a heterodimer with a unique alpha chain paired with a common beta subunit. In some embodiments, the antibody or antigen binding derivative thereof binds to an extracellular domain of the alpha chain. Exemplary alpha chain sequences are disclosed in UniProtKB accession no. P26951 or a sequence with at least about 85% sequence identity (e.g., about 85%, about 90%, about 95%, about 98% sequence identity) thereto.

The term "antibody" is used herein in the broadest sense and encompasses various antibody structures derived from any antibody-producing mammal (e.g., mouse, rat, rabbit, and primate including human), and which specifically bind to an antigen of interest. An antibody derivative refers to a molecule that incorporates one or more antibodies or one or more antibody fragments. An antibody fragment specifically refers to an intact portion or subdomain of a source antibody that still retains a desired function, such as contribution to antigen-binding capability or signaling capability. An "antibody fragment" comprises a portion of an intact antibody, preferably the antigen binding and/or the variable region of the intact antibody. Examples of antibody fragments include Fab. Fab', $F(ab')_2$ and Fv fragments; diabodies; linear antibodies (see U.S. Pat. No. 5,641,870. Example 2; Zapata et al., *Protein Eng.* 8(10): 1057-1062 [1995]); single-chain antibody molecules, and multispecific antibodies formed from antibody fragments. Typically, in a derivative there is at least some additional modification in the structure of the antibody or antibody fragment, or in the presentation or configuration of the antibody or antibody fragment.

Exemplary antibodies of the disclosure include polyclonal, monoclonal and recombinant antibodies. Exemplary antibodies or antibody derivatives of the disclosure also include multispecific antibodies (e.g., bispecific antibodies), human antibodies, murine antibodies, and chimeric antibodies, e.g., humanized antibodies.

The term "monoclonal antibody" as used herein refers to an antibody obtained from a population of substantially homogeneous antibodies. i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256:495-97 (1975); Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al. *J. Mol. Biol.* 222:581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/technology* 10:779-783 (1992); Lonberg et al., *Nature* 368: 856-859 (1994); Morrison. *Nature* 368:812-813 (1994); Fishwild et al., *Nature Biotechnol.* 14:845-851 (1996); *Neuberger, Nature Biotechnol.* 14:826 (1996); and Lonberg and Huszar, *Intern. Rev. Immunol.* 13:65-93 (1995).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al. *Proc. Natl. Acad. Sci. USA,* 81:6851-6855 (1984)).

"Humanized" forms of non-human (e.g., murine) antibodies are antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta. *Curr. Op. Struct. Biol.* 2:593-596 (1992). See also, for example, Vaswani and Hamilton. *Ann. Allergy. Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al. *Monoclonal Antibodies and Cancer Therapy*. Alan R. Liss, p. 77 (1985); Boerner et al., *J. Immunol.,* 147 (1): 86-95 (1991). See also van Dijk and van de Winkel, *Curr. Opin. Pharmacol.,* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

"Single-chain Fv" also abbreviated as "sFv or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90:6444-6448 (1993).

As indicated, the antibody or antibody derivative (including fragment) encompassed by the disclosure binds to CD123. In preferred embodiments, the antibody or antibody derivative specifically binds to CD123. As used herein, the term "specifically bind" or variations thereof refer to the ability of the binding domain (e.g., of the antibody, or fragment or derivative thereof) to bind to the antigen of interest (e.g., CD123), without significant binding to other molecules, under standard conditions known in the art. The antibody or antibody derivative can bind to other peptides, polypeptides, or proteins, but with lower affinity as determined by, e.g., immunoassays, Biacore, or other assays known in the art. However, the binding domain preferably does not substantially cross-react with other antigens. In some embodiments, the antibody or antibody derivative has a binding affinity for CD123 within a range characterized by a dissociation constant ($K_d$) from about 50 nM (lower binding affinity) to about 0.001 nM (higher binding affinity). For example, the antibody or antibody derivative has a binding affinity for the CD123 protein characterized by ($K_d$) of about 50 nM, 40 nM, 30 nM, 20 nM, 10 nM, 5 nM, 1 nM, 0.75 nM, 0.5 nM, 0.1 nM, 0.05 nM, 0.01 nM, 0.005 nM, and 0.001 nM, or even smaller. Typical ($K_d$) ranges characterizing the binding affinity of the cell-targeting domain for the antigen characteristic of the cell-type of interest include from about 30 nM to about 10 nM, from about 20 nM to about 1 nM, from about 10 nM to about 0.1 nM, from about 0.5 nM to about 0.05 nM, and from about 0.1 nM to about 0.001 nM, or even lower, or any subrange therein.

As used herein, the term "CDR" refers to the complementarity determining region within antibody variable sequences. The binding of the antibody or antibody derivative is conferred in a large part by the structure of the complementarity-determining regions (CDRs) (also known as hypervariable regions), which are held within framework regions of light chain variable ($V_L$) domain and the heavy chain variable ($V_H$) domain of the antibody or antibody derivative molecule. The CDRs in each chain are held together in close proximity by the framework regions and, with the CDRs from the other chain, contribute to the formation of the antigen-binding site of the antibody.

There are three CDRs in each of the variable regions of the heavy chain and of the light chain, which are designated CDR 1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al, Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). CDR region sequences also have been defined structurally by Chothia as those residues that are not part of the conserved β-sheet framework, and thus are able to adapt different conformations (Id.). Both terminologies are well recognized in the art. CDR region sequences have also been defined by AbM, Contact and IMGT.

The term "hypervariable region", "HVR", or "HV", when used herein refers to the regions of an antibody variable domain that are hypervariable in sequence and/or form structurally defined loops. Generally, antibodies comprise six hypervariable regions; three in the VH (H 1, H2, H3), and three in the VL (L1, L2, L3). A number of hypervariable region delineations are in use and are encompassed herein. The Kabat CDRs are based on sequence variability and are the most commonly used (Kabat et al., *Sequences of Proteins of Immunological Interest,* $5^{th}$ Ed. Public Health Service, National Institutes of Health, Bethesda, Md. (1991)). Chothia refers instead to the location of the structural loops (Chothia and Lesk *J Mol. Bioi.* 196:901-917 (1987)). The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM (Oxford Molecular) hypervariable regions represent a compromise between the Kabat CDRs and Chothia structural loops, and are used by Oxford Molecular's AbM antibody modeling software (Whitelegg N R, Rees A R. WAM: an improved algorithm for modelling antibodies on the WEB. Protein Eng. 2000 December; 13(12): 819-24). The "contact" hypervariable regions are based on an analysis of the available complex crystal structures.

Recently, a universal numbering system has been developed and widely adopted, ImMunoGeneTics (IMGT) Information System® (Lafranc et al., *Dev. Comp. Immunol.* 27(1): 55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. Correspondence between the Kabat numbering and the IMGT unique numbering system is also well known to one skilled in the art.

In some instances, a complementarity determining region can include amino acids from both a CDR region defined according to Kabat and a hypervariable loop. For example, the CDRH1 of the human heavy chain of antibody 4D5 includes amino acids 26 to 35. Chothia and coworkers (Chothia & Lesk, J. Mol. Biol, 196:901-917 (1987) and Chothia et al., Nature 342:877-883 (1989)) found that certain sub-portions within Kabat CDRs adopt nearly identical peptide backbone conformations, in spite of great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB). 9:133439 (1995)) and MacCallum (J Mot Biol 262(5): 732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CL domain of the light chain.

In some embodiments, the antibody or antigen binding derivative thereof that binds CD123 comprises at least one, two, three, four, five, or six CDRs selected from a $V_L$-CDR1 having a sequence set selected from SEQ ID NO: 3, 13, 23, 33, 43, 53, 63, 73, 83, 93, 103, 113, 123, 133, 143, 172, and 180, a $V_L$-CDR2 having a sequence set forth in SEQ ID NO: 4, 14, 24, 34, 44, 54, 64, 74, 84, 94, 104, 114, 124, 134, 144, 173, and 181, and a $V_L$-CDR3 having a sequence set forth in SEQ ID NO: 5, 15, 25, 35, 45, 55, 65, 75, 85, 95, 105, 115, 125, 135, 145, 174, and 182, a $V_H$-CDR1 having a sequence set forth in SEQ ID NO: 8, 18, 28, 38, 48, 58, 68, 78, 88, 98, 108, 118, 128, 138, 148, 176, and 184, a $V_H$-CDR2 having a sequence set forth in SEQ ID NO: 9, 19, 29, 39, 49, 69, 79, 89, 99, 109, 119, 129, 139, 149, 177, and 185, and a $V_H$-CDR3 having a sequence set forth in SEQ ID NO: 10, 20, 30, 40, 50, 60, 70, 80, 90, 100, 110, 120, 140, 150, 178, and 186.

As will be understood by a person skilled in the art, the boundaries between the CDRs and framework sequences for any of the VH regions and VL regions described herein can be determined using any one of the well-known methods in the art, including IMGT, Kabat, Chothia, Contact, or Kabat plus Chothia (e.g., "Exemplary" as described herein). Accordingly, any anti-CD123 antibody having one or more CDR or framework sequence as described herein includes a CDR or framework amino acid sequence as determined using IMGT, Kabat, Chothia, Contact, or Kabat plus Chothia.

Accordingly, in some embodiments, $V_L$ CDR1 comprises the amino acid residues SEQ ID NO: 3 or a sub portion thereof, the amino acid residues of SEQ ID NO: 13 or a sub portion thereof, the amino acid residues of SEQ ID NO: 23 or a sub portion thereof, the amino acid residues of SEQ ID NO: 33 or a sub portion thereof, the amino acid residues of SEQ ID NO: 43 or a sub portion thereof, the amino acid residues of SEQ ID NO: 53 or a sub portion thereof, the amino acid residues of SEQ ID NO: 63 or a sub portion thereof, the amino acid residues of SEQ ID NO: 73 or a sub portion thereof, the amino acid residues of SEQ ID NO: 83 or a sub portion thereof, the amino acid residues of SEQ ID NO: 93 or a sub portion thereof, the amino acid residues of SEQ ID NO: 103 or a sub portion thereof, the amino acid residues of SEQ ID NO: 113 or a sub portion thereof, the amino acid residues of SEQ ID NO: 123 or a sub portion thereof, the amino acid residues of SEQ ID NO: 133 or a sub portion thereof, the amino acid residues of SEQ ID NO: 143 or a sub portion thereof, the amino acid residues of SEQ ID: 172 or a sub portion thereof, or the amino acid residues of SEQ ID: 180 or a sub portion thereof.

In some embodiments, $V_L$ CDR2 comprises the amino acid residues of SEQ ID NO: 4 or a sub portion thereof, the amino acid residues of SEQ ID NO: 14 or a sub portion thereof, the amino acid residues of SEQ ID NO: 24 or a sub portion thereof, the amino acid residues of SEQ ID NO: 34 or a sub portion thereof, the amino acid residues of SEQ ID NO: 44 or a sub portion thereof, the amino acid residues of SEQ ID NO: 54 or a sub portion thereof, the amino acid residues of SEQ ID NO: 64 or a sub portion thereof, the amino acid residues of SEQ ID NO: 74 or a sub portion thereof, the amino acid residues of SEQ ID NO: 84 or a sub portion thereof, the amino acid residues of SEQ ID NO: 94 or a sub portion thereof, the amino acid residues of SEQ ID NO: 104 or a sub portion thereof, the amino acid residues of SEQ ID NO: 114 or a sub portion thereof, the amino acid residues of SEQ ID NO: 124 or a sub portion thereof, the amino acid residues of SEQ ID NO: 134 or a sub portion thereof, the amino acid residues of SEQ ID NO: 144 or a sub portion thereof, the amino acid residues of SEQ ID: 173 or a sub portion thereof, or the amino acid residues of SEQ ID: 181 or a sub portion thereof.

In some embodiments, $V_L$ CDR3 comprises the amino acid residues of SEQ ID NO: 5 or a sub portion thereof, the amino acid residues of SEQ ID NO: 15 or a sub portion thereof, the amino acid residues of SEQ ID NO: 25 or a sub portion thereof, the amino acid residues of SEQ ID NO: 35 or a sub portion thereof, the amino acid residues of SEQ ID NO: 45 or a sub portion thereof, the amino acid residues of SEQ ID NO: 55 or a sub portion thereof, the amino acid residues of SEQ ID NO: 65 or a sub portion thereof, the amino acid residues of SEQ ID NO: 75 or a sub portion thereof, the amino acid residues of SEQ ID NO: 85 or a sub portion thereof, the amino acid residues of SEQ ID NO: 95 or a sub portion thereof, the amino acid residues of SEQ ID NO: 105 or a sub portion thereof, the amino acid residues of SEQ ID NO: 115 or a sub portion thereof, the amino acid residues of SEQ ID NO: 125 or a sub portion thereof, the amino acid residues of SEQ ID NO: 135 or a sub portion thereof, the amino acid residues of SEQ ID NO: 145 or a sub portion thereof, the amino acid residues of SEQ ID: 174 or a sub portion thereof, or the amino acid residues of SEQ ID: 182 or a sub portion thereof.

In some embodiments, $V_H$ CDR1 comprises the amino acid residues of SEQ ID NO: 8 or a sub portion thereof, the amino acid residues of SEQ ID NO: 18 or a sub portion thereof, the amino acid residues of SEQ ID NO: 28 or a sub portion thereof, the amino acid residues of SEQ ID NO: 38 or a sub portion thereof, the amino acid residues of SEQ ID NO: 48 or a sub portion thereof, the amino acid residues of SEQ ID NO: 58 or a sub portion thereof, the amino acid residues of SEQ ID NO: 68 or a sub portion thereof, the amino acid residues of SEQ ID NO: 78 or a sub portion thereof, the amino acid residues of SEQ ID NO: 88 or a sub portion thereof, the amino acid residues of SEQ ID NO: 98 or a sub portion thereof, the amino acid residues of SEQ ID NO: 108 or a sub portion thereof, the amino acid residues of SEQ ID NO: 118 or a sub portion thereof, the amino acid residues of SEQ ID NO: 128 or a sub portion thereof, the amino acid residues of SEQ ID NO: 138 or a sub portion thereof, the amino acid residues of SEQ ID NO: 148 or a sub portion thereof, the amino acid residues of SEQ ID: 176 or a sub portion thereof, or the amino acid residues of SEQ ID: 184 or a sub portion thereof.

In some embodiments, $V_H$ CDR2 comprises the amino acid residues of SEQ ID NO: 9 or a sub portion thereof, the amino acid residues of SEQ ID NO: 19 or a sub portion thereof, the amino acid residues of SEQ ID NO: 29 or a sub portion thereof, the amino acid residues of SEQ ID NO: 39 or a sub portion thereof, the amino acid residues of SEQ ID NO: 49 or a sub portion thereof, the amino acid residues of SEQ ID NO: 59 or a sub portion thereof, the amino acid residues of SEQ ID NO: 69 or a sub portion thereof, the amino acid residues of SEQ ID NO: 79 or a sub portion thereof, the amino acid residues of SEQ ID NO: 89 or a sub portion thereof, the amino acid residues of SEQ ID NO: 99 or a sub portion thereof, the amino acid residues of SEQ ID NO: 109 or a sub portion thereof, the amino acid residues of SEQ ID NO: 119 or a sub portion thereof, the amino acid residues of SEQ ID NO: 129 or a sub portion thereof, the amino acid residues of SEQ ID NO: 139 or a sub portion thereof, the amino acid residues of SEQ ID NO: 149 or a sub portion thereof, the amino acid residues of SEQ ID: 177 or a sub portion thereof, or the amino acid residues of SEQ ID: 185 or a sub portion thereof.

In some embodiments, $V_H$ CDR3 comprises the amino acid residues of SEQ ID NO: 10 or a sub portion thereof, the amino acid residues of SEQ ID NO: 20 or a sub portion thereof, the amino acid residues of SEQ ID NO: 30 or a sub portion thereof, the amino acid residues of SEQ ID NO: 40 or a sub portion thereof, the amino acid residues of SEQ ID NO: 50 or a sub portion thereof, the amino acid residues of SEQ ID NO: 60 or a sub portion thereof, the amino acid residues of SEQ ID NO: 70 or a sub portion thereof, the amino acid residues of SEQ ID NO: 80 or a sub portion thereof, the amino acid residues of SEQ ID NO: 90 or a sub portion thereof, the amino acid residues of SEQ ID NO: 100 or a sub portion thereof, the amino acid residues of SEQ ID NO: 110 or a sub portion thereof, the amino acid residues of SEQ ID NO: 120 or a sub portion thereof, the amino acid residues of SEQ ID NO: 130 or a sub portion thereof, the amino acid residues of SEQ ID NO: 140 or a sub portion thereof, the amino acid residues of SEQ ID NO: 150 or a sub portion thereof, the amino acid residues of SEQ ID: 178 or a sub portion thereof, or the amino acid residues of SEQ ID: 186 or a sub portion thereof.

In some embodiments, the antibody or antigen binding derivative thereof that binds CD123 comprises a light chain variable ($V_L$) domain and a heavy chain variable ($V_H$) domain, wherein the $V_L$ domain comprises a $V_L$-CDR1 having a sequence set forth in one of SEQ ID NOS: 3, 13, 23, 33, 43, 53, 63, 73, 83, 93, 103, 113, 123, 133, 143, 172, and 180, a $V_L$-CDR2 having a sequence set forth in one of SEQ ID NOS: 4, 14, 24, 34, 44, 54, 64, 74, 84, 94, 104, 114, 124, 134, 144, 173, and 181, a $V_L$-CDR3 having a sequence set forth in one of SEQ ID NOS: 5, 15, 25, 35, 45, 55, 65, 75, 85, 95, 105, 115, 125, 135, 145, 174 and 182; and wherein the $V_H$ domain comprises a $V_H$-CDR1 having a sequence set forth in one of SEQ ID NOS: 8, 18, 28, 38, 48, 58, 68, 78, 88, 98, 108, 118, 128, 138, 148, 176, and 184, a $V_H$-CDR2 having a sequence set forth in one of SEQ ID NOS: 9, 19, 29, 39, 49, 69, 79, 89, 99, 109, 119, 129, 139, 149, 177, and 185, and a $V_H$-CDR3 having a sequence set forth in one of SEQ ID NOS: 10, 20, 30, 40, 50, 60, 70, 80, 90, 100, 110, 120, 140,150, 178, and 186.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 3, a $V_L$-CDR2 having a sequence set forth in SEQ ID NO: 4, and a $V_L$-CDR3 having a sequence set forth in SEQ ID NO: 5; and the $V_H$ domain comprises a $V_H$-CDR1 having a sequence set forth in SEQ ID NO: 8, a $V_H$-CDR2 having a sequence set forth in SEQ ID NO: 9, and a $V_H$-CDR3 having a sequence set forth in SEQ ID NO: 10.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 13, a $V_L$-CDR2 having a sequence set forth in SEQ ID NO: 14, and a $V_L$-CDR3 having a sequence set forth in SEQ ID NO: 15; and the $V_H$ domain comprises a $V_H$-CDR1 having a sequence set forth in SEQ ID NO: 18, a $V_H$-CDR2 having a sequence set forth in SEQ ID NO: 19, and a $V_H$-CDR3 having a sequence set forth in SEQ ID NO: 20.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 23, a $V_L$-CDR2 having a sequence set forth in SEQ ID NO: 24, and a $V_L$-CDR3 having a sequence set forth in SEQ ID NO: 25; and the $V_H$ domain comprises a $V_H$-CDR1 having a sequence set forth in SEQ ID NO: 28, a $V_H$-CDR2 having a sequence set forth in SEQ ID NO: 29, and a $V_H$-CDR3 having a sequence set forth in SEQ ID NO: 30.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 33, a $V_L$-CDR2 having a sequence set forth in SEQ ID NO: 34, and a $V_L$-CDR3 having a sequence set forth in SEQ ID NO: 35; and the $V_H$ domain comprises a $V_H$-CDR1 having a sequence set forth in SEQ ID NO: 38, a $V_H$-CDR2 having a sequence set forth in SEQ ID NO: 39, and a $V_H$-CDR3 having a sequence set forth in SEQ ID NO: 40.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 43, a $V_L$-CDR2 having a sequence set forth in SEQ ID NO: 44, and a $V_L$-CDR3 having a sequence set forth in SEQ ID NO: 45; and the $V_H$ domain comprises a $V_H$-CDR1 having a sequence set forth in SEQ ID NO: 48, a $V_H$-CDR2 having a sequence set forth in SEQ ID NO: 49, and a $V_H$-CDR3 having a sequence set forth in SEQ ID NO: 50.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 53, a $V_L$-CDR2 having a sequence set forth in SEQ ID NO: 54, and a $V_L$-CDR3 having a sequence set forth in SEQ ID NO: 55; and the $V_H$ domain comprises a $V_H$-CDR1 having a sequence set forth in SEQ ID NO: 58, a $V_H$-CDR2 having a sequence set forth in SEQ ID NO: 59, and a $V_H$-CDR3 having a sequence set forth in SEQ ID NO: 60.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 63, a $V_L$-CDR2 having a sequence set forth in SEQ ID NO: 64, and a $V_L$-CDR3 having a sequence set forth in SEQ ID NO: 65; and the $V_H$ domain comprises a $V_H$-CDR1 having a sequence set forth in SEQ ID NO: 68, a $V_H$-CDR2 having a sequence set forth in SEQ ID NO: 69, and a $V_H$-CDR3 having a sequence set forth in SEQ ID NO: 70.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 73, a $V_L$-CDR2 having a sequence set forth in SEQ ID NO: 74, and a $V_L$-CDR3 having a sequence set forth in SEQ ID NO: 75; and the $V_H$ domain comprises a $V_H$-CDR1 having a sequence set forth in SEQ ID NO: 78, a $V_H$-CDR2 having a sequence set forth in SEQ ID NO: 79, and a $V_H$-CDR3 having a sequence set forth in SEQ ID NO: 80.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 83, a $V_L$-CDR2 having a sequence set forth in SEQ ID NO: 84, and a $V_L$-CDR3 having a sequence set forth in SEQ ID NO: 85; and the $V_H$ domain comprises a $V_H$-CDR1 having a sequence set forth in SEQ ID NO: 88, a $V_H$-CDR2 having a sequence set forth in SEQ ID NO: 89, and a $V_H$-CDR3 having a sequence set forth in SEQ ID NO: 90.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 93, a $V_L$-CDR2 having a sequence set forth in SEQ ID NO: 94, and a $V_L$-CDR3 having a sequence set forth in SEQ ID NO: 95; and the $V_H$ domain comprises a $V_H$-CDR1 having a sequence set forth in SEQ ID NO: 98, a $V_H$-CDR2 having a sequence set forth in SEQ ID NO: 99, and a $V_H$-CDR3 having a sequence set forth in SEQ ID NO: 100.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 103, a $V_L$-CDR2 having a sequence set forth in SEQ ID NO: 104, and a $V_L$-CDR3 having a sequence set forth in SEQ ID NO: 105; and the $V_H$ domain comprises a $V_H$-CDR1 having a sequence set forth in SEQ ID NO: 108, a $V_H$-CDR2 having a sequence set forth in SEQ ID NO: 109, and a $V_H$-CDR3 having a sequence set forth in SEQ ID NO: 110.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 113, a $V_L$-CDR2 having a sequence set forth in SEQ ID NO: 114, and a $V_L$-CDR3 having a sequence set forth in SEQ ID NO: 115; and the $V_H$ domain comprises a $V_H$-CDR1 having a sequence set forth in SEQ ID NO: 118, a $V_H$-CDR2 having a sequence set forth in SEQ ID NO: 119, and a $V_H$-CDR3 having a sequence set forth in SEQ ID NO: 120.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 123, a $V_L$-CDR2 having a sequence set forth in SEQ ID NO: 124, and a $V_L$-CDR3 having a sequence set forth in SEQ ID NO: 125; and the $V_H$ domain comprises a $V_H$-CDR1 having a sequence set forth in SEQ ID NO: 128, a $V_H$-CDR2 having a sequence set forth in SEQ ID NO: 129, and a $V_H$-CDR3 having a sequence set forth in SEQ ID NO: 130.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 133, a $V_L$-CDR2 having a sequence set forth in SEQ ID NO: 134, and a $V_L$-CDR3 having a sequence set forth in SEQ ID NO: 135; and the $V_H$ domain comprises a $V_H$-CDR1 having a sequence set forth in SEQ ID NO: 138, a $V_H$-CDR2 having a sequence set forth in SEQ ID NO: 139, and a $V_H$-CDR3 having a sequence set forth in SEQ ID NO: 140.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 143, a $V_L$-CDR2 having a sequence set forth in SEQ ID NO: 144, and a $V_L$-CDR3 having a sequence set forth in SEQ ID NO: 145; and the $V_H$ domain comprises a $V_H$-CDR1 having a sequence set forth in SEQ ID NO: 148, a $V_H$-CDR2 having a sequence set forth in SEQ ID NO: 149, and a $V_H$-CDR3 having a sequence set forth in SEQ ID NO: 150.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 172, a $V_L$-CDR2 having a sequence set forth in SEQ ID NO: 173, and a $V_L$-CDR3 having a sequence set forth in SEQ ID NO: 174; and the $V_H$ domain comprises a $V_H$-CDR1 having a sequence set forth in SEQ ID NO: 176, a $V_H$-CDR2 having a sequence set forth in SEQ ID NO: 177, and a $V_H$-CDR3 having a sequence set forth in SEQ ID NO: 178.

In some embodiments, the antibody or antigen binding derivative thereof that binds CD123 comprises a $V_L$ domain and a $V_H$ domain, wherein the $V_L$ domain comprises a $V_L$-CDR1 having a sequence set forth in SEQ ID NO: 180, a $V_L$-CDR2 having a sequence set forth in SEQ ID NO: 181, and a $V_L$-CDR3 having a sequence set forth in SEQ ID NO: 182; and the $V_H$ domain comprises a $V_H$-CDR1 having a sequence set forth in SEQ ID NO: 184, a $V_H$-CDR2 having a sequence set forth in SEQ ID NO: 185, and a $V_H$-CDR3 having a sequence set forth in SEQ ID NO: 186.

It will be understood that in certain embodiments, substitutions, insertions, or deletions may occur within one or more CDRs without substantially reducing the ability of the antibody to bind antigen. For example, conservative alterations (e.g., conservative substitutions as provided herein) that do not substantially reduce binding affinity may be made in CDRs. In further embodiments, a CDR variant sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine. In yet further embodiments, a CDR variant sequence incorporates substitutions that enhance properties of the CDR such as increase in stability, resistance to proteases and/or binding affinities to CD123. In other embodiments, a CDR variant sequence is modified to change non-critical residues or residues in non-critical regions. Amino acids that are not critical can be identified by known methods, such as affinity maturation, CDR walking, site-directed mutagenesis, crystallization, nuclear magnetic resonance, photoaffinity labeling, or alanine-scanning mutagenesis. The binding affinity can be confirmed by routine testing known in the art, as described above. In certain embodiments, each CDR provided above either is unaltered, or contains one, two, three or four amino acid substitutions.

In some embodiments, the anti-CD123 antibody or derivative thereof comprises CDRs as defined in the preceding paragraphs in this section and a framework regions sequence having at least 90% identity, or at least 95% identity to a human immunoglobulin framework sequences. In some embodiments, each of framework region 1 (FR1), framework region 2 (FR2), framework region 3 (FR3), and framework region 4 (FR4) have at least 90% identity, or at least 95% identity to a corresponding human FR1, FR2, FR3, or FR4 sequence. In some embodiments, the light and heavy CDRs are selected without the surrounding framework sequences of the respective variable domains, which include framework sequences from other immunoglobulins or consensus framework regions, optionally are further mutated and/or replaced by other suitable framework sequences.

In some embodiments, the antibody or antigen binding derivative comprises a $V_L$ domain comprising an amino acid sequence with at least 80% (e.g., at least about 85%, 90%, 91%, 92%, 93%, 94%, 95%, 96%, 97%, 98%, 99%, 100%) sequence identity to the sequence set forth in one of SEQ ID NOS: 2, 12, 22, 32, 42, 52, 62, 72, 82, 92, 102, 112, 122, 132, 142, 171, and 175. In some embodiments, the antibody or antigen binding derivative comprises a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in one of SEQ ID NOS: 7, 17, 27, 37, 47, 57, 67, 77, 87, 97, 107, 117, 127, 137, 147, 179, and 183.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 2, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 7.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 12, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 17.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 22, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 27.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 32, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 37.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 42, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 47.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 52, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 57.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 62, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 67.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 72, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 77.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100% sequence identity to the sequence set forth in SEQ ID NO: 82, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 87.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100% sequence identity to the sequence set forth in SEQ ID NO: 92, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 97.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 102, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 107.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 112, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 117.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 122, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 127.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 132, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 137.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 142, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 147 or SEQ ID NO: 151.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 171, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 175.

In some embodiments, the antibody or antigen binding derivative thereof that binds CD123 comprises a $V_L$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 179, and a $V_H$ domain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 183.

In some embodiments, a variant heavy or light chain domain sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine.

In yet further embodiments, a variant heavy or light chain domain sequence incorporates substitutions that enhance properties of the CDR such as increase in stability, resistance to proteases and/or binding affinities to CD123. In other embodiments, a variant heavy or light chain domain sequence is modified to change non-critical residues or residues in non-critical regions. Amino acids that are not critical can be identified by known methods, such as affinity maturation, CDR walking, site-directed mutagenesis, crystallization, nuclear magnetic resonance, photoaffinity labeling, or alanine-scanning mutagenesis.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 196, 198, 202, 204, 208, 210, 214, 216, 220, 222, 226, 228, 232, 234, 238, 240, 248, 250, 258, 268, and 270.

In some embodiments, the antibody or antigen binding derivative thereof that binds CD123 comprises a light chain comprising an amino acid sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 200, 206, 212, 218, 224, 230, 236, 252, and 272.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 196 or SEQ ID NO: 198, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 200.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 202 or SEQ ID NO: 204, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 206.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 208 or SEQ ID NO: 210, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 212.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 214 or SEQ ID NO: 216, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 218.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 220 or SEQ ID NO: 222, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 224.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 226 or SEQ ID NO: 228, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 230.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 232 or SEQ ID NO: 234, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 236.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 238 or SEQ ID NO: 240, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 236.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 248 or SEQ ID NO: 250, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 252.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 258, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 252.

In some embodiments, the antibody or antigen binding derivative thereof that binds CD123 comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 268 or SEQ ID NO: 270, and a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 272.

In some embodiments, the antibody or antigen binding derivative thereof that binds CD123 comprises a heavy chain comprising nucleotide sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 195, 197, 201, 203, 207, 209, 213, 215, 219, 221, 225, 227, 231, 233, 237, 239, 247, 249, 253, 255, 257, 267, and 269.

In some embodiments, the antibody or antigen binding derivative thereof that binds CD123 comprises a light chain comprising a nucleotide sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 199, 205, 211, 217, 223, 229, 235, 251, and 271.

In some embodiments, the antibody is a monoclonal antibody. The term "monoclonal antibody" refers to a homogeneous antibody population involved in the highly specific recognition and binding of a single antigenic determinant or epitope. This is in contrast to polyclonal antibodies that typically include a mixture of different antibodies directed against a variety of different antigenic determinants. Monoclonal antibodies can be produced using hybridoma methods (see, e.g., Kohler, B. and Milstein, C. (1975) *Nature* 256: 495-497 or as modified by Buck, D. W., et al., *In Vitro*, 18:377-381(1982). In some embodiments, the antibody of interest can be sequenced, and the polynucleotide sequence may then be cloned into a vector for expression or propagation. The sequence encoding the antibody of interest can be maintained in the vector in a host cell, and the host cell can then be expanded and frozen for future use. As indicated, the disclosure also encompasses derivatives (including fragments) of monoclonal antibodies, which are described in more detail below.

In some embodiments, the antibody is a chimeric antibody, or the derivative is a derivative of a chimeric antibody. A "chimeric antibody" is a recombinant protein that contains domains from different sources. For example, the variable domains, or at least the complementarity-determining regions (CDRs) thereof, can be derived from a non-human species (e.g., rodent) antibody, while the remainder of the antibody molecule is derived from a human antibody. The chimeric antibody or derivative thereof can be a partially or fully humanized antibody or derivative thereof. A "humanized antibody" is a chimeric antibody that comprises a minimal sequence that conforms to specific CDRs derived from non-human immunoglobulin that is transplanted into a human antibody framework. In some embodiments, humanized antibodies are typically recombinant proteins in which only the antibody CDRs are of non-human origin. The term "human antibody" means an antibody produced by a human or an antibody having an amino acid sequence corresponding to an antibody produced by a human made using any technique known in the art. This definition of a human antibody includes intact or full-length antibodies, and fragments and other derivatives thereof.

In some embodiments, the antibody or antigen binding derivative thereof that binds CD123 comprises a chimeric antibody. In some embodiments the chimeric antibody comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 242 and 244

In some embodiments the chimeric antibody comprises a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 246.

In some embodiments the chimeric antibody comprises a heavy chain comprising an amino acid sequence set forth in SEQ ID NO: 242, and a light chain comprising an amino acid sequence set forth in SEQ ID NO: 246.

In some embodiments the chimeric antibody comprises a heavy chain comprising an amino acid sequence set forth in SEQ ID NO: 244, and a light chain comprising an amino acid sequence set forth in SEQ ID NO: 246.

In some embodiments the chimeric antibody comprises a heavy chain comprising a nucleotide sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 241 and 243.

In some embodiments the chimeric antibody comprises a light chain comprising a nucleotide sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 245.

In some embodiments, the antibody or antigen binding derivative thereof that binds CD123 comprises a humanized antibody. In some embodiments the humanized antibody comprises a heavy chain comprising an amino acid sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 248, 250, 254, 256, and 258.

In some embodiments the humanized antibody comprises a light chain comprising an amino acid sequence with at least about 80% (e.g., at least about 85%, 90%, 91%, 92%, 93%, 94%, 95%, 96%, 97%, 98%, 99%, 100%) sequence identity to the sequence set forth in SEQ ID NO: 252.

In some embodiments the humanized antibody comprises a heavy chain comprising a nucleotide sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 247, 249, 253, and 255.

In some embodiments the humanized antibody comprises a light chain comprising a nucleotide sequence with at least about 80% (e.g., at least about 85%, 90%, 91%, 92%, 93%, 94%, 95%, 96%, 97%, 98%, 99%, 100%) sequence identity to the sequences set forth in SEQ ID NO: 251.

The disclosure encompasses both intact and full-length antibodies, as described above, as well as derivative, such as fragments of the disclosed antibodies. In certain applications, antibody fragments and other smaller derivatives have an advantage over full-length antibodies because they can still serve as vehicles to specifically target radionuclides and other payloads, but, because they lack Fc interactions and are smaller, can yield improved tumor uptake/penetration and reduced toxicity relative to mAbs. The derivatives (including fragments) typically maintain the CD123 binding functionality and, thus, the structure of the derivatives typically maintain at least one, two, three, four, five, or all six of the CDRs, allowing for conservative mutations that do not negatively affect binding, as described above. the antigen binding derivative comprises an antigen binding antibody fragment. A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, NY, pp. 71-77, 1975; and Lewin, Genes IV, Oxford University Press, NY and Cell Press, Cambridge, MA, p. 8, 1990).

Illustrative antibody fragments encompassed by the disclosure include a nanobody, an Fab fragment, an Fab', an $F(ab)_2$ fragment, an $F(ab)_2$ fragment, an $F(ab')_2$ fragment, a $V_HH$ fragment, and a $V_{NAR}$ fragment. Antibody fragments that recognize specific epitopes can be generated by any technique known to those of skill in the art. For example, Fab and $F(ab')_2$ fragments of the disclosure can be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the CHI domain of the heavy chain. Further, the antibodies, or fragments or derivatives thereof, of the present disclosure can also be generated using various phage display methods known in the art. Finally, the antibodies, or fragments or derivatives thereof, can be produced recombinantly according to known techniques.

In some embodiments, the antigen binding derivative is or comprises a single-chain antibody. A single chain antibody refers to a derivative where the domain, e.g., the $V_L$ domain and $V_H$ domain, reside in a single polypeptide molecule instead of separate, associate molecules. The domains are typically covalently linked by flexible linker domains that do not interfere with antigen binding or cause steric hindrance. For example, an exemplary single chain antibody derivative encompassed by the disclosure is a "single-chain Fv" or "scFv" antibody fragment, which comprises the $V_L$ and $V_H$ domains of an antibody, wherein these domains are present in a single polypeptide chain. Another exemplary single-chain antibody encompassed by the disclosure is a single-chain Fab fragment (scFab), which comprise the $V_L$ and $C_L$ domains fused to the $V_H$ and $C_H$ domains in a single polypeptide chain. Other antigen-binding derivatives encompassed by the disclosure include minibodies, diabodies, triabodies, and scFv-Fc constructs. A minibody is a type of potentially bispecific derivative that contains two scFvs fused to a $C_H3$ (or similar) domains. For example, one scFv (e.g., targeting CD123) is fused to the N-terminus of one of the $C_H3$ domains and the scFv (e.g., targeting CD123 or a different antigen) to the other $C_H3$ domain. The two $C_H3$ domains heterodimerize and/or otherwise are stabilized by disulfide bonds.

In some embodiments, the antibody or antigen binding derivative thereof that binds CD123 comprises a humanized antibody. In some embodiments the humanized antibody comprises a minibody. In some embodiments the minibody comprises an amino acid sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 260 and 262. In some embodiments the minibody comprises an amino acid sequence set forth in SEQ ID NO: 260. In some embodiments the minibody comprises an amino acid sequence set forth in SEQ ID NO: 262. In some embodiments the minibody comprises a nucleotide sequence with at least about 80% (e.g., at least about 85%, 90%, 91%, 92%, 93%, 94%, 95%, 96%, 97%, 98%, 99%, 100%) sequence identity to the sequences set forth in one of SEQ ID NOS.: 259 and 261.

With a molecular weight of ~80 kDa, minibodies are large enough to escape renal glomerular filtration and have proven successful for delivery of therapeutic doses of radionuclides, including $^{211}$At, with very favorable efficacy/toxicity and pharmacokinetics. A diabody is a noncovalent dimer of single-chain Fv (scFv) fragments that contain the $V_H$ and $V_L$ domains connected by a small peptide linker. Another form of diabody is single-chain $(Fv)_2$ in which two scFv fragments are covalently linked to each other. A triabody is a trimer of scFv domains, which are connected by short linkers. Triabody constructs can be specific for one, two, or three different antigens. The multiple scFv or other antigen binding domains in these constructs can be the same or different, although at least one must bind to CD123, as described above.

In various embodiments of the derivatives, distinct domains can be separated within as single fusion polypeptide molecule by a linker domain. The linker domain can be a five to about 35 amino acid sequence that connects, e.g., the $V_L$ and $V_H$ domains. The linker domain provides a spacer function and flexibility sufficient for interaction of the two sub-binding domains so that the resulting single chain polypeptide retains a specific binding affinity to the same target molecule as an antibody or T cell receptor. In certain embodiments, a variable region linker comprises from about three to about 30 amino acids, from about 10 to about 30 amino acids, or from about 15 to about 25 amino acids. In particular embodiments, a variable region linker peptide comprises from one to ten repeats of $Gly_xSer_y$, wherein x and y are independently an integer from 1 to 5 (e.g., $Gly_4Ser$, $Gly_3Ser$, $Gly_2Ser$, or $(Gly_3Ser)_n(Gly_4Ser)_1$, $(Gly_3Ser)_n(Gly_4Ser)_n$, or $(Gly_4Ser)_n$, wherein n is an integer of 1, 2, 3, 4, or 5) and wherein In particular embodiments, a linker domain may contain an N-linked glycosylation motif. Exemplary linker domains encompassed by this disclosure are set forth in SEQ ID NOS.: 273 and 274.

The disclosed antibody or antigen binding derivative thereof described herein can further comprise a functional payload. Typically, a payload is a functional molecule that induces a change in target cell that expresses, at least transiently, CD123 on its surface. The change can be to a therapeutic effect if it is in vivo. Exemplary, non-limiting therapeutic payloads can comprise a nucleic acid, a protein or peptide, a lipid, a small molecule pharmaceutical, and/or a radioisotope/radionuclide, or other cytotoxic agent.

Nucleic acid payloads can be DNA (including cDNA), mRNA, siRNA, shRNA, and gRNA. Guide RNA molecules can be utilized in applications of DNA editing (e.g., CRISPR/Cas9 applications) and RNA editing. Some nucleic acid payloads can encode a protein with a therapeutic or other desired effect in the target cell. In some embodiments, the nucleic acid comprises an open reading frame operatively linked to a promoter sequence to provide for expression of the open reading frame in the target cell. This open reading frame can be referred to as a transgene. The term "promoter" refers to a regulatory nucleotide sequence that can activate transcription (expression) of the transgene and/or splice variant isoforms thereof. The promoter is typically located upstream of the gene, but can be located at other regions proximal to the gene, or even within the gene. The promoter typically contains binding sites for RNA polymerase and one or more transcription factors, which participate in the assembly of the transcriptional complex. As used herein, the term "operatively linked" indicates that the promoter and the encoding nucleic acid are configured and positioned relative to each other a manner such that the promoter can activate transcription of the encoding nucleic acid by the transcriptional machinery of the cell. The promoter can be constitutive or inducible. The nucleic acid therapeutic payload can be of any size and in any configuration, such as in linear form, in plasmid form (e.g., circular form), or in minicircle form.

The radioactive payload can be or comprise a radioactive ion or radionuclide. In one embodiment, the radioactive payload is or comprises a radioactive ion or radionuclide complexed with a chelator. A variety of radionuclides are available to serve as payloads in radioconjugated antibodies or antibody derivatives. For example, the radionuclide can be a β emitter, e.g., $^{86}$Y, $^{90}$Y, $^{186}$Re, $^{188}$Re, $^{131}$I, $^{177}$Lu, or $^{67}$Cu. More recently, increasing interest has centered around α-emitters such as astatine-211 ($^{211}$At) to eradicate neoplastic hematopoietic cells. α-emitters deposit higher decay energies (5-8 MeV) over short distances (55-70 μm) for potent, precise, and efficient target cell kill and minimized toxicity to normal surrounding cells compared to β-emitters (decay energies of 0.66-2.3 MeV delivered over 0.3-2.3 mm) For several α-emitters, including $^{211}$At, studies have documented that ≤10 hits per cell kill hematopoietic neoplasms, enabling the targeting of low-density antigens. With a t1/2 of 7.2 hours, $^{211}$At, is particularly suitable for the clinic. In animal models, $^{211}$At-labeled anti-CD45, anti-CD20, and anti-CD38 mAbs were highly efficacious against acute leukemia, B-cell lymphoma, and multiple myeloma in vivo, including measurable ('minimal') residual disease (MRD) burdens. Accordingly, in some embodiments, the radionuclide is an a emitter, e.g., $^{213}$Bi, $^{211}$At, $^{225}$Ac. In yet further embodiments, the radionuclide is a low-energy electron emitter, i.e., an Auger-emitter, e.g., $^{125}$I, $^{111}$In or $^{67}$Ga. In general, useful radionuclides include, for example, but are not limited to, $^{90}$Y, $^{111}$In, $^{67}$Ga, $^{68}$Ga, $^{177}$Lu, r$^{188}$Re, $^{223}$Ra, $^{57}$Gd, $^{64}$Cu, $^{67}$Cu, $^{89}$Zr, $^{47}$Sc, $^{153}$Sm, $^{166}$Tb, $^{166}$Tb, $^{166}$Ho, $^{212}$Pb, $^{212}$Bi, $^{213}$Bi, $^{225}$Ac, $^{227}$Th, $^{211}$At and $^{227}$Ac. In one embodiment, the radionuclide is Yttrium ($^{90}$Y). including but not limited to $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re, $^{212}$Bi and the like.

Exemplary nonlimiting small molecules or cytotoxic agents that can be configured as useful payloads are known in the art. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is a enzymatically active toxin of bacterial, fungal, plant, or animal origin, or fragments thereof, including but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, restrictocin, phenomycin, enomycin, and the tricothecenes. Additionally, small molecule toxins, such as a calicheamicin, maytansinoids, a trichothene, CC 1065, MMAE, MMAF, and the like, and the derivatives of these toxins that have toxin activity, can also be used.

Conjugation of such payloads to the antibody or antibody derivatives of the present disclosure can be implemented using standard techniques known in the art. The conjugation can be covalent or ionic. Conjugates of an antibody or antibody derivative and cytotoxic agent are made using a variety of protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), bis-active fluorine compounds (such as 1,5-difluoro-2,4-dinitrobenzene), and the like.

Bispecific Affinity Reagents

In another aspect, the disclosure provides a multi-specific affinity reagent. The multi-specific affinity reagent is configured to contain multiple binding domains that specifically bind to different antigens. In some embodiments, the affinity reagent is at least bi-specific, with a first binding domain that specifically binds a target of interest and a second binding domain that specifically binds the radioactive ligand. The first and second binding domains can be incorporated in the same fusion protein construct. In some embodiments, the affinity reagent is at least a bi-specific affinity reagent that comprises a first binding domain that specifically binds to an extracellular domain of interleukin-3 (IL-3) receptor α-chain (CD123) and a second binding domain that specifically binds to a radioactive ligand.

As used herein the term "binding domain" refers to a molecular domain, such as in a peptide, oligopeptide, polypeptide, or protein, that possesses the ability to specifically and non-covalently associate, unite, or combine with a target molecule (e.g., CD123 or a radioactive ligand). A binding domain includes any naturally occurring, synthetic, semi-synthetic, or recombinantly produced binding partner for the target biological molecule (e.g., CD123 or a radioactive ligand) or therapeutic compound (e.g., radioactive ligand, such as yttrium-DOTA (Y-DOTA)). In some embodiments, a binding domain is or comprises functional elements of an immunoglobulin or immunoglobulin-like molecule, such as an antibody (i.e., CDR(s), framework regions, variable domain fragments, etc.) The affinity reagents are especially suited for radioimmunotherapy (RIT) and pre-targeted radioimmunotherapy (PRIT) applications where the affinity reagent is administered in a therapeutic amount and either is bound to a radioactive ligand before administration (RIT) or the radioligand is administered separate (e.g., subsequently) to the administration of the affinity reagent (PRIT).

In some embodiments, the affinity reagent is a fusion protein, with the first binding domain and the second binding domain being separated by a hinge domain. Each binding domain can be independently an antibody or antibody derivative as generally defined above. For example, the first and second binding domain can each be an antigen binding antibody fragment (e.g., an Fab fragment, an Fab' fragment, an $F(ab)_2$ fragment, an $F(ab')_2$ fragment, an Fv fragment, a $V_H$H fragment, a $V_{NAR}$ fragment, and the like) or a single-chain antibody derivative (e.g., an scFv, a single-chain Fab (scFab), a diabody, a linear antibodies, a single-chain antibody molecule, and the like). These antibody derivative configurations are known in the art and are described in more detail above. In some embodiments, these derivatives serving as the binding domains are humanized or fully human.

In some embodiments, one or both of the first binding domain and the second binding domain comprises a $V_L$ domain and $V_H$ domain, for example of an antibody. These domains can be fully human or humanized. The $V_L$ domain and $V_H$ domain can be separated by a "linker domain", such as in a single-chain (e.g., scFv) configuration. The linker domain can be a five to about 35 amino acid sequence that connects the $V_L$ domain and the $V_H$ domain. Linker domains encompassed by the disclosure are described in more detail above.

The first binding domain binds to an extracellular domain of the alpha chain of CD123. Exemplary alpha chain sequences are disclosed in UniProtKB accession no. P26951 or a sequence with at least about 85% sequence identity (e.g., about 85%, about 90%, about 95%, about 98% sequence identity) thereto.

Exemplary, non-limiting binding domains that specifically bind to an extracellular domain of CD123 are disclosed herein. For example, exemplary binding domains that bind to CD123 can have at least one, two, three, four, five, or six CDRs selected from a $V_L$-CDR1 having a sequence set selected from SEQ ID NOS: 3, 13, 23, 33, 43, 53, 63, 73, 83, 93, 103, 113, 123, 133, 143, 172, and 180; a $V_L$-CDR2 having a sequence set forth in SEQ ID NOS.: 4, 14, 24, 34, 44, 54, 64, 74, 84, 94, 104, 114, 124, 134, 144, 173, and 181; and a $V_L$-CDR3 having a sequence set forth in SEQ ID NOS.: 5, 15, 25, 35, 45, 55, 65, 75, 85, 95, 105, 115, 125, 135, 145, 174, and 182; a $V_H$-CDR1 having a sequence set forth in SEQ ID NO: 8, 18, 28, 38, 48, 58, 68, 78, 88, 98, 108, 118, 128, 138, 148, 176, and 184; a $V_H$-CDR2 having a sequence set forth in SEQ ID NO: 9, 19, 29, 39, 49, 69, 79, 89, 99, 109, 119, 129, 139, 149, 176, and 184; and a $V_H$-CDR3 having a sequence set forth in SEQ ID NO: 10, 20, 30, 40, 50, 60, 70, 80, 90, 100, 110, 120, 140, 150, 178, and 186. Exemplary combinations of the select CDRs are described above in more detail and are not repeated here. Furthermore, exemplary variable $V_L$ and $V_H$ domain (and combinations thereof) are described above in more detail and are not repeated here. These exemplary binding domains are encompassed in this aspect of the disclosure.

As indicated, the second binding domain specifically binds the radioactive ligand. The radioactive ligand can be any ligand, typically a small molecule, which is radioactive and configured for administration into a subject. The radioactive ligand can be or comprise a radioactive ion or radionuclide. In one embodiment, the radioactive ligand is or comprises a radioactive ion or radionuclide complexed with a chelator.

In certain embodiments, the second binding domain that specifically binds to a radioactive ligand comprises a $V_L$ region. For example, a $V_L$ region in the first binding domain of the present disclosure is derived from or based on a $V_L$ of a known monoclonal antibody that binds to a radioactive ligand and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_L$ of a known monoclonal antibody that binds to a radioactive ligand. An insertion, deletion, or substitution may be anywhere in the $V_L$ region, including at the amino-terminus, carboxy-terminus, or both ends of the region, provided that each CDR comprises zero changes or at most one, two, three or four changes from a CDR of the $V_L$ region of a known monoclonal antibody that binds to a radioactive ligand, and provided a binding domain containing the modified $V_L$ region specifically binds to a radioactive ligand target with an affinity similar to the reference binding domain. Similarly, in certain embodiments, the second binding domain that specifically binds to a radioactive ligand comprises a $V_H$ region. For example, a $V_H$ region in the first binding domain of the present disclosure is derived from or based on a $V_H$ of a known monoclonal antibody that binds to a radioactive ligand and may contain one or more (e.g., 2, 3, 4, 5, 6, 7, 8, 9, or 10) insertions, one or more (e.g., 2, 3, 4, 5, 6, 7, 8, 9, or 10) deletions, one or more (e.g., 2, 3, 4, 5, 6, 7, 8, 9, or 10) amino acid substitutions (e.g., conservative amino acid substitutions), or a combination of the above-noted changes, when compared with the $V_H$ of a known monoclonal antibody that binds to a radioactive ligand. An insertion, deletion, or substitution may be anywhere in the $V_H$ region, including at the amino-terminus, carboxy-terminus, or both ends of the region, provided that each CDR comprises zero changes or at most one, two, three or four changes from a CDR of the $V_H$ region of a known monoclonal antibody that binds to a radioactive ligand, and provided a binding domain containing the modified $V_H$ region specifically binds to a radioactive ligand target with an affinity similar to the reference type binding domain.

The radionuclide can be, e.g., a beta emitter, an alpha emitter, or a low-energy electron emitter.

An exemplary chelator encompassed by the disclosure is DOTA, also known as tetraxetan. DOTA includes a central 12-membered tetraaza ring that can hold metal ions and radionuclides. DOTA is a macrocyclic chelating agent that forms stable complexes with metals that are essentially irreversible under physiological conditions. DOTA has a molecular weight of 405 Daltons, diffuses very rapidly, and exhibits rapid renal clearance. DOTA. A variant of DOTA that has a structure that differs to a certain limited extent from the structure of DOTA and that retains the ability to function (e.g., retains sufficient activity to be used for one or more of the purposes described herein) is an active variant of DOTA.

The chelated ion can be radionuclide, which confers radioactivity to the ligand. The radionuclide can be a β emitter, e.g., $^{86}$Y, $^{90}$Y, $^{186}$Re, $^{188}$Re, $^{131}$I, $^{177}$Lu, or $^{67}$Cu, an a emitter, e.g., $^{213}$Bi, $^{211}$At, $^{225}$Ac, or a low-energy electron emitter, i.e., an Auger-emitter, e.g., $^{125}$I, $^{111}$In or $^{67}$Ga. In general, useful radionuclides include, for example, but are not limited to, $^{90}$Y, $^{111}$In, $^{67}$Ga, $^{68}$Ga, $^{177}$Lu, r$^{188}$Re, $^{223}$Ra, $^{57}$Gd, $^{64}$Cu, $^{67}$Cu, $^{89}$Zr, $^{47}$Sc, $^{153}$Sm, $^{166}$Tb, $^{166}$Tb, $^{166}$Ho, $^{212}$Pb, $^{212}$Bi, $^{213}$Bi, $^{225}$Ac, $^{227}$Th, $^{211}$At and $^{227}$Ac. In one embodiment, the radionuclide is Yttrium ($^{90}$Y). Thus, in some embodiments, the radioactive ligand is or comprises $^{90}$Y-DOTA.

U.S. Pat. No. 8,648,176, incorporated herein by reference in its entirety, describes in more detail exemplary second binding domains that specifically binds to a metal chelate, such as DOTA. The second binding domain, e.g., an scFv domain, that binds a metal chelate with a radionuclide, can have a sequence at least or about 70% (e.g., at least or about 75%, 80%, 85%, 90%, 95% or 98%) identical to SEQ ID NO: 152, exclusive of the linker at residues 120-134. Residues 1-119 of SEQ ID NO: 152 represent the variable heavy chain of the antibody designated 2D 12.5 (Corneillie et al., J. Am. Chem. Soc. 125:15039-15048, 2003); residues 120-134 represent a linker; and residues 135-244 represent the variable light chain of 2D 12.5. These embodiments of the second domain can include a mutation at a position corresponding to one or more of the following positions within SEQ ID NO: 152: 29, 30, 31, 32, 33, 34, 36, 37, 47, 48, 49, 51, 54, 55, 56, 57, 58, 60, 69, 71, 73, 94, 95, 96, 97, 102, 103, 105, 106, 107, 164, 165, 166, 167, 169, 171, 172, 184, 185, 188, 189, 223, 224, 225, 226, 228, 229, 230, 231, 233, and 234. Alternatively, or in addition, the second binding domain can include a mutation at a position corresponding to one or more of the following positions within SEQ ID NO: 152: 60, 61, 63, 71, 80, 88, 108, 139, 157, 165, 187, 230, and 234. Alternatively, or in addition, the second binding domain can include a mutation at a position corresponding to one or more of the following positions within SEQ ID NO: 152: 100, 187, and 227. More specifically, the second binding domain can include the sequence of residues 1-244 of mutant C8.2-1 (SEQ ID NO: 153); C8.2-2 (SEQ ID NO: 154); C8.2-3 (SEQ ID NO: 155); C8.2-4 (SEQ ID NO: 156); C8.2-5 (SEQ ID NO: 157); C8.2-6 (SEQ ID NO: 158); C7.3 1 (SEQ ID NO: 159); C7.3 2 (SEQ ID NO: 160); C7.3 3 (SEQ ID NO: 161); C7.3 4 (SEQ ID NO: 162); C7.3 5 (SEQ ID NO: 163); C7.3 6 (SEQ ID NO: 164); C7.3 7 (SEQ ID NO: 165); C7.3 8 (SEQ ID NO: 166); C7.3 9 (SEQ ID NO: 167); or C7.3 10 (SEQ ID NO: 168).

As indicated above, in some embodiments the affinity reagent is a fusion protein, with the first binding domain and the second binding domain being separated by a hinge domain. As used herein, a "hinge region" or a "hinge" refers to a region that provides sufficient space and flexibility between the first and second binding domains to facilitate the binding of each binding domain to its respective specific antigen without mutual interference. Exemplary hinge domains that are encompassed by this disclosure, and detailed discussions thereof, are provided in WO 2018/151836, which is incorporated herein by reference in its entirety. In some embodiments, the hinge region can comprise (a) an immunoglobulin hinge sequence (made up of, for example, upper and core regions) or a functional fragment or variant thereof, (b) a type II C-lectin interdomain (stalk) region or a functional fragment or variant thereof, or (c) a cluster of differentiation (CD) molecule stalk region or a functional variant thereof. In some embodiments, the immunoglobulin hinge region can be a naturally occurring upper and middle hinge amino acid sequences interposed between and connecting the $C_{H_1}$ and $C_{H_2}$ domains (for IgG, IgA, and IgD) or interposed between and connecting the $C_{H_1}$ and $C_{H_3}$ domains (for IgE and IgM) found in the heavy chain of an antibody. In certain embodiments, the hinge region is human, and in particular embodiments, comprises a human IgG hinge region. In some embodiments, the IgG hinge region comprises a human IgG1 Fc hinge. In some embodiments, the IgG hinge region comprises a human IgG2 Fc hinge. In some embodiments, the IgG hinge region comprises a human IgG3 Fc hinge. In some embodiments, the IgG hinge region comprises a human IgG4 Fc hinge.

Figure 23B:
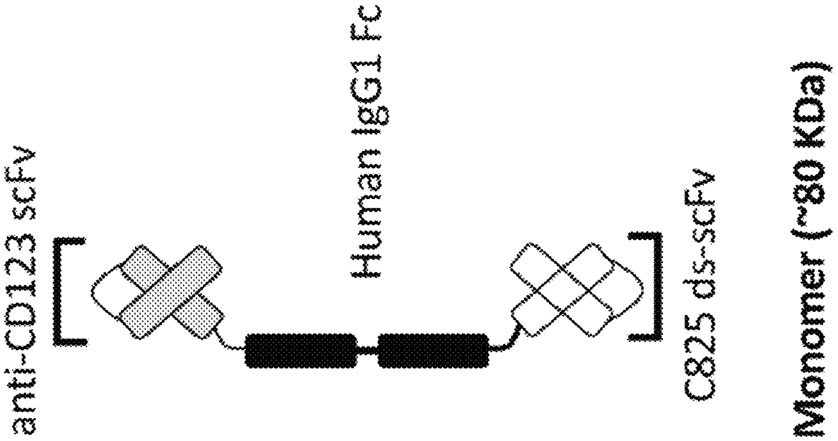
FIGS. 23A-23B. Schematically illustrate embodiments of a bispecific affinity reagent encompassed by the disclosure. 23A is a schematic illustration of a dimeric bispecific affinity reagent with first binding domains containing scFv domains that bind to CD123 and second binding domains that bind Y-DOTA radioligand each first binding domain is linked to a second binding domain by a human IgG1 Fc domain. 23B is a monomeric version of the bispecific reagent illustrated in 23A, where there is only a single first binding domain linked to the second binding domain via a human IgG1 Fc domain. Relative sizes are indicated.
Figure 23A:
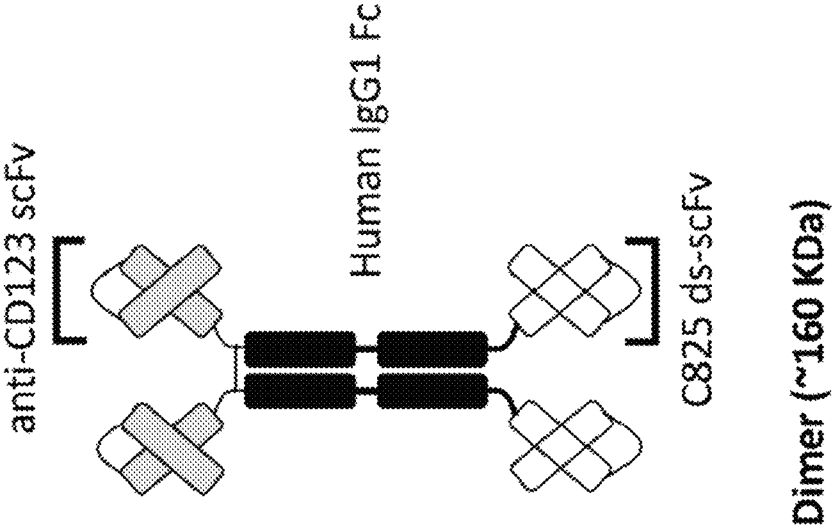

In some embodiments, the affinity reagent is a dimeric bispecific affinity reagent. A schematic of an illustrative, non-limiting dimeric bispecific affinity reagent is provided in FIG. 23A. The illustrated dimeric construct is a homodimer, with each monomer comprising the first binding domain (i.e., an antti-CD123 scFv) linked to the second binding domain (i.e., C825 ds-scFv as an exemplary, non-limiting embodiment) via a hinge region (i.e., hIgG1 Fc domain). In some embodiments the monomer comprises the amino acid sequence set forth in SEQ ID NOS.: 169 and 266. The dimeric structure is stabilized by, for example, one or more disulfide bonds. In FIG. 23A, an exemplary disulfide bond connecting the two monomers is shown at a location the region connecting the scFv of the first binding domain and the hinge region of each monomer. Persons of ordinary skill in the art can readily implement appropriate linkages, such as disulfide bonds, to stabilize the dimeric structure. In some embodiments the dimeric bispecific affinity reagent comprises an amino acid sequence as set forth in SEQ ID NO: 266. In some embodiments the dimeric bispecific affinity reagent comprises a nucleotide sequence as set forth in SEQ ID NO: 265. As provided in the listed sequence, the domains in order from amino terminal to carboxy terminal are: 10C4 $V_L$, Linker 1, 10C4 $V_H$, hinge and human IgG1 Fc, linker 2, C825 $V_H$, linker 3, and C825 $V_L$.

In other embodiments, the affinity reagent is a monomeric bispecific affinity reagent. A schematic of an illustrative, non-limiting monomeric bispecific affinity reagent is provided in FIG. 23B. The illustrated monomeric structure contains a single first binding domain (i.e., an andti-CD123 scFv) linked to the second binding domain (i.e., C825 ds-scFv as an exemplary, nonlimiting embodiment) via a hinge region (i.e., hIgG1 Fc domain). The hinge regions can be particularly configured for functionality in a monomer context such that the monomer maintains stability and avoids excessive interactions. US 200/0074225, incorporated herein by reference in its entirety, discloses several design parameters and embodiments of Fc domain variants that exhibit particular stability as monomers, which are encompassed by this disclosure. As described in more detail, such monomeric bispecific affinity reagents may confer an advantage of avoiding, reducing, or delaying internalization upon biding of the affinity reagent with CD123 on the cells surface. An exemplary amino acid sequence of one monomeric strand of a monomeric, bispecific affinity reagent encompassed by this disclosure is set forth in SEQ ID NO: 170 and SEQ ID NO: 264. In some embodiments the monomeric bispecific affinity reagent comprises an amino acid sequence as set forth in SEQ ID NO: 264. In some embodiments the monomeric bispecific affinity reagent comprises a nucleotide sequence as set forth in SEQ ID NO: 263. As provided in the listed sequence, the domains in order from amino terminal to carboxy terminal are: 10C4 $V_L$, Linker 1, 10C4 $V_H$, hinge and human IgG1 Fc, linker 2, C825 $V_H$, linker 3, and C825 $V_L$. The monomeric strand can remain monomeric due to the reduced ability for dimerization conferred by select amino acid substitutions with respect to the sequence of a dimerizing version (e.g., with a sequence set forth in SEQ ID NO: 169). In this embodiment, the substitutions comprise: a Ser at position 262, a Ser at position 265, and Arg at position 404, a His at position 441, and a Glu at position 443. These substitutions all fall within the hinge and human IgG1 Fc domain within the monomer.

Nucleic Acids, Vectors, Cells

In another aspect, the disclosure provides a nucleic acid molecule encoding any of the antibodies, antibody fragments, antibody derivatives, or multi-specific (e.g., bispecific) affinity reagents described herein, or components thereof. For example, the nucleic acid can comprise a sequence encoding one or more of SEQ ID NOS: 1-51. In some embodiments, the nucleic acid comprises a sequence encoding one, two, three, four, five, or six CDR domains, as described above. Exemplary combinations of CDR domains encompassed by these embodiments are also described above and not repeated here for brevity. In some embodiments, the nucleic acid comprises a sequence encoding a $V_H$ domain with an amino acid sequence described above, and a sequence encoding a $V_L$ with an amino acid sequence described above. Exemplary combinations of amino acid sequences for the $V_L$ and $V_H$ domains are described above and not repeated here. With respect to the multi-specific affinity reagents, embodiments of the nucleic acid have nucleic sequences encoding the first binding domain, the hinge region, and the second binding domain, as described above.

A person of ordinary skill in the art can use the genetic code to determine nucleic acid sequences that can encode antibodies, antibody fragments, antibody derivatives, or multi-specific (e.g., bispecific) affinity reagents described herein based on the above disclosures. In some embodiments, the nucleic acid further comprises a promoter sequence operatively linked to the sequence encoding the antibodies or fragments or derivatives thereof. The term “promoter” refers to a regulatory nucleotide sequence that can activate transcription (expression) of a gene and/or splice variant isoforms thereof. A promoter is typically located upstream of a gene, but can be located at other regions proximal to the gene, or even within the gene. The promoter typically contains binding sites for RNA polymerase and one or more transcription factors, which participate in the assembly of the transcriptional complex. As used herein, the term “operatively linked” indicates that the promoter and the encoding nucleic acid are configured and positioned relative to each other a manner such that the promoter can activate transcription of the encoding nucleic acid by the transcriptional machinery of the cell. The promoter can be constitutive or inducible. Constitutive promoters can be determined based on the character of the target cell and the particular transcription factors available in the cytosol. A person of ordinary skill in the art can select an appropriate promoter based on the intended person, as various promoters are known and commonly used in the art.

In some embodiments, the disclosure provides a vector comprising the nucleic acid described above. The vector can be any construct that facilitates the delivery of the nucleic acid to a target cell and/or expression of the nucleic acid within the cell. The vectors can be viral vectors, circular nucleic acid constructs (e.g., plasmids), or nanoparticles, and the like.

Various viral vectors are known in the art and are encompassed by the present disclosure. See, e.g., Machida, C. A. (ed.), *Viral Vectors for Gene Therapy: Methods and Protocols*, Humana Press, Totowa, New Jersey (2003); Muzyczka, N., (ed.), *Current Topics in Microbiology and Immunology: Viral Expression Vectors*, Springer-Verlag, Berlin, Germany (2012), each incorporated herein by reference in its entirety. In some embodiments, the viral vector is an adeno associated virus (AAV) vector, an adenovirus vector, a retrovirus vector, or a lentivirus vector. A specific embodiment of an AAV vector includes the AAV2.5 serotype.

In another aspect, the disclosure provides a cell comprising the nucleic acid encoding any antibodies, antibody fragments, antibody derivatives, or multi-specific (e.g., bispecific) affinity reagents described herein as described herein. In some embodiments, the cell comprises the disclosed vector construct, i.e., which comprises the nucleic acid encoding any antibodies, antibody fragments, antibody derivatives, or multi-specific (e.g., bispecific) affinity reagents described herein. The cell is capable of expressing the antibodies, antibody fragments, antibody derivatives, or multi-specific (e.g., bispecific) affinity reagents described herein from the nucleic acid. For example, the nucleic acid and/or vector can be configured for expression of antibodies, antibody fragments, antibody derivatives, or multi-specific (e.g., bispecific) affinity reagents described herein from the encoding nucleic acid within the cell. A promoter operatively linked to the nucleic acid can be appropriately configured to allow binding of the cell's RNA polymerase and one or more transcription factors to permit assembly of the transcriptional complex.

In some embodiments the present disclosure provides host cells comprising the expression vectors described herein. In some embodiments the host cell is an immune cell. In some embodiments the host cell is a Chimeric Antigen Receptor T (CAR-T) cell or a CAR-NK cell. Chimeric antigen receptors (CARs, also known as chimeric T cell receptors) are synthetic constructs that are designed to be expressed in host T cells or NK cells and to induce an immune response against a specific target antigen and cells expressing that antigen. The CAR typically comprises an antibody fragment, such as a scFv or Fab fragment, incorporated in a fusion protein that also comprises additional components, such as a CD3-ζ or CD28 transmembrane domain and selective T-cell activating moieties, including the endodomains of CD3-ζ, CD28, OX40, 4-1BB, Lck and/or ICOS. Various combinations of such elements have been used. In some aspects the present disclosure provides, e.g., a composition comprising one or more cells that express a CAR molecule that binds CD123. In some embodiments the CAR molecule is an antibody or antigen binding derivative thereof that binds to an extracellular domain of interleukin-3 (IL-3) receptor α-chain (CD123) as described herein. In some embodiments the antibody or antigen binding derivative thereof is a scFv or a scTCR as described herein.

The disclosure encompasses any type of cell for this aspect. In some embodiments, the antibody or antigen binding derivative thereof expressed by the cell is part of a chimeric antigen receptor and the cell is a lymphocyte.

Formulation and Administration

The disclosure also encompasses compositions that comprise the antibody or derivative thereof, described above. The compositions can be formulations appropriate for methods of administration for application to in vivo therapeutic settings in subjects (e.g., mammalian, e.g., human, subjects with a CD123+ neoplasm). According to skill and knowledge common in the art, the disclosed antibody or fragment or derivative thereof, encoding nucleic acids, and/or vectors comprising the nucleic acids, can be formulated with appropriate carriers, excipients, and/or non-active binders, and the like, for administration to target a CD123 expressing cell.

Methods of Treatment

The constructs described herein that specifically bind CD123, potentially as one of multiple target antigens, are useful for targeting CD123+ cells with toxic payloads, such as radionuclides for radioimmunotherapy. Accordingly, in another aspect, the disclosure provides a method of treating a neoplastic condition in a subject characterized by elevated expression of interleukin-3 (IL-3) receptor α-chain (CD123) The method comprises administering to the subject a therapeutically effective amount of a composition comprising: a) the antibody or antigen binding derivative thereof as described above; b) the bispecific affinity reagent as described above, c) the nucleic acid or the vector as described above, or d) the cell as described above.

The neoplastic condition is any neoplastic condition characterized by positive or elevated expression of CD123 on the transformed cell. Exemplary, non-limiting CD123+ neoplasms include myelodysplastic syndrome (MDS), blastic plasmacytoid dendritic cell neoplasm (BPDCN), classic hairy cell leukemia, acute myeloid leukemia (AML), lymphoblastic leukemia (AL), Hodgkin lymphoma, and systemic mastocytosis.

As used herein, the term "treat" refers to medical management of a disease, disorder, or condition (e.g., neoplasm, such as cancer) of a subject (e.g., a human or non-human mammal, such as a primate, horse, dog, mouse, rat, and the like). Treatment can encompass any indicia of success in the treatment or amelioration of the disease or condition (e.g., cancer, such as a leukemia), including any parameter such as abatement, remission, diminishing of symptoms or making the disease or condition more tolerable to the patient, slowing in the rate of degeneration or decline, or making the degeneration less debilitating. In non-limiting examples, the term "treat" in the context of cancer (e.g., a leukemia) can encompass slowing or inhibiting the rate of cancer growth, or reducing the likelihood of recurrence, compared to not having the treatment. In some embodiments, the treatment encompasses resulting in some detectable degree of cancer cell death in the patient. The treatment or amelioration of symptoms can be based on objective or subjective parameters, including the results of an examination by a physician. Accordingly, the term "treating" includes the administration of the compositions of the present disclosure to alleviate, or to arrest or inhibit development of the symptoms or conditions associated with disease or condition (e.g., cancer). The term "therapeutic effect" refers to the amelioration, reduction, or elimination of the disease or condition, symptoms of the disease or condition, or side effects of the disease or condition in the subject. The term "therapeutically effective" refers to an amount of the composition that results in a therapeutic effect and can be readily determined.

The method encompasses applications of radioimmunotherapy (RIT) targeting CD123 expressing cells, which comprise administering any antibody or antigen binding derivative thereof as described above which is coupled to a radionuclide or isotope, as described above.

In other embodiments, the method encompasses applications of pretargeted radioimmunotherapy (PRIT) targeting CD123 expressing cells. These embodiments comprise administering to the subject a therapeutically effective amount of the multispecific (e.g., bispecific) affinity reagent as described above. During or after this administration, the method further comprises administering to the subject a therapeutically effective amount of the radioactive ligand.

Effective doses of the multispecific (e.g., bispecific) affinity reagent can be readily determined by persons of ordinary skill in the art. Exemplary embodiments for dosing are equivalent dosing regiments that can be readily established for human subjects adjusting for body mass. For example, doses can range from 0.05 mg/kg to 100 mg/kg, 0.1 mg/kg to 75 mg/kg, 0.1 mg/kg to 50 mg/kg, 0.1 mg/kg to 25 mg/kg, 1 mg/kg to 30 mg/kg, 2 mg/kg to 25 mg/kg, 5 mg/kg to 25 mg/kg, 10 mg/kg to 20 mg/kg, or 15 mg/kg to 20 mg/kg. Exemplary doses include 0.05 mg/kg, 0.1 mg/kg, 0.5 mg/kg, 1 mg/kg, 2 mg/kg, 5 mg/kg, 10 mg/kg, 15 mg/kg, 20 mg/kg, 25 mg/kg, 30 mg/kg, 35 mg/kg, 40 mg/kg, 50 mg/kg, 60 mg/kg, 70 mg/kg, 80 mg/kg, 90 mg/kg, and 100 mg/kg.

The radioactive ligand of this aspect is described above. In an illustrative, non-limiting embodiment, the radioactive ligand comprises yttrium-DOTA. The radioactive ligand is administered to the subject after the bispecific affinity reagent is administered. In some embodiments, the radioactive ligand is administered to the subject about 1, 2, 3, 4, 5, 6, 7, 8, 9, 10, 15, 24, 10, 35, or 40 hours after the administration of the bispecific affinity reagent. In some embodiments, the radioactive ligand is administered to the subject about 10-to about 30, about 15 to about 25 hours, or about 20 to about 25 hours after the administration of the bispecific affinity reagent.

Effective doses of the radioactive ligand can be readily determined by persons of ordinary skill in the art to provide for sufficient ligand to specifically bind cell the present cell-bound bispecific affinity reagent in the subject. As described below, murine xenograft experiments utilized single injections of about 1.2 nM (2 μg) DOTA-biotin labeled with 20 to 40 μCi (0.74-1.48 MBq) of $^{90}$Y for successful effect on the grafted tumors. Equivalent dosing regiments can be readily established for human subjects adjusting for body mass.

In some embodiments, the method further comprises administering an effective amount of a clearing agent (CA). The CA accelerates the clearance of any unbound antibody from the subject's bloodstream to reduce the likelihood that the radioactive moiety will bind to bispecific fusion protein that is not bound to CD123. Accordingly, the CA is typically administered after administering the bispecific fusion protein but before administering the radioactive moiety. In some embodiments, the CA is administered 8 hours, 7 hours, 6 hours, about 5 hours, 4 hours, 3 hours, 2 hours, 1 hour, or just prior to administration of the radioactive ligand. In some embodiments, the CA is administered between about 0.5 and 4 hours or about 1-2 hours before administration of the radioactive ligand.

Any clearing agent effective to facilitate removal of unbound bispecific affinity reagent from circulation is encompassed by the disclosure. An exemplary CA is a DOTAY-Dextran clearing agent (Orcutt K D, et al., *Molecular cancer therapeutics.* 2012; 11(6): 1365-1372), incorporated herein by reference in its entirety.

Effective doses of the CA can be readily determined by persons of ordinary skill in the art to provide for at least some clearance of unbound bispecific affinity reagent. As described below, murine xenograft models utilized approximately 0.5 to 10 μg per individual mouse. Equivalent dosing regiments can be readily established for human subjects adjusting for body mass.

Additional Definitions

Unless specifically defined herein, all terms used herein have the same meaning as they would to one skilled in the art of the present invention. Practitioners are particularly directed to Sambrook J., et al. (eds.) *Molecular Cloning: A Laboratory Manual,* 3rd ed., Cold Spring Harbor Press, Plainsview, New York (2001); Ausubel, F. M., et al. (eds.), *Current Protocols in Molecular Biology*, John Wiley & Sons, New York (2010); and Coligan, J. E., et al. (eds.), *Current Protocols in Immunology*, John Wiley & Sons, New York (2010), Mirzaei, H. and Carrasco, M. (eds.), Modern Proteomics—Sample Preparation, Analysis and Practical Applications in *Advances in Experimental Medicine and Biology*, Springer International Publishing, 2016, and Comai, L, et al., (eds.), Proteomic: Methods and Protocols in *Methods in Molecular Biology*, Springer International Publishing, 2017, for definitions and terms of art. for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application. Unless stated otherwise, the term "about" implies minor variation around the stated value of no more than 10% (above or below), such as up to 10% variation above or below the reference sequence, up to 9% variation above or below the reference sequence, up to 8% variation above or below the reference sequence, up to 7% variation above or below the reference sequence, up to 6% variation above or below the reference sequence, up to 5% variation above or below the reference sequence, up to 4% variation above or below the reference sequence, up to 3% variation above or below the reference sequence, up to 2% variation above or below the reference sequence, or up to 1% variation above or below the reference sequence.

As used herein, the term "polypeptide" or "protein" refers to a polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

One of skill will recognize that individual substitutions, deletions or additions to a peptide, polypeptide, or protein sequence which alters, adds or deletes a single amino acid or a percentage of amino acids in the sequence is a "conservatively modified variant" where the alteration results in the substitution of an amino acid with a chemically similar amino acid. Conservative amino acid substitution tables providing functionally similar amino acids are well known to one of ordinary skill in the art. The following six groups are examples of amino acids that are considered to be conservative substitutions for one another:

(1) Alanine (A), Serine(S), Threonine (T), (2) Aspartic acid (D), Glutamic acid (E), (3) Asparagine (N), Glutamine (Q), (4) Arginine (R), Lysine (K), (5) Isoleucine (I), Leucine (L), Methionine (M), Valine (V), and (6) Phenylalanine (F), Tyrosine (Y), Tryptophan (W).

As used herein, the term "nucleic acid" refers to a polymer of nucleotide monomer units or "residues". The nucleotide monomer subunits, or residues, of the nucleic acids each contain a nitrogenous base (i.e., nucleobase) a five-carbon sugar, and a phosphate group. The identity of each residue is typically indicated herein with reference to the identity of the nucleobase (or nitrogenous base) structure of each residue. Canonical nucleobases include adenine (A), guanine (G), thymine (T), uracil (U) (in RNA instead of thymine (T) residues) and cytosine (C). However, the nucleic acids of the present disclosure can include any modified nucleobase, nucleobase analogs, and/or non-canonical nucleobase, as are well-known in the art. Modifications to the nucleic acid monomers, or residues, encompass any chemical change in the structure of the nucleic acid monomer, or residue, that results in a noncanonical subunit structure. Such chemical changes can result from, for example, epigenetic modifications (such as to genomic DNA or RNA), or damage resulting from radiation, chemical, or other means. Illustrative and nonlimiting examples of noncanonical subunits, which can result from a modification, include uracil (for DNA), 5-methylcytosine, 5-hydroxymethylcytosine, 5-formethylcytosine, 5-carboxycytosine b-glucosyl-5-hydroxy-methylcytosine, 8-oxoguanine, 2-amino-adenosine, 2-amino-deoxyadenosine, 2-thiothymidine, pyrrolo-pyrimidine, 2-thiocytidine, or an abasic lesion. An abasic lesion is a location along the deoxyribose backbone but lacking a base. Known analogs of natural nucleotides hybridize to nucleic acids in a manner similar to naturally occurring nucleotides, such as peptide nucleic acids (PNAs) and phosphorothioate DNA.

Reference to sequence identity addresses the degree of similarity of two polymeric sequences, such as protein sequences. Determination of sequence identity can be readily accomplished by persons of ordinary skill in the art using accepted algorithms and/or techniques. Sequence identity is typically determined by comparing two optimally aligned sequences over a comparison window, where the portion of the peptide or polynucleotide sequence in the comparison window may comprise additions or deletions (e.g., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. Various software driven algorithms are readily available, such as BLAST N or BLAST P to perform such comparisons.

Disclosed are materials and compositions that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

EXAMPLES

The following examples are provided for the purpose of illustrating, not limiting, the disclosure.

Example 1

Generation of CD123 Monoclonal Antibodies (mAbs).

Two immunization campaigns were conducted to raise new anti-CD123 mAbs as basis for therapeutics. In total, 15 mAbs were fully sequenced, 7 of which are derived from regular lab-strain mice (i.e. are murine mAbs) and 8 of which are Alloy mouse-derived mAbs (i.e. are human mAbs). While these antibodies have utility as anti-CD123 diagnostic and therapeutic compositions, the CDRs and variable domain sequences obtained from these antibodies can be the foundation for the development of further optimized therapeutic and diagnostic affinity reagents. This example describes the generation of new murine CD123 mAbs.

Figure 2:
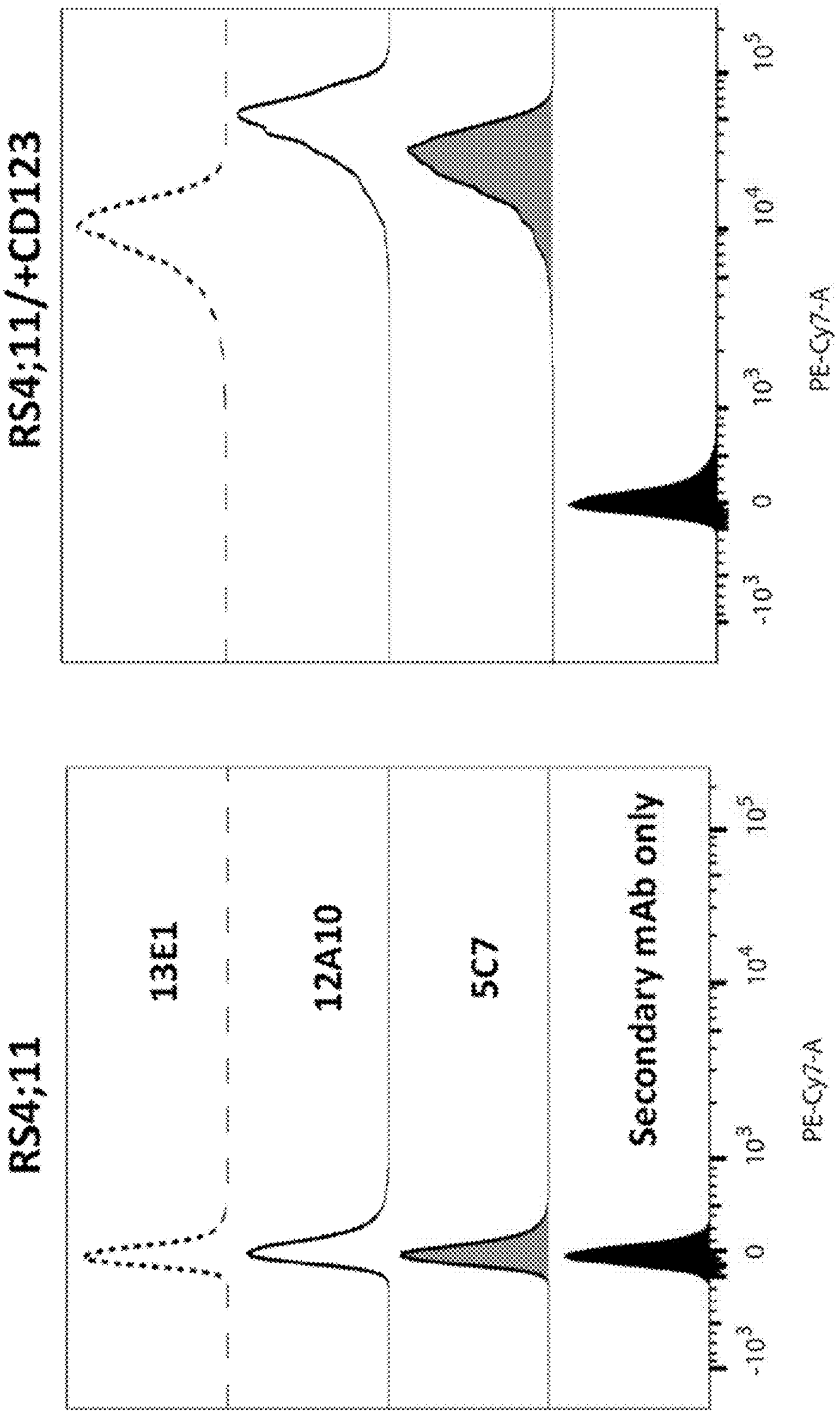
FIG. 2. Parental human (CD123-negative) RS4;11 acute lymphoblastic leukemia cells (left panel) and RS4;11 cells transduced with human CD123 (right panel) were left untreated or treated with murine anti-human CD123 antibodies (clones 5C7, 12A10, and 13E1) followed by a labeled secondary antibody before flow cytometric analysis.

To generate murine mAbs, BALB/c mice were immunized with peptides consisting of the extracellular domain (ECD) of human CD123 to generate murine anti-human CD123 mAbs. Several hybridomas were identified as secreting mAbs with the desired target specificity. Seven hybridomas (i.e., 1H8, 5C7, 5G4, 10C4, 11F11, 12A10, and 13E1) were selected, with 10C4 being the lead candidate antibody based on binding properties, as basis for radioimmunoconjugate compositions. See, e.g., FIG. 1 showing representative binding data for parental human RS4; 11 cells (endogenously lacking CD123), RS4; 11 cells transduced with human CD123, CD123-expressing human AML cells lines (TF-1, KG-1, MOLM-13), and MOLM-13 cells with CRISPR/Cas9-mediated knockout of the CD123 locus ($CD123^{KO}$) for monoclonal antibodies 10C4, 5G4, 11F11, and 1H8, with comparison to performance of commercially available antibodies 7G3 (and secondary antibody control) (FIG. 1) and for monoclonal antibodies 5C7, 12A10, and 13E1 (FIG. 2) confirmed specific binding of all mAbs to human CD123 (binding intensity: 10C4>5G4=11F11=1H8), with 10C4 yielding a higher median fluorescence intensity than the widely used commercial anti-CD123 mAb clones, 7G3. All seven murine anti-human CD123 mAbs were fully sequenced. See SEQ ID NOS: 1-70 in the Sequence Listing Section. Four of these mAbs (i.e., 10C4, 5G4, 11F11, and 1H8) were selected for further characterization.

Figure 3:
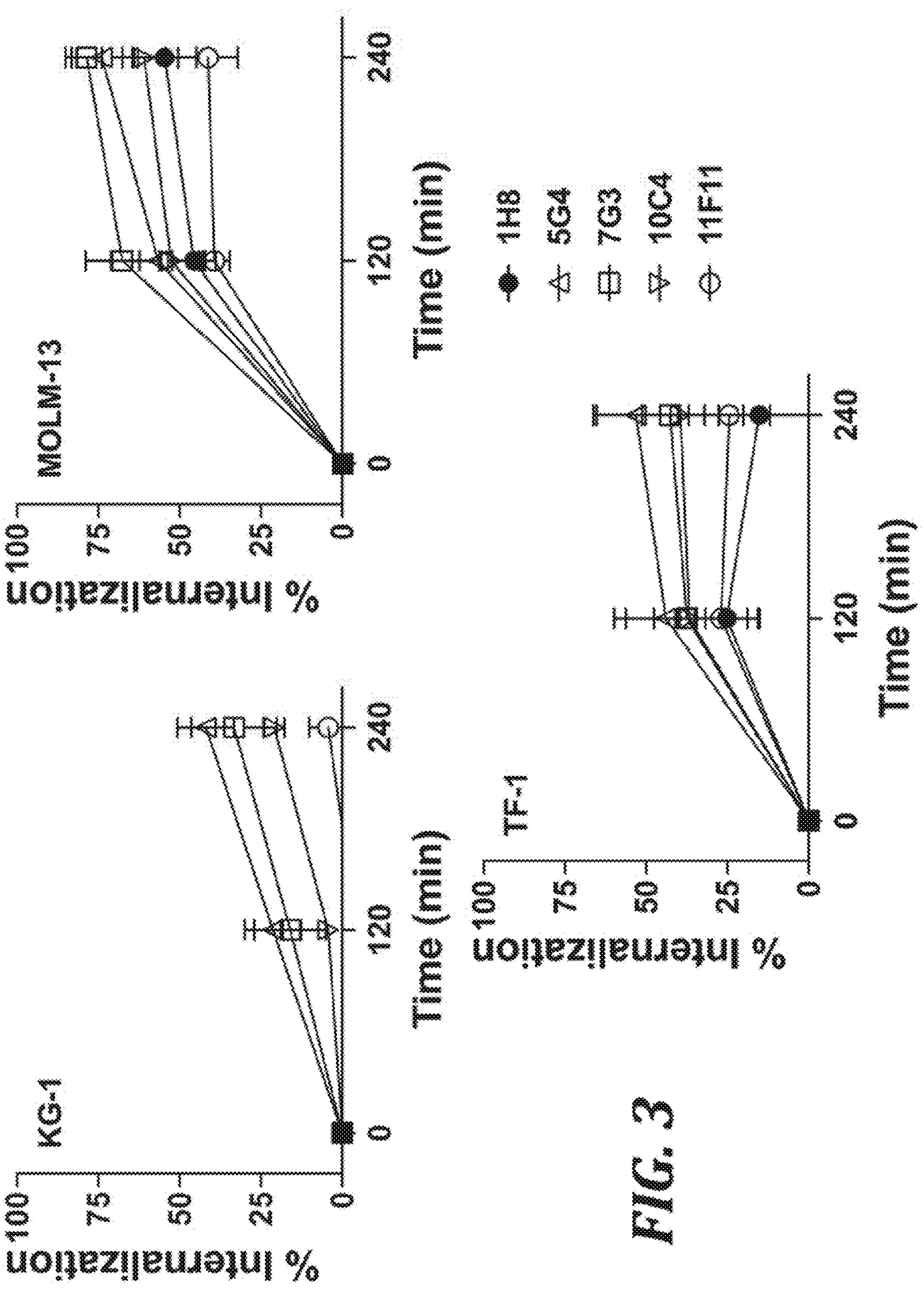
FIG. 3. Flow cytometry-based in vitro internalization assays of murine anti-human CD123 mAbs (1H8, 5G4, 10C4, 11F11) or a commercial anti-CD123 mAb (7G3) in CD123+ human acute leukemia cell lines (KG-1, MOLM-13, TF-1). $CD123^+$ acute leukemia cells were incubated with 2 μg/mL unlabeled CD123 antibody at 37° C. and aliquots were removed at multiple time points. Samples were then stained with APC-conjugated goat anti-mouse Ig to identify remaining antibody on the cell surface. Shown are mean±SEM values of 3-4 independent experiments.

In vitro internalization studies with a panel of human acute leukemia cell lines expressing CD123 (KG-1, MOLM-13, and TF-1) demonstrated uptake of all mAbs (10C4, 5G4, 11F11, and 1H8) by CD123+ target cells with a kinetic slower than that for anti-CD33 antibodies (typically, 30-50% of the anti-CD123 mAb internalized over 2-4 hours). See FIG. 3.

Example 2

This Example discloses the development of astatine-211 ($^{211}$At)-based radioimmunotherapy (RIT) targeting CD123 as proof-of-principle for efficacy of CD123-directed RIT.

For single-step mAb-based RIT, α-particle emitting radionuclides are currently of great interest as they deliver a very high amount of radiation over just a few cell diameters. Because of this, they enable highly potent, precise, and efficient target cell kill with minimal off-target toxicity. With a half-life of 7.2 hours, $^{211}$At is particularly well-suited for clinical use. So far, α-emitters including astatine-211 ($^{211}$At) have been primarily explored with mAbs targeting CD45 or CD33, but broad display of these antigens on non-malignant target-expressing cells can lead to marked "on-target, off-tumor cell" toxicities. It is believed that the targeting of RIT to the CD123 antigen will considerably reduce the off-tumor cell toxicities, considering CD123 is displayed widely on acute leukemia cells, including underlying leukemic stem cells, but is expressed only on a discrete subset of normal hematopoietic cells and is virtually absent on non-blood cells.

Figure 4:
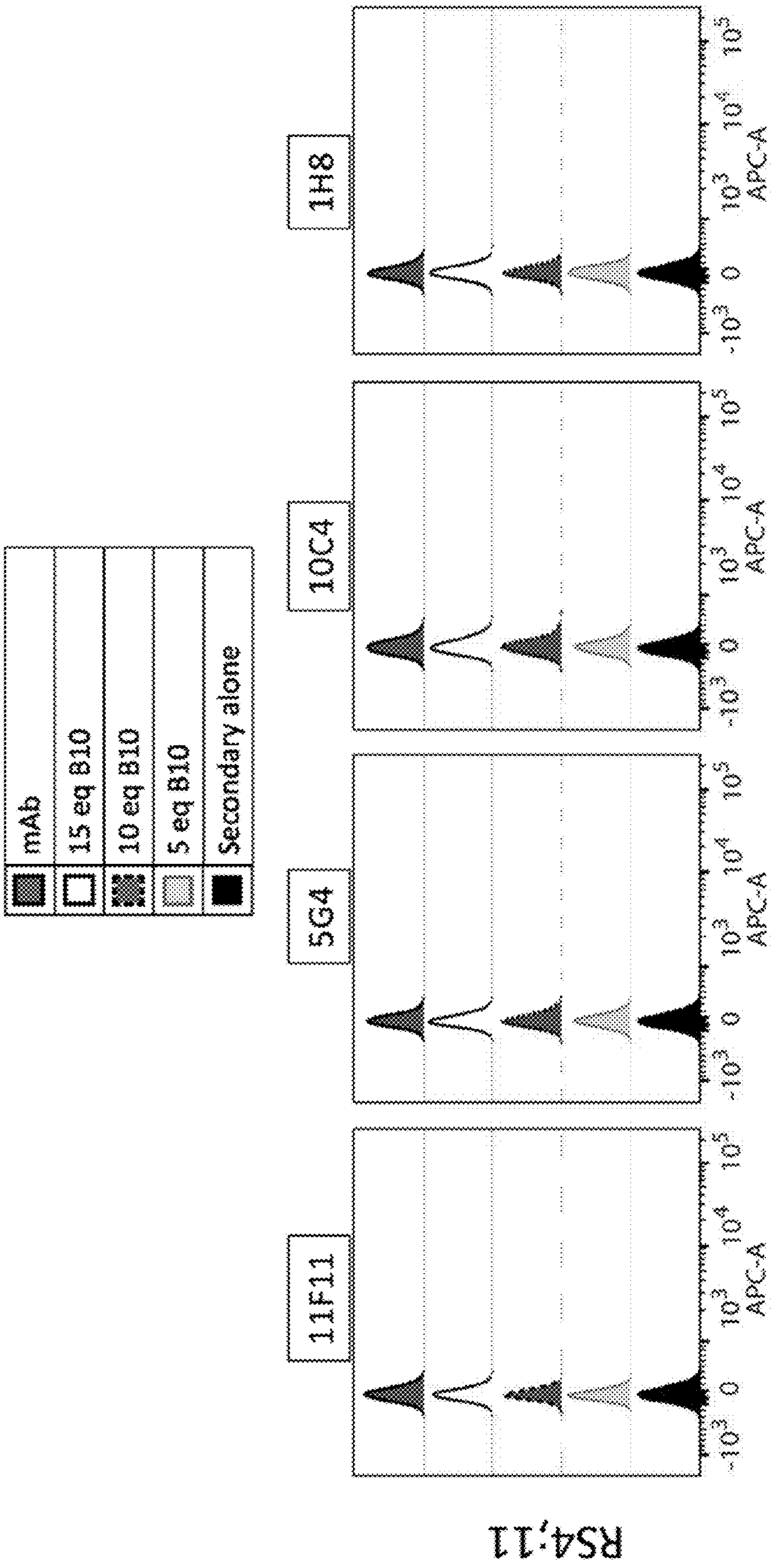
FIG. 4. Parental CD123-negative human RS4;11 ALL cells and RS4;11 cells engineered to overexpress human CD123 were used for flow cytometric phenotyping of a series of anti-CD123 mAbs (11F11, 5G4, 10C4, 1H8) that were either left unmodified or were reacted with 5, 10, or 15 equivalents of B10. A secondary mAb-only control is also shown.
Figure 4:
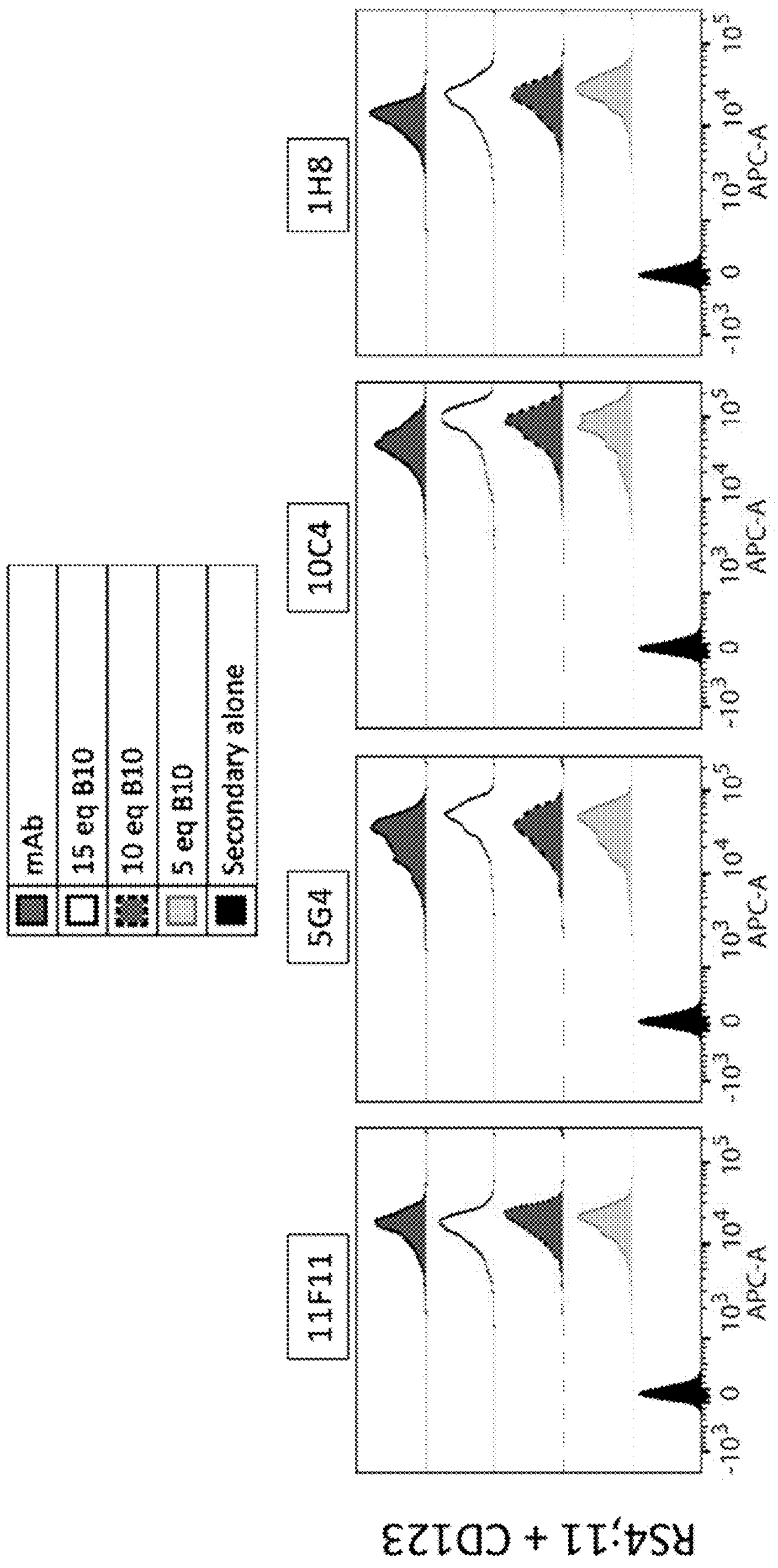

First, it was demonstrated that select murine mAbs described in Example 1 could be successfully conjugated with isothiocyantophenethyl-ureido-closo-decaborate(2-) (B10), a boron cage molecule for subsequent astatination using lysine amines (see, e.g., Wilbur D S, et al. Reagents for astatination of biomolecules. 4. Comparison of maleimido-closo-decaborate(2-) and meta-[(211)At]astatobenzoate conjugates for labeling anti-CD45 antibodies with [(211)At] astatine. *Bioconjug Chem.* 2009; 20:1983-91; and Wilbur D S, et al. Reagents for astatination of biomolecules. 6). An intact antibody conjugated with a maleimido-closo-decaborate(2-) reagent via sulfhydryl groups had considerably higher kidney concentrations than the same antibody conjugated with an isothiocyanato-closo-decaborate(2-) reagent via lysine amines. *Bioconjug Chem.* 2012; 23:409-20, each of which is incorporated herein by reference in its entirety). All tested anti-CD123 mAbs could be successfully conjugated with B10, with titration studies demonstrating optimal properties (highest amount of labeling with maintained CD123 binding) with 10 equivalents of B10 per mAb molecule. See FIG. 4.

Figure 5A:
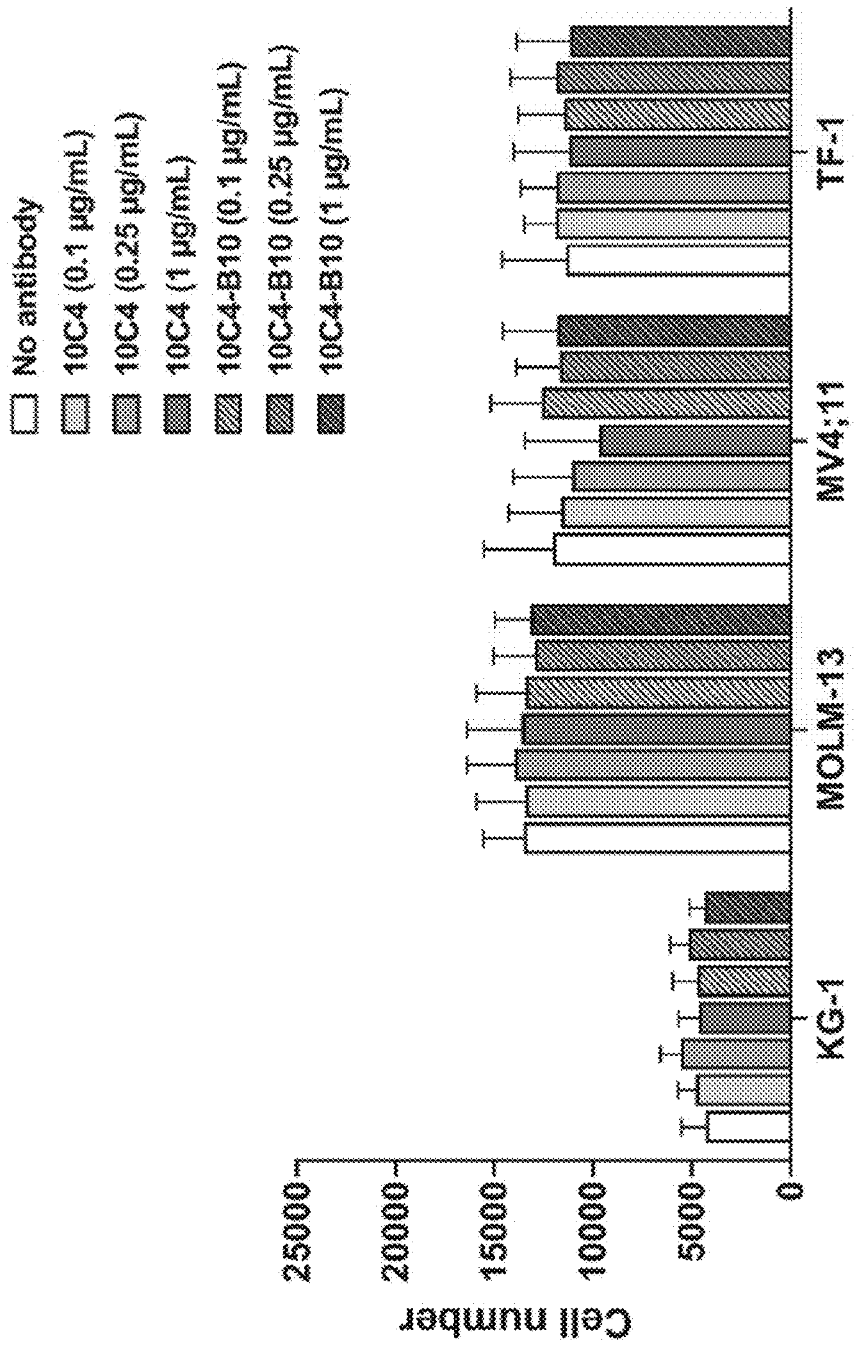
FIGS. 5A-5B. In vitro cytotoxic properties of 10C4 and 10C4-B10. CD123+ human acute leukemia cell lines (KG-1, MOLM-13, MV4;11, and TF-1) were incubated either alone or with unconjugated or B10-conjugated 10C4 at various concentrations as indicated. 3 days later, cell numbers (FIG. 5A) and the percentage of dead cells (FIG. 5B) were quantified by flow cytometry. Shown are mean±SEM values of 3 independent experiments.
Figure 5B:
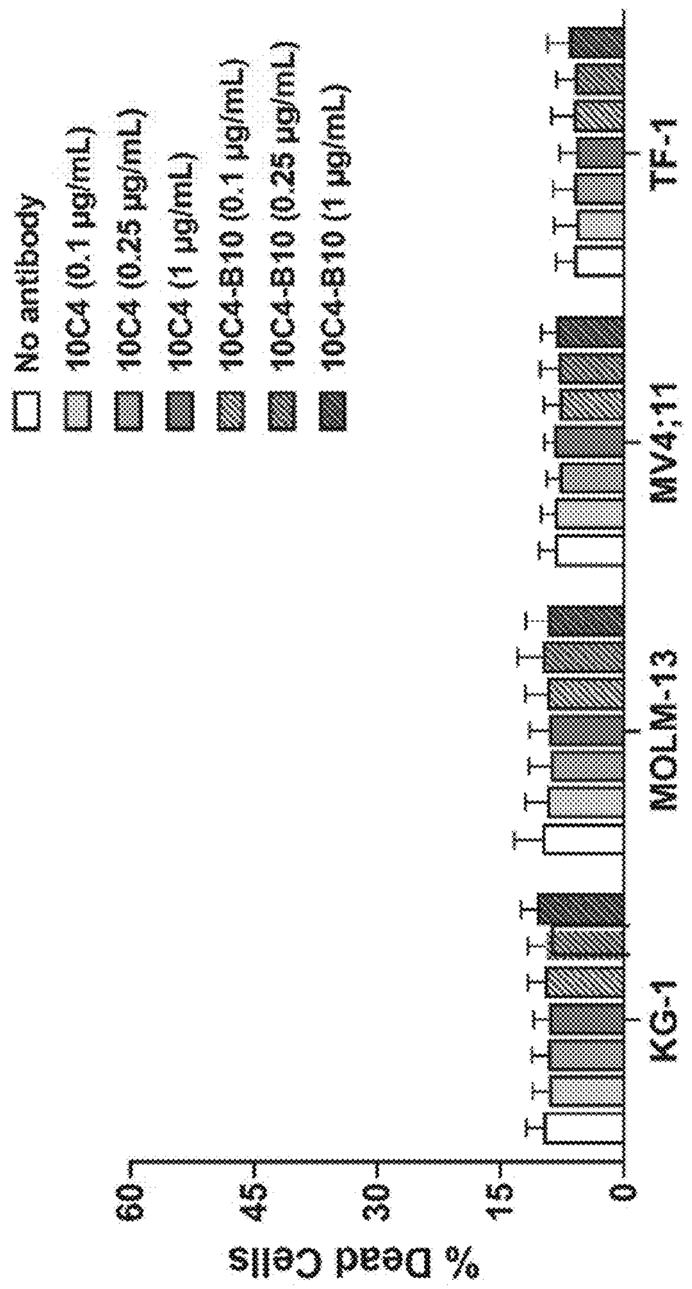

In vitro cytotoxicity evaluation for the antibody B10 conjugates revealed minimal cytotoxicity as measured by evaluation of cell number (FIG. 5A) and percentage of dead cells (FIG. 5B) following incubation of CD123+ human acute leukemia cell lines (KG-1, MOLM-13, MV4;11, and TF-1) alone or with unconjugated or B10-conjugated 10C4 at various concentrations.

Figure 6:
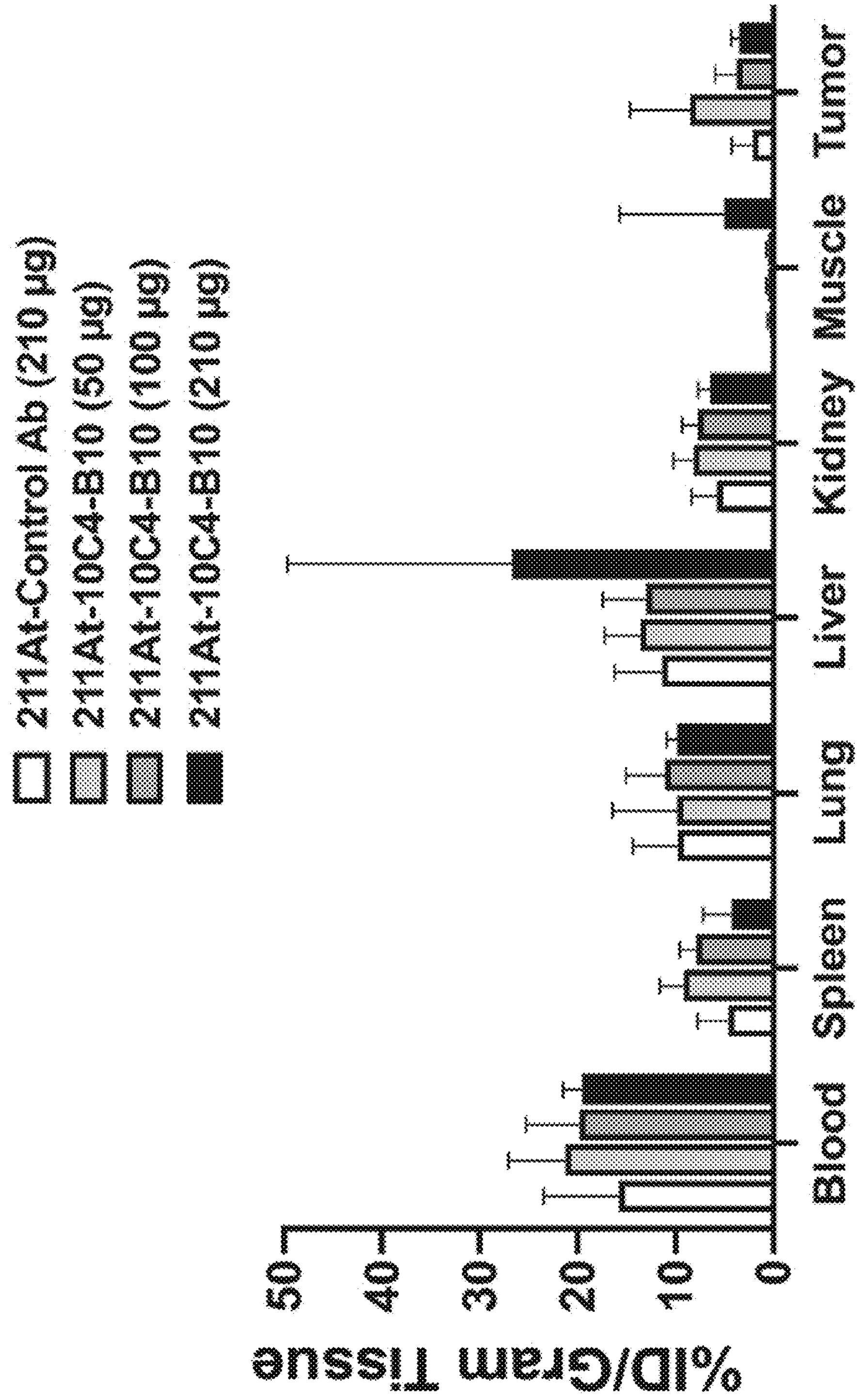
FIG. 6. In vivo anti-CD123 mAb dose finding study. $10^6$ parental (CD123+) MOLM-13 cells were implanted into the flanks of NRG mice. One week later, when tumors were palpable (~100 $mm^3$), animals (5/group) received 50 μg, 100 μg, or 210 μg a B10-cconjugated anti-CD123 mAb (10C4-B10) or 210 μg of a B10-conjugated murine IgG1 negative control mAb (BHV-1-B10), all labeled with 5 μCi $^{211}At$. 7 hours later, mice were euthanized, organs harvested, and tissues analyzed on a gamma counter to calculate the percent of injected dose/gram of organ tissue (% ID/g), and radiation absorbed doses for harvested organs calculated. Data are presented as mean±SD.
Figure 7:
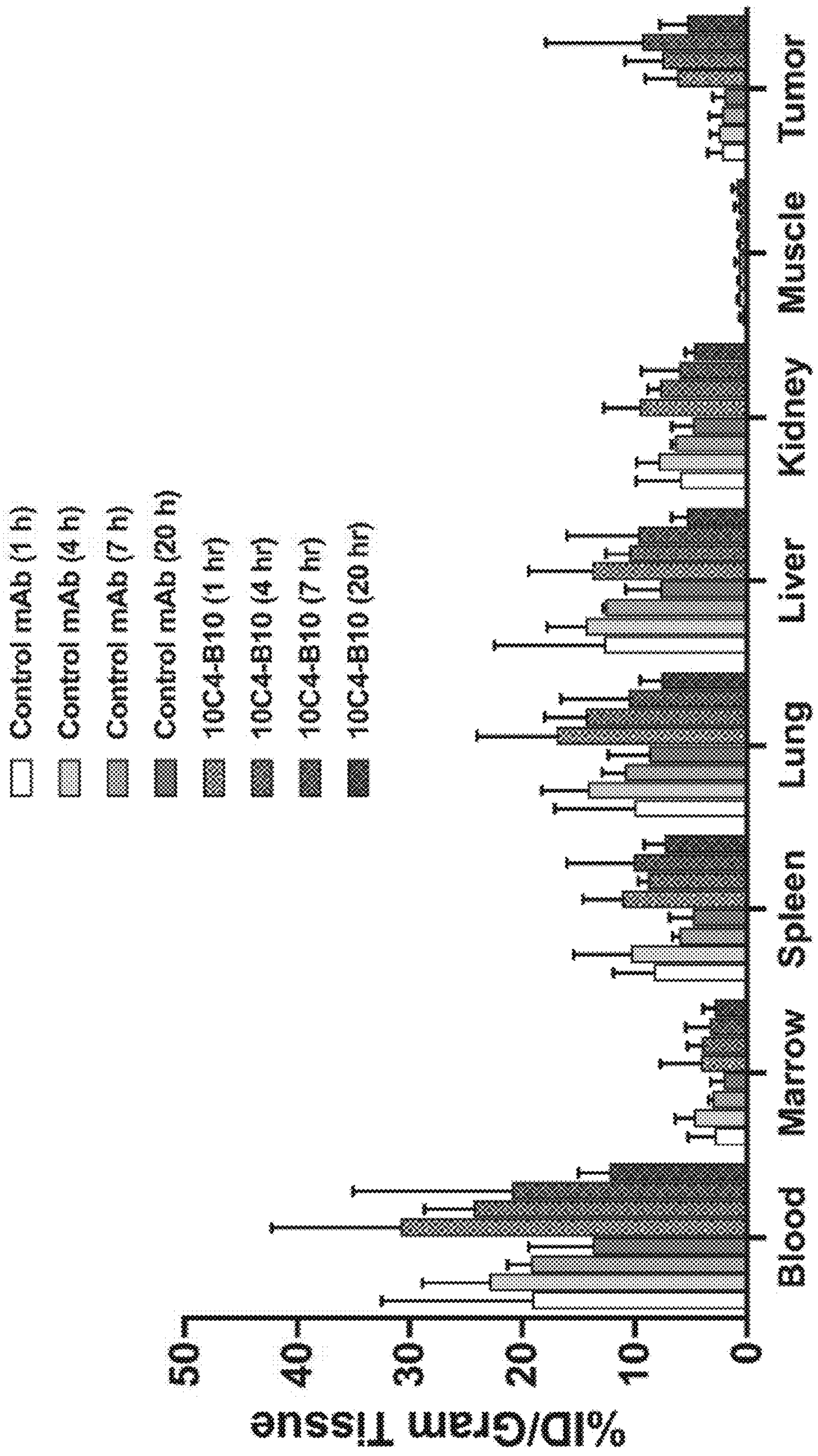
FIG. 7. In vivo CD123+ cell targeting with $^{211}At$-CD123 RIT. $10^6$ parental (CD123+) MOLM-13 cells were implanted into the flanks of NRG mice. One week later, animals (5/group) received 50 μg of either B10-conjugated anti-CD123 mAb (10C4-B10) or B10-conjugated murine IgG1 negative control mAb (BHV-1-B10) labeled with 5 μCi $^{211}At$. One hour, 4 hours, 7 hours, or 20 hours later, mice were euthanized, organs harvested, and tissues analyzed on a gamma counter to calculate the percent of injected dose/gram of organ tissue (% ID/g), and radiation absorbed doses for harvested organs calculated. Data are presented as mean±SD.

Next, it was demonstrated that $^{211}$At-labeled anti-CD123 mAbs have favorable human leukemia cell targeting ("biodistribution") properties in immunodeficient mice. In an initial leukemia cell targeting study, 3 mAb doses (50 μg, 100 μg, 210 μg) of $^{211}$At-labeled 10C4-B10 were tested in immunodeficient NOD-Rag1$^{null}$ IL2rγ$^{null}$/J (NRG) mice carrying MOLM-13 (CD45+/CD123+ human AML cell line) flank tumors. NRG mice tolerate higher levels of radiation and RIT than NSG mice and support transplanted cells from human acute leukemia cell lines without anti-asialo injections required to neutralize residual NK cell activity in athymic nude mice. Tissues were harvested 7 hours after RIT administration for analysis on a gamma counter to calculate the percent of injected dose/gram of organ tissue (% ID/g), and radiation absorbed doses for harvested organs calculated. The lowest mAb dose (50 μg) yielded the most optimal tumor cell accumulation of $^{211}$At and was used in subsequent studies. See FIG. 6. In a full time course experiment, significant accumulation of $^{211}$At-labeled 10C4-B10 was found in MOLM-13 flank tumors 1, 4, 7, and 20 hours after RIT administration, with values being comparable to those obtained with $^{211}$At-labeled anti-CD45 mAbs. See FIG. 7. This demonstrated favorable biodistribution properties of $^{211}$At-labeled anti-CD123 mAbs.

To facilitate in vivo efficacy assessments of radiolabeled anti-CD123 mAbs, MOLM-13 cells were transduced with luciferase. Following single cell sorting, a clonally derived MOLM-13$^{LUC}$ cell line was established and confirmed to show efficient engraftment in NRG mice, with all animals dying from leukemia within 3-4 weeks after injection of $2\times10^5$ cells per mouse. Using CRISPR/Cas9 followed by single cell cloning, a clonal CD123-deficient subline of these cells was then derived (MOLM-13$^{LUC}$/CD123KO).

Figure 8A:
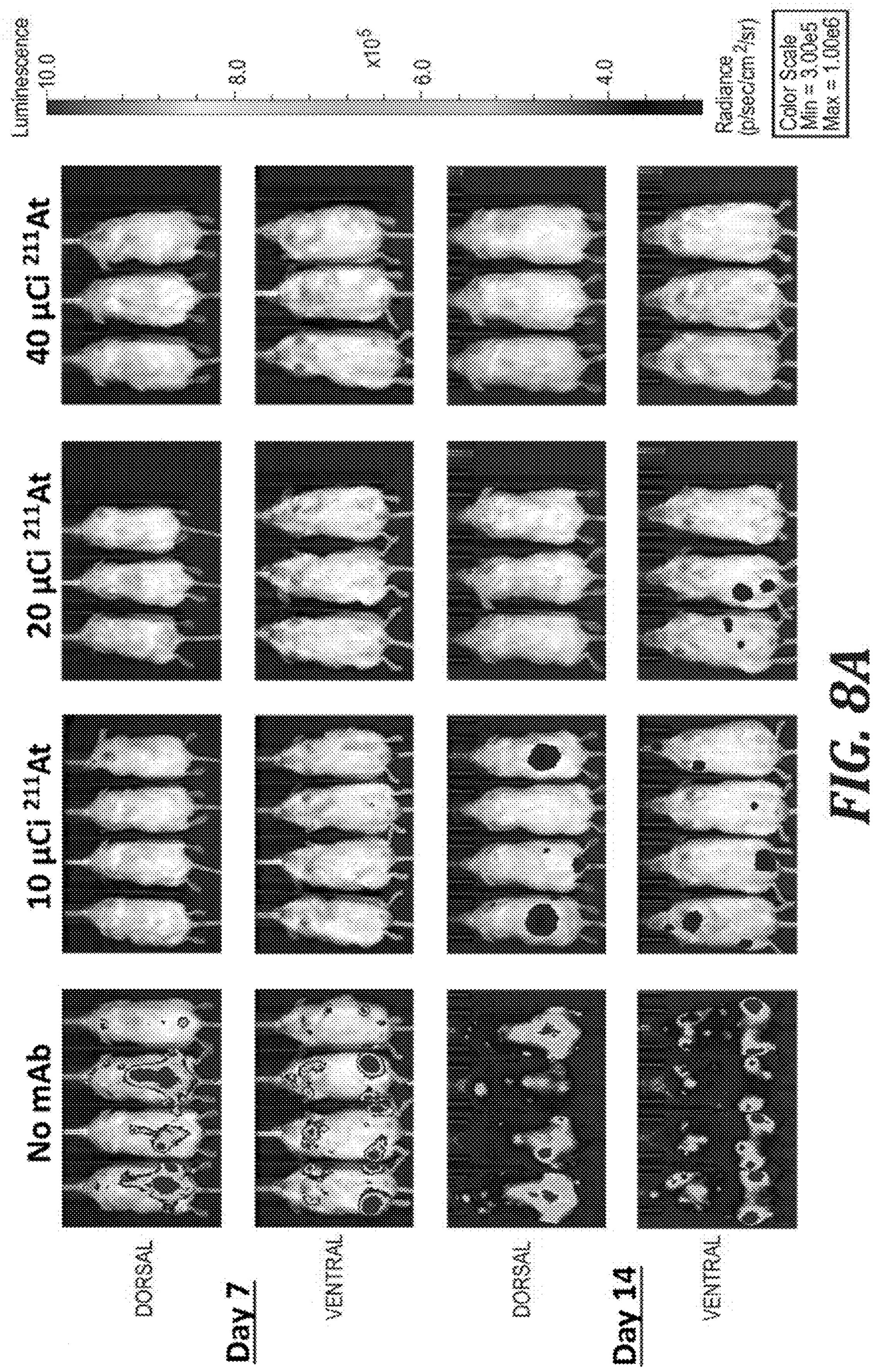
FIGS. 8A-8B. In vivo anti-AML efficacy of $^{211}At$-CD123 RIT. In vivo fluorescence imaging 7 and 14 days after administration of 10C4-B10 labeled with either 10 μCi, 20 μCi, or 40 μCi of $^{211}At$ (FIG. 8A). Control group was left untreated. Kaplan-Meier survival estimates. 8-11 animals per group (FIG. 8B). All deaths were attributed to progressive leukemia. P<0.0001 for Ctrl vs. 10 μCi, P<0.004 for 10 μCi vs. 40 μCi.
Figure 8B:
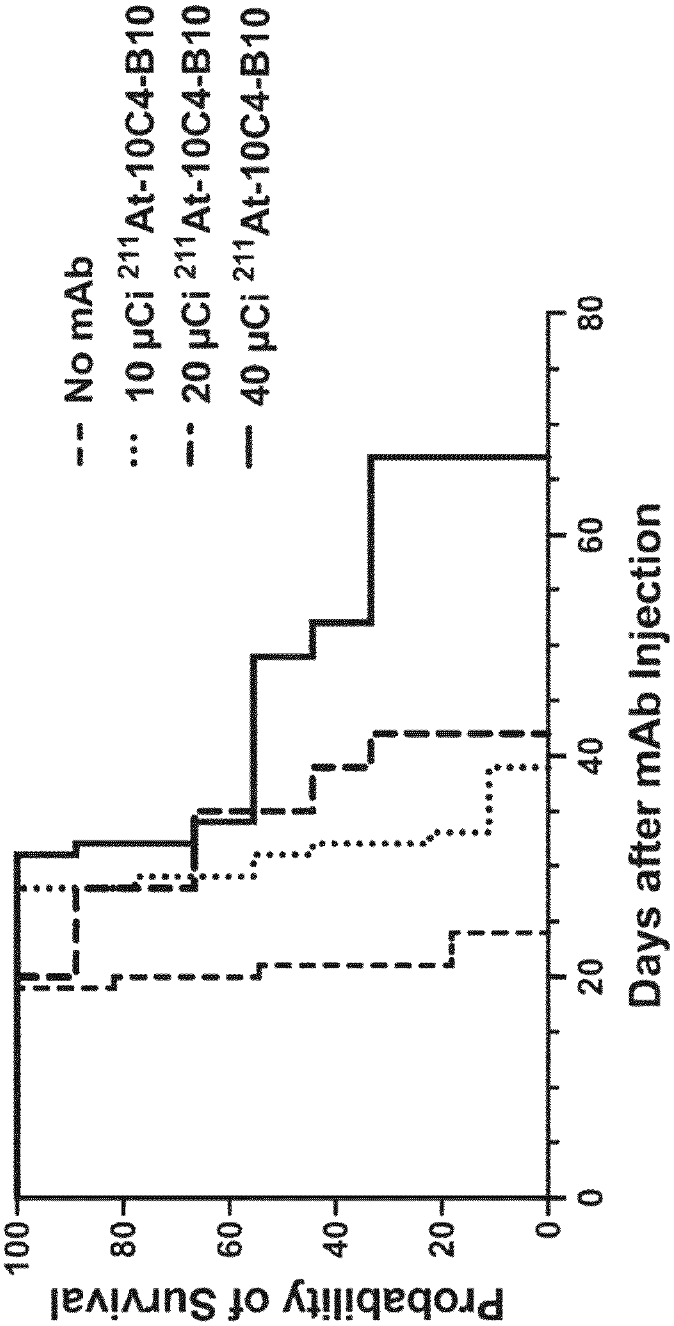

Unlike a non-binding $^{211}$At-labeled control mAb, $^{211}$At-labeled anti-CD123 mAbs showed uptake at MOLM-13 flank tumors in immunodeficient NRG mice xenotransplanted with human acute leukemia (MOLM-13) cells, resulting in prolonged survival. After completion of initial leukemia cell targeting ("biodistribution") studies to optimize the dosing of the 10C4 mAb (described above), a proof-of-concept efficacy study was conducted in immunodeficient mice. Specifically, NRG mice were injected with $2\times10^5$ MOLM-13$^{LUC}$ cells, the luciferase-transduced CD123+ human acute leukemia cell line described above, into tail veins to established disseminated leukemia. Two days later, animals were either left animals untreated or given 50 μg of 10C4-B10 mAb labeled with 10 μCi, 20 μCi, or 40 μCi of $^{211}$At (8-11 animals/group). Each animal then received $5\times10^6$ bone marrow cells from donor NRG mice as stem cell support 3 days later. As shown in FIGS. 8A-8B, $^{211}$At-labeled 10C4-B10 mAbs dose-dependently decreased the tumor burden in mice and significantly prolonged survival compared to untreated animals (median survival: 49 days [40 μCi of 211At] vs. 31 days [10 μCi of 211At] vs. 21 days [Ctrl]; $P<0.0001$ for Ctrl vs. 10 μCi, $P<0.004$ for 10 μCi vs. 40 μCi). These data demonstrate potent in vivo anti-leukemia efficacy of a single dose of $^{211}$At-CD123 RIT.

Figure 9A:
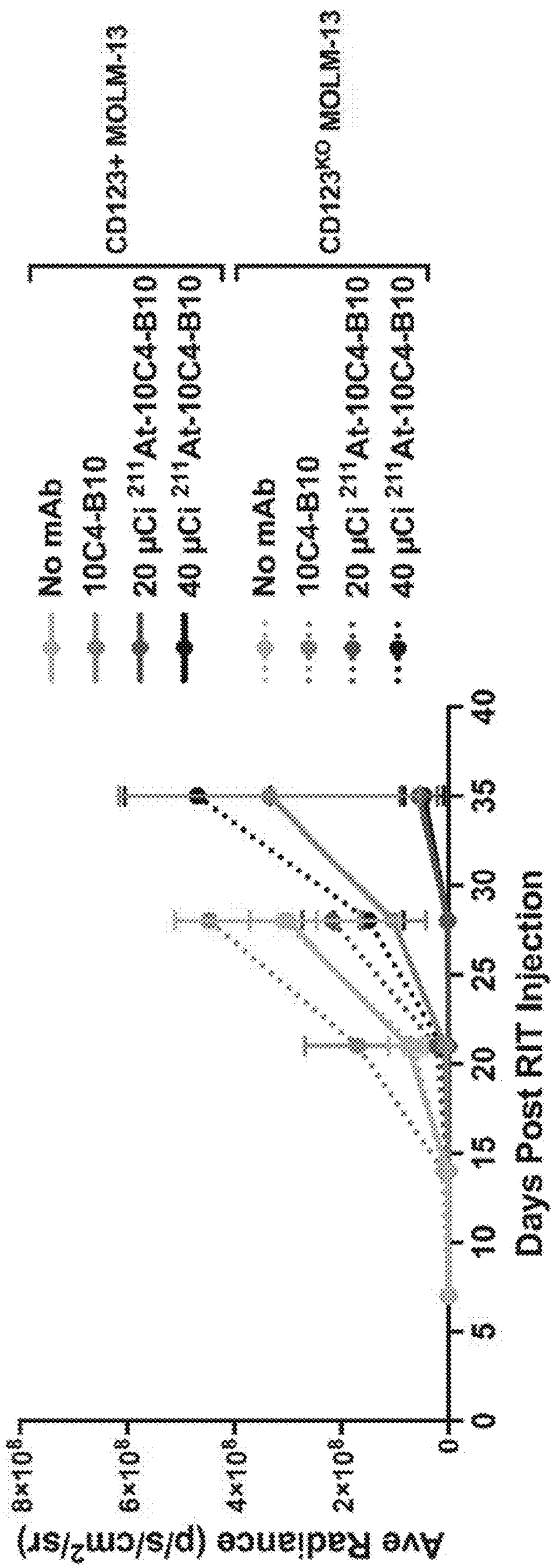
FIGS. 9A-9B. Target antigen specificity of $^{211}At$-CD123 RIT in vivo. Two days after injecting NRG mice intravenously with either luciferase-transduced parental CD123+ MOLM-13 cells or a clonally derived subline in which CD123 was deleted via CRISPR/Cas9 (CD123KO MOLM-13), mice were left untreated or injected with 50 μg of 10C4-B10 (i.e. B10-conjugated 10C4 anti-CD123 mAb without radioisotope) or 50 μg of 10C4-B10 labeled with either 20 μCi or 40 μCi of $^{211}At$.
Figure 9B:
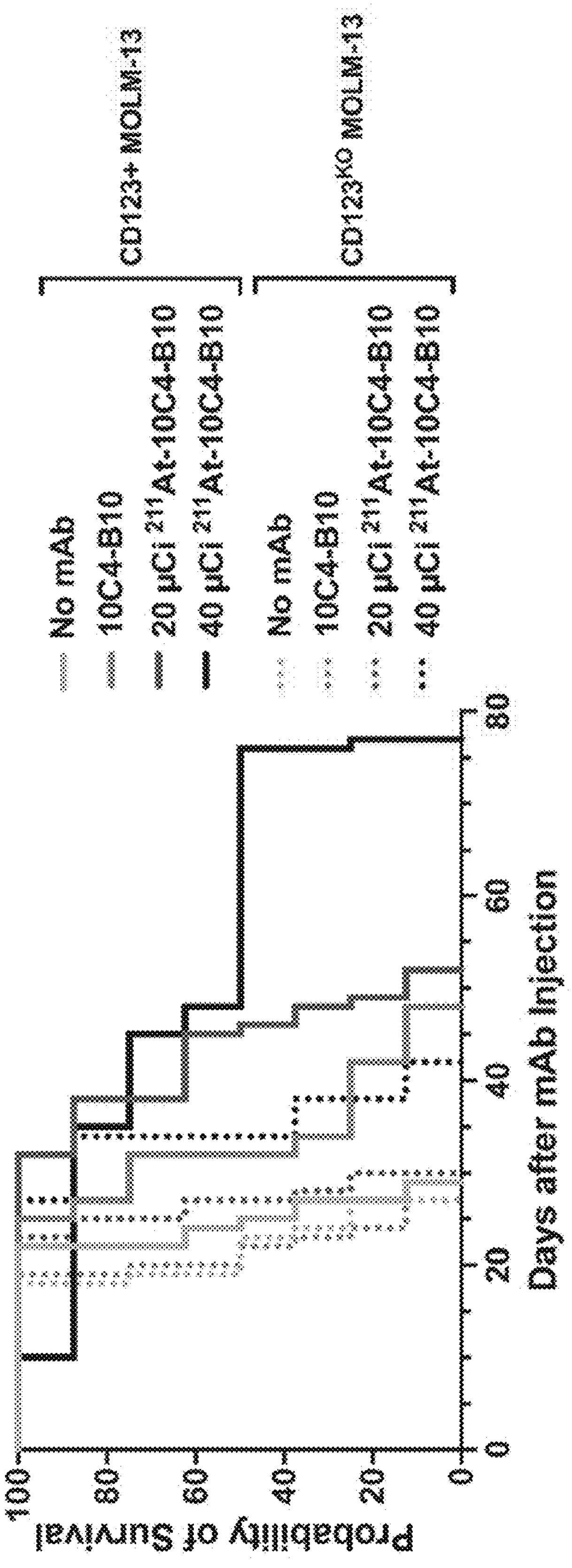

Next, target antigen specificity of $^{211}$At-CD123 RIT in vivo was demonstrated. As described in Example 1, luciferase-transduced MOLM-13 cells were used in addition to a single cell cloned subline in which CD123 was specifically deleted via CRISPR/Cas9. NRG mice were injected with either luciferase-transduced parental CD123+ MOLM-13 cells or a clonally derived subline in which CD123 was deleted via CRISPR/Cas9 ($2\times10^5$ cells per mouse). 2 days later, mice were left untreated or injected with 50 μg of 10C4-B10 (i.e., B10-conjugated 10C4 anti-CD123 mAb without radioisotope) or 50 μg of 10C4-B10 labeled with either 20 μCi or 40 μCi of $^{211}$At. Potent anti-leukemia efficacy with $^{211}$At-CD123 RIT was again observed in mice xenotransplanted with CD123+ MOLM-13 cells but not in mice xenotransplanted with CD123-MOLM-13 cells (FIG. 9A). FIG. 9B depicts Kaplan-Meier estimates of overall survival. These data demonstrate the viability of anti-CD123 affinity reagents as vehicles for radioisotope payloads to serve as an effective and highly-specific radioimmunotherapy (RIT) for patients with acute leukemia and other CD123+ neoplastic conditions, including other hematologic malignancies.

Example 3

Examples 1 and 2 described the generation and characterization of murine antibodies that specifically bind to CD123 and show promise as effective therapeutic reagents. Example 2 specifically demonstrates that the murine anti-CD123 affinity reagents can be conjugated with radioisotope payloads and used to specifically reduce tumor burden and prolong life in murine xenotransplant models.

This example describes the generation and characterization of fully human antibodies that specifically bind to CD123 for creation of optimized therapeutic compositions for use in humans, potentially including repeated administrations and show promise as effective therapeutic reagents.

Select human antibodies were generated from ATX-GX mice (Alloy Therapeutics) immunized with NIH 3T3 mouse embryo fibroblast cells transduced to express human CD123. Binding to CD123 was confirmed and the sequences of the antibodies were determined.

Six ATX-GX mice (Alloy Therapeutics) were immunized with NIH 3T3 mouse embryo fibroblast cells transduced to express human CD123. ATX-GX mice are transgenic animals developed as in vivo discovery platform and optimized for human antibody sequence developability and diversity, encompassing haplotype diversity and a full human heavy chain repertoire (40V, 23D, and 6J segments), with separate mice for human kappa (19V, 5J segments) and human lambda (22V, 5J segments) chain repertoires. Three strains of animals were used: 1) ATX-GK-BL/6, black 6 mice with full heavy chain and kappa light chain repertoires (n=2); 2) ATX-GK-MIX, with heavy chain repertoires split between two separate mouse lines (BL/6, BALB/c) to overcome immunodominant germlines and full kappa light chain diversity (n=2); and 3) ATX-GL, with full heavy chain repertoire and lambda light chain repertoire on a BL/6 background (n=2). More than 20 polyclonal hybridomas secreting mAbs recognizing human CD123 were isolated. Hybridomas of interest were subjected to single cell cloning. Eight hybridomas (i.e., ATX1B2, ATX1B5, ATX1B7, ATX1D9, ATX1E3, ATX1E5, ATX1F2, and ATX1G5) were selected for sequencing and development of radioimmunoconjugate compositions. See SEQ ID NOS: 71-151 in the Sequence Listing.

To generate recombinant fully human anti-CD123 mAbs optimized for therapeutic administration, the variable region sequences were derived from 5' RACE cloning to generate recombinant mAbs, using human IgG1 (most commonly used isotype in clinical therapeutics) and human kappa or lambda light chain frameworks as appropriate. For production of recombinant mAbs, a transient expression system that is based on pcDNA3.4 vectors and various HEK293 cell lines was used. Small-scale (~10 mL) productions were column purified before mAb characterization.

Figure 17:
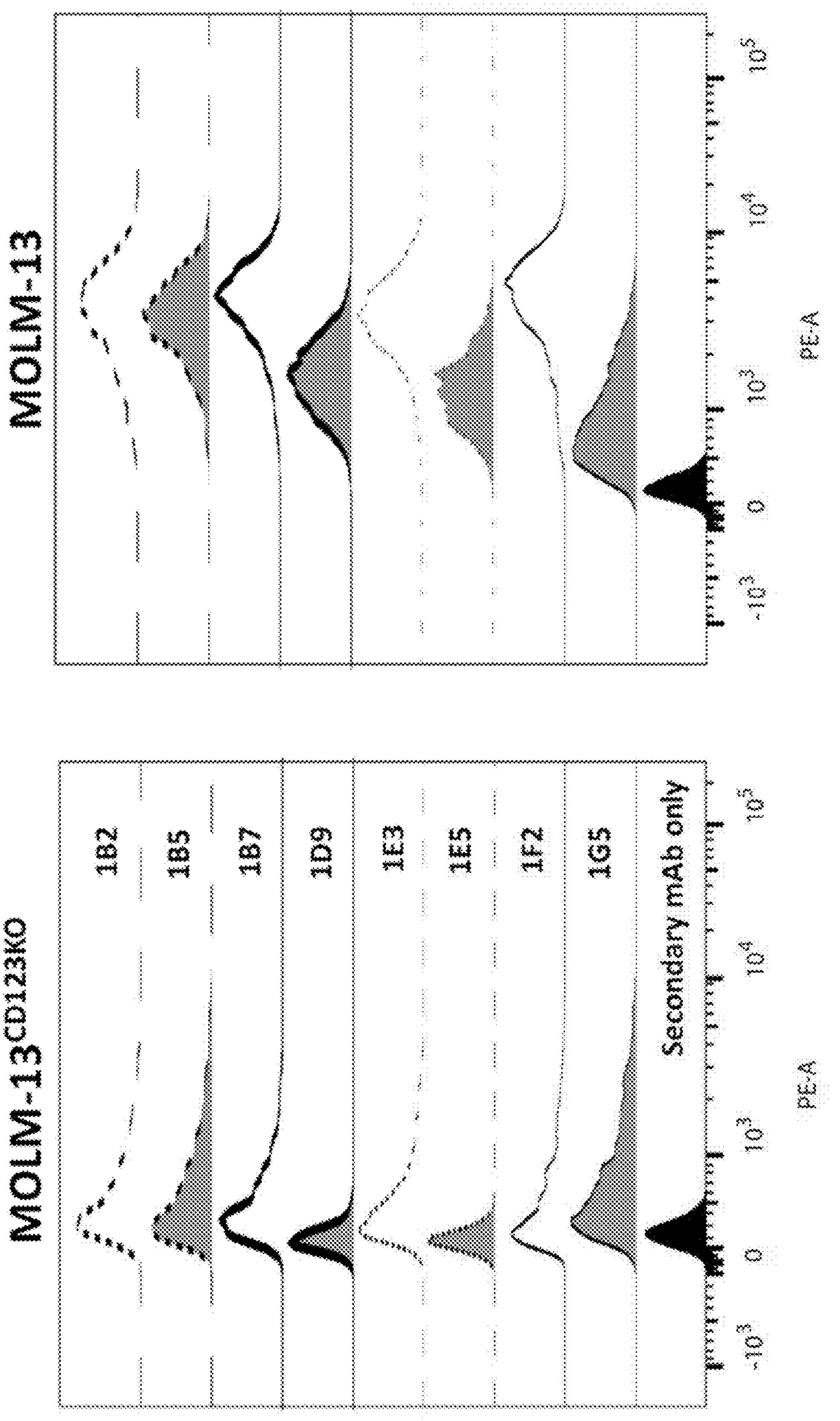
FIG. 17. MOLM-13 cells with CRISPR/Cas9-mediated knockout of the CD123 locus (CD123$^{KO}$) or parental MOLM-13 cells were left untreated or treated with recombinant fully human anti-human CD123 monoclonal antibodies (1B2, 1B5, 1B7, 1D9, 1E3, 1E5, 1F2, and 1G5); used at 2 μg/mL) or a labeled secondary antibody before flow cytometric analysis.
Figure 18A:
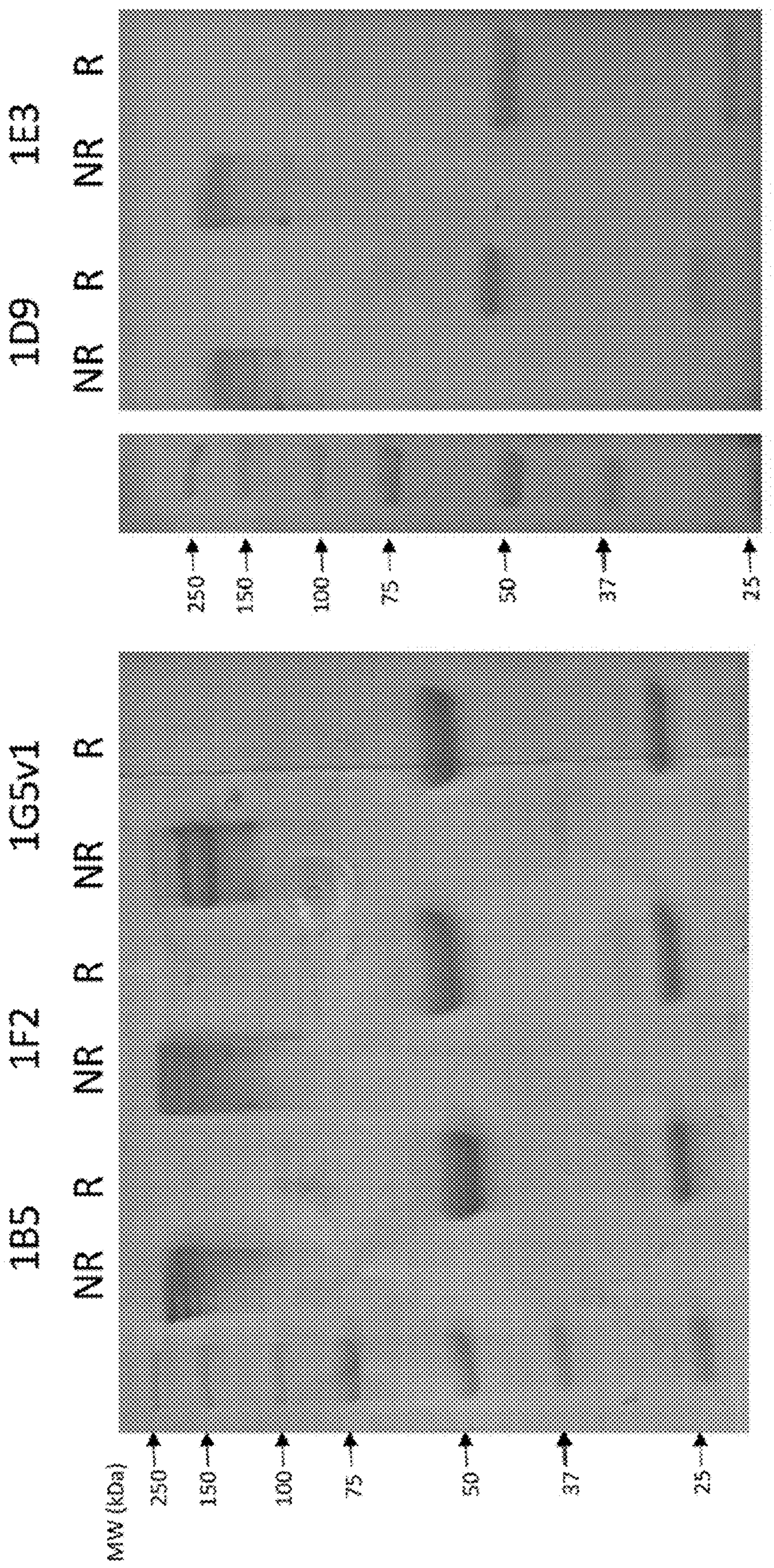
FIGS. 18A-18B. Protein gel analysis of recombinant fully human anti-human CD123 monoclonal antibodies. Monoclonal antibodies were produced using human IgG1 frameworks. 25 μg (left panel) or 5 μg (right panel) of purified antibodies were visualized via sodium dodecyl sulfate-polyacrylamide gel electrophoresis (SDS-PAGE) under non-reducing (NR) or reducing (R) conditions using a Coomassie Blue-based protein stain (FIG. 18A). A protein sizing ladder is shown to indicate relative molecular weight of protein bands. Monoclonal antibodies were produced using human IgG4 frameworks. 5 μg of purified antibodies were visualized via SDS-PAGE under non-reducing (NR) or reducing (R) conditions using a Coomassie Blue-based protein stain (FIG. 18B). A protein sizing ladder is shown to indicate relative molecular weight of protein bands FIG. 19. MOLM-13 cells with CRISPR/Cas9-mediated knockout of the CD123 locus (MOLM-13$^{CD123KO}$), parental MOLM-13 cells (endogenously expressing CD123) were left untreated or treated with recombinant human anti-human CD123 mAbs (clones 1B5, 1D9, 1E3, 1F2, and 1G5; all human IgG1 frameworks) and a labeled secondary antibody before flow cytometric analysis.
Figure 18B:
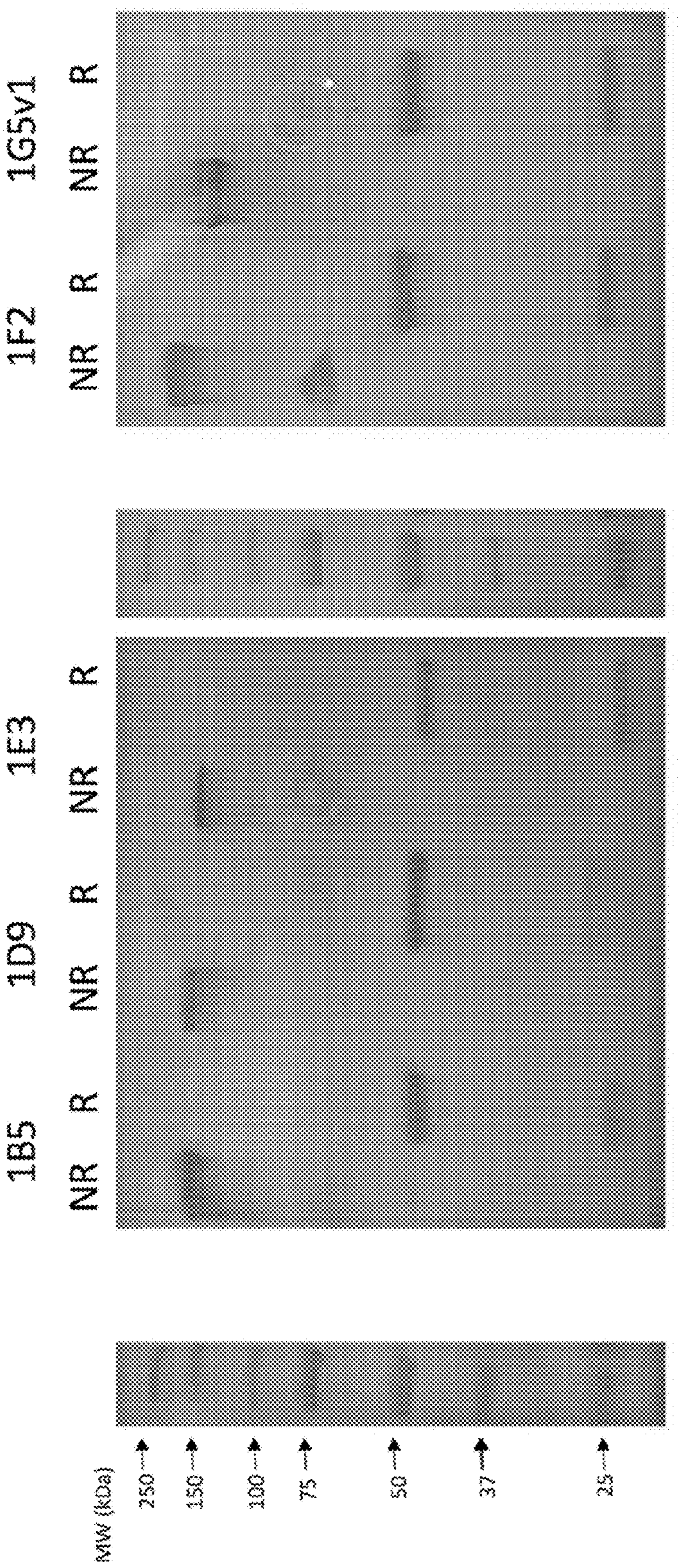

The recombinantly generated fully human anti-CD123 mAbs were subsequently characterized and selected and tested for binding to human CD123+ and CD123-human acute leukemia cells via flow cytometry, as demonstrated above. Specific binding to human CD123 was confirmed by flow cytometry using hybridoma cell culture supernatants (FIG. 17). After purification, the mAbs with IgG1 framework (FIG. 18A) and IgG4 framework (FIG. 18B) were analyzed by SDS-PAGE under reducing and non-reducing conditions.

Figure 19:
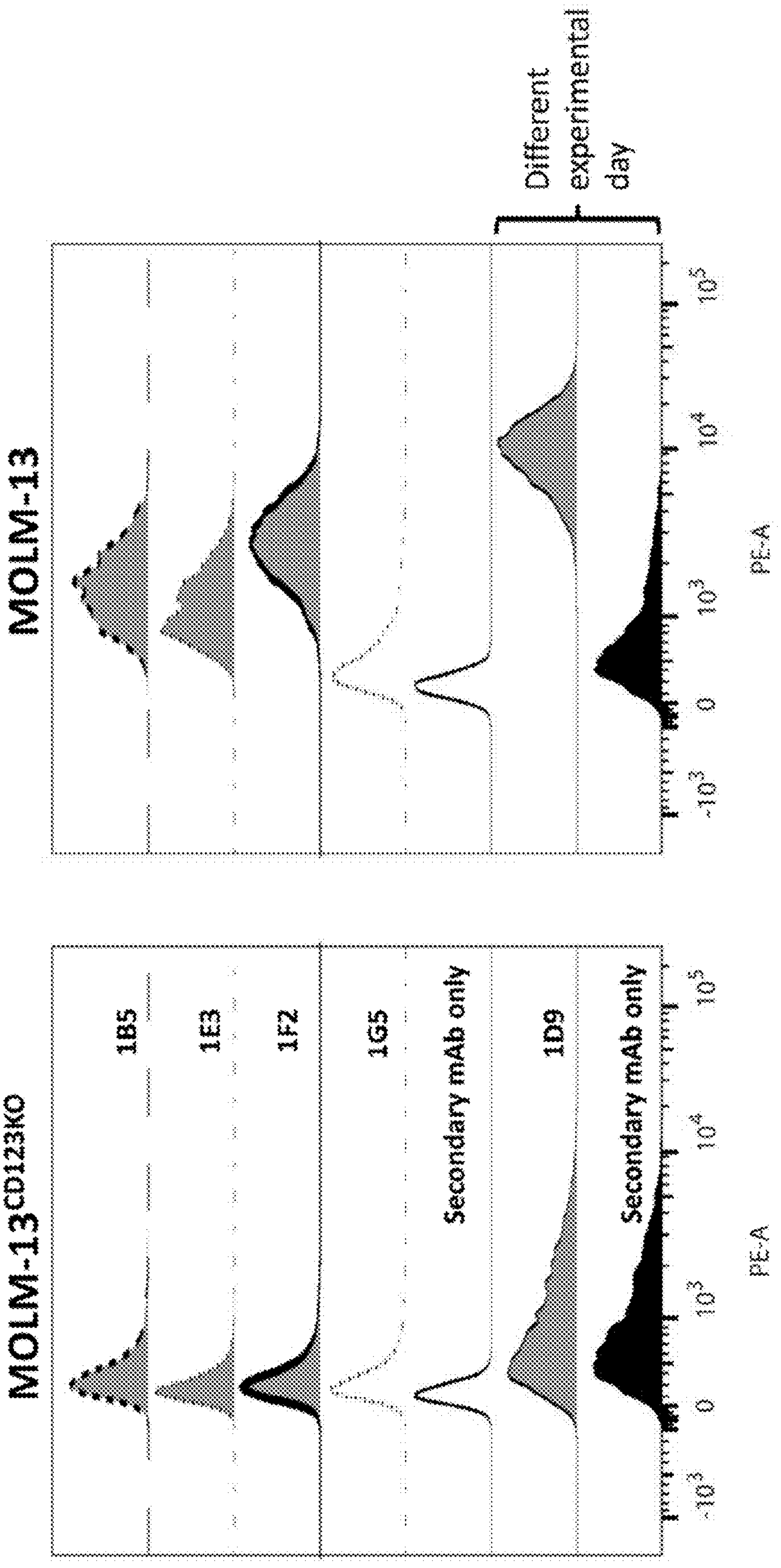
Figure 20A:
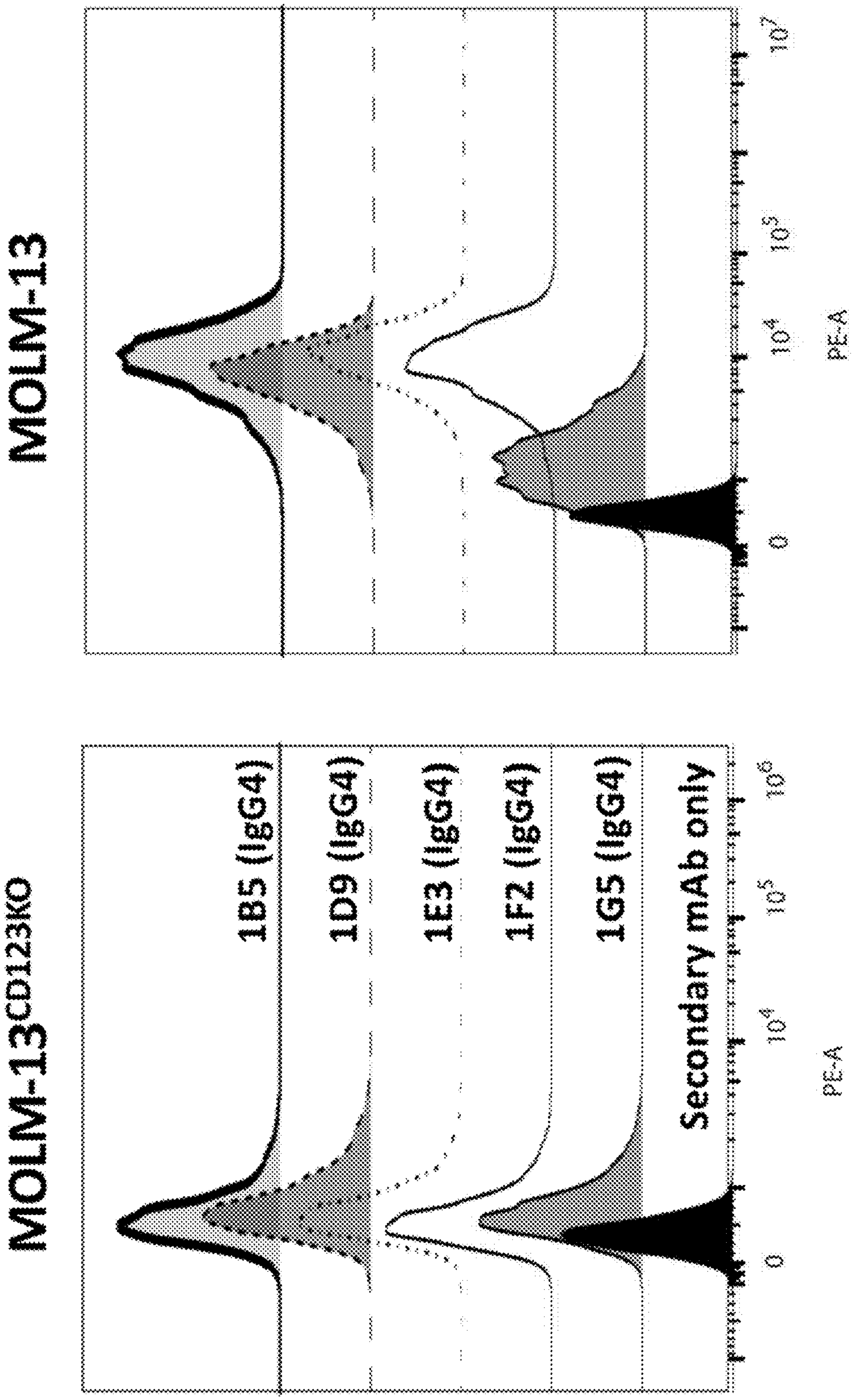
FIGS. 20A-20B. MOLM-13 cells with CRISPR/Cas9-mediated knockout of the CD123 locus (MOLM-13$^{CD123KO}$), parental MOLM-13 cells (endogenously expressing CD123) (FIG. 20A), ML-1 cells with CRISPR/Cas9-mediated knockout of the CD123 locus (ML-1$^{CD123KO}$), and ML-1$^{CD123KO}$ cells in which human CD123 was re-expressed via lentivirus-mediated gene expression (FIG. 20B) were left untreated or treated with recombinant human anti-human CD123 mAbs (clones 1B5, 1D9, 1E3, 1F2, and 1G5; all human IgG4 frameworks) and a labeled secondary antibody before flow cytometric analysis.
Figure 20B:
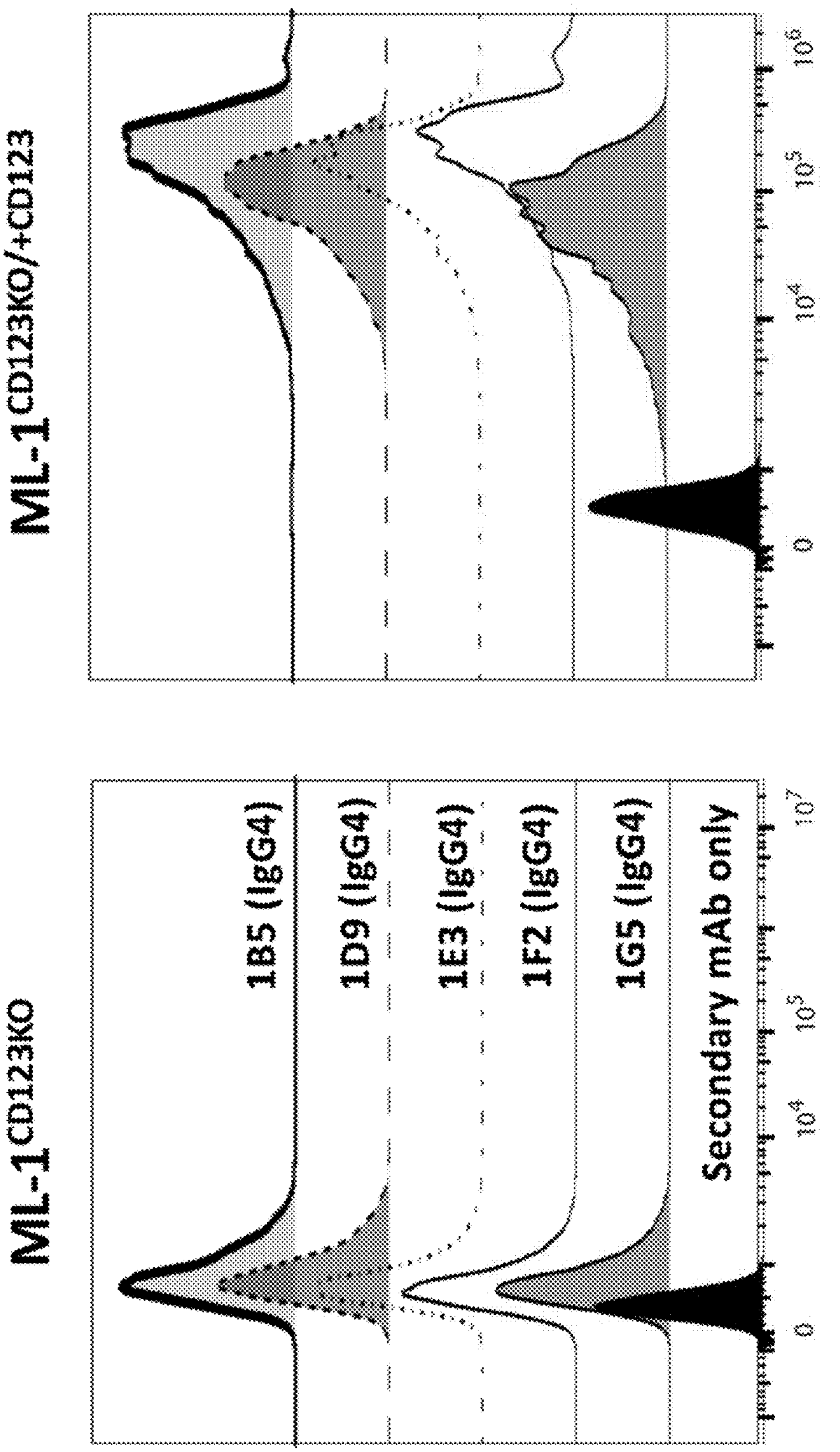

To illustrate, specific binding for the selected human mAb clones, with either all human IgG1 frameworks (FIG. 19) or human IgG4 frameworks (FIGS. 20A-20B) to human CD123, was determined. All selected human mAb clones (i.e., ATX1B5, ATX1D9, ATX1E3, ATX1F2, and ATX1G5) exhibited binding to human CD123-expressing cells, but not to cells devoid of CD123 expression.

Figure 21A:
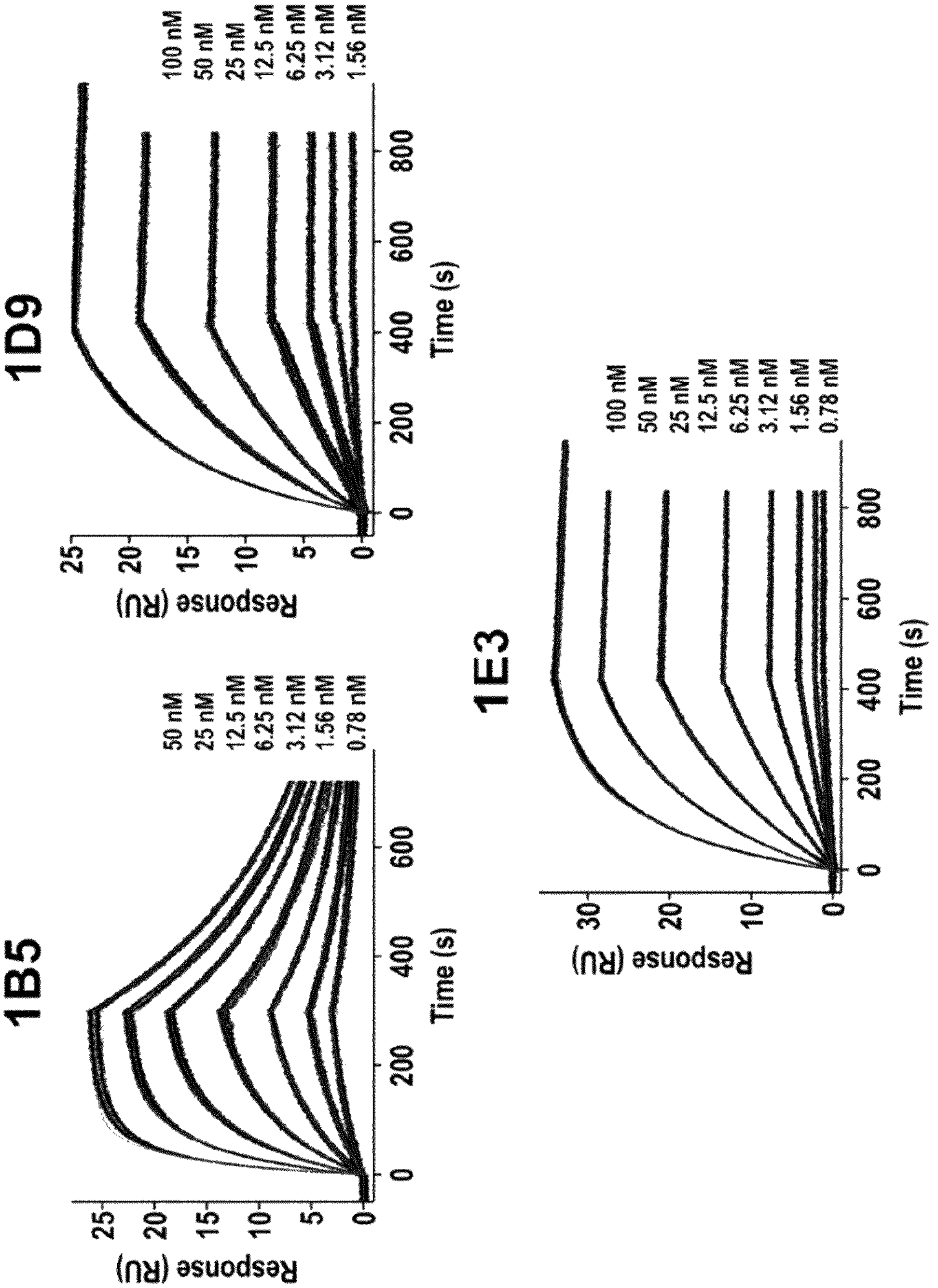
FIGS. 21A-21B. Surface plasmon resonance (Biacore T-100) analyses were performed to rigorously/precisely determine univalent binding affinities of recombinant, fully human versions of the anti-human CD123 monoclonal antibodies 1B5, 1D9, and 1E3, using human IgG1 (FIG. 21A) and human IgG4 frameworks (FIG. 21B). For these experiments, a peptide encoding the complete extracellular portion of human CD123 was used, and the antibodies were captured on the biosensor chip (CM4) via a Fc gamma-specific goat anti-human IgG and amine coupling.
Figure 21B:
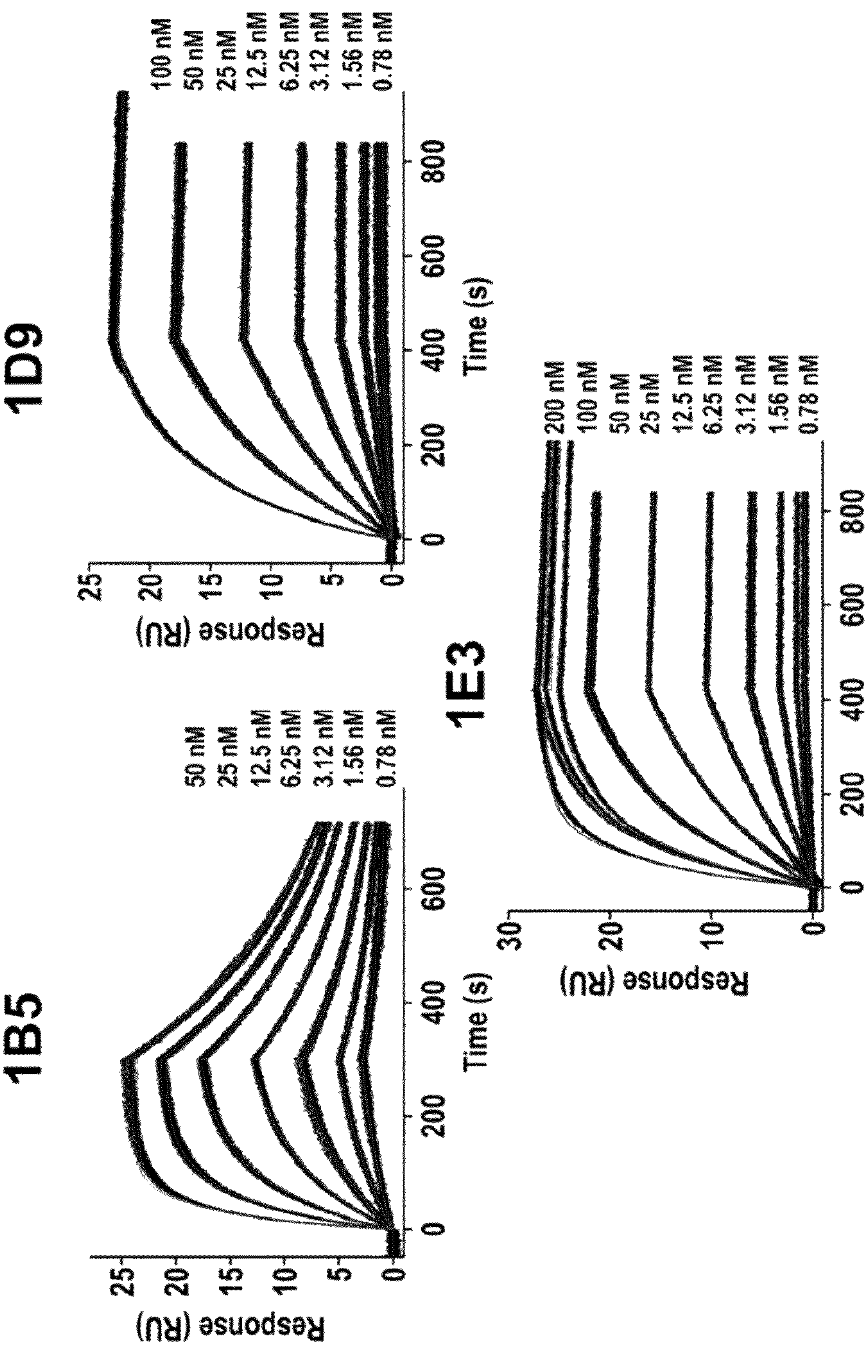

A His-Avi tagged peptide encompassing the ECD of human CD123 was used to enable SPR (Biacore) analysis to precisely determine binding affinities of the recombinant fully human CD123 antibodies using both human IgG1 and IgG4 frameworks. See FIGS. 21A-21B. mAbs were selected based on binding intensity to CD123 (flow cytometrically determined) and/or binding affinity (Biacore determined). The recombinant mAbs can be produced in larger quantity for subsequent B10 conjugation.

Summary of surface plasmon resonance (Biacore T-100) analyses performed to rigorously/precisely determine univalent binding affinities of recombinant fully human anti-human CD123 antibodies to human CD123 and nonhuman primate CD123, using both human IgG1 and human IgG4 frameworks. See FIG. 22.

To optimize conjugation of anti-CD123 mAbs with B10, assays can be readily conducted to conjugate B10 moieties with anti-CD123 mAbs wherein ~5, 10 or 15 equivalents of B10 are reacted with mAbs to identify optimal conjugation conditions. The B10-conjugated mAbs can be purified, e.g., over size-exclusion (SE) PD10 columns. After purification, the B10-conjugated mAbs can be analyzed by SE-HPLC, IEF and SDS-PAGE and assayed by mass spectral analysis to identify the average number of B10 moieties on them. The mAbs can then be assayed for binding with CD123+ target cells and CD123-control cells by flow cytometry, as demonstrated above. Optimal B10 conjugation conditions can be defined as those yielding the highest number of B10 moieties per mAb molecule while preserving high CD123 binding. This optimization typically provides labeling efficiencies >90%. Radiochemical purity can be verified by size-exclusion radio-HPLC for radioimmunoconjugates.

$^{211}$At-labeling of mAbs can then be performed. Specifically, $^{211}$At can be produced on a Scanditronix MC-50 cyclotron with 29 MeV α beam irradiation of a bismuth metal target. See, e.g., Gagnon K, et al. Design and evaluation of an external high-current target for production of 211At. *J Label Compd Radiopharm.* 2012; 55:436-440, incorporated herein by reference in its entirety. After irradiation, $^{211}$At can be isolated in a "wet chemistry" isolation procedure. See Balkin E R, et al. Evaluation of a wet chemistry method for isolation of cyclotron produced [At-$^{211}$] astatine. *Appl Sci-Basel.* 2013; 3:636-655, incorporated herein by reference in its entirety.

The therapeutic efficacy and toxicity of the fully human $^{211}$At-labeled anti-CD123 mAbs can be determined using disseminated in vivo human leukemia models to support further clinical development.

In vivo human leukemia cell targeting ("biodistribution") studies can be performed to identify optimal mAb dose for therapeutic studies. Mice can receive s.c. injections of human acute leukemia cells expressing either relatively high levels of CD123 or relatively low levels of CD123 but comparable levels of CD45 (e.g. MOLM-13 [CD123$^{high}$] and NB4 cells [CD123$^{low}$]) in the flank. $10^5$-$10^6$ cells/mouse can be given as dictated by line-specific tumor take rate studies. When tumors are palpable (~100 mm$^3$), mice can receive variable amounts of anti-CD123 mAb or negative control mAb radioimmunoconjugates (e.g., 10 μg, 25 μg, and 50 μg B10-conjugated mAb labeled with 5 μCi $^{211}$At based on the data described above) by tail vein injection to define the optimal radiommunoconjugate dose. Mice are euthanized and organs harvested at multiple time points, e.g., within 2-24 hours, in line with the 7.2 hour half-life of $^{211}$At. Retroorbital blood can be collected serially at 5-1,440 min after injection to estimate clearance of the radiolabeled mAb. Tissues can be analyzed on a gamma counter to calculate the % ID/g, and radiation absorbed doses for harvested organs can be calculated. Tumor-to-normal organ ratios can be calculated by comparing % ID/g of target tumor to that of uninvolved normal organs. To better model acute leukemia biology, confirmatory leukemia targeting studies can be performed in mice with disseminated disease, and accumulation of radioimmunoconjugates in expected disease sites (spleens, marrow) with multiple mAb doses assessed.

Non-specific (i.e. "off-target, off-leukemia cell") toxicity of radiolabeled mAb can also be assessed. To obtain initial data on possible non-specific (i.e. "off-leukemia, off-target cell") toxicities of $^{211}$At-labeled anti-CD123 mAbs, limited toxicity assessments can be performed in NRG mice treated with $^{211}$At-labeled anti-human CD123 mAbs. Data from such toxicity assessments can be used to refine the selection of RIT doses to test in the leukemia models. As shown previously with $^{211}$At-labeled mAbs, immunodeficient mice are helpful in determining such non-specific toxicities to bone marrow, kidneys or liver, among other organs. Non-leukemia-bearing NRG mice can be used without stem cell support for this purpose to fully characterize any long-term organ toxicity. Mice can be treated with $^{211}$At-labeled mAbs (one amount of mAb as defined in biodistribution studies; at 3 $^{211}$At doses (e.g., 10, 20, and 40 μCi) and monitored for toxicity. This includes blood draws via retro-orbital bleeds, analyzing weekly for one month then monthly for 6 months, and finally at 1 year, characterizing any acute or long term hematopoietic, hepatic, or renal dysfunction by measuring complete blood counts, liver enzymes, BUN, and creatinine as known in the art. Several mice/group can be followed for blood counts and serum chemistries. Representative animals from each group can be bled in a staggered schedule to adhere to animal care protocols.

Like the studies described in Example 2, murine xenografts can be used to model human acute leukemia supporting assessment of the antibody therapeutic reagents in this context. Similar to the studies described above, luciferase-transduced CD123+ human acute leukemia cells can be used for efficacy assessments. Limited studies can also use sublines of such cells in which CD123 is deleted (e.g., via CRISPR/Cas9) to validate CD123-targeting requirement for efficacy. Disseminated leukemia can be established by giving mice 0.2-2×10$^{5}$ leukemia cells by tail vein injections (as dictated by tumor take rate studies that establish lethal disease in 3-6 weeks). Studies testing RITs in MRD settings can treat mice with radioimmunoconjugates 1-2 days after receiving leukemia cells. Studies investigating higher-volume disease settings can treat mice with radioimmunoconjugates ~1-2 weeks after injection of leukemia cells before disease becomes fatal if untreated. Initial studies can use MOLM-13 cells, which express CD123 at relatively high levels. Additional assays can also include luciferase-transduced human acute leukemia cell lines that express CD123 at relatively low levels that have, however, comparable CD45 levels to MOLM-13 cells (e.g. NB4$^{LUC}$ cells).

Multiple assays can be performed to confirm and quantify the anti-leukemia efficacy of the radiolabeled mAbs. In one, the anti-leukemia efficacy of the selected anti-CD123 mAbs with each other can be compared. For example, MOLM-13$^{LUC}$ and NB4$^{LUC}$ cells can be used, and each of the selected mAbs used at multiple $^{211}$At doses (e.g., 20 and 40 μCi; see FIGS. 4 and 5) and a negative control mAb labeled similarly with $^{211}$At. Together with data from the toxicity assessments, this will enable the selection preferred mAb(s). Once selected, a second set of experiments can then be conducted in which the selected mAb(s) (with $^{211}$At ~20-40 μCi, as determined in the first efficacy assessment experiment) is further tested not only in MOLM-13$^{LUC}$ and NB4$^{LUC}$ cells but also CD123KO sublines and against positive ($^{211}$At-labeled anti-CD45 mAb) and negative ($^{211}$At-labeled 13R4, B10-conjugated anti-CD123 mAb without 211At) control. For all of these in vivo experiments, NRG mice/group can be used, and human acute leukemia cells can be given by IV injection to establish disseminated disease models. Mice can then receive optimal amounts of the B10-conjugated anti-CD123 mAb with or without $^{211}$At. As done in the proof-of-principle study described above, stem cell support can be used for all animals, typically using 5×10$^{6}$ bone marrow cells from donor NRG mice 3 days after mAb administration. Mice can be monitored for survival.

Based on the preliminary results described above, the protocols described herein are expected to confirm eligibility of candidate anti-CD123 mAbs for therapeutic applications.

Example 4

Example 3 describes potential optimizations to the fully human mAbs that enhance the therapeutic potential of such compositions. This Example describes further optimizations that can be performed to minimize potential non-specific toxicities often observed with antibody-based therapeutics.

mAbs built in human IgG1 frameworks (most widely used therapeutic mAb format) widely interact with Fc receptors. Thus, Fc receptor interactions may contribute to non-specific toxicities observed with $^{211}$At-based RIT, especially when administered at higher doses.

Experimental Approach for Generating Different Anti-CD123 mAb Variants:

Chimeric and humanized monoclonal antibodies were generated using the murine 10C4 anti-CD123 monoclonal antibody. Chimeric antibodies are molecules made up of domains from different species. For example, the Fc region or all the constant regions of a mouse mAb may be replaced with those of a human or (any other species) antibody.

Figure 10:
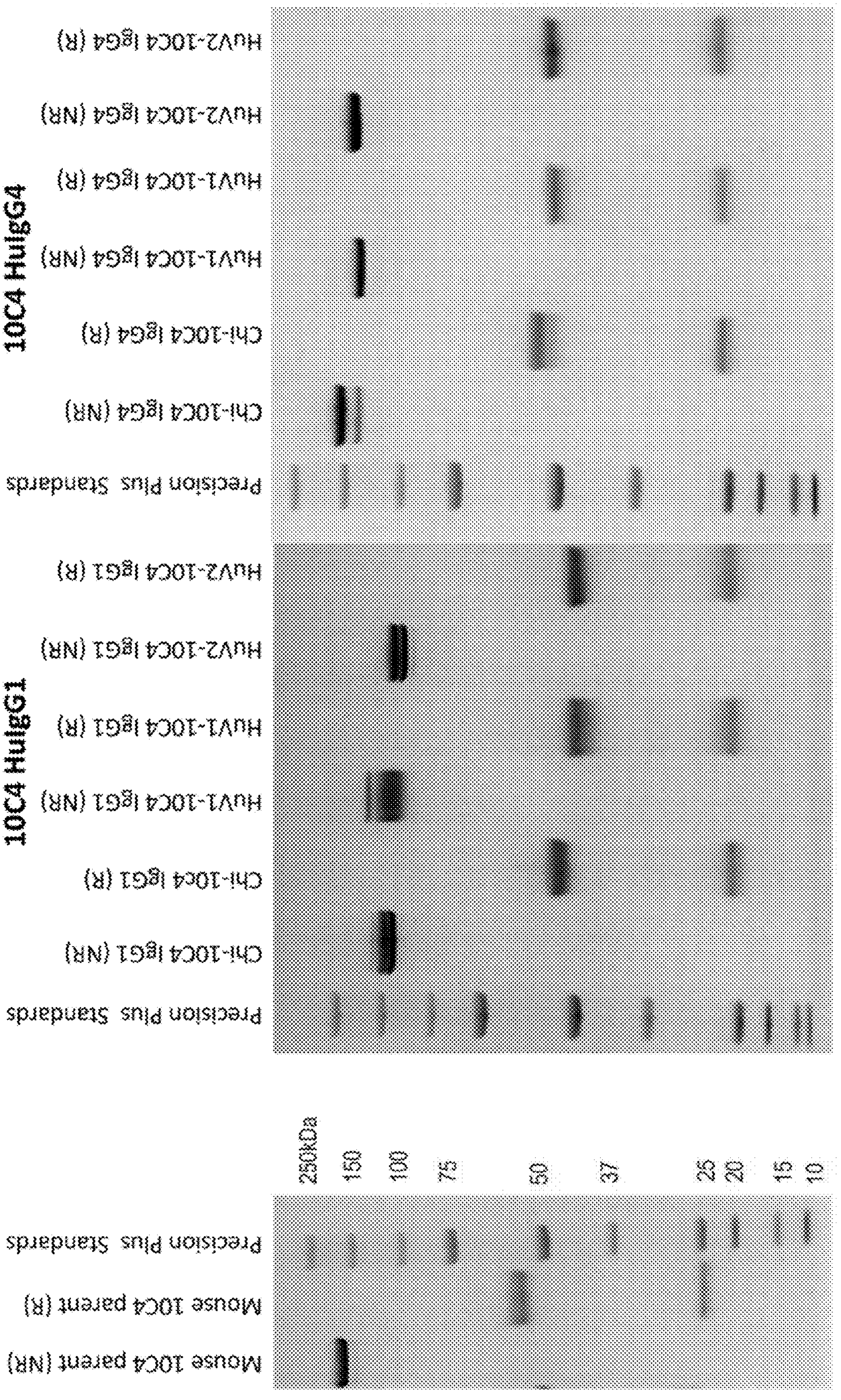
FIG. 10. Protein gel analysis of parent murine 10C4 as well as of recombinant chimeric and humanized 10C4 IgG1 and IgG4 monoclonal antibodies. Protein gels were stained with a Coomassie blue-based dye to visualize proteins. A molecular weight marker was included to help identify molecular weights of intact antibodies and reduced antibody chains.
Figure 11A:
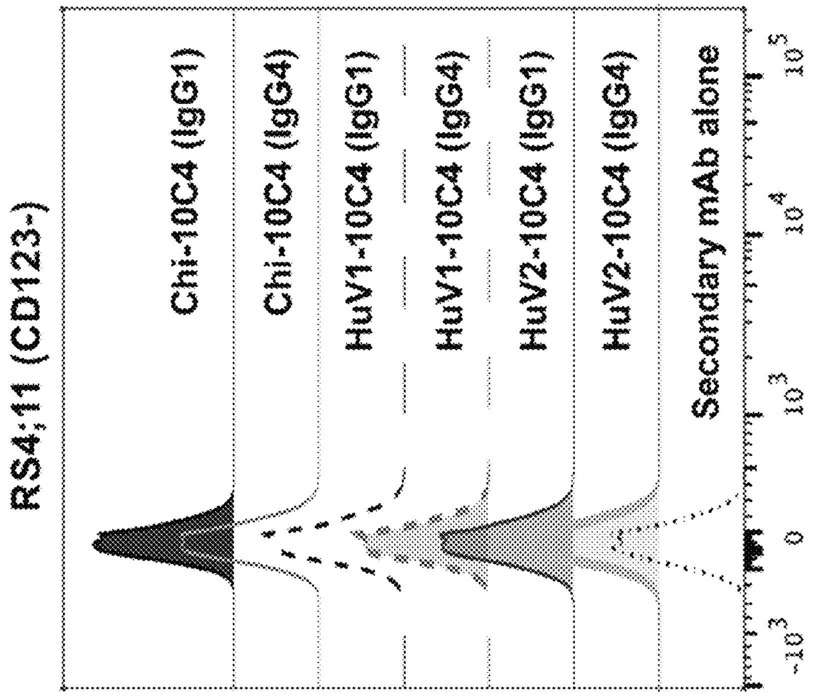
FIGS. 11A-11B. Flow cytometry-based binding studies of chimeric and humanized 10C4 monoclonal antibodies, using human IgG1 and IgG4 framework, on (FIG. 11A) parental human RS4;11 acute lymphoblastic leukemia cells (endogenously CD123-negative) and (FIG. 11B) RS4;11 cells transduced with human CD123. A secondary mAb-only control is also shown.
Figure 11B:
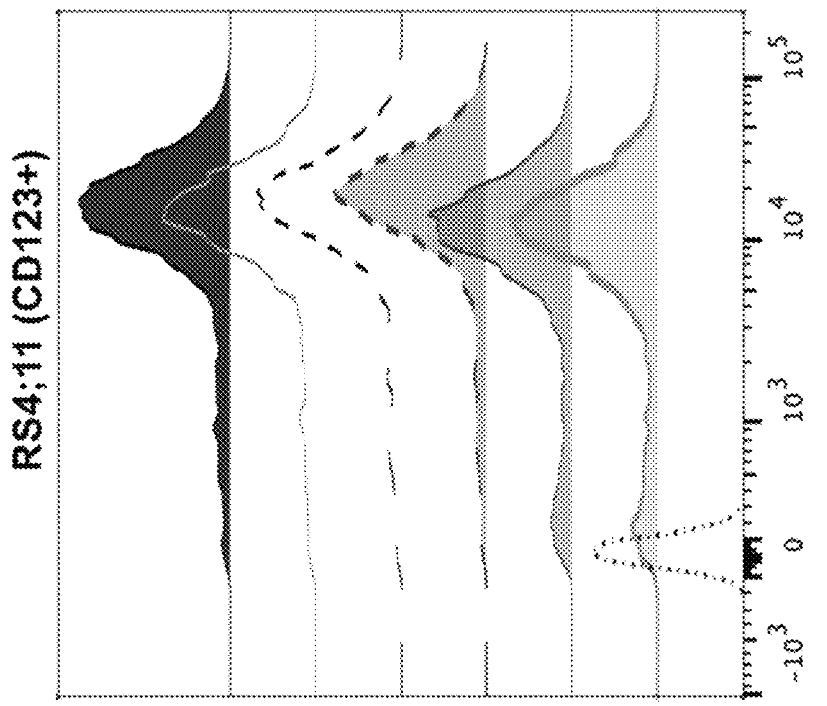

After purification, the parent murine 10C4, as well as the chimeric and humanized 10C4 IgG1 and IgG4 monoclonal antibodies were analyzed by SDS-PAGE under reducing and non-reducing conditions (FIG. 10) and tested for binding to human CD123+ and CD123− human acute leukemia cells via flow cytometry, as demonstrated above. See FIGS. 11A-11B. Specific binding to human CD123 was confirmed by flow cytometry using hybridoma cell culture supernatants. Binding of HuV1-10C4, but not HuV2-10C4, is comparable to binding of the parent antibody construct and chimeric-10C4, while in contrast, none of the antibodies bind to cells that lack CD123 expression.

Figure 12A:
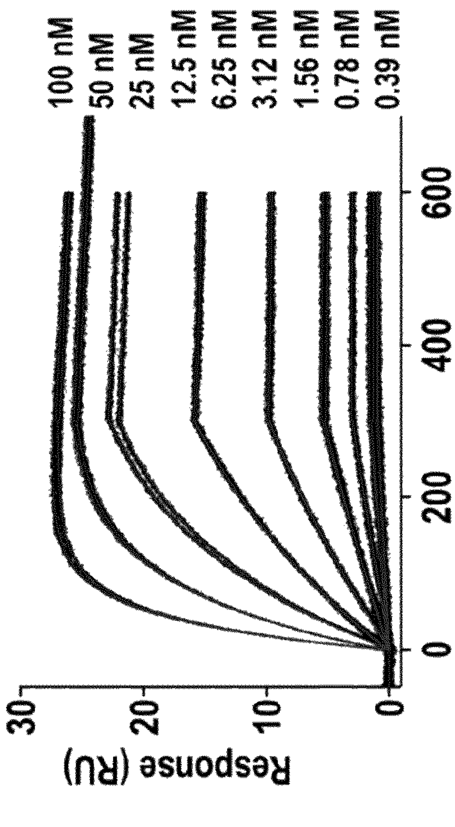
FIGS. 12A-12B. Surface plasmon resonance (Biacore T-100) analyses were performed to rigorously/precisely determine univalent binding affinities of the murine anti-human CD123 monoclonal antibody 10C4 to (FIG. 12A) human CD123 and (FIG. 12B) nonhuman primate CD123. For these experiments, peptides encoding the complete extracellular portion of human CD123 or nonhuman primate CD123 were used, and the antibodies were captured on the biosensor chip (CM4) via Protein A/G and amine coupling.
Figure 12B:
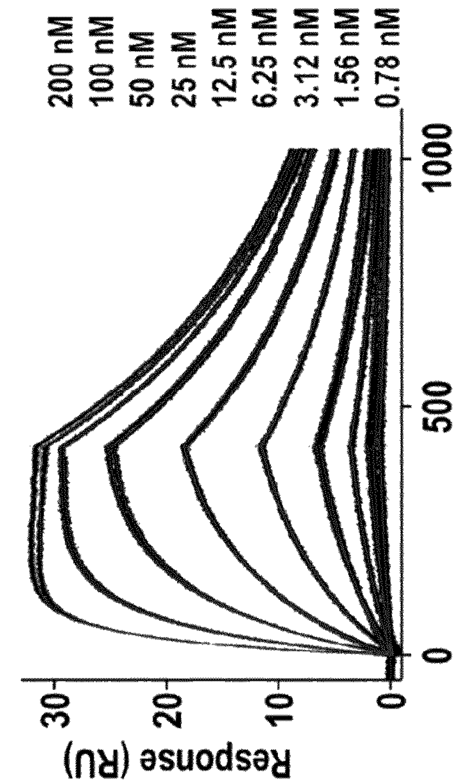
Figure 13A:
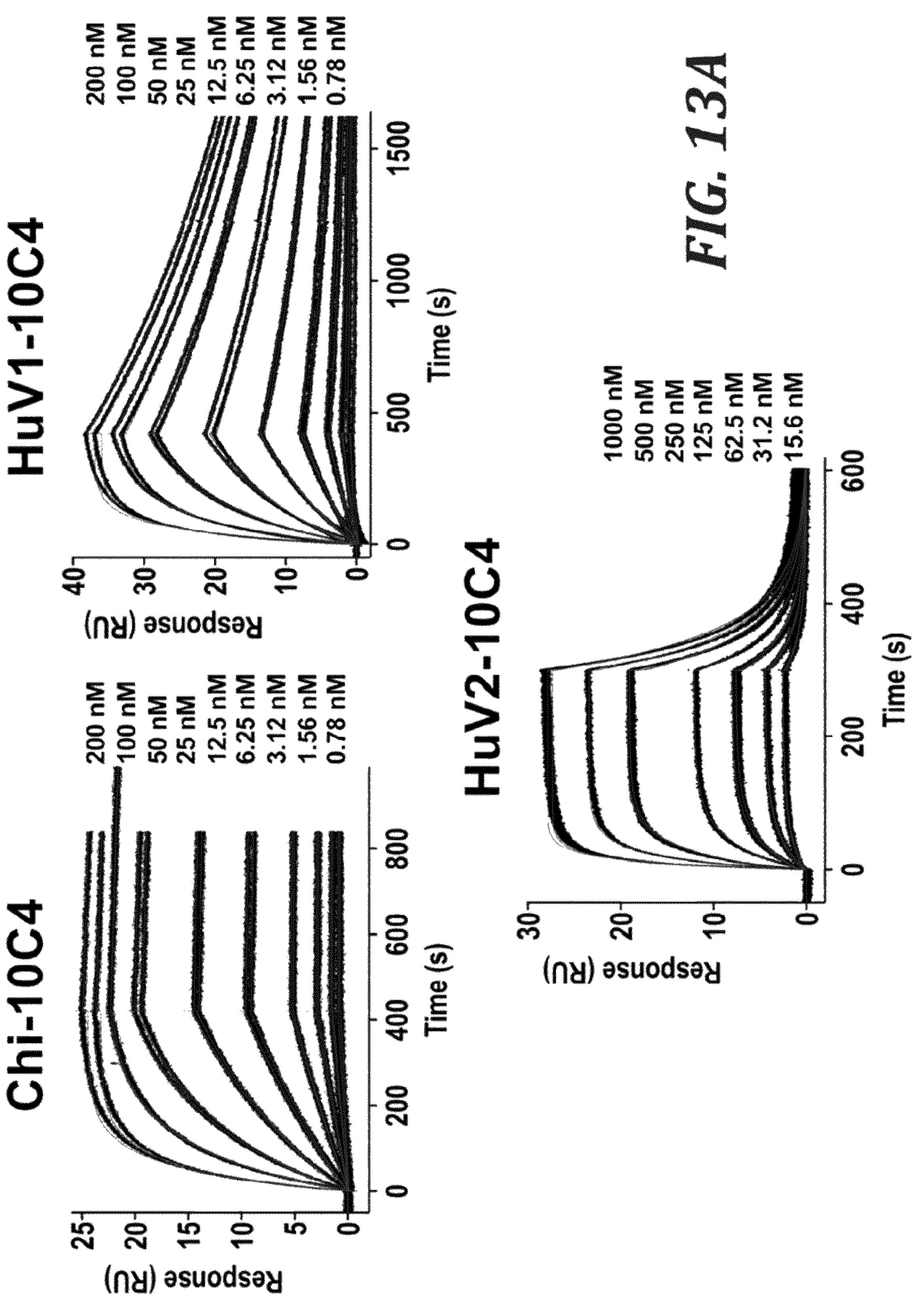
FIGS. 13A-13B. Surface plasmon resonance (Biacore T-100) analyses were performed to rigorously/precisely determine univalent binding affinities of recombinant chimeric and humanized versions of the anti-human CD123 monoclonal antibody 10C4, using (FIG. 13A) human IgG1 and (FIG. 13B) human IgG4 frameworks. For these experiments, a peptide encoding the complete extracellular portion of human CD123 was used, and the antibodies were captured on the biosensor chip (CM4) via a Fc gamma-specific goat anti-human IgG and amine coupling.
Figure 13B:
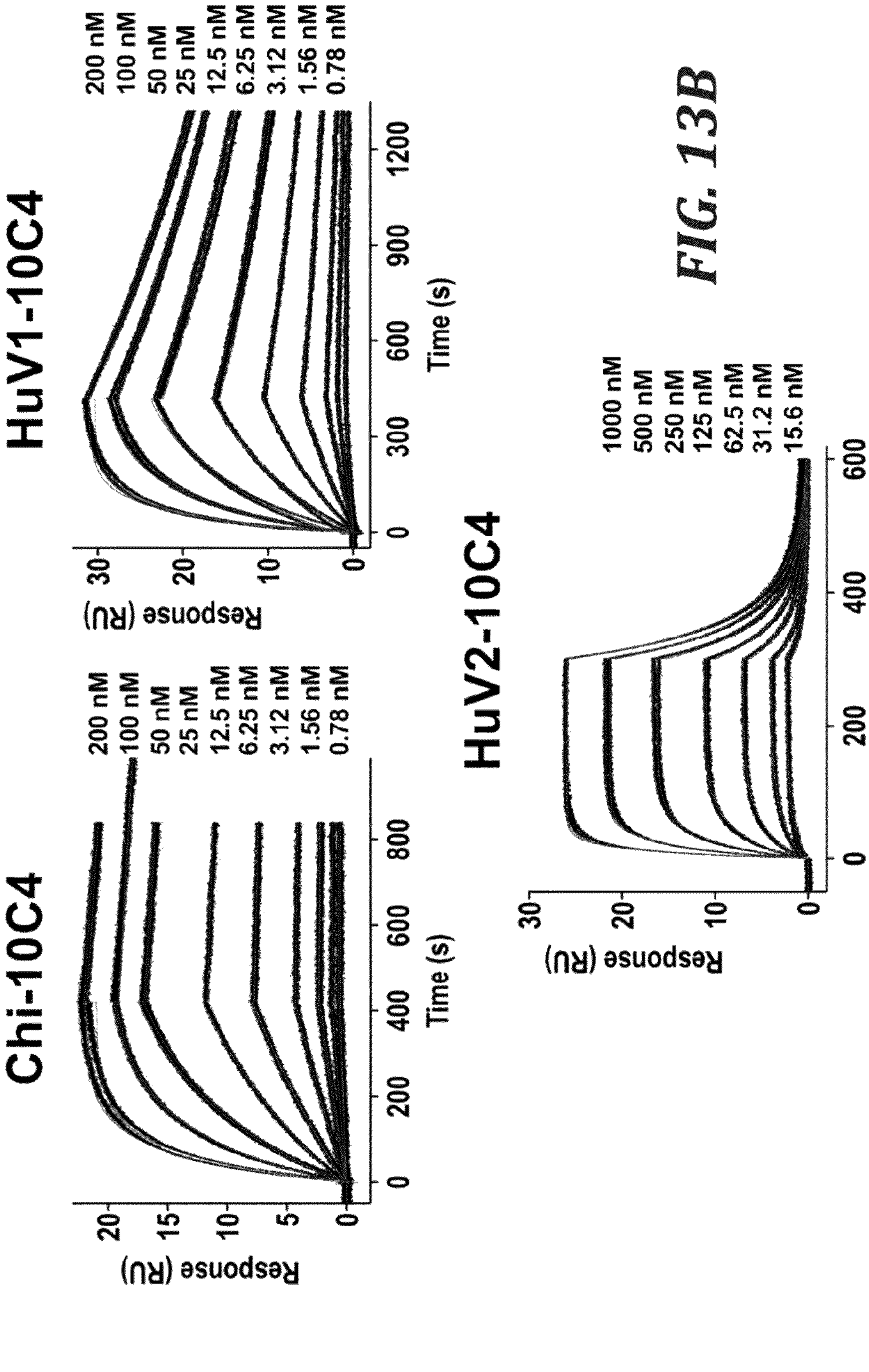
Figure 15A:
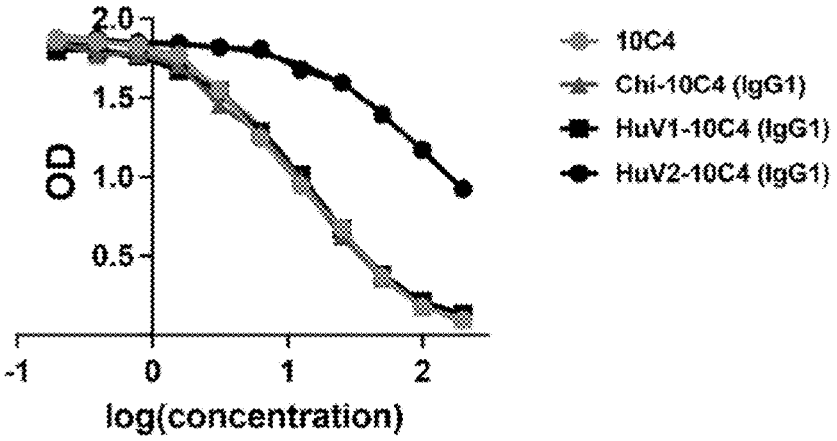
FIGS. 15A-15B. Enzyme-linked immunosorbent assay (ELISA) with the original mouse 10C4 antibody and peptide encompassing the entire extracellular domain (ECD) of CD123 was used to test competitive binding of 10C4 compared to recombinant (FIG. 15A) human IgG1 versions and (FIG. 15B) human IgG4 versions of chimeric 10C4 and humanized 10C4 monoclonal antibodies. Plates were coated with CD123 ECD-His-Avi fusion protein and bound to biotinylated 10C4 antibody in the presence or absence of increasing amounts of competing unlabeled antibodies, as detected by HRP-Streptavidin.
Figure 15B:
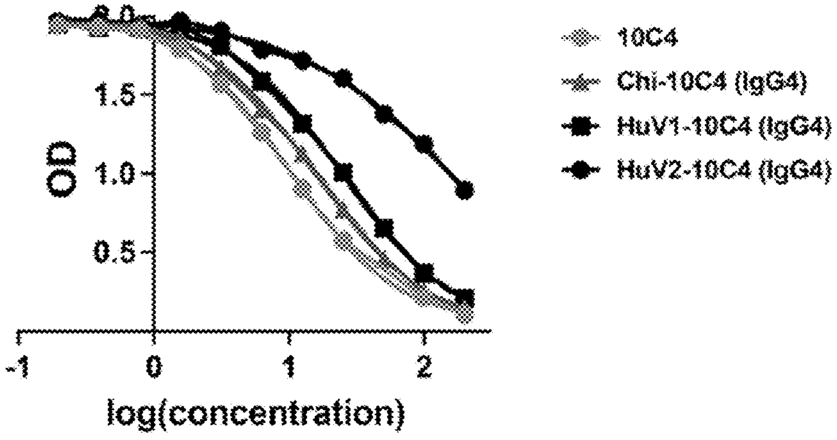

Precise univalent binding affinities of the murine anti-human CD123 monoclonal antibody 10C4 was determined using surface plasmon resonance (SPR) to human CD123 and nonhuman primate CD123. See FIGS. 12A-12B. The binding affinities of the recombinant chimeric (Chi) (Chi-10c4) and humanized (Hu) (HuV1-10C4 and HuV2-10C4) versions of the anti-human CD123 monoclonal antibody 10C4, using human IgG1 (FIG. 13A) and human IgG4 (FIG. 13B) frameworks, was also characterized. FIG. 14 summarizes the binding affinities of the parent murine anti-human CD123 antibody 10C4 as well as recombinant chimeric and humanized versions of 10C4, using both human IgG1 and human IgG4 frameworks, to human CD123 and nonhuman primate CD123. Competitive binding of 10C4 compared to recombinant human IgG1 versions (FIG. 15A) and human IgG4 versions (FIG. 15B) of chimeric 10C4 and humanized 10C4 monoclonal antibodies demonstrated that only one of the humanized 10C4 monoclonal antibodies (HuV1-10C4) displayed competition very similar to the parent 10C4 antibody, while the other (HuV2-10C4) did not compete well, as indicated by binding affinities.

Figure 16A:
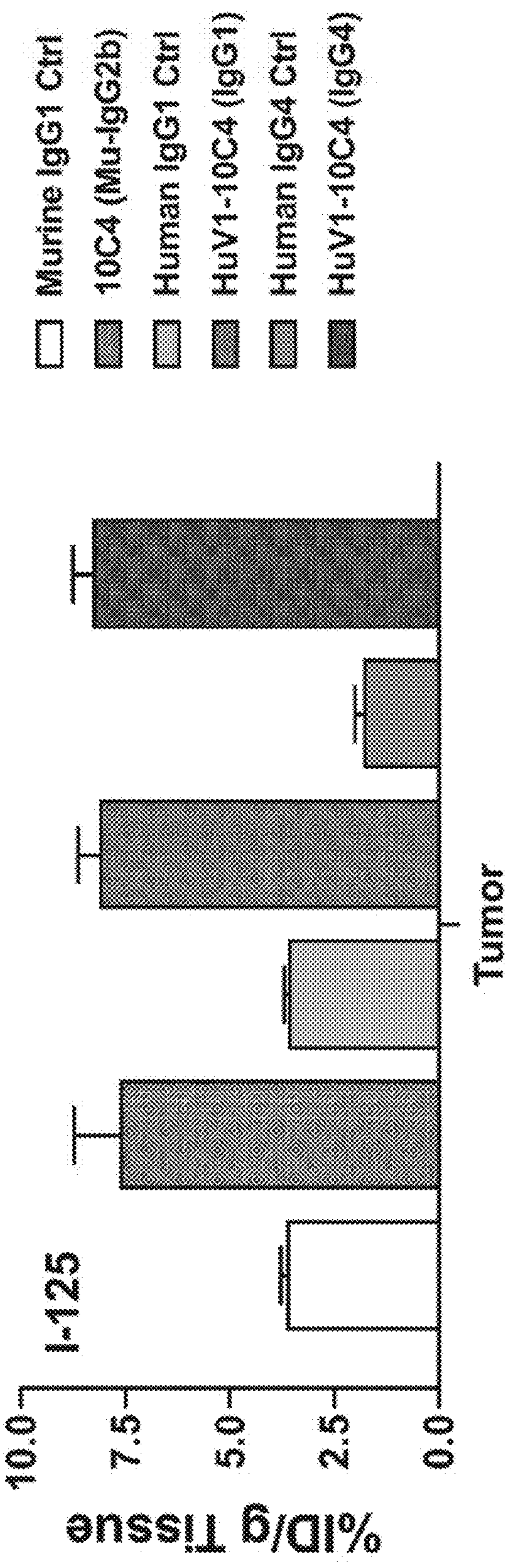
FIGS. 16A-16B. In vivo CD123+ cell targeting with $^{211}$At-CD123 RIT (10C4 vs. humanized 10C4). $10^6$ parental (CD123+) MOLM-13 cells were implanted into the flanks of NRG mice. One week later, animals (4/group) received 50 μg of B10-conjugated antibody (murine IgG1 control antibody, murine 10C4, human IgG1 control antibody, human IgG1 version of HuV1-10C4, human IgG4 control antibody, and human IgG4 version of HuV1-10C4) dual labeled with 5 μCi of I-125 (FIG. 16A) or 10 μCi $^{211}$At (FIG. 16B) and 24 hours later, mice were euthanized, flank tumors harvested, and analyzed on a gamma counter to calculate the percent of injected dose/gram of tumor tissue (% ID/g). Data are presented as mean±SEM.
Figure 16B:
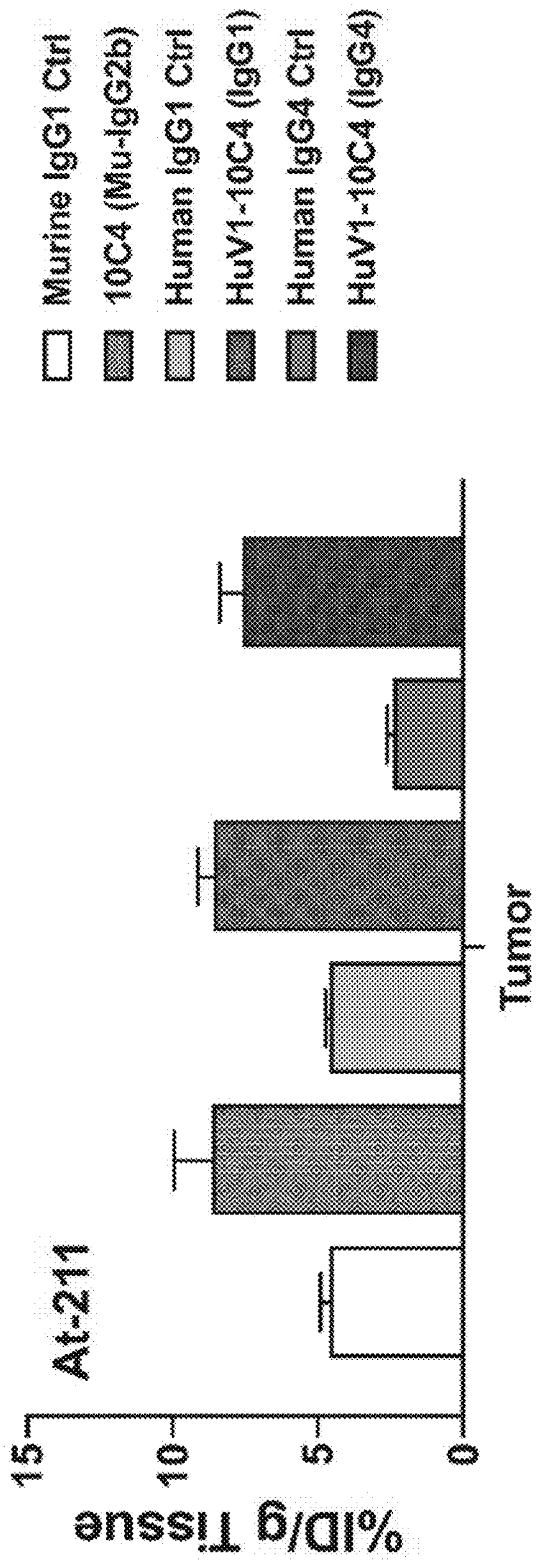

A comparison of in vivo CD123+ cell targeting with $^{211}$At-CD123 RIT demonstrated that all three antibodies (the parent murine antibody 10C4 compared against the humanized version of 10C4) deliver radioactivity to tumors as $^{211}$At-CD123 RIT in amounts greater than control non-targeting antibodies. See FIGS. 16A-16B.

Minibodies are single-chain antibody fragment composed of the scFv of a mAb fused to the human IgG1 CH3 domain via short linker, have been previously characterized for radioimmunoimaging and RIT. The linker can be short, e.g., two amino acids, or longer to provide for additional flexibility and disulfide bridges for disulfide bonding. The molecule self-assembles into a bivalent protein of ~80 kDa. In mice, minibodies have shown excellent tumor targeting and biodistribution properties. Very recently, $^{211}$At-labeled minibodies with a flex linker proved highly effective in eradicating tumors in murine models of prostate cancer, with biodistribution studies showing a t1/2 that matched the t1/2 of $^{211}$At much better than when $^{211}$At was delivered via full-size mAb.

Anti-CD123 minibodies using the anti-CD123 mAb binding sequences and a 'flex' linker can be generated using standard cloning techniques. Molecules can be cloned into pcDNA3.4 vectors and expressed as described above. As negative control, a matching minibody using binding sequences from irrelevant antibody can be used.

B10 conjugation and $^{211}$At-labeling of minibodies can be performed as described above.

In vivo leukemia cell targeting studies can be conducted similar to studies described above, using mice (both genders, randomly assigned)/group/time point and flank tumors of acute leukemia cells that either express relatively high levels of CD123 or relatively low levels of CD123 but comparable levels of CD45 (e.g. MOLM-13 [CD123$^{high}$] and NB4 cells [CD123$^{low}$]). Disseminated disease models can be performed subsequently for confirmation. Exemplary treatment groups include: Negative minibody control ($^{211}$At-labeled irrelevant minibody) and $^{211}$At-CD123 minibody. Multiple minibody amounts, e.g., with 5 μCi of $^{211}$At, can be tested multiple time points within 24 hours of administration.

Non-specific (i.e. "off-target, off-leukemia cell") toxicity of radiolabeled minibodies can be assessed in non-leukemia-bearing NRG mice similar to studies described above, for example, using ~8 groups as above with ~8 mice/group; 1 mAb amount; 3 doses of $^{211}$At.

Anti-leukemia efficacy of radiolabeled minibodies can be quantified. As described above, MOLM-13$^{LUC}$ and NB4$^{LUC}$ cells and 8 mice/group (both genders, randomly assigned can be used. Treatment groups can include: 1) Negative control (irrelevant minibody); 2) $^{211}$At-CD123-IgG1 (positive control); 3) best/optimal alternative $^{211}$At-CD123 minibody variant as identified in leukemia cell targeting studies. Mice are monitored for survival. Mice exhibiting excessive toxicity, morbidity, or weight loss are euthanized.

These minibody-based optimizations and assays can identify therapeutic reagent configurations (i.e., the format providing high anti-leukemia efficacy with the lowest amount of Fc-mediated non-specific toxicity) in the mouse models. While the minibodies are predicted to have less non-specific uptake in the liver and/or other non-targeted organs, although it is possible the reference IgG1 mAb already provides the best combination of efficacy and toxicity.

Example 5

Examples 1-2 describe generation of murine and human antibodies that specifically bind CD123, and which can be conjugated to radioisotope payloads to specifically target CD123 expressing cells, e.g., in leukemias, with reduced off target toxicity. Examples 3-4 describe exemplary optimizations and characterization assays for development of enhanced anti-CD123 therapeutic reagents that can enhance specific binding while reducing off-target toxicities in a therapeutic application. This Example describes illustrative assays to assess the anti-leukemia efficacy and "on-target, off-leukemia cell" toxicity of $^{211}$At-CD123 RIT when used alone or before haplo-identical allogeneic hematopoietic cell transplantation (HCT), and to assess whether $^{211}$At-CD123 RIT facilitates allogeneic cell engraftment at higher radiation doses.

To establish efficacy of anti-CD123 targeting as a therapeutic strategy, a comprehensive in vivo assessment, including testing of "on-target, off-leukemia cell" toxicities, can be performed in the context of an intact immune system. The disseminated murine syngeneic SYL leukemia model developed previously (Orozco J J, et al. Anti-CD45 radioimmunotherapy using (211) At with bone marrow transplantation prolongs survival in a disseminated murine leukemia model. *Blood.* 2013; 121:3759-67; Orozco J J, et al. Anti-CD45 radioimmunotherapy with 90Y but not 177Lu is effective treatment in a syngeneic murine leukemia model. *PLOS One.* 2014; 9: e113601; and Orozco J J, et al. Anti-CD45 radioimmunotherapy without TBI before transplantation facilitates persistent haploidentical donor engraftment. *Blood.* 2016; 127:352-9, each of which is incorporated herein by reference in its entirety) is ideally suited for this purpose and, additionally, allows RIT testing in an allogeneic HCT setting.

Experimental approach for assessing anti-CD123 targeting in vivo, alone or in conjunction with HCT.

Radiolabeled mAbs produced as described above, or any commercially available CD123 antibody reagent (e.g., rat IgG2a isotype, clone 5B11; Biolegend) can be assessed. The antibody or derivative can be conjugated to B10 before labeling with $^{211}$At as described above. Appropriate negative controls can be selected.

The preparative regimen for Haploidentical HCT regimen with $^{211}$At-CD123 RIT in B6SJLF1/J mice. Can be optimized. For conditioning, mice can receive CY (~200 mg/kg) followed 1 day later by the IV administration of anti-CD123-B10 mAb (~2 amounts between 10 and 50 μg, selected based on studies described above) labeled with 3 doses of $^{211}$At (~10-40 μCi) using 8 mice/group. Mice will then be given $1.5\times10^7$ haploidentical marrow cells 2 days after RIT injections. This high marrow cell dose is used to minimize the likelihood of graft rejection and the confounding effect of cell dose. Post-HCT CY (200 mg/kg) can be given 2 days after marrow transplantation for GVHD prophylaxis. Mice can be bled monthly to measure the percent donor-derived (H-2D$^{d}$) cells by flow cytometry. Optimization of $^{211}$At-CD123 RIT conditioning can be assumed when engraftment >75% from haploidentical donors is achieved across all interrogated lineages. To determine donor chimerism, about 50 μL of peripheral blood from transplanted mice can be assayed by flow cytometry for multiple lineages. Briefly, blood will have erythrocytes lysed before incubation with mAb cocktail (fluorophore-labeled anti-CD4, anti-CD8, anti-CD3, anti-CD25, anti-Fox3P, anti-CD11b, and anti-B220 antibodies to identify T-cell subsets, myeloid and B-cells as previously published). Controls used for gating and voltage setting can be artificial "chimeras", i.e., a 1:1 mixture of donor and recipient peripheral blood stained with single mAb conjugates to help define positive and negative populations and facilitate compensation. Chimerism levels at the various time points can be measured as the percentage of lineage-specific positive cells that are of donor (H-2D$^{d}$-positive) origin.

Kinetics of haploidentical lymphoid and myeloid cell engraftment can be determined. Once the $^{211}$At dose is defined, a separate cohort of mice (5/group) can be treated with $^{211}$At-labeled anti-CD123 mAb (~2 doses of $^{211}$At) or TBI and haploidentical HCT and followed for recovery of hematopoiesis via measurement of complete blood counts and chimerism by flow cytometric quantification of H-2 allotype on leukocytes in the peripheral blood at, e.g., day +28, +56, +84 and +180, all of which are clinically relevant time points. Donor derived CD4+, CD8+ or all CD3+ T-cells, $CD11b^+$ myeloid cells and $B220^+$ B-cells can be quantified by flow cytometry as described above.

"On-target, off-leukemia cell" toxicity of $^{211}$At-anti-murine CD123 RIT can be assessed as stand-alone treatment or prior to haploidentical HCT: Toxicity studies evaluating anti-murine CD123 RIT as stand-alone treatment can be performed with non-leukemia-bearing B6SJLF1/J mice (8/group) treated with 10-50 μg of $^{211}$At-labeled anti-murine CD123 mAb, $^{211}$At-labeled anti-murine CD45 mAb, or $^{211}$At-labeled control mAb (~1 mAb amount, ~2 doses of $^{211}$At). Blood can be analyzed weekly (for 1 month) and then monthly for leukocyte and platelet counts, hemoglobin, AST/ALT, bilirubin, BUN and serum creatinine to characterize acute and long-term hematopoietic, hepatic or renal (dys)function. Mice can be assessed for weight loss after RIT and HCT as a measure of well-being and/or toxicity. At the end of study, surviving mice can be euthanized for histological analysis of the skin, gut and liver to document evidence of delayed radiation damage. For characterization of toxicity associated with anti-murine CD123 RIT prior to haploidentical HCT, non-leukemia-bearing B6SJLF1/J mice (8/group) can be treated with $^{211}$At-labeled anti-murine CD123 mAb, $^{211}$At-labeled anti-murine CD45 mAb, $^{211}$At-labeled negative control mAb, or 10 Gy myeloablative TBI before haploidentical HCT as defined above and monitored for toxicity. Similarly, blood can be analyzed weekly (for ~1 month) and then monthly for leukocyte and platelet counts, hemoglobin, AST/ALT, bilirubin, BUN and serum creatinine to characterize acute or long term hematopoietic, hepatic or renal dysfunction. Mice can be assessed for weight loss after RIT and HCT as a simple measure of well-being and/or GVHD. At the end of study, surviving mice can be euthanized for histological analysis of the skin, gut and liver to document evidence of delayed radiation damage and/or GVHD. Data from such toxicity assessments can be used to refine the selection of RIT doses to test in the leukemia models.

In addition to SJL leukemia, the results can be validated using other commercially available murine leukemia cell lines confirmed to express CD123. Disseminated murine leukemia models can be established by giving mice $10^5$-$10^6$ leukemia cells by IV tail vein injections (as dictated by tumor take rate studies that establish lethal disease in 3-6 weeks). Studies investigating RIT in MRD settings can treat mice with radioimmunoconjugates 1-2 days after receiving disseminated leukemia as done previously (Orozco J J, et al. Anti-CD45 radioimmunotherapy using (211) At with bone marrow transplantation prolongs survival in a disseminated murine leukemia model. *Blood.* 2013; 121:3759-67, incorporated herein by reference in its entirety), whereas those studying RIT in higher-volume disease settings can treat mice with radioimmunoconjugates ~1-2 weeks after injection of leukemia cells before disease becomes fatal.

Anti-leukemia efficacy of radiolabeled mAbs can be quantified. Leukemia-bearing mice can be given $10^5$-$10^6$ leukemia cells by IV injection. To investigate anti-leukemia effects, mice can be given 10-50 μg (optimal dose from prior studies) of anti-murine CD123 mAb, anti-murine CD45 mAb (30F11), or negative control mAb with $^{211}$At (0, ~20, or ~40 μCi). Mice will be monitored for survival. Any mouse exhibiting excessive toxicity, morbidity or weight loss are euthanized per institutional protocol.

Finally, efficacy of $^{211}$At-CD123 RIT with haploidentical HCT can be determined. Groups of 8 recipient B6SJLF1/J female mice bearing SJL leukemia for a minimum of 2 days can be treated with ~10-50 μg of $^{211}$At-labeled anti-murine CD123 mAb, $^{211}$At-anti-murine CD45 mAb ($^{211}$At-30F11), non-targeting $^{211}$At-labeled mAb, or myeloablative-dose TBI (~10 Gy) before haploidentical HCT. $^{211}$At groups can receive the maximum tolerated radioactivity of $^{211}$At as determined above. Mice can receive $1.5\times10^7$ bone marrow cells from haploidentical donor male CB6F1/J mice 2 days after RIT, or the same day as TBI for TBI control mice. RIT-treated mice can receive pre-HCT CY as above. All mice receive post-transplant CY for GVHD prophylaxis. Mice are followed for survival.

The described murine studies are expected to show efficacy of $^{211}$At-CD123 RIT with minimal "on target, off-leukemia cell" toxicity, and will determine the optimal preparative regimen and radioactivity of this RIT format to augment radiation doses delivered to sites of disease and inform the translation of this approach to human trials.

Example 6

This Example discloses the development of a novel bispecific antibody construct and its incorporation in an alternative pre-targeted RIT (PRIT) strategy that targets CD123.

Once administered, radiolabeled antibody reagents can deliver radiation to normal (non-target) tissues before docking at their target sites. One strategy to minimize this potential non-specific toxicity from circulating radioimmunoconjugates is to use of a two-step delivery approach ("pre-targeted RIT (PRIT)"), in which an unlabeled target-specific antibody (or fragment or derivative thereof) is infused first, with administration of the radiolabeled secondary reagent after inbound circulating antibody is cleared with a 'clearing agent' to allow target binding/saturation of the targeting antibody. Therefore, our vision is to develop CD123-directed PRIT for patient application. As described above in Example 1, a series of murine anti-human CD123 and human anti-human CD123 antibodies were developed and can serve as basis for the development of a PRIT strategy.

In initial studies, dimeric anti-CD123×anti-DOTA-Y bispecific antibody (BiAb) molecules were generated and tested. Prior PRIT approaches conjugated affinity regents specific for a target antigen with an affinity reagent specific for a radiolabeled secondary reagent of preference. Such conjugations have been accomplished using biotin and streptavidin as binding partners, which are easily incorporated into their respective affinity reagents. A classic example of PRIT is based on initial administration of an antibody-streptavidin conjugate, followed by a radiolabeled biotin molecule. This leads to improved biodistribution properties compared to directly labeled radio immunoconjugates. However, streptavidin is immunogenic and thus will limit repeat dosing of therapy period furthermore, and endogenous biotin may interfere with targeting of the therapeutic radiolabeled ligand. Accordingly, alternative approaches to conjugate affinity reagents specific for the target antigen and the radiolabeled secondary reagent are pursued.

A first design strategy was similar to construct previously implement to target CD20 (for lymphoma), CD38 (for multiple myeloma), and CD45 (for acute leukemia) for PRIT with the beta-emitting radionuclide yttrium-90 ($^{90}$Y). A biAb fusion construct was generated with separate domains that bind to CD123 and yttrium-DOTA, respectively. In this approach, a fusion protein is constructed that contains the heavy and light chain variable regions from a tumor recognizing antibody at the amino terminus and the heavy and light chain variable regions of an antibody recognizing Y-DOTA as the capture moiety at the carboxyl end of human IgG1 Fc fragment to provide a dimeric bi-specific affinity reagent. See FIG. 23A. These constructs were expressed in CHO cells, with fusion protein purified from supernatant and assayed for target binding via flow cytometry and ELISA. In biodistribution, bispecific fusion proteins were infused to dock at tumor target, and the following day a synthetic DOTAY-dextran clearing agent was given to clear any unbound circulating fusion protein. One or two hours later, the radiolabeled second reagent ($^{90}$Y-DOTA) was infused.

Figure 24:
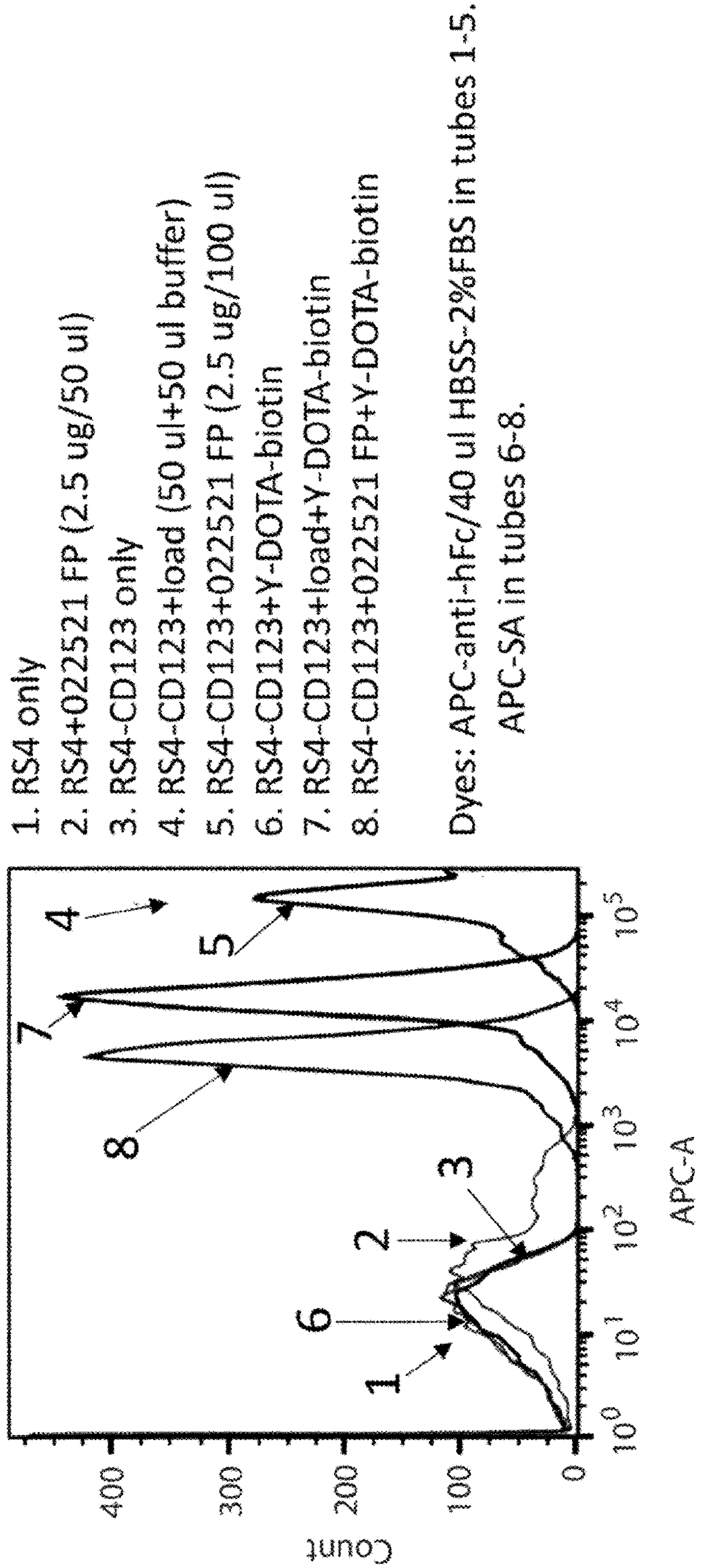
FIG. 24. Flow cytometry-based binding assay of monomeric anti-CD123 BsAb derived from 10C4 binding sequences. $0.4 \times 10^6$ CD123-negative parental RS4;11 cells (RSA) or RSA cells engineered to express human CD123 (RS4-CD123) were incubated with or without CD123 bispecific fusion protein from purification (FP) or crude supernatant (load), with or without Y-DOTA-biotin. After incubating for 30 min at 4° C. cells were washed twice and assayed by flow cytometry with fluorophore-labeled anti-human Fc receptor secondary Ab (tubes 1-5) to detect bound bispecific fusion protein, or fluorophore labeled anti-streptavidin secondary Ab (tubes 6-8) to detect functional capacity of bispecific fusion protein to bind both CD123+ target cells and the radioligand, Y-DOTA-biotin.
Figure 25:
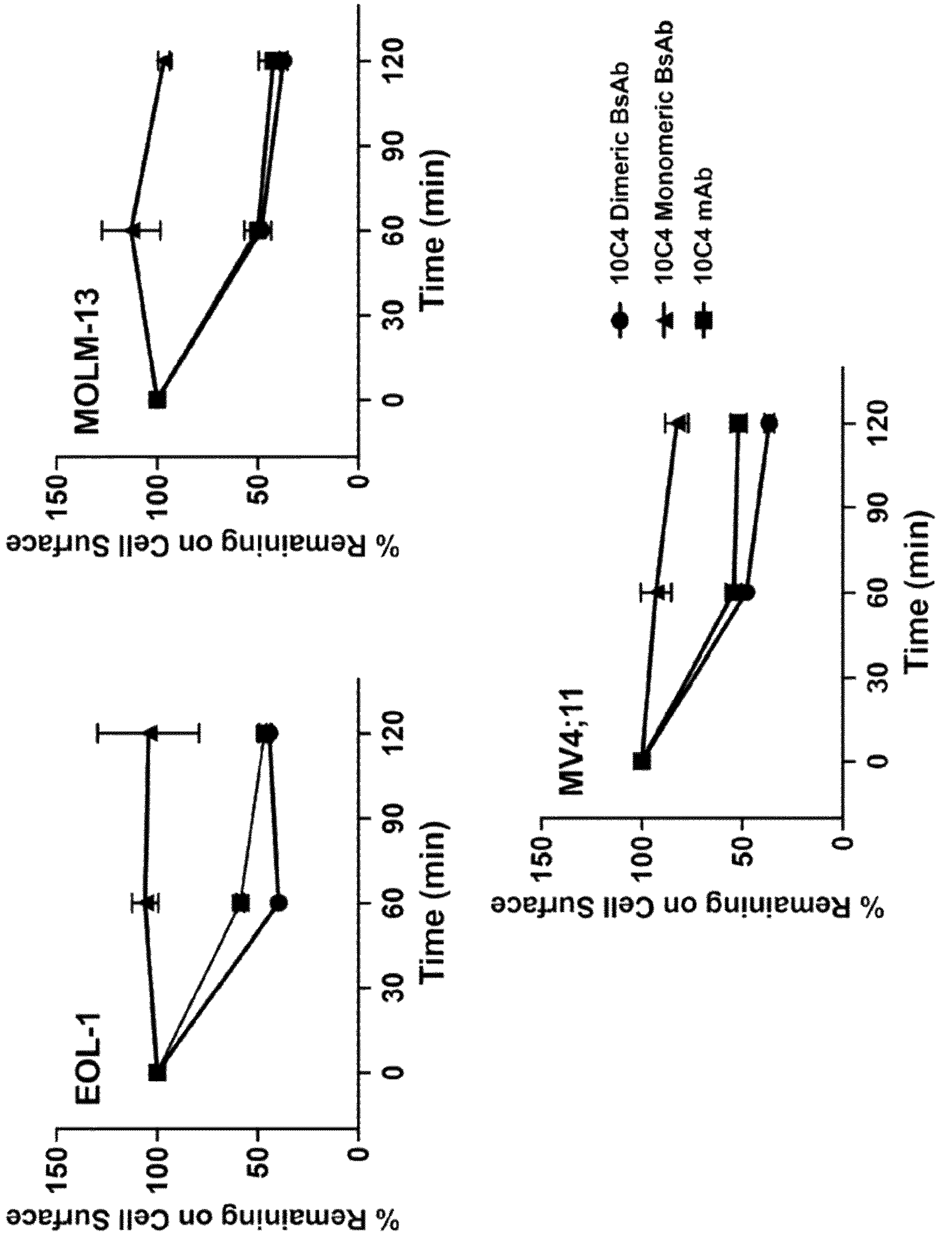
FIG. 25. Comparative flow cytometry-based in vitro internalization assay of 10C4 as mAb, the monomeric 10C4 BsAb, and the dimeric 10C4 BsAb in 3 CD123+ human AML cell lines (EOL-1, MOLM-13, MV4;11). Shown are mean±SEM values of 3 independent experiments.
Figure 26:
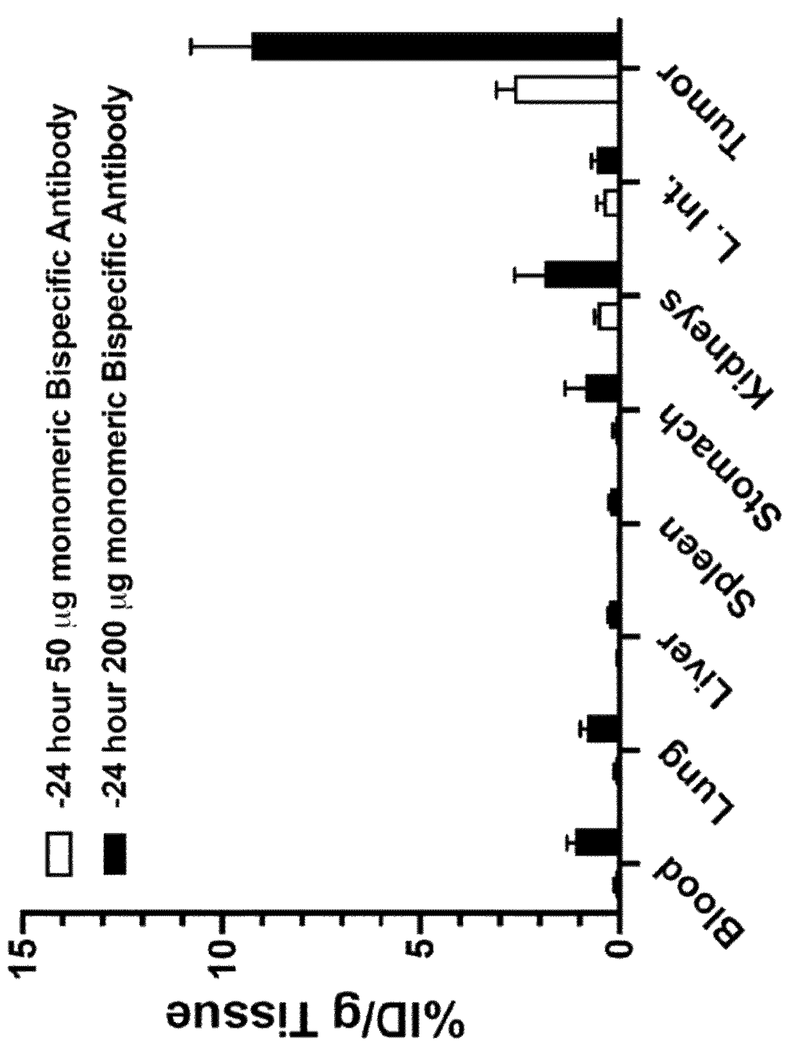
FIG. 26 Anti-CD123 monomeric bispecific antibody targets $CD123^+$ tumors. To characterize targeting, biodistribution studies used NRG mice (4 mice/group) that were given $CD123^+$ MOLM-13 tumors, $2\times10^6$ cells/mouse injected subcutaneously in the flank approximately 8 days prior. Once tumors were approximately 100 $m^3$, mice were given 50 or 200 μg of monomeric bispecific (anti-CD123×anti-Y-DOTA) antibody by tail vein (IV) injections. After 24 hours for bispecific antibody to localize to target tumor, radioligand $^{90}$Y-DOTA-biotin (50 μCi $^{90}$Y on 2 μg DOTA-biotin) was given IV. Mice were sacrificed 2 hours later after non-bound radioligand would have been excreted, and organs harvested and assayed by gamma counter to measure counts per minute to calculate the percent of injected dose per gram of tissue (% ID/g tissue). L int=large intestine.

However, this approach did not result in significant accumulation of radiation from the radiolabeled agent in AML tumors engrafted in immunodeficient mice. Without being bound to any theory, this effect was likely due to CD123 being internalized when bound by a bivalent ligand, thus rendering it inaccessible for subsequent binding by the radiolabeled secondary reagent. Accordingly, a new bispecific targeting molecule was developed that was monomeric instead of dimeric, and which still was bispecific (i.e., binding to CD123 and DOTA-Y). See FIGS. 23B and 24. Using in vitro flow cytometry-based endocytosis assays, this monomeric molecule was demonstrated to be internalized to a significantly lesser extent than the dimeric formulation (see FIG. 25), thus permitting accessibility to binding by the radiolabeled secondary reagent and successful PRIT-based accumulation of radiation specifically on target cells expressing CD123. Using immunodeficient mice engrafted with CD123$^+$-AML cell tumors in the flank, this monomeric bispecific Ab-based construct led to positive biodistribution (FIG. 26), further confirming usefulness for PRIT applications targeting CD123 expressing cells.

Various embodiments encompassed by this disclosure are further described below.

1. 123-1H8 (murine anti-CD123 antibody, IgG1 isotype, Kappa Light Chain); Light Chain SP domain sequence (SEQ ID NO: 1) METDTLLLWVLLLWVPGSTG
2. 123-1H8 (murine anti-CD123 antibody, IgG1 isotype, Kappa Light Chain); Light Chain Variable Domain sequence (SEQ ID NO: 2) DIVLTQSPASLAVSLGQRATISCRASQSVSSSSYSFMHWYQKKPRQPPKLLIK YASTLEAGVPARFSGSGSGTDFTLNIHPVEEEDTATYYCQHSWEIPYTFGGGT KLEIK
3. 123-1H8 (murine anti-CD123 antibody, IgG1 isotype, Kappa Light Chain); Light Chain CDR1 sequence (SEQ ID NO: 3) RASQSVSSSSYSFMHY
4. 123-1H8; murine andi-CD123 antibody; IgG1 isotype; Kappa Light Chain; Light Chain CDR2 sequence ((SEQ ID NO: 4) LLIKYASTLEA
5. 123-1H8; murine andi-CD123 antibody; IgG1 isotype; Kappa Light Chain; Light Chain CDR3 sequence (SEQ ID NO: 5) QHSWEIPYT
6. 123-1H8 (murine anti-CD123 antibody, IgG1 isotype, Kappa Light Chain); Heavy Chain SP domain sequence (SEQ ID NO: 6) MYFRLSSVFLVLILKGVQC
7. 123-1H8 (murine anti-CD123 antibody, IgG1 isotype, Kappa Light Chain); Heavy Chain Variable Domain sequence (SEQ ID NO: 7) EVKLVESEGGLVQPGSSMKLSCTASGFTFSDYYMAWVRQVPEKGLEWVANI DDEGSSTYYLDSLKSRFIISRDNAKNILYLQMTSLKSEDTATYYCARGTTQTS FFVHWGQGTLVTVSA
8. 123-1H8 (murine anti-CD123 antibody, IgG1 isotype, Kappa Light Chain); Heavy Chain CDR1 sequence (SEQ ID NO: 8) TASGFTFSDYYMA
9. 123-1H8 (murine anti-CD123 antibody, IgG1 isotype, Kappa Light Chain); Heavy Chain CDR2 sequence (SEQ ID NO: 9) WVANIDDEGSSTYYLDSLKS
10. 123-1H8 (murine anti-CD123 antibody, IgG1 isotype, Kappa Light Chain); Heavy Chain CDR3 sequence (SEQ ID NO: 10) ARGTTQTSFFVH
11. 123-5C7 (murine anti-CD123 antibody, IgG2b isotype, Kappa Light Chain); Light Chain SP domain sequence (SEQ ID NO: 11) MDSQAQVLMLLLLWVSGTCG
12. 123-5C7 (murine anti-CD123 antibody, IgG2b isotype, Kappa Light Chain); Light Chain Variable Domain sequence (SEQ ID NO: 12) DFVMSQSPSSLAVSVGEKITINCKSSQSLFFGSTQKNYLAWYQQKPGQSPKLL IFWSSTRESGVPDRFTGSGSGTDFTLSINSVKAEDLAVYYCQQYYNYPWTFG GGTKLEIK
13. 123-5C7 (murine anti-CD123 antibody, IgG2b isotype, Kappa Light Chain); Light Chain CDR1 sequence (SEQ ID NO: 13) KSSQSLFFGSTQKNYLAWY
14. 123-5C7 (murine anti-CD123 antibody, IgG2b isotype, Kappa Light Chain); Light Chain CDR2 sequence (SEQ ID NO: 14) LLIFWSSTRES
15. 123-5C7 (murine anti-CD123 antibody, IgG2b isotype, Kappa Light Chain); Light Chain CDR3 sequence (SEQ ID NO: 15) QQYYNYPWT
16. 123-5C7 (murine anti-CD123 antibody, IgG2b isotype, Kappa Light Chain); Heavy Chain SP domain sequence (SEQ ID NO: 16) MKVLSLLYLLTAIPGILS
17. 123-5C7 (murine anti-CD123 antibody, IgG2b isotype, Kappa Light Chain); Heavy Chain Variable Domain sequence (SEQ ID NO: 17) DVQLQESGPGLVKPSQSLSLTCSVTGYSITSSYYWNWIRQFPGNKLEWMGYI SYDGSNNYNPSLKNRISITRDTSKTQFFLNLNSVTTEDTATYYC ARGDGYYFD YWGQGTTLTVSS
18. 123-5C7 (murine anti-CD123 antibody, IgG2b isotype, Kappa Light Chain); Heavy Chain CDR1 sequence (SEQ ID NO: 18) SVTGYSITSSYYWN
19. 123-5C7 (murine anti-CD123 antibody, IgG2b isotype, Kappa Light Chain); Heavy Chain CDR2 sequence: (SEQ ID NO: 19) WMGYISYDGSNNYNPSLKN
20. 123-5C7 (murine anti-CD123 antibody, IgG2b isotype, Kappa Light Chain); Heavy Chain CDR3 sequence: (SEQ ID NO: 20) ARGDGYYFDY
21. 123-5G4 (murine anti-CD123 antibody, IgG2a isotype, Kappa Light Chain); Light Chain SP domain sequence: (SEQ ID NO: 21) MDFQVQIFSFLLISASVIMSRG
22. 123-5G4 (murine anti-CD123 antibody, IgG2a isotype, Kappa Light Chain); Light Chain Variable Domain sequence: (SEQ ID NO: 22) QIVLTQSPAIMSVSLGERVTMTCTASSSVTSSYFHWYQQKPGSSPKLWIYSTS NLASGVPARFSGSGSGTSYSLTISSMEAEDAATYYCHQYHRSPRTFGGGTKL EIK
23. 123-5G4 (murine anti-CD123 antibody, IgG2a isotype, Kappa Light Chain); Light Chain CDR1 sequence: (SEQ ID NO: 23) TASSSVTSSYFHWY 24. 123-5G4 (murine anti-CD123 antibody, IgG2a isotype, Kappa Light Chain); Light Chain CDR2 sequence: (SEQ ID NO: 24) LWIYSTSNLAS
25. 123-5G4 (murine anti-CD123 antibody, IgG2a isotype, Kappa Light Chain); Light Chain CDR3 sequence: (SEQ ID NO: 25) HQYHRSPRT
26. 123-5G4 (murine anti-CD123 antibody, IgG2a isotype, Kappa Light Chain); Heavy Chain SP domain sequence: (SEQ ID NO: 26) HQYHRSPRT
27. 123-5G4 (murine anti-CD123 antibody, IgG2a isotype, Kappa Light Chain); Heavy Chain Variable Domain sequence: (SEQ ID NO: 27) DVQLQESGPGLVKPSQSLSLTCTVTGYSITSDYVWNWIRQFPGNKLEWMAYI SYSGTTSYNPSLSSRISITRDTSSNQFFLQLNSVTS EDTATYYCARGLDYWGQ GTSVTVSS
28. 123-5G4 (murine anti-CD123 antibody, IgG2a isotype, Kappa Light Chain); Heavy Chain CDR1 sequence: (SEQ ID NO: 28) TVTGYSITSDYVWN
29. 123-5G4 (murine anti-CD123 antibody, IgG2a isotype, Kappa Light Chain); Heavy Chain CDR2 sequence: (SEQ ID NO: 29) WMAYISYSGTTSYNPSLSS
30. 123-5G4 (murine anti-CD123 antibody, IgG2a isotype, Kappa Light Chain); Heavy Chain CDR3 sequence: (SEQ ID NO: 30) ARGLDY
31. 123-10C4 (murine anti-CD123 antibody, IgG2b isotype, Kappa Light Chain); Light Chain SP domain sequence: (SEQ ID NO: 31) MDSQAQVLILLLLWVSGTCG
32. 123-10C4 (murine anti-CD123 antibody, IgG2b isotype, Kappa Light Chain); Light Chain Variable Domain sequence: (SEQ ID NO: 32) DIVMSQSPSSLAVSAGEKVTMSCKSSQSLLSSGTRKNYLAWYQQKPGQSPKL LIYWASTRESGVPDRFTGSGSGTDFTLTISSVQAEDLAVYYCKQSYILFTFGSG TKLEIK
33. 123-10C4 (murine anti-CD123 antibody, IgG2b isotype, Kappa Light Chain); Light Chain CDR1 sequence: (SEQ ID NO: 33) KSSQSLLSSGTRKNYLA
34. 123-10C4 (murine anti-CD123 antibody, IgG2b isotype, Kappa Light Chain); Light Chain CDR2 sequence: (SEQ ID NO: 34) LLIYWASTRES
35. 123-10C4 (murine anti-CD123 antibody, IgG2b isotype, Kappa Light Chain); Light Chain CDR3 sequence: (SEQ ID NO: 35) KQSYILFT
36. 123-10C4 (murine anti-CD123 antibody, IgG2b isotype, Kappa Light Chain); Heavy Chain SP domain sequence: (SEQ ID NO: 36) MAVLALLLCLVAFPSCTLS
37. 123-10C4 (murine anti-CD123 antibody, IgG2b isotype, Kappa Light Chain); Heavy Chain Variable Domain sequence: (SEQ ID NO: 37) QVQLKESGPGLVAPSQNLSITCTVSGFSLTTYDINWIRQPPGKGLEWLGVIWT GGGTNYNSAFMSRLSISKDNSKSQVFLK MNSLQTDDTAMYYCVRGDTYHY ALDFWGQGTSVTVSS
38. 123-10C4 (murine anti-CD123 antibody, IgG2b isotype, Kappa Light Chain); Heavy Chain CDR1 sequence: (SEQ ID NO: 38) TVSGFSLTTYDIN
39. 123-10C4 (murine anti-CD123 antibody, IgG2b isotype, Kappa Light Chain); Heavy Chain CDR2 sequence: (SEQ ID NO: 39) WLGVIWTGGGTNYNSAFMS
40. 123-10C4 (murine anti-CD123 antibody, IgG2b isotype, Kappa Light Chain); Heavy Chain CDR3 sequence: (SEQ ID NO: 40) VRGDTYHYALDF
41. 123-11F11 (murine anti-CD123 antibody, IgG1 isotype, Kappa Light Chain); Light Chain SP domain sequence: (SEQ ID NO: 41) VRGDTYHYALDF
42. 123-11F11 (murine anti-CD123 antibody, IgG1 isotype, Kappa Light Chain); Light Chain Variable Domain sequence: (SEQ ID NO: 42) DIVLTQSPASLAVSLGQRATISCRASESLDFYGNSFMHWYQQKSGQPPKLLIS RASNLESGIPPRFSGSGSRTDFTLTIDPVEADDVATYYCQQSYEDPYTFGGGT KLEIK
43. 123-11F11 (murine anti-CD123 antibody, IgG1 isotype, Kappa Light Chain); Light Chain CDR1 sequence: (SEQ ID NO: 43) RASESLDFYGNSFMHWY
44. 123-11F11 (murine anti-CD123 antibody, IgG1 isotype, Kappa Light Chain); Light Chain CDR2 sequence: (SEQ ID NO: 44) LLISRASNLES
45. 123-11F11 (murine anti-CD123 antibody, IgG1 isotype, Kappa Light Chain); Light Chain CDR3 sequence: (SEQ ID NO: 45) QQSYEDPYT
46. 123-11F11 (murine anti-CD123 antibody, IgG1 isotype, Kappa Light Chain); Heavy Chain SP domain sequence: (SEQ ID NO: 46) MKLWLNWIFLVTLLNGIQC
47. 123-11F11 (murine anti-CD123 antibody, IgG1 isotype, Kappa Light Chain); Heavy Chain Variable Domain sequence: (SEQ ID NO: 47) EVTLVESGGGLEQPGGSLSLSCAASGFTFTDYYMSWVRQPPGKALEWLALIR NKANGYTTEYSASVKGRFTISRDNSQSILYLQMNALRAEDSATYYCARQVR NYYGYEEDALDYWGQGTSVTVSS
48. 123-11F11 (murine anti-CD123 antibody, IgG1 isotype, Kappa Light Chain); Heavy Chain CDR1 sequence: (SEQ ID NO: 48) AASGFTFTDYYMS
49. 123-11F11 (murine anti-CD123 antibody, IgG1 isotype, Kappa Light Chain); Heavy Chain CDR2 sequence: (SEQ ID NO: 49) WLALIRNKANGYTTEYSASVKG
50. 123-11F11 (murine anti-CD123 antibody, IgG1 isotype, Kappa Light Chain); Heavy Chain CDR3 sequence: (SEQ ID NO: 50) ARQVRNYYGYEEDALDY
51. 123-12A10 (murine anti-CD123 antibody, IgG2b isotype, Kappa Light Chain); Light Chain SP domain sequence: (SEQ ID NO: 51) MDSQAQVLMLLLLWVSGTCG
52. 123-12A10 (murine anti-CD123 antibody, IgG2b isotype, Kappa Light Chain); Light Chain Variable Domain sequence: (SEQ ID NO: 52) DIVMSQSPSSLAVSVGEKVTMSCKSSQSLLHSSNQKNYLAWYQQKPGQSPKL LIYWASTRESGVPDRFTGSGSGTDFTLTISSVKAEDLAVYYCQQYYSFPRTFG GGTKLEIK
53. 123-12A10 (murine anti-CD123 antibody, IgG2b isotype, Kappa Light Chain); Light Chain CDR1 sequence: (SEQ ID NO: 53) KSSQSLLHSSNQKNYLAWY
54. 123-12A10 (murine anti-CD123 antibody, IgG2b isotype, Kappa Light Chain); Light Chain CDR2 sequence: (SEQ ID NO: 54) LLIYWASTRES
55. 123-12A10 (murine anti-CD123 antibody, IgG2b isotype, Kappa Light Chain); Light Chain CDR3 sequence: (SEQ ID NO: 55) QQYYSFPRT 56. 123-12A10 (murine anti-CD123 antibody, IgG2b isotype, Kappa Light Chain); Heavy Chain SP domain sequence: (SEQ ID NO: 56) MGWSWI-FLFLLSGTAGVLS
57. 123-12A10 (murine anti-CD123 antibody, IgG2b isotype, Kappa Light Chain); Heavy Chain Variable Domain sequence: (SEQ ID NO: 57) EVQLQQSG-PELVKPGASVKISCK-TSGYTFTDYYMNWVKQSHGKSLEWIGDII PNNGGTSYHQKFKGKATLTVDKSSN-TAYMELRSLTSEDSAVYYCARYGSSW FFDVWGTGTTVTVSS
58. 123-12A10 (murine anti-CD123 antibody, IgG2b isotype, Kappa Light Chain); Heavy Chain CDR1 sequence: (SEQ ID NO: 58) KTSGYTFTDYYMN
59. 123-12A10 (murine anti-CD123 antibody, IgG2b isotype, Kappa Light Chain); Heavy Chain CDR2 sequence: (SEQ ID NO: 59) WIGDIIPNNGGT-SYHQKFKG
60. 123-12A10 (murine anti-CD123 antibody, IgG2b isotype, Kappa Light Chain); Heavy Chain CDR3 sequence: (SEQ ID NO: 60) ARYGSSWFFDV
61. 123-13E1 (murine anti-CD123 antibody, IgG2b isotype, Kappa Light Chain); Light Chain SP domain sequence: (SEQ ID NO: 61) MESQTRVLMFLLL-WVSGASA
62. 123-13E1 (murine anti-CD123 antibody, IgG2b isotype, Kappa Light Chain); Light Chain Variable Domain sequence: (SEQ ID NO: 62) DIVLTQSPSSLAMSVGQKVTMSCK-SSQSLLNSSNQKNYLAWYQQKPGQSPK LLVYFAS-TRESGVPDRFTGSGSGTDFTLTISTVQAED-LAFYYCHQHYSIPRTFG GGTKLEIT
63. 123-13E1 (murine anti-CD123 antibody, IgG2b isotype, Kappa Light Chain); Light Chain CDR1 sequence: (SEQ ID NO: 63) KSSQSLLNSSNQK-NYLAWY
64. 123-13E1 (murine anti-CD123 antibody, IgG2b isotype, Kappa Light Chain); Light Chain CDR2 sequence: (SEQ ID NO: 64) LLVYFASTRES
65. 123-13E1 (murine anti-CD123 antibody, IgG2b isotype, Kappa Light Chain); Light Chain CDR3 sequence: (SEQ ID NO: 65) HQHYSIPRT
66. 123-13E1 (murine anti-CD123 antibody, IgG2b isotype, Kappa Light Chain); Heavy Chain SP domain sequence: (SEQ ID NO: 66) MGWSWI-FLFLLSGTAGVLS
67. 123-13E1 (murine anti-CD123 antibody, IgG2b isotype, Kappa Light Chain); Heavy Chain Variable Domain sequence: (SEQ ID NO: 67) EVQLQQSG-PELVKPGASVKISCK-ASGYTFTDHYMNWVKQSHGERLEWIGDII PNNGGS-TYSQKFKGKATLTVDKSSSTAYMELRSLTSED-SAVYYCARNGYYW YFDVWGTGTTVTVSS
68. 123-13E1 (murine anti-CD123 antibody, IgG2b isotype, Kappa Light Chain); Heavy Chain CDR1 sequence: (SEQ ID NO: 68) KASGYTFTDHYMN
69. 123-13E1 (murine anti-CD123 antibody, IgG2b isotype, Kappa Light Chain); Heavy Chain CDR2 sequence: (SEQ ID NO: 69) WIGDIIPNNGGS-TYSQKFKG
70. 123-13E1 (murine anti-CD123 antibody, IgG2b isotype, Kappa Light Chain); Heavy Chain CDR3 sequence: (SEQ ID NO: 70) ARNGYYWYFDV
71. 123-ATX1B2 (Human anti-CD123 antibody from ATX-GX mouse, Kappa Light Chain); Light Chain SP domain sequence: (SEQ ID NO: 71) METPAQLL-FLLLLWLPDTTG
72. 123-ATX1B2 (Human anti-CD123 antibody from ATX-GX mouse, Kappa Light Chain); Light Chain Variable Domain sequence: (SEQ ID NO: 72) DIQMTQSPSSLSASVGDRVTITCQASQDIT-NYLNWYQQKPGKAPKLQIYDAS NLETGVPSRFSGSGSGTDFTFTISSLQPEDI-ATYYCQQHDDLPLTFGGGTKVEI K
73. 123-ATX1B2 (Human anti-CD123 antibody from ATX-GX mouse, Kappa Light Chain); Light Chain CDR1 sequence: (SEQ ID NO: 73) QASQDIT-NYLNWY
74. 123-ATX1B2 (Human anti-CD123 antibody from ATX-GX mouse, Kappa Light Chain); Light Chain CDR2 sequence: (SEQ ID NO: 74) LQIYDASNLET
75. 123-ATX1B2 (Human anti-CD123 antibody from ATX-GX mouse, Kappa Light Chain); Light Chain CDR3 sequence: (SEQ ID NO: 75) QQHDDLPLT
76. 123-ATX1B2 (Human anti-CD123 antibody from ATX-GX mouse, Kappa Light Chain); Heavy Chain SP domain sequence: (SEQ ID NO: 76) MEFGLNWIF-LAAILKGVQC
77. 123-ATX1B2 (Human anti-CD123 antibody from ATX-GX mouse, Kappa Light Chain); Heavy Chain Variable Domain sequence: (SEQ ID NO: 77) QVQLVQSGAEVKKPGASVEVSCK-ASGYTFTGYYIHWVRQAPGQGLEWMG WINPNSGGTNYAQKFQGRVTMTWDTSIS-TAFMELSRLRSDDTAVYSCARDR GGPYFDYWGQGTLVIVSS
78. 123-ATX1B2 (Human anti-CD123 antibody from ATX-GX mouse, Kappa Light Chain); Heavy Chain CDR1 sequence: (SEQ ID NO: 78) KASGYTFTGYYIH
79. 123-ATX1B2 (Human anti-CD123 antibody from ATX-GX mouse, Kappa Light Chain); Heavy Chain CDR2 sequence: (SEQ ID NO: 79) WMGWINPNSGGTNYAQKFQG
80. 123-ATX1B2 (Human anti-CD123 antibody from ATX-GX mouse, Kappa Light Chain); Heavy Chain CDR3 sequence: (SEQ ID NO: 80) ARDRGGPYFDY
81. 123-ATX1B5 (Human anti-CD123 antibody from ATX-GX mouse, Kappa Light Chain); Light Chain SP domain sequence: (SEQ ID NO: 81) MDMRVPAQLLGLLLLWLPGAKC
82. 123-ATX1B5 (Human anti-CD123 antibody from ATX-GX mouse, Kappa Light Chain); Light Chain Variable Domain sequence: (SEQ ID NO: 82) DIQMTQSPSTLSASVGDRVTITCRASQSISS-WLAWYQQKPGKAPKILIYKASS LESGVPSRFSGSGSGTEFTLTISSLQPDDFA-TYYCQQYNSYWTFGQGTK VEIK
83. 123-ATX1B5 (Human anti-CD123 antibody from ATX-GX mouse, Kappa Light Chain); Light Chain CDR1 sequence: (SEQ ID NO: 83) RASQSISSWLA
84. 123-ATX1B5 (Human anti-CD123 antibody from ATX-GX mouse, Kappa Light Chain); Light Chain CDR2 sequence: (SEQ ID NO: 84) ILIYKASSLES
85. 123-ATX1B5 (Human anti-CD123 antibody from ATX-GX mouse, Kappa Light Chain); Light Chain CDR3 sequence: (SEQ ID NO: 85) QQYNSYWT 86. 123-ATX1B5 (Human anti-CD123 antibody from ATX-GX mouse, Kappa Light Chain); Heavy Chain SP domain sequence: (SEQ ID NO: 86) MELGLSWVFLVAILEGVQC
87. 123-ATX1B5 (Human anti-CD123 antibody from ATX-GX mouse, Kappa Light Chain); Heavy Chain Variable Domain sequence: (SEQ ID NO: 87) EVOLVESGGGLVQPGGSLRLSCATSGFTFSNYDMHWVRQVTGKGLEWVSGI GIAGDTYYPGSVKGRFTISREDAKNSLYLQMNSLRAEDTAVYYCATERGSSS WYNYFDYWGQGTLVTVSS
88. 123-ATX1B5 (Human anti-CD123 antibody from ATX-GX mouse, Kappa Light Chain); Heavy Chain CDR1 sequence: (SEQ ID NO: 88) ATSGFTFSNYDMH
89. 123-ATX1B5 (Human anti-CD123 antibody from ATX-GX mouse, Kappa Light Chain); Heavy Chain CDR2 sequence: (SEQ ID NO: 89) WVSGIGIAGDTYYPGSVKG
90. 123-ATX1B5 (Human anti-CD123 antibody from ATX-GX mouse, Kappa Light Chain); Heavy Chain CDR3 sequence: (SEQ ID NO: 90) ATERGSSSWYNYFDY
91. 123-ATX1B7 (Human anti-CD123 antibody from ATX-GX mouse, Kappa Light Chain); Light Chain SP domain sequence: (SEQ ID NO: 91) METPAQLLFLLLLWLPDTTG
92. 123-ATX1B7 (Human anti-CD123 antibody from ATX-GX mouse, Kappa Light Chain); Light Chain Variable Domain sequence: (SEQ ID NO: 92) EIVLTQSPGT LSLSPGERAT LSCRASQSFS DRYLAWYQQK PGQAPRLLIY GTSSRATGIP DRFSGSGSGT DFTLTISRLE SEDSAVYYCQ QYGRSPFTFG PGTKVDIK
93. 123-ATX1B7 (Human anti-CD123 antibody from ATX-GX mouse, Kappa Light Chain); Light Chain CDR1 sequence: (SEQ ID NO: 93) RASQSFSDRYLAWY
94. 123-ATX1B7 (Human anti-CD123 antibody from ATX-GX mouse, Kappa Light Chain); Light Chain CDR2 sequence: (SEQ ID NO: 94) LLIYGTSSRAT
95. 123-ATX1B7 (Human anti-CD123 antibody from ATX-GX mouse, Kappa Light Chain); Light Chain CDR3 sequence: (SEQ ID NO: 95) QQYGRSPF
96. 123-ATX1B7 (Human anti-CD123 antibody from ATX-GX mouse, Kappa Light Chain); Heavy Chain SP domain sequence: (SEQ ID NO: 96) MEFGLSWVFLVAIIKGVHC
97. 123-ATX1B7 (Human anti-CD123 antibody from ATX-GX mouse, Kappa Light Chain); Heavy Chain Variable Domain sequence: (SEQ ID NO: 97) QVQLVQSGAEVKKPGASVKVSCKASGYTFTSFGLTWVRQAPGQGLEWMG WFNAYSGKTYYAPTLQDRVTMTTDPSTSTAYMELMSLTSDD TAIYYCARDL VFDYWGQGTL VTVSS
98. 123-ATX1B7 (Human anti-CD123 antibody from ATX-GX mouse, Kappa Light Chain); Heavy Chain CDR1 sequence: (SEQ ID NO: 98) KASGYTFTSF GLT
99. 123-ATX1B7 (Human anti-CD123 antibody from ATX-GX mouse, Kappa Light Chain); Heavy Chain CDR2 sequence: (SEQ ID NO: 99) WMGWFNAYSG KTYYAPTLQD
100. 123-ATX1B7 (Human anti-CD123 antibody from ATX-GX mouse, Kappa Light Chain); Heavy Chain CDR3 sequence: (SEQ ID NO: 100) ARDLVFDY
101. 123-ATX1D9 (Human anti-CD123 antibody from ATX-GX mouse, Lambda Light Chain); Light Chain SP domain sequence: (SEQ ID NO: 101) MAWALLLLTLLTQGTGSWA
102. 123-ATX1D9 (Human anti-CD123 antibody from ATX-GX mouse, Lambda Light Chain); Light Chain Variable Domain sequence: (SEQ ID NO: 102) QSALTQPPSASGSPGQSVTISCTGTSSDVGGYNYVSWYQQHPGKAPKIMIYE VNKRPAGVPDRFSGSKSGNTASLTVSGLQAEDEAHYYCNSYTDSNNLIFGGG TKLTVL
103. 123-ATX1D9 (Human anti-CD123 antibody from ATX-GX mouse, Lambda Light Chain); Light Chain CDR1 sequence: (SEQ ID NO: 103) TGTSSDVGGYNYVSWY
104. 123-ATX1D9 (Human anti-CD123 antibody from ATX-GX mouse, Lambda Light Chain); Light Chain CDR2 sequence: (SEQ ID NO: 104) IMIYEVNKRPA
105. 123-ATX1D9 (Human anti-CD123 antibody from ATX-GX mouse, Lambda Light Chain); Light Chain CDR3 sequence: (SEQ ID NO: 105) NSYTDSNNLI
106. 123-ATX1D9 (Human anti-CD123 antibody from ATX-GX mouse, Lambda Light Chain); Heavy Chain SP domain sequence: (SEQ ID NO: 106) MELGLSWIFLLAILKGVQC
107. 123-ATX1D9 (Human anti-CD123 antibody from ATX-GX mouse, Lambda Light Chain); Heavy Chain Variable Domain sequence: (SEQ ID NO: 107) EVOLVESGGGLVQPGRSLRLSCAASGFTFGDYAMHWVRQAPGKGLEWVSGI NWNNKNIGYADSVKGRFTISKNNAKNSLYLQMNSLRVEDTALYYCAKDRG YSYGYWYFDLWGRGTLVTVSS
108. 123-ATX1D9 (Human anti-CD123 antibody from ATX-GX mouse, Lambda Light Chain); Heavy Chain CDR1 sequence: (SEQ ID NO: 108) AASGFTFGDYAMH
109. 123-ATX1D9 (Human anti-CD123 antibody from ATX-GX mouse, Lambda Light Chain); Heavy Chain CDR2 sequence: (SEQ ID NO: 109) WVSGINWNNKNIGYADSVKG
110. 123-ATX1D9 (Human anti-CD123 antibody from ATX-GX mouse, Lambda Light Chain); Heavy Chain CDR3 sequence: (SEQ ID NO: 110) AKDRGYSYGYWYFDL
111. 123-ATX1E3 (Human anti-CD123 antibody from ATX-GX mouse, Kappa Light Chain); Light Chain SP domain sequence: (SEQ ID NO: 111) METPAQLLFLLLLWLPDATG
112. 123-ATX1E3 (Human anti-CD123 antibody from ATX-GX mouse, Kappa Light Chain); Light Chain Variable Domain sequence: (SEQ ID NO: 112) EIVLMQSPGTLSLSPGERVTLSCRASQTFSSSYLAWYQQKPGQAPRLLIYGAS SRATGIPDRFSGSGSGTDFTLTINRLEPEDFAVYYCQQYGRSPFTFGPGTKLDI K
113. 123-ATX1E3 (Human anti-CD123 antibody from ATX-GX mouse, Kappa Light Chain); Light Chain CDR1 sequence: (SEQ ID NO: 113) RASQTFSSSYLA
114. 123-ATX1E3 (Human anti-CD123 antibody from ATX-GX mouse, Kappa Light Chain); Light Chain CDR2 sequence: (SEQ ID NO: 114) LLIYGASSRAT
115. 123-ATX1E3 (Human anti-CD123 antibody from ATX-GX mouse, Kappa Light Chain); Light Chain CDR3 sequence: (SEQ ID NO: 115) QQYGRSPFT 116. 123-ATX1E3 (Human anti-CD123 antibody from ATX-GX mouse, Kappa Light Chain); Heavy Chain SP domain sequence: (SEQ ID NO: 116) MDWTWSIL-FLVAAATGAHS 117. 123-ATX1E3 (Human anti-CD123 antibody from ATX-GX mouse, Kappa Light Chain); Heavy Chain Variable Domain sequence: (SEQ ID NO: 117) QVQLVQSGAEVKKPGASVKVSCKASGYTFNSY-GISWVRQAPGQGLEWMGW FNAY-SGITNYAQKFQDRITMTTDTST-STAYMELRSLRSDDTAVYYCARDLVF DFWGQGTLVTVSS 118. 123-ATX1E3 (Human anti-CD123 antibody from ATX-GX mouse, Kappa Light Chain); Heavy Chain CDR1 sequence: (SEQ ID NO: 118) KASGYTFNSY-GIS 119. 123-ATX1E3 (Human anti-CD123 antibody from ATX-GX mouse, Kappa Light Chain); Heavy Chain CDR2 sequence: (SEQ ID NO: 119) WMGWFNAY-SGITNYAQKFQD 120. 123-ATX1E3 (Human anti-CD123 antibody from ATX-GX mouse, Kappa Light Chain); Heavy Chain CDR3 sequence: (SEQ ID NO: 120) ARDLVFDF 121. 123-ATX1E5 (Human anti-CD123 antibody from ATX-GX mouse, Kappa Light Chain); Light Chain SP domain sequence: (SEQ ID NO: 121) MVLQTQVFIS-LLLWISGAYG 122. 123-ATX1E5 (Human anti-CD123 antibody from ATX-GX mouse, Kappa Light Chain); Light Chain Variable Domain sequence: (SEQ ID NO: 122) EIVLTQSPGTLSLSPGERATLSCRASQSFSDRY-LAWYQQKPGQAPRLLIYGTFS RAT-GIPDRFSGSGSGTDFTLTISRLDSED-FAVYYCQQYGSSPFTFGPGTKVDIK 123. 123-ATX1E5 (Human anti-CD123 antibody from ATX-GX mouse, Kappa Light Chain); Light Chain CDR1 sequence: (SEQ ID NO: 123) RASQSFSDRY-LAWY 124. 123-ATX1E5 (Human anti-CD123 antibody from ATX-GX mouse, Kappa Light Chain); Light Chain CDR2 sequence: (SEQ ID NO: 124) LLIYGTFSRAT 125. 123-ATX1E5 (Human anti-CD123 antibody from ATX-GX mouse, Kappa Light Chain); Light Chain CDR3 sequence: (SEQ ID NO: 125) QQYGSSPF 126. 123-ATX1E5 (Human anti-CD123 antibody from ATX-GX mouse, Kappa Light Chain); Heavy Chain SP domain sequence: (SEQ ID NO: 126) MDWTWRIL-FLVAAATGAHS 127. 123-ATX1E5 (Human anti-CD123 antibody from ATX-GX mouse, Kappa Light Chain); Heavy Chain Variable Domain sequence: (SEQ ID NO: 127) QVQLVQSGAEVKKPGASVKVSCKASGYTFTSF-GISWVRQAPGQGLEWMGW FNAYSGNTYY-APTLQDRVTMTTDTSTSTAYMELMSLRSDD-TAIYYCARDLV FDYWGQGTLVTVSS 128. 123-ATX1E5 (Human anti-CD123 antibody from ATX-GX mouse, Kappa Light Chain); Heavy Chain CDR1 sequence: (SEQ ID NO: 128) KASGYTFTSF-GIS 129. 123-ATX1E5 (Human anti-CD123 antibody from ATX-GX mouse, Kappa Light Chain); Heavy Chain CDR2 sequence: (SEQ ID NO: 129) WMGWFNAY-SGNTYYAPTLQD 130. 123-ATX1E5 (Human anti-CD123 antibody from ATX-GX mouse, Kappa Light Chain); Heavy Chain CDR3 sequence: (SEQ ID NO: 130) ARDLVFDY 131. 123-ATX1F2 (Human anti-CD123 antibody from ATX-GX mouse, Kappa Light Chain); Light Chain SP domain sequence: (SEQ ID NO: 131) MRVPAQLLGLLLLWFPGARC 132. 123-ATX1F2 (Human anti-CD123 antibody from ATX-GX mouse, Kappa Light Chain); Light Chain Variable Domain sequence: (SEQ ID NO: 132) DIQMTQSPSSLSASVGDRVTITCRASQ-GIRNDLGWYQQRPGKAPKRLIYAASS LQSGVPSRFSGSGSGTEFTLAISSLQPEDFATY-SCLQHNSYPWTFGQGTKVEIK 133. 123-ATX1F2 (Human anti-CD123 antibody from ATX-GX mouse, Kappa Light Chain); Light Chain CDR1 sequence: (SEQ ID NO: 133) RASQ-GIRNDLGWY 134. 123-ATX1F2 (Human anti-CD123 antibody from ATX-GX mouse, Kappa Light Chain); Light Chain CDR2 sequence: (SEQ ID NO: 134) RLIYAASSLOS 135. 123-ATX1F2 (Human anti-CD123 antibody from ATX-GX mouse, Kappa Light Chain); Light Chain CDR3 sequence: (SEQ ID NO: 135) LOHNSYPWT 136. 123-ATX1F2 (Human anti-CD123 antibody from ATX-GX mouse, Kappa Light Chain); Heavy Chain SP domain sequence: (SEQ ID NO: 136) MDCTWRIL-FLVAAATGTHA 137. 123-ATX1F2 (Human anti-CD123 antibody from ATX-GX mouse, Kappa Light Chain); Heavy Chain Variable Domain sequence: (SEQ ID NO: 137) QVQLVQSGAEVKKP-GASVKVSCKVSGYTLTEFSMHWVRQAPGK-GLEWMG VFDPEHGATIYAQKFQGRVTMTEDT-STDTAYMDLSYLRSEDTAVYYCATYF DFWSGYSHFDFWGQGTLVTVSS 138. 123-ATX1F2 (Human anti-CD123 antibody from ATX-GX mouse, Kappa Light Chain); Heavy Chain CDR1 sequence: (SEQ ID NO: 138) KVSGYTLTEFSMH 139. 123-ATX1F2 (Human anti-CD123 antibody from ATX-GX mouse, Kappa Light Chain); Heavy Chain CDR2 sequence: (SEQ ID NO: 139) WMGVFDPEH-GATIYAQKFQG 140. 123-ATX1F2 (Human anti-CD123 antibody from ATX-GX mouse, Kappa Light Chain); Heavy Chain CDR3 sequence: (SEQ ID NO: 140) ATYFDFWSGYSHFDF 141. 123-ATX1G5 (Human anti-CD123 antibody from ATX-GX mouse, Kappa Light Chain); Light Chain SP domain sequence: (SEQ ID NO: 141) MDMRV-LAQLLGLLLLCFPGARC 142. 123-ATX1G5 (Human anti-CD123 antibody from ATX-GX mouse, Kappa Light Chain); Light Chain Variable Domain sequence: (SEQ ID NO: 142) DIQMTQSPSSLSASVGDRVTITCRASQGIS-NYLAWFQQKPGKAPKSLIYAASS LQSGVPSKFSGSGSGTDFTLTISSLQPED-LATYYCQQYNSYPYTFGQGTKLEIK 143. 123-ATX1G5 (Human anti-CD123 antibody from ATX-GX mouse, Kappa Light Chain); Light Chain CDR1 sequence: (SEQ ID NO: 143) RASQGISNYLA 144. 123-ATX1G5 (Human anti-CD123 antibody from ATX-GX mouse, Kappa Light Chain); Light Chain CDR2 sequence: (SEQ ID NO: 144) SLIYAASSLQS 145. 123-ATX1G5 (Human anti-CD123 antibody from ATX-GX mouse, Kappa Light Chain); Light Chain CDR3 sequence: (SEQ ID NO: 155) QQYNSYPYT 146. 123-ATX1G5 (Human anti-CD123 antibody from ATX-GX mouse, Kappa Light Chain); Heavy Chain SP domain sequence: (SEQ ID NO: 146) MDWTWRFLFVVAAATGVQS 147. 123-ATX1G5 (Human anti-CD123 antibody from ATX-GX mouse, Kappa Light Chain); Heavy Chain Variable Domain sequence: (SEQ ID NO: 147) QVQLVQSGSEVKKPGSSVKVSCK-ASGGTFSSYAISWVRQAPGQGLEWMGGII PIFGTVTYAQKFQGRVTITA-DESTNTVYMELSSLRSEDTAVYYCARDDFWTG DYWGQGTLVTVSS 148. 123-ATX1G5 (Human anti-CD123 antibody from ATX-GX mouse, Kappa Light Chain); Heavy Chain CDR1 sequence: (SEQ ID NO: 148) KASGGTFSSYAIS 149. 123-ATX1G5 (Human anti-CD123 antibody from ATX-GX mouse, Kappa Light Chain); Heavy Chain CDR2 sequence: (SEQ ID NO: 149) WMGGIIP-IFGTVTYAQKFQG 150. 123-ATX1G5 (Human anti-CD123 antibody from ATX-GX mouse, Kappa Light Chain); Heavy Chain CDR3 sequence: (SEQ ID NO: 150) ARDDFWTGDY 151. 123-ATX1G5 (Human anti-CD123 antibody from ATX-GX mouse, Kappa Light Chain); Heavy Chain Variable Domain variant sequence: (SEQ ID NO: 151) QVQLVQSGSEVKKPGSSVKVSCK-ASGGTFSSYAISWVRQAPGQGLEWMGGII PIFGTVTYAQKFQGGVTITA-DESTNTVYMELSSLRSEDTAVYYCARDDFWTG DYWGQGTLVTVSS 152. <Protein/3; Artificial sequence> (SEQ ID NO: 152) QVKLQESGPG LVQPSQSLSI TCTVSGFSLT DYGVHWVRQS PGKGLEWLGV IWSGGGTATYAAFISRLNIY KDNSKNQVFF EMNSLQANDT AMYYCARRGS YPYNYFDVWG QGTTVTVSSGGGGSGGGGSG GGGSQAVVTQ ESALTTSPGE TVTLTCRSST GAVTTSNYAN WVQEKPDHLFTGLIGGNNNR PPGVPARFSG SLIGDKAALT IAGTQTEADA IYFCALWYSN HWVFGGGFRGRVLG 153. <Seq21; Protein/3; Artificial sequence> (SEQ ID NO: 153) QVKLQESGPG LVQPSQSLSI TCTVSGFSLT DYGVHWVRQS PGKGLEWLGV IWSGGGTAYNTALISRLNIY RDNSKNQVFL EMNSLQADDT AMYYCARRGS YPYNYFDAWG RGTTVTVSSGGGGSGGGGSG GGGSQAVVIQ ESALTTSPGE TVTLTCGSST GAVTASNYAN WVQEKPDHCFTGLIGGHNNR PPGVPARFSG SLIGDKAALT IAGTQTEDEA IYFCALWYSD HWVIGGGTRLTVLG 154. <Protein/3; Artificial sequence> (SEQ ID NO: 154) LVKLQESGPG LVQPSQSLSI TCTVSGFSLT DYGVHWVRQS PGKGLEWLGV IWSGGGTAYN-TALISRLNIY RDNSKNQVFL EMNSLQAEDT AMYYCARRGS YPYNYFDAWG RGTTVTVSSEGGGSGGGGSG GGGSQAVVIQ ESALTTSPGE TVTLTCGSST GAVTASNYAN WVQEKPDHCFTGLIGGHNNR PPGVPARFSG SLIGDKAALT IAGTQTEDEA IYFLCFVVF 155. <Protein/3; Artificial sequence> (SEQ ID NO: 155) QAKLQESGPG LVQPSQSLSI TCTVSGFSLT DYGVHWVRQS PGKGLEWLGV IWSGGGTAYN-TALISRLNIY RDNSKNQVFL EMNSLQADDT AMYYCARRGS YPYNYFDAWG CGTTVTVSSGGGGSGGGGSG GGGSQAVVIQ ESALTTSPGE TVTLTCGSST GAVTASNYAN WVQEKPDHCFTGLIGGHNNR PPGVPARFSG SLIGDKAALT IAGTQTEDEA IYFCALWYSD HWVIGGGTRLTVLG 156. <Protein/3; Artificial sequence> (SEQ ID NO: 156) QVKLQESGPG LVQPSQSLSI TCTVSGFSLT DYGVHWVRQS PGKGLEWLGV IWSGGGTAYN-TALISRLNIY RDNSKNQVFL EMNSLQADDT AMYYCARRGS YPYNYFDAWG CGTTVTVSSGGGGPGGGGSG GGGSQAVVIQ ESALTTSPGE TVTLTCGSST GAVTASNYAN WVQEKPDHCFTGLIGGHNNR PPGVPARFSG SLIGDKAALT IAGTQTEDEA IYFCALWYSD HWVIGGGTRLTVLS 157. <Protein/3; Artificial sequence> (SEQ ID NO: 157) HVKLQESGPG LVQPSQSLSL TCTVSGFSLT DYGVHWVRQS PGKGLEWLGV IWSGGGTAYN-TALISRLNIY RDNSKNQVFL EMNSLQAEDT AMYYCARRGS YPYNYFDAWG CGTTVTVSSGGGGSGGGGSG GGGSQAVVIQ ESALTTPPGE TVTLTCGSST GAVTASNYAN WVQEKPDHCFTGLIGGHNNR PPGVPARFSG SLIGDKAALT IAGTQTEDEA IYFCALWYSD HWVIGGGTRL 158. <Protein/3; Artificial sequence> (SEQ ID NO: 158) QVKLQESGPGLVRPSQPL-SITCTVSGFSLTDYGVHWVRQSPGKGLEWLGV IWSGGGTAYNTALISRLNIY RDNSKNQVFL EMNSLQADDT AMYYCARRGS YPYNYFDAWGCGTTVTVSSGGGGSGGGGSG GGGSQAVVIQ ESALTTSPGE TVTLTCGSST-GAVTAFNYAN WVQEKPDHCFTGLIGGHNNR PPGVPARFSG SLIGGKAALT IAGTQTEDEA IYFCALWYSDHWVIGGGTRLTVLG 159. <Protein/3; Artificial sequence> (SEQ ID NO: 159) QVKLQESGPG LVQPSQSLSI TCTVSGFSLT DYGVHWVRQS PGKGLEWLGV IWSGGGTAYN-TALISRLNIY RDNSKNQVFF EMNSLQADDT AMYYCARRGS YPYNYFDAWG CGTTVTVSSGGGGSGGGGSG GGGSQAVVIQ ESALITSPGE TVTLTCGSST GAVTASNYAN WVQEKPDHCFTGLIGGHNNR PPGVPARFSG SLIGDKAALT IAGTQTGDEA IYFCALWYSD HWVIGGGTRLTVLG 160. <Protein/3; Artificial sequence> (SEQ ID NO: 160) QVKLQESGPG LVQPSQSLSI TCTVSGFSLT DYGVHWVRQS PGKGLEWLGV IWSGGGTAYN-TALISRLNIY RDNSKNQVFL EMNSLQADDT AMYYCARRGS YPYNYFDAWG CGTTVTVSSGGGGSGGGGSG GGGSQAVVIQ ESALTTSPGE TVTLTCGSST GAVTASNYAN WVQEKPDHCFTGLIGGHNNR PPGVPARFSG SLIGDKAALT IAGTQTEDEA IYFCALWYSD HWVIGGGTRLTVLG 161. <Protein/3; Artificial sequence> (SEQ ID NO: 161) QVKLQESGPG LVQPSQSLSI TCTVSGFSLT DYGVHWVRQS PGKGLEWLGV IWSGGGTAYN-TALISRLNIY RDNSKNQVFL EMNSLQADDT AMYYCARRGS YPYNYFDAWG CGTTVTVSSG GGGSGGGGSG GGGSQAVVIQ ESALTTSPGE TVTLTCGSST GAVTASNYAN WVQEKPDHCFTGLIGGHNNR PPGVPARFSG SLIGDKAALT IAGTQTEDEA IYFCALWYSD HWVIGGGTRL TVLG 162. <Protein/3; Artificial sequence> (SEQ ID NO: 162) QVKLQESGPG LVQPSQSLSI TCTVSGFSLT DYGVHWVRQS PGKGLEWLGV IWSGGGTAYN TALISRLNIY RDNSKNQVFF EMNSLQADDT AMYYCARRGS YPYNYFDAWG CGTTVTVSSG GGGSGSGGSG GGGSQAVVIQ ESALTTSPGE TVTLTCGSST GAVTASNYAN WVQEKPDHCF TGLIGGHNNR PPGVPARFSG SLIGDKAALT IAGTQTEDEA IYFCALWYSD HWVIGGGTRL TVLG 163. <Protein/3; Artificial sequence> (SEQ ID NO: 163) QVKLQESGPG LVQPPQSLSI TCTVSGFSLT DYGVHWVRQS PGKGLEWLGV IWSGGGTAYN TALISRLNIY RDNSKNQVFF EMNSLQADDT AMYYCARRGS YPYNYFDAWG CGTTVTVSSG GGGSGGGGSG GGGSQAVVIQ ESALTTSPGE TVTLTCGSST GAVTASNYAN WVQEKPDHCF TGLIGGHNNR PPGVPARFSG SLIGDKATLT IAGTQTEDEA IYFCALWYSD HWVIGGGTRL TVLG 164. <Protein/3; Artificial sequence> (SEQ ID NO: 164) QVKLQESGPG LVQPSQSLSI TCTVSGFSLT DYGVHWVRQS PGKGLEWLGV IWSGGGTAYN TALISRLNIY RDNSKNQVFF EMNSLQAEDT AMYYCARRGS YPYNYFDAWG CGTTVTVSSG GGGPGGGGSG GGGSQAVVIQ ESALTTSPGE TVTLTCGSST GAITTSNYAN WVQEKPDHCF TGLIGGHNNR PPGVPARFSG SLIGDKAALT IAGTQTEDEA IYFCALWYSD HWVIGGGTRL TVLG 165. <Protein/3; Artificial sequence> (SEQ ID NO: 165) QVKLQESGPG LVQPSQSLSI TCTVSGFSLT DYGVHWVRQS PGKGLEWLGV IWSGGGTAYN TALISRLNIY RDNSKNQVFL EMNSLQAEDT AMYYCARRGS YPYNYFDAWG CGTTVTVSSG GGGSGGGGSG GGGSQAVVIQ ESALTTSPGE TVTLTCGSST GAVTASNYAN WVQEKPDHCF TGLIGGHNNR PPGVPARFSG SLIGDKAALT IVGTQTEDEA IYFCALWYSD HWVIGGGTRL TVLG 166. <Protein/3; Artificial sequence> (SEQ ID NO: 166) QVKLQESGPG LVQPSQSLSI TCTVSGFSLT DYGVHWVRQS PGKGLEWLGV IWSGGGTAYN TALISRLNIY RDNSKNQVFF EMNSLQADDT AMYYCARRGR YPYNYFDAWG CGTTVTVSSG GGGSGGGGSG GGGSQAVVIQ ESALTTSPGE TVTLTCGSST GAVTASNYAN WVQEKPDHCF TGLIGGHNNR PPGVPARFSG SLIGDKAALT IAGTQTEDEA IYFCALWYSD HWVIGGGTRL TVLG 167. <Protein/3; Artificial sequence> (SEQ ID NO: 167) QVKLQESGPG LVQPSQSLSI TCTVSGFSLT DYGVHWVRQS PGKSLEWLGV IWSGGGTAYN TALISRLNIY KDNSKNQVFF EMNSLQAEDT AMYYCARRGS YPYNYFDAWG CGTTVTVSSG GGGSGGGGSG GGGSQAVVIQ ESALTTSPGE TVTLTCGSST GAVTASNYAN WVQEKPDHCF TGLIGGHNNR PPGVPARFSG SLIGDKAALT IAGTQTEDEA IYYCALWYSD HWVIGGGTRL TVLG 168. <Protein/3; Artificial sequence> (SEQ ID NO: 168) QVKLQESGPG LVQPSQSLSI TCTVSGFSLT DYGVHWVRQS PGKGLEWLGV IWSGGGTAYN TALISRLNIY RDNSKNQVFL EMNSLQADDT AMYYCARRGS YPYNYFDAWG RGTTVTVSSG GGGSGGGGSG GGGSQAVVIQ ESALTTSPGE TVTLTCGSST GAVTASNYAN WVQEKPDHCF TGLIGGHNNR PPGVPARFSG SLIGDKAALT IAGTQTEDEA IYFCALWYSD HWVIGWWY 169. Dimeric construct (only one chain is shown); (SEQ ID NO: 169) DIVMSQSPSS LAVSAGEKVT MSCKSSQSLL SSGTRKNYLA WYQQKPGQSP KLLIYWASTR ESGVPDRFTG SGSGTDFTLT ISSVQAEDLA VYYCKQSYIL FTFGSGTKLE IKGGGSGGGG SGGGGSGGGG SSQVQLKESG PGLVAPSQNL SITCTVSGFS LTTYDINWIR QPPGKGLEWL GVIWTGGGTN YNSAFMSRLS ISKDNSKSQV FLKMNSLQTD DTAMYYCVRG DTYHYALDFW GQGTSVTVSS LEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEGLHN HYTQKSLSLS PGKVDGASSH VNVSSPSVQD IHVKLQESGP GLVQPSQSLS LTCTVSGFSL TDYGVHWVRQ SPGKGLEWLG VIWSGGGTAY NTALISRLNI YRDNSKNQVF LEMNSLQAED TAMYYCARRG SYPYNYFDAW GCGTTVTVSS GGGGGGGGS GGGGSQAVVI QESALTTPPG ETVTLTCGSS TGAVTASNYA NWVQEKPDHC FTGLIGGHNN RPPGVPARFS GSLIGDKAAL TIAGTQTEDE AIYFCALWYS DHWVIGGGTR LTVLG 170. Monomeric construct (only one chain is shown); (SEQ ID NO: 170) DIVMSQSPSS LAVSAGEKVT MSCKSSQSLL SSGTRKNYLA WYQQKPGQSP KLLIYWASTR ESGVPDRFTG SGSGTDFTLT ISSVQAEDLA VYYCKQSYIL FTFGSGTKLE IKGGGSGGGG SGGGGGGGG SSQVQLKESG PGLVAPSQNL SITCTVSGFS LTTYDINWIR QPPGKGLEWL GVIWTGGGTN YNSAFMSRLS ISKDNSKSQV FLKMNSLQTD DTAMYYCVRG DTYHYALDFW GQGTSVTVSS LEPKSSDKTH TSPPSPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCRVKGFYP SDIAVEWESN GQPENNYKTT PPVLDSDGSF HLESKLTVDK SRWQQGNVFS CSVMHEGLHN HYTQKSLSLS PGKVDGASSH VNVSSPSVQD IHVKLQESGP GLVQPSQSLS LTCTVSGFSL TDYGVHWVRQ SPGKGLEWLG VIWSGGGTAY NTALISRLNI YRDNSKNQVF LEMNSLQAED TAMYYCARRG SYPYNYFDAW GCGTTVTVSS GGGGSGGGGS GGGGSQAVVI QESALTTPPG ETVTLTCGSS TGAVTASNYA NWVQEKPDHC FTGLIGGHNN RPPGVPARFS GSLIGDKAAL TIAGTQTEDE AIYFCALWYS DHWVIGGGTR LTVLG 171. CD123-HuV1-10C4 Light Chain variable domain sequence (SEQ ID NO: 171) DIVMTQSPDS LAVSLGERAT INCKSSQSLL SSGTRKNYLA WYQQKPGQPP KLLIYWASTR ESGVPDRFSG SGSGTDFTLT ISSLQAEDVA VYYCKQSYIL FTFGQGTKLE IK 172. CD123-HuV1-10C4 Light Chain CDR1 (SEQ ID NO: 172) KSSQSLLSSGTRKNYLAWY 173. CD123-HuV1-10C4 Light Chain CDR2 (SEQ ID NO: 173) LLIYWASTRES 174. CD123-HuV1-10C4 Light Chain CDR3 (SEQ ID NO: 174) KQSYILF 175. CD123-HuV1-10C4 Heavy Chain variable domain sequence (SEQ ID NO: 175) QVQLQESGPG LVKPSETLSL TCTVSGFSLT TYDINWIRQP PGKGLEWIGV IWTGGGTNYN SAFMSRVTIS

VDTSKNQFSL KLSSVTAADT AVYYCARADT YHYALDFWGQ GTLVTVSS

176. CD123-HuV1-10C4 Heavy Chain CDR1 (SEQ ID NO: 176) TVSGFSLTTYDIN

177. CD123-HuV1-10C4 Heavy Chain CDR2 (SEQ ID NO: 177) WIGVIWTGGGTNYNSAFMS

178. CD123-HuV1-10C4 Heavy Chain CDR3 (SEQ ID NO: 178) ARADTYHYALDF

179. CD123-HuV2-10C4 Light Chain variable domain sequence (SEQ ID NO: 179) DIVMTQSPDS LAVSLGERAT INCKSSQSLL SSGTRKNYLA WYQQKPGQPP KLLIYWASTR ESGVPDRFSG SGSGTDFTLT ISSLQAEDVA VYYCKQSYIL FTFGQGTKLE IK 180. CD123-HuV2-10C4 Light Chain CDR1 (SEQ ID NO: 180) KSSQSLLSSGTRKNYLAWY 181. CD123-HuV2-10C4 Light Chain CDR2 (SEQ ID NO: 181) LLIYWASTRES 182. CD123-HuV2-10C4 Light Chain CDR3 (SEQ ID NO: 182) KQSYILFT 183. CD123-HuV2-10C4 Heavy Chain variable domain sequence (SEQ ID NO: 183) QVQLQESGPG LVKPSETLSL TCTVSGFSLT TYDWSWIRQP PGKGLEWIGY IWTGGGTNYN PSLKSRVTIS VDTSKNQFSL KLSSVTAADT AVYYCVRGDT YHYALDFWGQ GTLVTVSS 184. CD123-HuV2-10C4 Heavy Chain CDR1 (SEQ ID NO: 184) TVSGFSLTTYDWSWY 185. CD123-HuV2-10C4 Heavy Chain CDR2 (SEQ ID NO: 185) WIGYIWTGGGTNYNPSLKS 186. CD123-HuV2-10C4 Heavy Chain CDR3 (SEQ ID NO: 186) VRGDTYHYALDF 187. Hs_CD123_mmFc (Human immunogen for antibody campaign) (SEQ ID NO: 187) ADYSMPAVNNSYCOFGAISLCEVTNYTVRVANPPFSTWILFPENSGKPWAGAENLT CWIHDVDFLSCSWAVGPGAPADVOYDLYLNVANRRQQYECLHYKTDAQGTRIGCR FDDISRLSSGSQSSHILVRGRSAAFGIPCTDKFVVFSQIEILTPPNMTAKCNKTHSFMH WKMRSHFNRKFRYELQIQKRMQPVITEQVRDRTSFOLLNPGTYTVQIRARERVYEFL SAWSTPORFECDQEEGANTRAGGGSGCKPCICTVPEVSSVFIFPPKPKDVLTITLTPK VTCVVVDISKDDPEVQFSWFVDDVEVHTAQTQPREEQFNSTFRSVSELPIMHQDWL NGKEFKCRVNSAAFPAPIEKTISKTKGRPKAPQVYTIPPPKEQMAKDKVSLTCMITDF FPEDITVEWQWNGQPAENYKNTQPIMNTNGSYFVYSKL NVQKSNWEAGNTFTCSV LHEGLHNHHTEKSLSHSPGK BOLD=signal peptide, underline=human CD123 ECD, italics=linker region, regular font=mouse Fc region 188. Mf_CD123_mmFc (monkey immunogen for antibody campaign)) (SEQ ID NO: 188) MTLLWLTLLLVATPCLLRTKEDPNAPIRNLRMKEKAQQLMWDLNRNVTDVECIK GTDYSMPAMNNSYCQFGAISLCEVTNYTVRVASPPFSTWILFPENSGTPRAGAENLT CWVHDVDFLSCSWVVGPAAPADVQYDLYLNNPNSHEQYRCLHYKTDARGTQIGC RFDDIAPLSRGSQSSHILVRGRSAAVSIPCTDKFVFFSQIERLTPPNMTGECNETHSFM HWKMKSHFNRKFRYELRIQKRMQPVRTEQVRDTTSFQLPNPGTYTVQIRARETVYE FLSAWSTPQRFECDQEEGASSRAGGGSGCKPCICTVPE- VSSVFIFPPKPKDVLTITLTP KVTCVVVDISKDDPEVQFSWFVDDVEVHTAQTQPREEQFNSTFRSVSELPIMHQDW LNGKEFKCRVNSAAFPAPIEKTISKTKGRPKAPQVYTIPPPKEQMAKDKVSLTCMITD FFPEDITVEWQWNGQPAENYKNTQPIMNTNGSYFVYSKL NVQKSNWEAGNTFTCS VLHEGLHNHHTEKSLSHSPGK BOLD=signal peptide, underline=human CD123 ECD, italics=linker region, regular font=mouse Fc region 189. Hs_CD123 (human cell based immunogen)) (SEQ ID NO: 189) ATGGTCCTCCTTTGGCTCACGCTGCTCCTGATCGCCCTGCCCTGTCTCCTGCAAAC GAAGGAAGATCCAAACCCACCAATCACGAACCTAAGGATGAAAGCAAAGGCTC AGCAGTTGACCTGGGACCTTAACAGAAATGTGACCGATATCGAGTGTGTTAAAG ACGCCGACTATTCTATGCCGGCAGTGAACAATAGCTATTGCCAGTTTGGAGCAA TTTCCTTATGTGAAGTGACCAACTACACCGTCCGAGTGGCCAACCCACCATTCTC CACGTGGATCCTCTTCCCTGAGAACAGTGGGAAGCCTTGGGCAGGTGCGGAGAA TCTGACCTGCTGGATTCATGACGTGGATTTCTTGAGCTGCAGCTGGGCGGTAGGC CCGGGGGCCCCCGCGGACG TCCAGTACGACCTGTACTTGAACGTTGCCAACAGG CGTCAACAGTACGAGTGTCTTCACTACAAAACGGATGCTCAGGGAACACGTATC GGGTGTCGTTTCGATGACATCTCTCGACTCTCCAGCGGTTCTCAAAGTTCCCACA TCCTGGTGCGGGGCAGGAGCGCAGCCTTCGGTATCC CCTGCACAGATAAGTTTG TCGTCTTTTCACAGATTGAGATATTAACTCCACCCAACATGACTGCAAAGTGTAA TAAGACACATTCCTTTATGCACTGGAAAA TGAGAAGTCATTTCAATCGCAAATTT CGCTATGAGCTTCAGATACAAAAGAGAATGCAGCCTGTAATCACAGAACAGGTC AGAGACAGAACCTCCTTCCAG CTACTCAATCCTGGAACGTACACAGTACAAATA AGAGCCCGGGAAAGAGTGTATGAATTCTTGAGCGCCTGGAGCACCCCCCAGCGC TTCGAGTGCGACCAGGAGGAGGGCGCAAACACACGTGCCT GGCGGACGTCGCTG CTGATCGCGCTGGGGACGCT GCTGGCCCTGGTCTGTGTCTTCGTGATCTGCAGAA GGTATCTGGTGATGCAGAGACTCTTTCCCCGCATCCCTCACATGAAAGACCCCAT CGGTGACAGCTTCCAAAACGACAAGCTGGTGGTCTGGGAGGCGGGCAAAGCCG GCCTGGAGGAGTGTCTGGTGACTGA AGTACAGGTCGTGCAGAAAACTTGA 190. Hs_CD123 (human cell based immunogen)) (SEQ ID NO: 190) ADYSMPAVNNSYCQFGAISLCEVTNYTVRVANPPFSTWILFPENSGKPWAGAENLT CWIHDVDFLSCSWAVGPGAPADVOYDLYLNVANRRQQYECLHYKTDAQGTRIGCR FDDISRLSSGSQSSHILVRGRSAAFGIPCTDKFVVFSQIEILTPPNMTAKCNKTHSFMH WKMRSHFNRKFRYELQIQKRMQPVITE-QVRDRTSFOLLNPGTYTVQIRARERVYEFL SAW-STPQRFECDQEEGANTRAWRTSLLIALGTLLA-LVCVFVICRRYLVMQRLFPRIP HMKDPIGDSFQNDKLVVWEAGKAGLEECLVTE-VQVVQKT BOLD=signal peptide, underline=human CD123 ECD, regular font=human CD123 transmembrane (TM) domain and intracellular (IC) domain 191. Mm_CD33_Hs_CD123 (mouse/human chimera cell based immunogen)) (SEQ ID NO: 191) ATGCTCTGGCCGCTGCC CCTCTTTCTCCTCTGCGCGGG-GAGTCTCGCCCAGGACC TTGAAT-TTCAGCTTGTAGCGCCT-GAGTCCGTAACGGTAGAAGAGGGTCTCTGTGT TCACGTACCGTGCTCAGTGTTTACCCAAGTAT-TAAGCTCACATTGGGGCCCGTG ACCG-GATCCTGGCTTCGCAAGGGTGTTTCATTGCAT-GAAGACAGTCCTGTCGCTA CCTCCGACCCGAGACAACTCGTTCAAAAAGC-TACACAGGGTAGATTTCAGCTGC TCGGA-GACCCCCCAGAAACATGACTGCAGTCTGTTT-ATTAGAGACGCTCAAAAAA ATGACACAGGAATGTACTTTTTCCGGGTGGT TCGAGAACCGTTCGTACGATACTC CTATAAGAAGTCCCAGTTGTCCCTCCATGT-CACAGGAGGTGGAGGATCAGGCGG TGGTGG-GAGTGGAGGTGGAGGGTCTCCTTGCACAGA-TAAATTCGTGGTATTTTCA CAAATAGAGATACTCACGCCACCGAA-CATGACGGCAAAGTGCAATAAAACCCA CTCTTTCATGCATTGGAAAATGCGAAGC-CACTTTAACAGGAAATTTCGGTACGA GTTGCAAATCCAGAAAA GAATGCAACCAGTAAT-CACCGAGCAAGTGCGCGACA GAACTTCATTC-CAACTTTTGAATCCAGGCACGTACACGGTA-CAAATACGGGCTA GAGAGCGGGTTTACGAATTTCTTTCCGCATG-GAGCACCCCCCAGCGCTTCGAGTG CGACCAG-GAGGAGGGCGCAAACACACGTG CCTGGCGGACGTCGCTGCTGATCGC GCTGGGGACGCTGCTGGC CCTGGTCTGTGTCTTCGT-GATCTGCAGAAGGTATCTG GTGATGCAGA-GACTCTTTCCCCGCATCCCTCACATGAAA-GACCCCATCGGTGAC AGCTTCCAAAACGACAAGCTGGTGGTCTGG-GAGGCGGGCAAAGCCGGCCTGGA GGAGTGTCTGGTGACTGAAGTA-CAGGTCGTGCAGAAAACTTGA 192. Mm_CD33_Hs_CD123 (mouse/human chimera cell based immunogen)) (SEQ ID NO: 192) MLWPLPLFLLCAGSLAQDLEF QLVAPESVTVEEGLCVHVPCSVFYPSIKLTLGPVT GSWLRKGVSLHEDSP-VATSDPRQLVQKATQGRFQLLGDPQKHDCSL-FIRDAQKNDT GMYFFRVVREPFVRYSYKKSQ LSLHVTGGGGSGGGGSGGG GSPCTDKFVVFSQIEIL TPPNMTAKCNKTHSFMHWKMRSHFNRKFRY-ELQIQKRMQPVITEQVRDRTSFQLLN PGTYTVQIRARERVYEFLSAWSTPQRFECDQEE-GANTRAWRTSLLIALGTLLALVCV FVICRRYL-VMQRLFPRIPHMKDPIGDSFQNDKL VVWEAGKAGLEECLVTEVQVVQK T BOLD=signal peptide, underline=mouse CD33 V-set domain, italics=linker, regular font=human CD123 ECD domain 3, TM and IC domains sequenc 193. Hs_CD123_6His-Avi (human affinity measurements, ELISA and biacore reagent)) (SEQ ID NO: 193) MVLLWLTLLLIALPCLLQTKEDPNP-PITNLRMKAKAQQLTWDLNRNVTDIECVKD ADYSMPAVNNSYCQFGAISLCEVTNYTVR-VANPPFSTWILFPENSGKPWAGAENLT CWIHDVDFLSCSWAVGPGAPADVOYDLYLN-VANRRQQYECLHYKTDAQGTRIGCR FDDIS-RLSSGSQSSHILVRGRSAAFGIPCTDKFVVFSQIE-ILTPPNMTAKCNKTHSFMH WKMRSHFNRKFRYELQIQKRMQPVITE-QVRDRTSFQLLNPGTYTVQIRARERVYEFL SAW-STPQRFECDQEEGANTRAGSHHHHHHGSGLN-DIFEAQKIEWHE BOLD=signal peptide, underline=human CD123 ECD, italics=linker region, regular font=6-histidine tag, italics=linker region, BOLD and underline=Avidin tag 194. Mf_CD123_6His-Avi (mouse affinity measurements, ELISA and biacore reagent)) (SEQ ID NO: 194) MTLLWLTLLLVATPCLLRTKEDPNA-PIRNLRMKEKAQQLMWDLNRNVTDVECIK GTDYSMPAMNNSYCQFGAISLCEVTNYTVR-VASPPFSTWILFPENSGTPRAGAENLT CWVHDVDFLSCSWVVGPAAPADVQYD-LYLNNPNSHEQYRCLHYKTDARGTQIGC RFD-DIAPLSRGSQSSHIL VRGRSAAVSIPCTDKFVFF-SQIERLTPPNMTGECNETHSFM HWKMKSHFNRKFRYELRIQKRMQPVRTE-QVRDTTSFQLPNPGTYTVQIRARETVYE FLSAW-STPQRFECDQEEGASSRAGSHHHHHHGSGLN-DIFEAQKIEWHE BOLD=signal peptide, underline=human CD123 ECD, italics=linker region, regular font=6-histidine tag, italics=linker region, BOLD and underline=Avidin tag 195. 123-ATX1B2_Hs_IgG1_HC-fully human recombinant antibody heavy chain (nucleotide sequence) (SEQ ID NO: 195)
ATGGAGACAGATACTTTGCTCCTTTGGG TACTCTTGCTGTGGGTTCCCGGT AGCACCGGCCAGGTA-CAACTGGTGCAATCTGGGGCCGAAGT-CAAGAAGCCCGGT GCGTCCGTCGAAGTAT-CATGTAAAGCCTCAGGATA CACGTTCACCGGATATTAC ATCCAT-TGGGTCAGACAAGCACCTGGACAAGGACTT-GAATGGATGGGCTGGATA AACCCAAAT-TCCGGCGGTACAAACTATGC TCAAAAGTTCCAAGGGAGAGTGACT ATGACTTGGGACACGTCTATTTC-CACAGCTTTTATG-GAGTTGTCTAGGTTGCGAA GCGATGA-TACTGCGGTTTACTCCTGT GCGCGGGATAGGGGGGGACCATATTTCG ATTATTGGGGACAGGGTA-CACTTGTAATCGTCTCCTCCGCTAGCAC-CAAAGGAC CCTCCGTCTTTCCGCT CGCGCCGAGCAGCAAGTC-CACGAGCGGGGGGACAGCCG CCCTTGGGTGTCTGGTCAAGGATTAT-TTTCCTGAGCCCGTTACTGTCTCCTGGAA TAGCGGTGCCTTGACTTCTGGGGTACAT-ACCTTCCCGGCGGTTTTGCAATCATCA GGACTGTATAGCCTCTCTAGCGTTGT AACGGTACCATCTTCATCACTTGGCACAC AAACATATATTTGTAATGTAAAT-
CACAAACCTT-
CAAATACTAAAGTTGACAAAA AAGTG-
GAGCCGAAGAGCTGTGA
TAAAACGCAT-
ACTTGCCCGCCTTGCCCCGCTC CAGAAT-
TGCTGGGCGGGCCGTCTGTGTTCCTCTTCC-
CACCGAAACCGAAGGATA
CGCTGATGATAAGTCGAACGCCCGAAGTAA-
CATGCGTGGTTGTTGATGTAAGCC ACGAA-
GATCCGGAAGTAAAGTTCAACTGGTACGTA-
GATGGAGTAGAAGTGCATA
ACGCGAAAACTAAGCCCCGCGAG-
GAGCAATATAATTCAACCTATCGGGTTGTTA
GTGTGCTCACCGTTCTCCATCAGGATTGGCT-
TAACGGGAAAGAGTATAAGTGCA AGGT-
TAGCAATAAAGCATTGCCAGCACC-
TATAGAGAAGACAATTAGCAAAGCG
AAGGGACAGCCACGAGAGCCCCAAGTCTA-
CACGCTGCCTCCCAGCCGCGACGAG
TTGACGAAGAATCAAGTGTCACTCA-
CATGTCTTGTCAAGGGATTCTATCCCTCAG
ATATTGCAGTAGAATGG-
GAGTCTAATGGACAACCAGAGAACAAC-
TATAAAACTA CTCCACCGGTGCTTGA-
TAGTGACGGTAGTTTTTTCCT
TTATAGTAAGCTGACTGTC
GATAAGAGTCGCTGGCAACAGG-
GAAATGTTTTTTCTTGTAGTGTTATGCAT-
GAAG CACTTCATAACCATTA-
CACACAAAAGTCTCTGTC
ACTTTCCCCTGGCAAATGA 196. 123-ATX1B2_Hs_IgG1_HC—fully human recombinant antibody heavy chain (amino acid sequence) (SEQ ID NO: 196)

METDTLLLWVLLLWVPGSTGQVOLVOS-
GAEVKKPGASVEVSCKASGYTF
TGYYIHWVRQAPGQ-
GLEWMGWINPNSGGTNYAQKF
QGRVTMTWDTSISTAFMELS RLRSDDTAVYS-
CARDRGGPYFDYWGQGTLVIVSSAS-
TKGPSVFPLAPSSKSTSGGTA ALGCLVKDYF-
PEPVTVSWNSGALTSGVHTFPAVLQSS
GLYSLSSVVTVPSSSLGTQT
YICNVNHKPSNTKVDKKVEPKSCDKTH-
TCPPCPAPELLGGPSVFLFPPKPKDTLMISR
TPEVTCVVVDVSHEDPE-
VKFNWYVDGVEVHNAKTKPREEQYN-
STYRVVSVLTVLH QDWLNGKEYKCKVSNKA-
LPAPIEKTISKAKGQPRE
PQVYTLPPSRDELTKNQVSLTC LVKGFYPS-
DIAVEWESNGQPENNYKTTPPVLDSDGSFFLY-
SKLTVDKSRWQQGNVF SCSVMHEALHN-
HYTQKSLSLSPGK

BOLD=signal peptide, underline=antibody variable region, regular font=antibody constant region 197. 123-ATX1B2_Hs_IgG4_HC—fully human recombinant antibody heavy chain (nucleotide sequence) (SEQ ID NO: 197)

ATGGAGACAGATACTTTGCTCCTTTGGGTACT
CTTGCTGTGGGTTCCCGGT
AGCACCGGCCAGGTA-
CAACTGGTGCAATCTGGGGCCGAAGT-
CAAGAAGCCCGGT GCGTCCGTCGAAGTAT-
CATGTAAAGCCTCAGGATAC
ACGTTCACCGGATATTAC ATCCATTGGGTCA-
GACAAGCACCTGGACAAGGACTTGAATG-
GATGGGCTGGATA AACCCAAAT-
TCCGGCGGTACAAACTATGC
TCAAAAGTTCCAAGGGAGAGTGACT
ATGACTTGGGACACGTCTATTTC-
CACAGCTTTTATG-
GAGTTGTCTAGGTTGCGAA GCGATGA-
TACTGCGGTTTACTCCTGTGCG
CGGGATAGGGGGGGACCATATTTCG ATTAT-
TGGGGACAGGGTA-
CACTTGTAATCGTCTCCTCCGCTAGCAC-
CAAAGGAC
CCTCCGTCTTTCCGCTCGCGCCGTGCTCTC-
GATCCACGAGCGAGTCTACGGCGGC
CTTGGGCTGTCTCGTGAAAGACTAT-
TTCCCAGAGCCAGTGACCGTTTCCTGGAAC
TCCGGAGCGCTCACATCAGGTGTGCAT-
ACCTTTCCAGCCGTACTTCAATCTTCAG
GGCTGTATAGCTTGTCCTCT
GTCGTGACCGTACCCTCCAGT
TCTCTCGGGACAAA GACC-
TATACCTGTAACGTAGACCATAAGCCATC-
CAATACCAAAGTAGATAAGAG GGTG-
GAATCTAAATATGGACCGCCTTGTC
CGCCGTGCCCGGCTCCTGAGTTCCTT
GGAGGGCCGTCCGTCTTTCTGT
TTCCCCCTAAACCTAAGGACACCCTGATGA-
TAA GTAGGACGCCG-
GAAGTAACCTGTGTCGTGGTTGATGTGT-
CACAGGAAGACCCGG
AGGTACAATTTAATTGGTACGTCGATG-
GAGTCGAGGTGCATAATGCGAAAACCA AGC-
CACGAGAGGAGCAATTCAACAGCACC-
TACCGAGTAGTTTCAGTCTTGACTG
TGCTGCACCAAGACTGGCT-
GAATGGCAAGGAGTA-
CAAATGCAAGGTCAGTAATA AAGGAT-
TGCCGTCTTCAATAGAGAA
GACTATCAGTAAGGCGAAGGGACAACCTC
GCGAGCCTCAGGTATA-
CACTTTGCCGCCCAGC-
CAAGAAGAAATGACGAAGAACC
AAGTCTCTTTGACTTGCCTGGT-
CAAAGGCTTCTACCCCTCTGA-
TATAGCAGTCGA ATGGGAGTCCAACGGT-
CAACCGGAGAACAATTAT
AAGACAACTCCACCTGTGCT TGATTCA-
GACGGCTCTTTTTTCTTGTATAGCCGCCT-
TACCGTAGACAAGAGTCGA TGGCAG-
GAAGGTAATGTATTTTC
TTGTAGTGTAATGCACGAGGCACTTCAT-
AATC ACTACACACAAAAGTCTCTGT-
CACTTTCCCTGGGCAAATGA 198. 123-ATX1B2_Hs_IgG4_HC—fully human recombinant antibody heavy chain (amino acid sequence) (SEQ ID NO: 198)

METDTLLLWVLLLWVPGSTGQVOLVOS-
GAEVKKPGASVEVSCKASGYTF
TGYYIHWVRQAPGQ-
GLEWMGWINPNSGGTNYAQKFQ
GRVTMTWDTSISTAFMELS RLRSDDTAVYS-
CARDRGGPYFDYWGQGTLVIVSSAS-
TKGPSVFPLAPCSRSTSESTA ALGCLVKDYF-
PEPVTVSWNSGALTSGVHTFP
AVLQSSGLYSLSSVVTVPSSSLGTKT
YTCNVDHKPSNTKVDKRVESKYGPPCPPCPA-
PEFLGGPSVFLFPPKPKDTLMISRTPE
VTCVVVDVSQEDPE-

VQFNWYVDGVEVHNAKTKPREEQFN-
STYRVVSVLTVLHQD
WLNGKEYKCKVSNKGLPSSIEK
TISKAKGQPREPQVYTLPPSQEEMTKNQVSLT-
CLV KGFYPSDIA VEWESNGQPEN-
NYKTTPPVLDSDGSFFLY-
SRLTVDKSRWQEGNVFSCS
VMHEALHNHYTQKSLSLSLGK

BOLD=signal peptide, underline=antibody variable region, regular font=antibody constant region 199. 123-ATX1B2_Hs_IgK_LC—fully human recombinant antibody light chain (SEQ ID NO: 199)

ATGAGAGCCTGGATCTTCTTCCTGCTT
TGTTTGGCAGGACGAGCGCTAGC CGATATA-
CAGATGACGCAATCCCCTTCTA
GCTTGTCAGCTAGTGTTGGCGACCGA
GTAACAATCACGTGTCAAGCGAGTCAAGA-
CATAACCAACTACCTGAACTGGTAT
CAACAAAAACCTGGAAAGGCACC-
CAAACTTCAAATTTACGATGCGAGCAATCTC
GAGACGGGCGTTCCCAGCAGATTTTCAG-
GATCAGGCTCAGGCACCGACTTTACT
TTCACTATCAGTTCCTTGCAACCCGAGGA-
CATCGCCACATACTATTGTCAACAAC
ACGATGACTTGCCCCTCACTTTCG-
GAGGTGGCACGAAGGTCGAGATCAAACGTA
CGGTAGCTGCGCCTAGCGTGTTTAT-
TTTTCCGCCCTCTGACGAACAACTCAAAAG
TGGCACTGCCTCTGTAGTCTGTCTCCT-
GAACAATTTTTATCCAAGGGAAGCTAAG
GTACAGTGGAAAGTCGATAACGCGCTC-
CAAAGTGGCAACAGTCAAGAATCTGTAACG-
GAGCAAGATAGTAAAGACAGCACTTA-
CAGCTTGAGCAGCACACTCACATTG
TCCAAGGCCGACTACGAAAAACAT-
AAAGTGTACGCCTGTGAGGTAACACACCAG
GGTCTGAGCAGCCCAGTGACGAAGTCATT-
TAATCGCGGTGAGTGCTGA 200. 123-ATX1B2_Hs_IgK_LC—fully human recombinant antibody light chain (SEQ ID NO: 200)

MRAWIFFLLCLAGRALADIQMTQSPSSL-
SASVGDRVTITCQASQDITNYLN
WYQQKPGKAPKLQIYDASN-
LETGVPSRFSGSGSGTDFTFTISSLQPEDI-
ATYYCQQHD
DLPLTFGGGTKVEIKRTVAAPSVFIFPPSD-
EQLKSGTASVVCLLNNFYPREAKVQWK
VDNALQSGNSQESVTEQDSKDSTYSLSSTLTL-
SKADYEKHKVYACEVTHQGLSSPV
TKSFNRGEC

BOLD=signal peptide, underline=antibody variable region, regular font=antibody constant region 201. 123-ATX1B5_Hs_IgG1_HC fully human recombinant antibody heavy chain (SEQ ID NO: 201)

ATGGAGACAGA-
TACTTTGCTCCTTTGGGTTTTGT
TGCTGTGGGTTCCAGGA TCCACGGGG-
GAAGTACAGCTGGTTGAGTCTGGAGGCG-
GATTGGTTCAGCCTGGG
GGGTCCCTCCGCCTTTCCTGTGC-
TACCAGCGGATTTACATTTTCTAACTACGA-
TAT GCATTGGGTCCGACAAGTGAC
TGGCAAGGGCCTTGAATGGGTCTCAGGCAT-
TGG CATAGCTGGTGACACATAC-
TACCCTGGCTCCGTAAAAGGAAGGTTTACT-
ATTTCA
AGAGAGGACGCAAAGAACTCTCTCTACCTC-
CAAATGAATTCTCTGCGAGCAGAG
GATACTGCTGTGTATTATTGTGCTA-
CAGAGCGCGGGAGTAGCAGTTGGTATAATT
ATTTCGACTATTGGGGCCAGGGCAC
TCTGGTAACGGTGTCTAGCGCTAGCACCA
AAGGACCCTCCGTCTTTCCGCTCG
CGCCGAGCAGCAAGTC-
CACGAGCGGGGGGA
CAGCCGCCCTTGGGTGTCTGGTCAAGGATT-
ATTTTCCTGAGCCCGTTACTGTCTC CTG-
GAATAGCGGTGCCTTGACTTCTGGGGTACAT-
ACCTTCCCGGCGGTTTTGCAA
TCATCAGGACTGTATAGCCT
CTCTAGCGTTGTAACGGTACCATCTTCAT-
CACTTG GCACACAAACATATAT-
TTGTAATGTAAATCACAAACCTT-
CAAATACTAAAGTTG
ACAAAAAAGTGGAGCCGAAGAGCTGTGA-
TAAAACGCATACTTGCCCGCCTTGCC
CCGCTCCAGAAT-
TGCTGGGCGGGCCGTCTGTGTTCCTCTTCC-
CACCGAAACCGAA GGATACGCTGATGA-
TAAGTCGAACGCCCGAAGTAA
CATGCGTGGTTGTTGATGT AAGCCACGAA-
GATCCGGAAGTAAAGTTCAACTGGTACGTA-
GATGGAGTAGAAG TGCAT-
AACGCGAAAACTAAGCCCCG
CGAGGAGCAATATAATTCAACCTATCGGG
TTGTTAGTGTGCTCACCGTTCTCCATCAG-
GATTGGCTTAACGGGAAAGAGTATAA
GTGCAAGGTTAGCAATAAAGCAT-
TGCCAGCACCTATAGAGAAGACAATTAGCAA
AGCGAAGGGACAGCCACGAGAGCCC-
CAAGTCTACACGCTGCCTCCCAGCCGCGA
CGAGTTGACGAAGAATCAAGTGTCACTCA-
CATGTCTTGTCAAGGGATTCTATCCC TCAGA-
TATTGCAGTAGAATGG-
GAGTCTAATGGACAACCAGAG
AACAACTATAAA ACTACTCCACCGGTGCTT-
GATAGTGACGGTAGTTTTTTCCTT-
TATAGTAAGCTGA CTGTCGA-
TAAGAGTCGCTGGCAACAGGGA
AATGTTTTTTCTTGTAGTGTTATGCA
TGAAGCACTTCATAACCATTA-
CACACAAAAGTCTCTGT-
CACTTTCCCCTGGCAAA TGA 202. 123-ATX1B5_Hs_IgG1_HC fully human recombinant antibody heavy chain (SEQ ID NO: 202)

METDTLLLWVLLLWVPGSTGEVOLVESGG-
GLVQPGGSLRLSCATSGFTFS
NYDMHWVRQVTGKGLEWVSGI-
GIAGDTYYPGSVKGRFTISREDAKNSLY-
LOMNSL RAEDTAVYYCATERGSSSWYN-
YFDYWGQGTLVTVSSASTKGPSVFPLAPSSKST-
SG
GTAALGCLVKDYFPEPVTVSWNSGALT-
SGVHTFPAVLQSSGLYSLSSVVTVPSSSLG
TQTYICNVNHKPSNTKVDKKVEPKSCDKTH-
TCPPCPAPELLGGPSVFLFPPKPKDTL MISRT-
PEVTCVVVDVSHEDPE-
VKFNWYVDGVEVHNAKTKPRE
EQYNSTYRVVSVL
TVLHQDWLNGKEYKCKVSNKALPA-
PIEKTISKAKGQPREPQVYTLPPSRDELTKNQ
VSLTCLVKGFYPSDIA VEWESNGQPEN-
NYKTTPPVLDSDGSFFLYSKLTVDKSRWQ
QGNVFSCSVMHEALHNHYTQKSLSLSPGK

BOLD=signal peptide, underline=antibody variable region, regular font=antibody constant region 203. 123-ATX1B5_Hs_IgG4_HC fully human recombinant antibody heavy chain (SEQ ID NO: 203)

ATGGAGACAGATACTTTGCTCCTTTGGGTTTT GTTGCTGTGGGTTCCAGGA TCCACGGGG-GAAGTACAGCTGGTTGAGTCTGGAGGCG-GATTGGTTCAGCCTGGG GGGTCCCTCCGCCTTTCCTGTGC-TACCAGCGGATTTACATTTTCTAACTACGA-TAT GCATTGGGTCCGACAAGT GACTGGCAAGGGCCTTGAATGGGTCTCAGG-CATTGG CATAGCTGGTGACACATAC-TACCCTGGCTCCGTAAAAGGAAGGTTTACT-ATTTCA AGAGAGGACGCAAAGAACTCTCTCTACCTC-CAAATGAATTCTCTGCGAGCAGAG GATACTGCTGTGTATTATTGTGCTA-CAGAGCGCGGGAGTAGCAGTTGGTATAATT ATTTCGACTAT-TGGGGCCAGGGCACTCTGGTAA CGGTGTCTAGCGCTAGCACCA AAGGACCCTCCGTCTTTCC GCTCGCGCCGTGCTCTCGATC-CACGAGCGAGTCTAC GGCGGCCTTGGGCTGTCTCGTGAAAGACT-ATTTCCCAGAGCCAGTGACCGTTTCC TGGAACTCCGGAGCGCTCACATCAGGTGTG-CATACCTTTCCAGCCGTACTTCAAT CTTCAGGGCTGTATAGCTTGTCCT CTGTCGTGACCGTACCCTCCAGTTCTCTCGG GACAAAGACCTATACCTGTAACGTAGACCAT-AAGCCATCCAATACCAAAGTAGA TAAGAGGGTGGAATCTAAATATGGACCGCC TTGTCCGCCGTGCCCGGCTCCTGA GTTCCTTGGAGGGCCGTCCGTCTTTCTGTTT CCCCCTAAACCTAAGGACACCCTG ATGA-TAAGTAGGACGCCG-GAAGTAACCTGTGTCGTGGTTGATGTGT-CACAGGAA GACCCGGAGGTACAATTTAATTGGTACGTC-GATGGAGTCGAGGTGCATAATGCG AAAAC-CAAGCCACGAGAGGAGCAATT-CAACAGCACCTACCGAGTAGTTTCAGTC TTGACTGTGCTGCACCAAGACTGGCT-GAATGGCAAGGAGTACAAATGCAAGGTC AGTAATAAAGGATTGCCGTCTT-CAATAGAGAAGAC-TATCAGTAAGGCGAAGGGA CAACCTCGCGAGCCTCAGGTATA-CACTTTGCCGCCCAGC-CAAGAAGAAATGACG AAGAAC-CAAGTCTCTTTGACTTGCC TGGTCAAAGGCTTCTACCCCTCTGATATAG CAGTCGAATGGGAGTCCAACGGTCAACCG-GAGAACAATTATAAGACAACTCCAC CTGTGCTTGATTCA-GACGGCTCTTTTTTCTTGTATAGCCGCCT-TACCGTAGACAA GAGTCGATGGCAG-GAAGGTAATGTATTTTCTTGT AGTGTAATGCACGAGGCACTT CATAATCAC-TACACACAAAAGTCTCTGT-CACTTTCCCTGGGCAAATGA 204. 123-ATX1B5_Hs_IgG4_HC fully human recombinant antibody heavy chain (SEQ ID NO: 204)

METDTLLLWVLLLWVPGSTGEVOLVESGG-GLVQPGGSLRLSCATSGFTFS NYDMHWVRQVTGKGLEWVSGI-GIAGDTYYPGSVKGRFTISREDAKNSLY-LOMNSL RAEDTAVYYCATERGSSSWYN-YFDYWGQGTLVTVSSASTKGPSVFP LAPCSRSTSE STAALGCLVKDYF-PEPVTVSWNSGALTSGVHTFPAVLQSSGLYS-LSSVVTVPSSSLG TKTYTCNVDHKPSNTKVDKRVESKY-GPPCPPCPAPEFLGGPSVFLFPPKPKDTLMISR TPEVTCVVVDVSQEDPE-VQFNWYVDGVEVHNAKTKPREEQFN-STYRVVSVLTVLH QDWLNGKEYKCKVSNKGLPS SIEKTISKAKGQPREPQVYTLPPSQEEMT-KNQVSLTC LVKGFYPSDIA VEWESNGQPEN-NYKTTPPVLDSDGSFFLY-SRLTVDKSRWQEGNVFS CSVMHEALHNHYTQKSLSLSLGK

BOLD=signal peptide, underline=antibody variable region, regular font=antibody constant region 205. 123-ATX1B5 fully human recombinant antibody light chain (SEQ ID NO: 205)

ATGAGAGCCTG-GATCTTCTTCCTGCTTTGTTTGG CAGGACGAGCGCTAGC CGACATC-CAAATGACTCAATCACCGTC-TACCTTGTCAGCAAGCGTGGGGGACCG CGT-TACGATAACTTGCAGAGCCAGTC AGAGCATAAGCAGTTGGCTGGCATGGTA TCAGCAGAAGCCCGGAAAAGCACCCAA-GATCCTGATTTACAAAGCCTCAAGCCT CGAATCTGGTGTCCCAAGTCGGTTTAGTG-GAAGCGGTTCTGGTACAGAGTTTACC CTCACAATTAGTAGTCTTCAACCCGATGAT-TTTGCTACCTACTATTGTCAGCAGT ATAAT-TCTTATTGGACTTTCGGACAGG-GAACAAAGGTCGAAATCAAACGTACGG TAGCTGCGCCTAGCGTGTTTAT-TTTTCCGCCCTCTGACGAACAACT-CAAAAGTGG CACTGCCTCTGTAGTCTGTCTCCTGAACAAT-TTTTATCCAAGGGAAGCTAAGGTA CAGTG-GAAAGTCGATAACGCGCTC-CAAAGTGGCAACAGTCAAGAATCTGTAACG GAGCAAGATAGTAAAGACAGCACTTA-CAGCTTGAGCAGCACACTCACATTGTCC AAGGCCGACTACGAAAAACAT-AAAGTGTACGCCTGT-GAGGTAACACACCAGGG TCT-GAGCAGCCCAGTGACGAAG TCATTTAATCGCGGTGAGTGCTGA 206. 123-ATX1B5 fully human recombinant antibody light chain (SEQ ID NO: 206)

MRAWIFFLLCLAGRALADIQMTQSPSTL-SASVGDRVTITCRASQSISSWLA WYQQKPGKAPKIL-IYKASSLESGVPSRFSGSGSG TEFTLTISSLQPDDFATYYCQQYN SYWTFGQGTKVEIKRTVAAPSVFIFPPSD-EQLKSGTASVVCLLNNFYPREAKVQWKV DNALQSGNSQESVTEQDSKDSTYSLSSTLTL-SKADYEKHKVYACEVTHQGLSSPVT KSFNRGEC

BOLD=signal peptide, underline=antibody variable region, regular font=antibody constant region 207. 123-ATX1D9_Hs_IgG1_HC-fully human recombinant antibody heavy chain (SEQ ID NO: 207)

ATGGAGACAGATACTTTGCTCCTTTGGGTT
TTGTTGCTGTGGGTTCCAGGA TCCACGGGG-
GAGGTACAACTGGTT-
GAATCAGGTGGCGGACTTGTCCAGCCGGGG
AGGTCTCTTCGAT-
TGTCTTGCGCGGCGAGCGGCTT-
TACGTTCGGTGACTACGCTA
TGCACTGGGTTCGACAAGCTCCA
GGCAAGGGTCTTGAATGGGTGTCAGGCATTA
ACTGGAATAACAAAAATATAGGCTATGCC-
GATTCTGTGAAGGGGAGATTCACGA TTT-
CAAAAAACAACGCGAAGAATAGCCTT-
TATCTGCAAATGAACTCTCTTAGGG
TTGAAGACACAGCATTGTAC-
TACTGTGCAAAGGATAGGGGGTATTCTTACG-
GAT ATTGGTATTTTGACCTTTGGGGTCGGG-
GAACATTGGTCACTGTCAGCTCTGCTAG
CACCAAAGGACCCTCCGTCTT
TCCGCTCGCGCCGAGCAGCAAGTC-
CACGAGCGG
GGGGACAGCCGCCCTTGGGTGTCTGGT-
CAAGGATTATTTCCTGAGCCCGTTACT
GTCTCCTG-
GAATAGCGGTGCCTTGACTTCTGGGGTACAT-
ACCTTCCCGGCGGTTT TGCAAT-
CATCAGGACTGTATAGCC
TCTCTAGCGTTGTAACGGTACCATCTTCATC
ACTTGGCACACAAACATATAT-
TTGTAATGTAAATCACAAACCTT-
CAAATACTAA AGTTGACAAAAAAGTG-
GAGCCGAAGAGCTGTGATAAA
ACGCATACTTGCCCGCC
TTGCCCCGCTCCAGAAT-
TGCTGGGCGGGCCGTCTGTGTTCCTCTTCC-
CACCGAAA CCGAAGGATACGCTGATGA-
TAAGTCGAACGCCCGAAGTA
ACATGCGTGGTTGTT GATGTAAGCCACGAA-
GATCCGGAAGTAAAGTTCAACTGGTACGTA-
GATGGAGTA GAAGTGCAT-
AACGCGAAAACTAAGCCCCGC
GAGGAGCAATATAATTCAACCTAT
CGGGTTGTTAGTGTGCTCACCGTTCTC-
CATCAGGATTGGCTTAACGGGAAAGAGT
ATAAGTGCAAGGTTAGCAATAAAGCAT-
TGCCAGCACCTATAGAGAAGACAATTA
GCAAAGCGAAGGGACAGCCACGAGAGCCC-
CAAGTCTACACGCTGCCTCCCAGCC
GCGACGAGTTGACGAAGAATCAAGTGT-
CACTCACATGTCTTGTCAAGGGATTCT
ATCCCTCAGATATTGCAGTAGAATGG-
GAGTCTAATGGACAACCAGAGAACAACT
ATAAAACTACTCCACCGGTGCTTGA-
TAGTGACGGTAGTTTTTTCCTTTATAGTAA
GCTGACTGTCGA-
TAAGAGTCGCTGGCAACAGG-
GAAATGTTTTTTCTTGTAGTGTT ATGCAT-
GAAGCACTTCATAACCAT
TACACACAAAAGTCTCTGTCACTTTCCCCTG
GCAAATGA 208. 123-ATX1D9_Hs_IgG1_HC—fully human recombinant antibody heavy chain (SEQ ID NO: 208)

METDTLLLWVLLLWVPGSTGEVQLVESGG-
GLVQPGRSLRLSCAASGFTFG DYAM-
HWVRQAPGKGLEWVSGINWNNKNIG-
YADSVKGRFTISKNNAKNSLYLQMN
SLRVEDTALYYCAKDR-
GYSYGYWYFDLWGRGTLVTVSSAS-
TKGPSVFPLAPSSKST SGGTAALGCLVKDYF-
PEPVTVSWNSGALTSGVHTFPAV
LQSSGLYSLSSVVTVPSSS
LGTQTYICNVNHKPSNTKVDKKVE-
PKSCDKTHTCPPCPAPELLGGPSVFLFPPKPKD
TLMISRTPEVTCVVVDVSHEDPE-
VKFNWYVDGVEVHNAKTKPREEQYN-
STYRVVS VLTVLHQDWLNGKEYKCKVSNKA-
LPAPIEKTISKAKGQPREPQVYTLPPSRDELTKN
QVSLTCLVKGFYPSDIA VEWESNGQPEN-
NYKTTPPVLDSDGSFFLYSKLTVDKSRW
QQGNVFSCSVMHEALHNHYTQKSLSLSPGK 209. 123-ATX1D9_Hs_IgG4_HC—fully human recombinant antibody heavy chain (SEQ ID NO: 209)

ATGGAGACAGATACTTTGCTCCTTTGGGTTTTG
TTGCTGTGGGTTCCAGGA TCCACGGGG-
GAGGTACAACTGGTT-
GAATCAGGTGGCGGACTTGTCCAGCCGGGG
AGGTCTCTTCGAT-
TGTCTTGCGCGGCGAGCGGCTT-
TACGTTCGGTGACTACGCTA
TGCACTGGGTTCGACAAGCTCCAG
GCAAGGGTCTTGAATGGGTGTCAGGCATTA
ACTGGAATAACAAAAATATAGGCTATGCC-
GATTCTGTGAAGGGGAGATTCACGA TTT-
CAAAAAACAACGCGAAGAATAGCCTT-
TATCTGCAAATGAACTCTCTTAGGG
TTGAAGACACAGCATTGTAC-
TACTGTGCAAAGGATAGGGGGTATTCTTACG-
GAT ATTGGTATTTTGACCTTTGGGGTCGGG-
GAACATTGGTCACTGTCAGCTCTGCTAG
CACCAAAGGACCCTCCGTCTTTCCGC
TCGCGCCGTGCTCTCGATCCACGAGCGAG
TCTACGGCGGCCTTGGGCTGTCTCGTGAAA-
GACTATTTCCCAGAGCCAGTGACCG
TTTCCTGGAACTCCGGAGCGCTCA-
CATCAGGTGTGCATACCTTTCCAGCCGTACT
TCAATCTTCAGGGCTGTATAGCTT
GTCCTCTGTCGTGACCGTACCCTCCAGTTCTC
TCGGGACAAAGACCTATACCTGTAACGTA-
GACCATAAGCCATCCAATACCAAAG TAGA-
TAAGAGGGTG-
GAATCTAAATATGGACCGCCTTG
TCCGCCGTGCCCGGCTC CTGAGTTCCTTG-
GAGGGCCGTCCGTCTTTCTGTTTC
CCCCTAAACCTAAGGACAC CCTGATGA-
TAAGTAGGACGCCG-
GAAGTAACCTGTGTCGTGGTTGATGTGT-
CACA
GGAAGACCCGGAGGTACAATTTAAT-
TGGTACGTCGATGGAGTCGAGGTGCATAA
TGCGAAAACCAAGCCACGAGAGGAGCAAT-
TCAACAGCACCTACCGAGTAGTTTC
AGTCTTGACTGTGCTGCACCAAGACTGGCT-
GAATGGCAAGGAGTACAAATGCAA
GGTCAGTAATAAAGGATTGCCGTCTT-
CAATAGAGAAGACTATCAGTAAGGCGAA
GGGACAACCTCGCGAGCCTCAGGTATA-
CACTTTGCCGCCCAGCCAAGAAGAAAT
GACGAAGAAC-
CAAGTCTCTTTGACTTGCCTGGT-
CAAAGGCTTCTACCCCTCTGAT
ATAGCAGTCGAATGGGAGTCCAACGGT-
CAACCGGAGAACAATTATAAGACAACT
CCACCTGTGCTTGATTCA-
GACGGCTCTTTTTTCTTGTATAGCCGCCT-
TACCGTAGA CAAGAGTCGATGGCAG-

GAAGGTAATGTATTTTCTTGTA GTGTAATGCACGAGGC ACTTCATAATCAC-TACACACAAAAGTCTCTGT-CACTTTCCCTGGGCAAATGA 210. 123-ATX1D9_Hs_IgG4_HC—fully human recombinant antibody heavy chain (SEQ ID NO: 210)

METDTLLLWVLLLWVPGSTGEVOLVESGG-GLVQPGRSLRLSCAASGFTFG DYAM-HWVRQAPGKGLEWVSGINWNNKNIG-YADSVKGRFTISKNNAKNSLYLQMN SLRVEDTALYYCAKDR-GYSYGYWYFDLWGRGTLVTVSSAS-TKGPSVFPLAPCSRST SESTAALGCLVKDYF-PEPVTVSWNSGALTSGVHTF PAVLQSSGLYSLSSVVTVPSSSL GTKTYTCNVDHKPSNTKVDKRVESKY-GPPCPPCPAPEFLGGPSVFLFPPKPKDTLMIS RTPEVTCVVVDVSQEDPE-VQFNWYVDGVEVHNAKTKPREEQFN-STYRVVSVLTVL HQDWLNGKEYKCKVSNKGL PSSIEKTISKAKGQPREPQVYTLPPSQEEMT-KNQVSLT CLVKGFYPSDIAVEWESNGQPEN-NYKTTPPVLDSDGSFFLY-SRLTVDKSRWQEGNV FSCSVMHEALHNHYTQKSLSLSLGK*

BOLD=signal peptide, underline=antibody variable region, regular font=antibody constant region 211. 123-ATX1D9_Hs_IgL_LC (SEQ ID NO: 211)

ATGAGAGCCTG-GATCTTCTTCCTGCTTTGTTTGG CAGGACGAGCGCTAGC CCAGTCAGCGCT-CACACAGCCCC-CATCAGCCAGCGGGTCCCCAGGGCAGTCCGT AACTATTAGCTGCACGGGGACCTCCA GCGACGTGGGGGGTTACAATTATGTTTCT TGGTACCAGCAACATCCTGGAAAAGCAC-CAAAGATTATGATATATGAAGTTAAT AAAAGGCCGGCTGGCGTGCCT-GATCGGTTCTCCGGTTCTAAGAG CGGCAACACC GCATCCTTGACTGTATCCGGTCT CCAGGCAGAAGACGAAGCCCATTAC-TACTGC AATTCT-TATACCGACAGTAATAACCTCATATTCGGGG-GAGGCACAAAACTTACA GTGCTGGGACAGCCTAAAGCAAATC-CAACCGTAACCTTGTTTCCACCGTCCAGC GAAGAGCTTCAGGCTAACAAAGCTA-CACTCGTATGCCTGATCAGTGACTTCTATC CTGGGGCCGTAACAGTAGCGTGGAAAGCA-GATGGGTCACCCGTCAAAGCAGGG GTGGA-GACGACCAAACCCTCCAAGCAGTC-CAACAATAAGTACGCAGCCTCAAGT TATTTGTCACTTACTCCTGAACAATGGAAAT-CACATCGATCCTATTCCTGTCAAG TTACC-CATGAGGGGAGCACTGTT-GAAAAAACTGTCGCCCCAACTGAATGTAGTT AATGA 212. 123-ATX1D9_Hs_IgL_LC (SEQ ID NO: 212)

MRAWIFFLLCLAGRALAQSALTQPP-SASGSPGQSVTISCTGTSSDVGGYNYVS WYQQHPGKAPKIMIYEVNKRPAGVPDRFSG-SKSGNTASLTVSGLQAEDEAHYYCNS YTDSNNLIFGGGTKLTVLGQP-KANPTVTLFPPSSEELQANKATLVCLISDFYP-GAVTV AWKADGSPVK-AGVETTKPSKQSNNKYAASSYL SLTPEQWKSHRSYSCQVTHEGST VEKTVAPTECS

BOLD=signal peptide, underline=antibody variable region, regular font=antibody constant region 213. 123-ATX1E3_Hs_IgG1_HC (SEQ ID NO: 213)

ATGGAGACAGA-TACTTTGCTCCTTTGGGTACTCTT GCTGTGGGTTCCCGGT AGCACCGGCCAGGTA-CAACTTGTGCAGTCCGGGGCTGAAGT-TAAAAAGCCCGGC GCGTCCGTAAAGGTCAGT TGTAAGGCTAGTGGGTACACGTTTAACAGT-TATGGA ATCTCATGGGT-TAGGCAAGCCCCCGGACAAGGGCTT-GAGTGGATGGGATGGTTT AACGCGTATAGCGGGATAACTAAC-TATGCCCAGAAGTTCCAAGACAGGATAACA ATGACCACCGACACATCCACAAGTACAG-CATACATGGAATTGCGAAGTCTTCGC TCA-GACGACACAGCCGTGTATTATTGTGCTCGC-GATCTTGTGTTCGATTTTTGGG GGCAAGGCACTCTGGTAACGGTGT CTAGCGCTAGCACCAAAGGACCCTCCGTCT TTCCGCTCGCGCCGAGCAGCAAGTC-CACGAGCGGGGGGACAGCCGCCCTTGGGT GTCTGGTCAAGGATTATTTTCCTGAGCCCGT-TACTGTCTCCTGGAATAGCGGTGC CTTGACTTCTGGGGTACAT-ACCTTCCCGGCGGTTTTGCAAT-CATCAGGACTGTAT AGCCTCTCTAGCGTTGTAACGGTACCATCTT-CATCACTTGGCACACAAACATATA TTTGTAATGTAAATCACAAACCTT-CAAATACTAAAGTTGACAAAAAAGTGGAGC CGAAGAGCTGTGATAAAACGCAT-ACTTGCCCGCCTTGCCCCGCTCCAGAAT-TGCT GGGCGGGCCGTCTGTGTTCCTCTTCC-CACCGAAACCGAAGGATACGCTGATGAT AAGTCGAACGCCCGAAGTAA-CATGCGTGGTTGTTGATGTAAGCCACGAA-GATCC GGAAGTAAAGTTCAACTGGTACGTA-GATGGAGTAGAAGTGCATAACGCGAAAA CTAAGCCCCGCGAGGAGCAATATAATT-CAACCTATCGGGTTGTTAGTGTGCTCAC CGTTCTCCATCAGGATTGGCTTAACGG-GAAAGAGTATAAGTGCAAGGTTAGCAA TAAAGCATTGCCAGCACCTATAGAGAA-GACAATTAGCAAAGCGAAGGGACAGC CACGAGAGCCCCAAGTCTA-CACGCTGCCTCCCAGCCGCG ACGAGTTGACGAAGAATCAAGTGTCACTCA-CATGTCTTGTCAAGGGATTCTATCCCTCAGA-TATTGCAGT AGAATGG-GAGTCTAATGGACAACC AGAGAACAACTATAAAACTACTCCACCGGT GCTTGATAGTGACGGTAGTTTTTTCCTT-TATAGTAAGCTGACTGTCGATAAGAGT CGCTGGCAACAGG-GAAATGTTTTTTCTTGTAGTGTTATGCAT-GAAGCACTTCATA ACCATTA-CACACAAAAGTCTCTGTCACTTTC CCCTGGCAAATGA 214. 123-ATX1E3_Hs_IgG1_HC (SEQ ID NO: 214)

METDTLLLWVLLLWVPGSTGQVOLVOS-GAEVKKPGASVKVSCKASGYTF NSY-

GISWVRQAPGQGLEWMGWFNAY-SGITNYAQKFQDRITMTTDTSTSTAYMELR SLRSDDTAVYYCARDLVFDFWGQGTLVTVS-SASTKGPSVFPLAPSSKSTSGGTAALG CLVKDYFPEPVTVSWNSGALT-SGVHTFPAVLQSSGLYS-LSSVVTVPSSSLGTQTYICN VNHKPSNTKVDKKVEPKSCDKTHTCPPCPA-PELLGGPSVFLFPPKPKDTLMISRTPEV TCVVVDVSHEDPE-VKFNWYVDGVEVHNAKTKPREEQYN-STYRVVSVLTVLHQDW LNGKEYKCKVSNKA-LPAPIEKTISKAKGQPREPQ VYTLPPSRDELTKNQVSLTCLVK GFYPSDIA VEWESNGQPENNYKTTPPVLDSDGSFFLYSK-LTVDKSRWQQGNVFSCS VMHEALHN-HYTQKSLSLSPGK

BOLD=signal peptide, underline=antibody variable region, regular font=antibody constant region 215. 123-ATX1E3_Hs_IgG4_HC (SEQ ID NO: 215)

ATGGAGACAGA-TACTTTGCTCCTTTGGGTACTCTT GCTGTGGGTTCCCGGT AGCACCGGCCAGGTA-CAACTTGTGCAGTCCGGGGCTGAAGT-TAAAAAGCCCGGC GCGTCCGTAAAGGTCAGTTGTAAGG CTAGTGGGTACACGTTTAACAGTTATGGA ATCTCATGGGT-TAGGCAAGCCCCCGGACAAGGGCTT-GAGTGGATGGGATGGTTT AACGCGTATAGCGGGATAACTAAC-TATGCCCAGAAGTTCCAAGACAGGATAACA ATGACCACCGACACATCCACAAGTACAG-CATACATGGAATTGCGAAGTCTTCGC TCA-GACGACACAGCCGTGTATTATTGTGCTCGC-GATCTTGTGTTCGATTTTTGGG GGCAAGGCACTCTGGTAACGGTG TCTAGCGCTAGCACCAAAGGACCCTCCGTCT TTCCGCTCGCGCCGTGCTCTCGATC-CACGAGCGAGTCTACGGCGGCCTTGGGCTG TCTCGTGAAAGACTAT-TTCCCAGAGCCAGTGACCGTTTCCTG-GAACTCCGGAGCG CTCACATCAGGTGTG-CATACCTTTCCAGCCGTACTTCAAT CTTCAGGGCTGTATA GCTTGTCCTCTGTCGTGACCGTAC CCTCCAGTTCTCTCGGGACAAAGACCTATAC CTGTAACGTAGACCATAAGCCATCCAATAC-CAAAGTAGATAAGAGGGTGGAATC TAAATATGGACCGCCTTGTCCGCCGT GCCCGGCTCCTGAGTTCCTTGGAGGGCCG TCCGTCTTTCTGTTTCCCCCTAAAC CTAAGGACACCCTGATGATAAGTAGGACGC CGGAAGTAACCTGTGTCGTGGTTGATGTGT-CACAGGAAGACCCGGAGGTACAAT TTAAT-TGGTACGTCGATGGAGTCGAGGTGCAT-AATGCGAAAACCAAGCCACGAG AGGAGCAATTCAACAGCACC-TACCGAGTAGTTTCAGTCTTGACT GTGCTGCACC AAGACTGGCT-GAATGGCAAGGAGTA-CAAATGCAAGGTCAGTAATAAAGGATTG CCGTCTTCAATAGAGAAGAC-TATCAGTAAGGCGAAGGGAC AACCTCGCGAGCCT CAGGTATA-CACTTTGCCGCCCAGC-CAAGAAGAAATGACGAAGAACCAAGTCTCT TTGACTTGCCTGGTCAAAGGCTTC-TACCCCTCTGATATAGCAGTCGAATGGGAGT CCAACGGTCAACCGGAGAACAATTATAA-GACAACTCCACCTGTGCTTGATTCAG ACGGCTCTTTTTTCTTGTATAGCCGCCT-TACCGTAGACAAGAGTCGATGGCAGGA AGGTAATGTAT-TTTCTTGTAGTGTAATGCACGAGGCACTT-CATAATCACTACACA CAAAAGTCTCTGT-CACTTTCCCTGGGCAAATGA 216. 123-ATX1E3_Hs_IgG4_HC (SEQ ID NO: 216)

METDTLLLWVLLLWVPGSTGQVQLVQS-GAEVKKPGASVKVSCKASGYTF NSY-GISWVRQAPGQGLEWMGWFNAY-SGITNYAQKFQDRITMTTDTSTSTAYMELR SLRSDDTAVYYCARDLVFDFWGQGTLVTVS-SASTKGPSVFPLAPCSRSTSESTAALG CLVKDYFPEPVTVSWNSGALT-SGVHTFPAVLQSSGLYS-LSSVVTVPSSSLGTKTYTC NVDHKPSNTKVDKRVESKYGPPCPPCPAPE-FLGGPSVFLFPPKPKDTLMISRTPEVTC VVVDVSQEDPE-VQFNWYVDGVEVHNAKTKPREEQFN-STYRVVSVLTVLHQDWLN GKEYKCKVSNKGLPSSIEKTISKAKGQ PREPQVYTLPPSQEEMTKNQVSLTCLVKGF YPSDIA VEWESNGQPEN-NYKTTPPVLDSDGSFFLY-SRLTVDKSRWQEGNVFSCSVM HEALHN-HYTQKSLSLSLGK

BOLD=signal peptide, underline=antibody variable region, regular font=antibody constant region 217. 123-ATX1E3 IgK_LC (SEQ ID NO: 217)

ATGAGAGCCTG-GATCTTCTTCCTGCTTTGTTTGGCAGG ACGAGCGCTAGC CGAAATCGTATT-GATGCAAAGTCCCGGCACACTCTCATT-GAGCCCTGGGGAGAG AGT-CACGCTCTCTTGTAGAGCCAGTCA AACATTCTCTAGCAGCTATCTCGCCTGG TAC-CAACAGAAACCTGGACAGGC GCCTAGACTCCTGATATATGGCGCAAGCAGT CGGGCCACAGGTATTCCA-GATCGGTTTTCAG-GATCTGGCTCTGGCACTGACTTCA CCCT-TACTATCAACCGATTGGAACCAGAG GACTTTGCTGTCTATTATTGTCAACA GTATGGCAGGTCACCCTT-TACTTTTGGCCCCGGTACCAAGCTCGATAT-TAAGCGT ACGGTAGCTGCGCCTAGCGTGTT-TATTTTTCCGCCCTCTGACGAA CAACTCAAAA GTGGCACTGCCTCTGTAGTCTGTCTCCT-GAACAATTTTTATCCAAGGGAAGCTAA GGTACAGTGGAAAGTCGATAACGCGCTC-CAAAGTGGCAACAGTCAAGAATCTGT AACGGAGCAAGATAGTAAAGACAGCACTTA-CAGCTTGAGCAGCACACTCACATT GTC-CAAGGCCGACTACGAAAAACAT-AAAGTGTACGCCTGTGAGGTAACACACCA GGGTCTGAGCAGCCCAGTGACGAAGTCATT-TAATCGCGGTGAGTGCTGA 218. 123-ATX1E3 IgK_LC (SEQ ID NO: 218)

MRAWIFFLLCLAGRALAEIVLMQSPGTLSL-SPGERVTLSCRASQTFSSSYLA WYQQKPGQAPRLLIYGASSRAT-

GIPDRFSGSGSGTDFTLTINRLEPED-
FAVYYCQQY
GRSPFTFGPGTKLDIKRTVAAPSVFIFPPSD-
EQLKSGTASVVCLLNNFYPREAKVQWK
VDNALQSGNSQESVTEQDSKDSTYSLSSTLTL-
SKADYEKHKVYACEVTHQGLSSPV
TKSFNRGEC

BOLD=signal peptide, underline=antibody variable region, regular font=antibody constant region 219. 123-ATX1E5_Hs_IgG1_HC (SEQ ID NO: 219)

ATGGAGACAGA-
TACTTTGCTCCTTTGGGTACTCTTGC
TGTGGGTTCCCGGT AGCACCGGCCAGGTC-
CAACTTGTTCAGTCAGGCGC
AGAAGTAAAAAAACCGGGT GCCTCAGT-
GAAAGTAAGCTGTAAAGCAAGTGGGTA-
CACGTTCACGAGTTTTGGG ATTAGCTGGGT-
TAGACAAGCTCCGGGTCAGGG
GCTTGAATGGATGGGATGGTTT AACGCAT-
ACTCTGGAAATACCTAC-
TATGCACCGACCCTTCAGGACAGAGTGACG
ATGACTACTGACACCAGCACATC-
TACGGCGTACATGGAATTGATGTCCTTGC-
GAT CAGACGATACTGCAATCTACTAT-
TGCGCACGGGATTTGGTTTTCGAT
TATTGGGG
CCAGGGCACTCTGGTAACGGTGT
CTAGCGCTAGCAC-
CAAAGGACCCTCCGTCTTT
CCGCTCGCGCCGAGCAGCAAGTC-
CACGAGCGGGGGGACAGCCGC
CCTTGGGTGT CTGGTCAAGGATTATTTTCCT-
GAGCCCGTTACTGTCTCCTG-
GAATAGCGGTGCCT TGACTTCTGGGGTA-
CATACCTTCCCGGCGGTTTTGC
AATCATCAGGACTGTATAG
CCTCTCTAGCGTTGTAACGGTACCATCTT-
CATCACTTGGCACACAAACATATATT
TGTAATGTAAATCACAAACCTT-
CAAATACTAAAGTTGACAAAAAAGTG-
GAGCCG AAGAGCTGTGATAAAACGCAT-
ACTTGCCCGCCTTGCCCCGCTC
CAGAATTGCTG
GGCGGGCCGTCTGTGTTCCTCTTCC-
CACCGAAACCGAAGGATACGCTGATGATA
AGTCGAACGCCCGAAGTAA-
CATGCGTGGTTGTTGATGTAAGCCACGAA-
GATCCG GAAGTAAAGTTCAACTGGTACGTA-
GATGGAGTAGAAGTGCATAACGCGAAAACT
AAGCCCCGCGAGGAGCAATATAATTCAACC-
TATCGGGTTGTTAGTGTGCTCACC GTTCTC-
CATCAGGATTGGCTTAACGG-
GAAAGAGTATAAGTGCAAGGTTAGCAAT
AAAGCATTGCCAGCACCTATAGAGAA-
GACAATTAGCAAAGCGAAGGGACAGCC
ACGAGAGCCCCAAGTCTA-
CACGCTGCCTCCCAGCCGCGAC
GAGTTGACGAAGAA TCAAGTGTCACTCA-
CATGTCTTGTCAAGGGATTCTATCCCTCAGA-
TATTGCAGTA GAATGG-
GAGTCTAATGGACAACCAGAG
AACAACTATAAAACTACTCCACCGGTG CTT-
GATAGTGACGGTAGTTTTTTCCTT-
TATAGTAAGCTGACTGTCGATAAGAGTC
GCTGGCAACAGG-
GAAATGTTTTTTCTTGTAGTGTTATGCAT-
GAAGCACTTCATAA CCATTA-
CACACAAAAGTCTCTGTCACTT
TCCCCTGGCAAATGA 220. 123-ATX1E5_Hs_IgG1_HC (SEQ ID NO: 220)

METDTLLLWVLLLWVPGSTGQVOLVOS-
GAEVKKPGASVKVSCKASGYTF TSF-
GISWVRQAPGOGLEWMGWFNAYSGNTYY-
APTLQDRVTMTTDTSTSTAYMEL
MSLRSDDTAIYYCARDLVFDYWGQGTLVTVS-
SASTKGPSVFPLAPSSKSTSGGTAAL
GCLVKDYFPEPVTVSWNSGALT-
SGVHTFPAVLQSSGLYS-
LSSVVTVPSSSLGTQTYIC
NVNHKPSNTKVDKKVEPKSCDKTHTCPPCPA-
PELLGGPSVFLFPPKPKDTLMISRTPE
VTCVVVDVSHEDPE-
VKFNWYVDGVEVHNAKTKPREEQYN-
STYRVVSVLTVLHQD WLNGKEYKCKVSNKA-
LPAPIEKTISKAKGQPREPQVYTLPPS
RDELTKNQVSLTCLV KGFYPSDIA-
VEWESNGQPENNYKTTPPVLDSDGSFFLYSK-
LTVDKSRWQQGNVFSC SVMHEALHN-
HYTQKSLSLSPGK

BOLD=signal peptide, underline=antibody variable region, regular font=antibody constant region 221. 123-ATX1E5_Hs_IgG4_HC (SEQ ID NO: 221)

ATGGAGACAGATACTTTGCTCCTTTGGGTACTC
TTGCTGTGGGTTCCCGGT
AGCACCGGCCAGGTC-
CAACTTGTTCAGTCAGGCGCAGAA
GTAAAAAAACCGGGT GCCTCAGT-
GAAAGTAAGCTGTAAAGCAAGTGGGTA-
CACGTTCACGAGTTTTGGG ATTAGCTGGGT-
TAGACAAGCTCCGGGTCAGGGG
CTTGAATGGATGGGATGGTTT AACGCAT-
ACTCTGGAAATACCTAC-
TATGCACCGACCCTTCAGGACAGAGTGACG
ATGACTACTGACACCAGCACATC-
TACGGCGTACATGGAATTGATGTCCTTGC-
GAT CAGACGATACTGCAATCTACTAT-
TGCGCACGGGATTTGGTTTTCGATTATTGGGG
CCAGGGCACTCTGGTAACGGTG
TCTAGCGCTAGCAC-
CAAAGGACCCTCCGTCTTT
CCGCTCGCGCCGTGCTCTCGATC-
CACGAGCGAGTC-
TACGGCGGCCTTGGGCTGTC TCGTGAAA-
GACTATTTCCCAGAGCCAGTGACCGT
TTCCTGGAACTCCGGAGCGCT
CACATCAGGTGTGCAT-
ACCTTTCCAGCCGTACTT-
CAATCTTCAGGGCTGTATAGC
TTGTCCTCTGTCGTGACCGT
ACCCTCCAGTTCTCTCGGGACAAAGACC-
TATACCT GTAACGTAGACCATAAGCCATC-
CAATACCAAAGTAGATAAGAGGGTG-
GAATCTA AATATGGACCGCCTTGTCCGCC
GTGCCCGGCTCCTGAGTTCCTTG-
GAGGGCCGTC
CGTCTTTCTGTTTCCCCCTAAAC
CTAAGGACACCCTGATGA-
TAAGTAGGACGCCG
GAAGTAACCTGTGTCGTGGTTGATGTGT-
CACAGGAAGACCCGGAGGTACAATTT AAT-
TGGTACGTCGATGGAGTCGAGGTGCAT-
AATGCGAAAACCAAGCCACGAGA
GGAGCAATTCAACAGCACC-

TACCGAGTAGTTTCAGTCTT
GACTGTGCTGCACCA AGACTGGCT-
GAATGGCAAGGAGTA-
CAAATGCAAGGTCAGTAATAAAGGATTGC
CGTCTTCAATAGAGAAGAC-
TATCAGTAAGGCGAAGGGACAACC
TCGCGAGCCTC AGGTATA-
CACTTTGCCGCCCAGC-
CAAGAAGAAATGACGAAGAAC-
CAAGTCTCTT
TGACTTGCCTGGTCAAAGGCTTC-
TACCCCTCTGATATAGCAGTCGAATGG-
GAGTC CAACGGTCAACCGGAGAACAAT-
TATAAGACAACTCCACCTGTGCTTGATTCAGA
CGGCTCTTTTTCTTGTATAGCCGCCT-
TACCGTAGACAAGAGTCGATGGCAGGAA
GGTAATGTAT-
TTTCTTGTAGTGTAATGCACGAGGCACTT-
CATAATCACTACACAC AAAAGTCTCTGT-
CACTTTCCCTGGGCAAATGA

BOLD=signal peptide, underline=antibody variable region, regular font=antibody constant region 222. 123-ATX1E5_Hs_IgG4_HC (SEQ ID NO: 222)

METDTLLLWVLLLWVPGSTGQVOLVOS-
GAEVKKPGASVKVSCKASGYTF TSF-
GISWVRQAPGOGLEWMGWFNAYSGNTYY-
APTLQDRVTMTTDTSTSTAYMEL
MSLRSDDTAIYYCARDLVFDYWGQGTLVTVS-
SASTKGPSVFPLAPCSRSTSESTAAL
GCLVKDYFPEPVTVSWNSGALT-
SGVHTFPAVLQSSGLYS-
LSSVVTVPSSSLGTKTYT
CNVDHKPSNTKVDKRVESKYGPPCPPCPAPE-
FLGGPSVFLFPPKPKDTLMISRTPEVT
CVVVDVSQEDPE-
VQFNWYVDGVEVHNAKTKPREEQFN-
STYRVVSVLTVLHQDWL
NGKEYKCKVSNKGLPSSIEKTISKA
KGQPREPQVYTLPPSQEEMTKNQVSLTCLVKG
FYPSDIA VEWESNGQPEN-
NYKTTPPVLDSDGSFFLY-
SRLTVDKSRWQEGNVFSCSV MHEALHN-
HYTQKSLSLSLGK 223. 123-ATX1E5_Hs_IgK_LC (SEQ ID NO: 223)

ATGAGAGCCTG-
GATCTTCTTCCTGCTTTGTTTGGCAGG
ACGAGCGCTAGC CGAGATCGTGCTTACC-
CAAAGCCCTGGCACTCTTTCCCTC
AGCCCCGGTGAAAGA
GCGACCCTTTCCTGTCGCGCCT-
CACAGAGTTTTTCAGACAGGTACTTGG-
CATGGT
ATCAACAAAAACCGGGACAAGCACCT
AGGCTGCTCATATACGGCACTTTCAGCC
GCGCGACTGGAATACCTGACAGGTTTTCTGG
GTCTGGTTCAGGAACGGACTTCA CTCTTA-
CAATTTCTCGACTCGATTCTGAA-
GACTTCGCTGTCTACTACTGTCAACA
ATACGGTAGCTCTCCATTCACAT-
TTGGTCCGGGCACTAAGGTCGA-
TATAAAGCGT
ACGGTAGCTGCGCCTAGCGTGTTTAT-
TTTTCCGCCCTCTGACGAACAACTCAAAA
GTGGCACTGCCTCTGTAGTCTGTCTCCT-
GAACAATTTTTATCCAAGGGAAGCTAA
GGTACAGTGGAAAGTCGATAACGCGCTC-
CAAAGTGGCAACAGTCAAGAATCTGT
AACGGAGCAAGATAGTAAAGACAGCACTTA-
CAGCTTGAGCAGCACACTCACATT GTC-
CAAGGCCGACTACGAAAAACAT-
AAAGTGTACGCCTGTGAGGTAACACACCA
GGGTCTGAGCAGCCCAGTGACGAAGTCATT-
TAATCGCGGTGAGTGCTGA 224. 123-ATX1E5_Hs_IgK_LC (SEQ ID NO: 224)

MRAWIFFLLCLAGRALAEIVLTQSPGTLSL-
SPGERATLSCRASQSFSDRYLA
WYQQKPGQAPRLLIYGTFSRAT-
GIPDRFSGSGSGTDFTLTISRLDSED-
FAVYYCQQYG
SSPFTFGPGTKVDIKRTVAAPSVFIFPPSD-
EQLKSGTASVVCLLNNFYPREAKVQWKV
DNALQSGNSQESVTEQDSKDSTYSLSSTLTL-
SKADYEKHKVYACEVTHQGLSSPVT
KSFNRGEC

BOLD=signal peptide, underline=antibody variable region, regular font=antibody constant region 225. 123-ATX1F2_Hs_IgG1_HC (SEQ ID NO: 225)

ATGGAGACAGA-
TACTTTGCTCCTTTGGGTACTCTTGCT
GTGGGTTCCCGGT
AGCACCGGCCAGGTTCAGCTTGTC-
CAAAGTGGTGCAGAGGTTAAAAAGCCTGGT
GCCTCTGT-
GAAAGTCAGTTGTAAGGTCAGCGGCTATA-
CATTGACTGAGTTTAGCA
TGCACTGGGTACGC-
CAAGCCCCCGGTAAGGGACTGGAATG-
GATGGGCGTCTTTG
ACCCAGAACACGGGGCTACGATATACGCT-
CAAAAGTTCCAGGGGCGGGTAACG
ATGACAGAA-
GACACTAGCACGGACACCGCCTA-
CATGGACCTCTCCTATCTGAGG TCCGAGGA-
TACAGCGGTTTATTATTGTGCAAC
GTACTTTGACTTCTGGTCAGGTT ACAGCCAT-
TTTGATTTCTGGGGTCAGGGCACTCTG
GTAACGGTGTCTAGCGCTAG CAC-
CAAAGGACCCTCCGTCTTTCCGCTCG
CGCCGAGCAGCAAGTCCACGAGCGG
GGGGACAGCCGCCCTTGGGTGTCTGGT-
CAAGGATTATTTTCCTGAGCCCGTTACT
GTCTCCTG-
GAATAGCGGTGCCTTGACTTCTGGGGTACAT-
ACCTTCCCGGCGGTTT TGCAAT-
CATCAGGACTGTATAGCCTCTC
TAGCGTTGTAACGGTACCATCTTCATC
ACTTGGCACACAAACATATAT-
TTGTAATGTAAATCACAAACCTT-
CAAATACTAA AGTTGACAAAAAAGTG-
GAGCCGAAGAGCTGTGATAAAA
CGCATACTTGCCCGCC
TTGCCCCGCTCCAGAAT-
TGCTGGGCGGGCCGTCTGTGTTCCTCTTCC-
CACCGAAA CCGAAGGATACGCTGATGA-
TAAGTCGAACGCCCGAAGTAACATG
CGTGGTTGTT GATGTAAGCCACGAA-
GATCCGGAAGTAAAGTTCAACTGGTACGTA-
GATGGAGTA GAAGTGCAT-
AACGCGAAAACTAAGCCCCGCGA
GGAGCAATATAATTCAACCTAT CGGGTTGT-
TAGTGTGCTCACCGTTCTCCATCAGGAT-
TGGCTTAACGGGAAAGAGT
ATAAGTGCAAGGTTAGCAATAAAGCAT-
TGCCAGCACCTATAGAGAAGACAATTA

GCAAAGCGAAGGGACAGCCACGAGAGCCC-
CAAGTCTACACGCTGCCTCCCAGCC
GCGACGAGTTGACGAAGAATCAAGTGT-
CACTCACATGTCTTGTCAAGGGATTCT
ATCCCTCAGATATTGCAGTAGAATGG-
GAGTCTAATGGACAACCAGAGAACAACT
ATAAAACTACTCCACCGGTGCTTGA-
TAGTGACGGTAGTTTTTCCTTTATAGTAA
GCTGACTGTCGA-
TAAGAGTCGCTGGCAACAGG-
GAAATGTTTTTCTTGTAGTGTT ATGCAT-
GAAGCACTTCATAACCATTACACAC
AAAAGTCTCTGTCACTTTCCCCTG
GCAAATGA 226. 123-ATX1F2_Hs_IgG1_HC (SEQ ID NO: 226)

METDTLLLWVLLLWVPGSTGQVQLVQS-
GAEVKKPGASVKVSCKVSGYTL
TEFSMHWVRQAPGKGLEWMGVFDPEHGATI-
YAQKFQGRVTMTEDTSTDTAYMDL
SYLRSEDTAVYY-
CATYFDFWSGYSHFDFWGQGTLVTVSSAS-
TKGPSVFPLAPSSKST SGGTAALGCLVKDYF-
PEPVTVSWNSGALTSGVHTFPAVL
QSSGLYSLSSVVTVPSSS
LGTQTYICNVNHKPSNTKVDKKVE-
PKSCDKTHTCPPCPAPELLGGPSVFLFPPKPKD
TLMISRTPEVTCVVVDVSHEDPE-
VKFNWYVDGVEVHNAKTKPREEQYN-
STYRVVS VLTVLHQDWLNGKEYKCKVSNKA-
LPAPIEKTISKAKGQPREPQVYTLPPSRDELTKN
QVSLTCLVKGFYPSDIA VEWESNGQPEN-
NYKTTPPVLDSDGSFFLYSKLTVDKSRW
QQGNVFSCSVMHEALHNHYTQKSLSLSPGK*

BOLD=signal peptide, underline=antibody variable region, regular font=antibody constant region 227. 123-ATX1F2_Hs_IgG4_HC (SEQ ID NO: 227)

ATGGAGACAGA-
TACTTTGCTCCTTTGGGTACTCTTGC
TGTGGGTTCCCGGT
AGCACCGGCCAGGTTCAGCTTGTC-
CAAAGTGGTGCAGAGGTTAAAAAGCCTGGT
GCCTCTGT-
GAAAGTCAGTTGTAAGGTCAGCGGCTATA-
CATTGACTGAGTTTAGCA
TGCACTGGGTACGC-
CAAGCCCCCGGTAAGGGACTGGAATG-
GATGGGCGTCTTTG
ACCCAGAACACGGGGCTACGATATACGCT-
CAAAAGTTCCAGGGGGGGGTAACG
ATGACAGAA-
GACACTAGCACGGACACCGCCTA-
CATGGACCTCTCCTATCTGAGG TCCGAGGA-
TACAGCGGTTTATTATTGTGCAAC
GTACTTTGACTTCTGGTCAGGTT ACAGCCAT-
TTTGATTTCTGGGGTCAGGGCACTCTGGTA
ACGGTGTCTAGCGCTAG CAC-
CAAAGGACCCTCCGTCTTTCCG
CTCGCGCCGTGCTCTCGATCCACGAGCGAG
TCTACGGCGGCCTTGGGCTGTCTCGTGAAA-
GACTATTTCCCAGAGCCAGTGACCG
TTTCCTGGAACTCCGGAGCGCTCA-
CATCAGGTGTGCATACCTTTCCAGCCGTACT
TCAATCTTCAGGGCTGTATAGCTTG
TCCTCTGTCGTGACCGTACCCTCCAGTTCTC
TCGGGACAAAGACCTATACCTGTAACGTA-
GACCATAAGCCATCCAATACCAAAG TAGA-
TAAGAGGGTGGAATCTAAATATGGACCGCC
TTGTCCGCCGTGCCCGGCTC
CTGAGTTCCTTG-
GAGGGCCGTCCGTCTTTCTG
TTTCCCCCTAAACCTAAGGACAC CCTGAT-
GATAAGTAGGACGCCG-
GAAGTAACCTGTGTCGTGGTTGATGTGT-
CACA
GGAAGACCCGGAGGTACAATTTAAT-
TGGTACGTCGATGGAGTCGAGGTGCATAA
TGCGAAAACCAAGCCACGAGAGGAGCAAT-
TCAACAGCACCTACCGAGTAGTTTC
AGTCTTGACTGTGCTGCACCAAGACTGGCT-
GAATGGCAAGGAGTACAAATGCAA
GGTCAGTAATAAAGGATTGCCGTCTT-
CAATAGAGAAGACTATCAGTAAGGCGAA
GGGACAACCTCGCGAGCCTCAGGTATA-
CACTTTGCCGCCCAGCCAAGAAGAAAT
GACGAAGAAC-
CAAGTCTCTTTGACTTGCCTGGT-
CAAAGGCTTCTACCCCTCTGAT
ATAGCAGTCGAATGGGAGTCCAACGGT-
CAACCGGAGAACAATTATAAGACAACT
CCACCTGTGCTTGATTCA-
GACGGCTCTTTTTTCTTGTATAGCCGCCT-
TACCGTAGA CAAGAGTCGATGGCAG-
GAAGGTAATGTATTTTCTT
GTAGTGTAATGCACGAGGC ACTTCATAAT-
CACTACACACAAAAGTCTCTGT-
CACTTTCCCTGGGCAAATGA 228. 123-ATX1F2_Hs_IgG4_HC (SEQ ID NO: 228)

METDTLLLWVLLLWVPGSTGQVQLVQS-
GAEVKKPGASVKVSCKVSGYTL
TEFSMHWVRQAPGKGLEWMGVFDPEHGATI-
YAQKFQGRVTMTEDTSTDTAYMDL
SYLRSEDTAVYY-
CATYFDFWSGYSHFDFWGQGTLVTVSSAS-
TKGPSVFPLAPCSRST SESTAALGCLVKDYF-
PEPVTVSWNSGALTSGVHTFP
AVLQSSGLYSLSSVVTVPSSSL
GTKTYTCNVDHKPSNTKVDKRVESKY-
GPPCPPCPAPEFLGGPSVFLFPPKPKDTLMIS
RTPEVTCVVVDVSQEDPE-
VQFNWYVDGVEVHNAKTKPREEQFN-
STYRVVSVLTVL
HQDWLNGKEYKCKVSNKGLP
SSIEKTISKAKGQPREPQVYTLPPSQEEMT-
KNQVSLT CLVKGFYPSDIAVEWESNGQPEN-
NYKTTPPVLDSDGSFFLY-
SRLTVDKSRWQEGNV
FSCSVMHEALHNHYTQKSLSLSLGK*

BOLD=signal peptide, underline=antibody variable region, regular font=antibody constant region 229. 123-ATX1F2_Hs_IgK_LC (SEQ ID NO: 229)

ATGAGAGCCTGGATCTTCTTCCTGCTTTGTT
TGGCAGGACGAGCGCTAGC CGACATC-
CAAATGACTCAAAGTCCGTCAAGTCT-
TAGTGCGAGTGTGGGTGACCG AGTTACGAT-
TACCTGCCGAGCTAGTCAGGGCATCC
GCAACGACCTTGGCTGGTA TCAACAGA-
GACCTGGAAAAGCGCCTAAGCGACTCATC-
TATGCGGCGTCCTCACT
TCAAAGCGGCGTACCTT-
CAAGGTTTTCTGGTTCTGG-
GAGTGGGACCGAGTTCACC CTTGCCATT-
AGTTCCTTGCAACCTGAAGACTT
CGCTACTTACTCTTGTCTCCAACA TAATAGT-
TACCCCTGGACCTTTGGACAGG-

GAACAAAGGTCGAAATCAAACGTAC
GGTAGCTGCGCCTAGCGTGTTTAT-
TTTTCCGCCCTCTGACGAACAACTCAAAAGT
GGCACTGCCTCTGTAGTCTGTCTCCT-
GAACAATTTTTATCCAAGGGAAGCTAAGG
TACAGTGGAAAGTCGATAACGCGCTC-
CAAAGTGGCAACAGTCAAGAATCTGTAA
CGGAGCAAGATAGTAAAGACAGCACTTA-
CAGCTTGAGCAGCACACTCACATTGT
CCAAGGCCGACTACGAAAAACAT-
AAAGTGTACGCCTGTGAGGTAACACACCAG
GGTCTGAGCAGCCCAGTGACGAAGTCATT-
TAATCGCGGTGAGTGCTGA 230. 123-ATX1F2_Hs_IgK_LC (SEQ ID NO: 230)

MRAWIFFLLCLAGRALADIQMTQSPSSL-
SASVGDRVTITCRASQGIRNDLG
WYQQRPGKAPKRLI-
YAASSLOSGVPSRFSGSGSGTEFTLAISSLOPE-
DFATYSCLOHN
SYPWTFGQGTKVEIKRTVAAPSVFIFPPSD-
EQLKSGTASVVCLLNNFYPREAKVQWK
VDNALQSGNSQESVTEQDSKDSTYSLSSTLTL-
SKADYEKHKVYACEVTHQGLSSPV
TKSFNRGEC

BOLD=signal peptide, underline=antibody variable region, regular font=antibody constant region 231. 123-ATX1G5v1_Hs_IgG1_HC (SEQ ID NO: 231)

ATGGAGACAGA-
TACTTTGCTCCTTTGGGTACTCTT
GCTGTGGGTTCCCGGT
AGCACCGGCCAGGTA-
CAGCTCGTTCAGTCAGGGAGTGAGGT-
CAAGAAACCGGGT TCCTCTGT-
CAAAGTTTCCTGCAAGGCCAGT
GGAGGCACCTTTAGTTCTTACGCAA
TTAGCTGGGTACGACAGGCACCCGGC-
CAAGGGCTGGAATGGATGGGAGGGATA
ATTCCCATTTTCGGTACAGTGACTTACGCC-
CAAAAGTTCCAAGGCGGCGTAACG
ATCACAGCAGACGAGTCTAC-
CAATACTGTGTACATGGAATTGAGTAGCCT-
TAGA AGCGAGGACACAGCAGTCTAT-
TACTGTGCGCGGGACGA
CTTTTGGACTGGTGAC
TACTGGGGCCAGGGCACTC
TGGTAACGGTGTCTAGCGCTAGCAC-
CAAAGGACCC
TCCGTCTTTCCGCTCGCGCCGAGCAGC
AAGTCCACGAGCGGGGGGACAGCCGCC
CTTGGGTGTCTGGTCAAGGATTATTTTCCT-
GAGCCCGTTACTGTCTCCTGGAATA
GCGGTGCCTTGACTTCTGGGGTACAT-
ACCTTCCCGGCGGTTTTGCAATCATCAGG
ACTGTATAGCCTCTCTAGCGTT
GTAACGGTACCATCTTCAT-
CACTTGGCACACAA ACATATAT-
TTGTAATGTAAATCACAAACCTT-
CAAATACTAAAGTTGACAAAAAA
GTGGAGCCGAAGAGCTGTGATAAAACGCAT-
ACTTGCCCGCCTTGCCCCGCTCCA GAAT-
TGCTGGGCGGGCCGTCTGTGTTCCTCTTCC-
CACCGAAACCGAAGGATACG
CTGATGATAAGTCGAACGCCCGAAGTAA-
CATGCGTGGTTGTTGATGTAAGCCAC GAA-
GATCCGGAAGTAAAGTTCAACTGGTACGTA-
GATGGAGTAGAAGTGCATAAC
GCGAAAACTAAGCCCCGCGAG-

GAGCAATATAATTCAACCTATCGGGTTGT-
TAGT GTGCTCACCGTTCTCCATCAGGAT-
TGGCTTAACGGGAAAGAGTATAAGTGCAAG
GTTAGCAATAAAGCATTGCCAGCACC-
TATAGAGAAGACAATTAGCAAAGCGAA
GGGACAGCCACGAGAGCCCCAAGTCTA-
CACGCTGCCTCCCAGCCGCGACGAGTT
GACGAAGAATCAAGTGTCACTCA-
CATGTCTTGTCAAGGGATTCTATCCCTCAGAT
ATTGCAGTAGAATGG-
GAGTCTAATGGACAACCAGAGAACAAC-
TATAAAACTACT CCACCGGTGCTTGA-
TAGTGACGGTAGTTTTTTC
CTTTATAGTAAGCTGACTGTCG
ATAAGAGTCGCTGGCAACAGG-
GAAATGTTTTTTCTTGTAGTGTTATGCAT-
GAAGC ACTTCATAACCATTA-
CACACAAAAGTCTCTGTCAC
TTTCCCCTGGCAAATGA 232. 123-ATX1G5v1_Hs_IgG1_HC (SEQ ID NO: 232)

METDTLLLWVLLLWVPGSTGQVOLVOSG-
SEVKKPGSSVKVSCKASGGTFS
SYAISWVRQAPGOGLEWMGGIIP-
IFGTVTYAQKFQGGVTITA-
DESTNTVYMELSSLR SEDTAVYY-
CARDDFWTGDYWGQGTLVTVSSASTKGPSVF-
PLAPSSKSTSGGTAALG
CLVKDYFPEPVTVSWNSGALT-
SGVHTFPAVLQSSGLYS-
LSSVVTVPSSSLGTQTYICN
VNHKPSNTKVDKKVEPKSCDKTHTCPPCPA-
PELLGGPSVFLFPPKPKDTLMISRTPEV
TCVVVDVSHEDPE-
VKFNWYVDGVEVHNAKTKPREEQYN-
STYRVVSVLTVLHQDW LNGKEYKCKVSNKA-
LPAPIEKTISKAKGQPREPQVYTLPP
SRDELTKNQVSLTCLVK GFYPSDIA
VEWESNGQPENNYKTTPPVLDSDGSFFLYSK-
LTVDKSRWQQGNVFSCS VMHEALHN-
HYTQKSLSLSPGK

BOLD=signal peptide, underline=antibody variable region, regular font=antibody constant region 233. 123-ATX1G5v1_Hs_IgG4_HC (SEQ ID NO: 233)

ATGGAGACAGA-
TACTTTGCTCCTTTGGGTACTCT
TGCTGTGGGTTCCCGGT
AGCACCGGCCAGGTA-
CAGCTCGTTCAGTCAGGGAGTGAGGT-
CAAGAAACCGGGT TCCTCTGT-
CAAAGTTTCCTGCAAGGCCAG
TGGAGGCACCTTTAGTTCTTACGCAA
TTAGCTGGGTACGACAGGCACCCGGC-
CAAGGGCTGGAATGGATGGGAGGGATA
ATTCCCATTTTCGGTACAGTGACTTACGCC-
CAAAAGTTCCAAGGCGGCGTAACG
ATCACAGCAGACGAGTCTAC-
CAATACTGTGTACATGGAATTGAGTAGCCT-
TAGA AGCGAGGACACAGCAGTCTAT-
TACTGTGCGCGGGACGACTT
TTGGACTGGTGAC
TACTGGGGCCAGGGCACTC
TGGTAACGGTGTCTAGCGCTAGCAC-
CAAAGGACCC
TCCGTCTTTCCGCTCGCGCCGTGCTCTC-
GATCCACGAGCGAGTCTACGGCGGCCT
TGGGCTGTCTCGTGAAAGACTAT-
TTCCCAGAGCCAGTGACCGTTTCCTG-

GAACTC CGGAGCGCTCACATCAGGTGTG-
CATACCTTTCCAGCCGTACTTCA
ATCTTCAGGG CTGTATAGCTTGTCCTCTGTC
GTGACCGTACCCTCCAGTTCTCTCG
GGACAAAGA CCTATACCTGTAACGTAGAC-
CATAAGCCATCCAATACCAAAGTAGA-
TAAGAGGG TGGAATCTAAATATGGACCGCC
TTGTCCGCCGTGCCCGGCTCCT-
GAGTTCCTTGG
AGGGCCGTCCGTCTTTCTGTTTCC
CCCTAAACCTAAGGACACCCTGATGATAAGT
AGGACGCCGGAAGTAACCTGTGTCGTGGTT-
GATGTGTCACAGGAAGACCCGGAG GTA-
CAATTTAATTGGTACGTCGATG-
GAGTCGAGGTGCATAATGCGAAAACCAAG
CCACGAGAGGAGCAATTCAACAGCACC-
TACCGAGTAGTTTCAGTCTTGACTGTG
CTGCACCAAGACTGGCT-
GAATGGCAAGGAGTA-
CAAATGCAAGGTCAGTAATAA AGGAT-
TGCCGTCTTCAATAGAGAAG
ACTATCAGTAAGGCGAAGGGACAACCTCG
CGAGCCTCAGGTATA-
CACTTTGCCGCCCAGC-
CAAGAAGAAATGACGAAGAACCA
AGTCTCTTTGACTTGCCTGGT-
CAAAGGCTTCTACCCCTCTGA-
TATAGCAGTCGAA TGGGAGTCCAACGGT-
CAACCGGAGAACAATTATAAGA
CAACTCCACCTGTGCTT GATTCA-
GACGGCTCTTTTTTCTTGTATAGCCGCCT-
TACCGTAGACAAGAGTCGAT GGCAG-
GAAGGTAATGTATTTTCT
TGTAGTGTAATGCACGAGGCACTTCAT-
AATCA CTACACACAAAAGTCTCTGT-
CACTTTCCCTGGGCAAATGA 234. 123-ATX1G5v1_Hs_IgG4_HC (SEQ ID NO: 234)
METDTLLLWVLLLWVPGSTGQVQLVQSG-
SEVKKPGSSVKVSCKASGGTFS
SYAISWVRQAPGQGLEWMGGIIP-
IFGTVTYAQKFQGGVTITA-
DESTNTVYMELSSLR SEDTAVYY-
CARDDFWTGDYWGQGTLVTVS
SASTKGPSVFPLAPCSRSTSESTAALG
CLVKDYFPEPVTVSWNSGALT-
SGVHTFPAVLQSSGLYS-
LSSVVTVPSSSLGTKTYTC
NVDHKPSNTKVDKRVESKYGPPCPPCPAPE-
FLGGPSVFLFPPKPKDTLMISRTPEVTC
VVVDVSQEDPE-
VQFNWYVDGVEVHNAKTKPREEQFN-
STYRVVSVLTVLHQDWLN
GKEYKCKVSNKGLPSSIEKTI
SKAKGQPREPQVYTLPPSQEEMTKNQVSLT-
CLVKGF YPSDIAVEWESNGQPEN-
NYKTTPPVLDSDGSFFLY-
SRLTVDKSRWQEGNVFSCSVM
HEALHNHYTQKSLSLSLGK

BOLD=signal peptide, underline=antibody variable region, regular font=antibody constant region 235. 123-ATX1G5v1_Hs_IgK_LC (SEQ ID NO: 235)
ATGAGAGCCTGGATCTTCTTCCTGCTTTG
TTTGGCAGGACGAGCGCTAGC CGATATTCA-
GATGACGCAGTCTC-
CAAGTAGCCTTTCCGCCTCTGTAGGCG
ACAGG GTGACAATTACCTGCCGGGCGAGC-
CAAGGCATCTCCAATTATCTCGCGTGGTTTC
AGCAGAAACCAG-
GAAAAGCTCCGAAGTCCCTTATC-
TATGCAGCTTCTAGTCTTC AAAGTG-
GAGTCCCTTCAAAGTTCT
CCGGGTCCGGCAGCGGCACGGACTTCACCC
TCACAATATCATCACTCCAGCCAGAGGAT-
TTGGCAACGTACTATTGCCAGCAAT
ACAATAGTTACCCTTA-
CACTTTTGGGCAAGGCACTAAGCTCGAAAT-
TAAGCGTA CGGTAGCTGCGCCTAGCGTGTT-
TATTTTTCCGCCCTCTGACGAAC
AACTCAAAAG
TGGCACTGCCTCTGTAGTCTGTCTCCT-
GAACAATTTTTATCCAAGGGAAGCTAAG
GTACAGTGGAAAGTCGATAACGCGCTC-
CAAAGTGGCAACAGTCAAGAATCTGTAACG-
GAGCAAGATAGTAAAGACAGCACTTA-
CAGCTTGAGCAGCACACTCACATTG
TCCAAGGCCGACTACGAAAAACAT-
AAAGTGTACGCCTGTGAGGTAACACACCAG
GGTCTGAGCAGCCCAGTGACGAAGTCATT-
TAATCGCGGTGAGTGCTGA 236. 123-ATX1G5v1_Hs_IgK_LC (SEQ ID NO: 236)
MRAWIFFLLCLAGRALADIQMTQSPSSL-
SASVGDRVTITCRASQGISNYLA
WFQQKPGKAPKSLI-
YAASSLOSGVPSKFSGSGSGTDFTLTISSLOPE-
DLATYYCQQYN SYPY-
TFGQGTKLEIKRTVAAPSVFIFPP
SDEQLKSGTASVVCLLNNFYPREAKVQWK
VDNALQSGNSQESVTEQDSKDSTYSLSSTLTL-
SKADYEKHKVYACEVTHQGLSSPV
TKSFNRGEC BOLD=signal peptide, underline=antibody variable region, regular font=antibody constant region 237. 123-ATX1G5v2_Hs_IgG1_HC (SEQ ID NO: 237)
ATGGAGACAGATACTTTGCTCCTTTGGGT
ACTCTTGCTGTGGGTTCCCGGT
AGCACCGGCCAGGTA-
CAGCTCGTTCAGTCAGGGAGTGAGGT-
CAAGAAACCGGGT TCCTCTGT-
CAAAGTTTCCTGCAAGGCC
AGTGGAGGCACCTTTAGTTCTTACGCAA
TTAGCTGGGTACGACAGGCACCCGGC-
CAAGGGCTGGAATGGATGGGAGGGATA
ATTCCCATTTTCGGTACAGTGACTTACGCC-
CAAAAGTTCCAAGGCCGCGTAACGA
TCACAGCAGACGAGTCTAC-
CAATACTGTGTACATGGAATTGAGTAGCCT-
TAGAA GCGAGGACACAGCAGTCTAT-
TACTGTGCGCGGGACGACTTTT
GGACTGGTGACT
ACTGGGGCCAGGGCACTCTGG
TAACGGTGTCTAGCGCTAGCAC-
CAAAGGACCCT
CCGTCTTTCCGCTCGCGCCGAGC
AGCAAGTC-
CACGAGCGGGGGGACAGCCGCCC
TTGGGTGTCTGGTCAAGGATTATTTTCCT-
GAGCCCGTTACTGTCTCCTGGAATAG
CGGTGCCTTGACTTCTGGGGTACAT-
ACCTTCCCGGCGGTTTTGCAATCATCAGGA
CTGTATAGCCTCTCTAGCGTTGTAACGGTAC-
CATCTTCATCACTTGGCACACAAA CATATAT-
TTGTAATGTAAATCACAAACCTT-
CAAATACTAAAGTTGACAAAAAAG
TGGAGCCGAAGAGCTGTGATAAAACGCAT- ACTTGCCCGCCTTGCCCCGCTCCAG AAT-
TGCTGGGCGGGCCGTCTGTGTTCCTCTTCC-
CACCGAAACCGAAGGATACGCT
GATGATAAGTCGAACGCCCGAAGTAA-
CATGCGTGGTTGTTGATGTAAGCCACGA
AGATCCGGAAGTAAAGTT-
CAACTGGTACGTAGATGGAGTAGAAGTG-
CATAACGC GAAAACTAAGCCCCGCGAG-
GAGCAATATAATTCAACCT
ATCGGGTTGTTAGTGT GCTCACCGTTCTC-
CATCAGGATTGGCTTAACGG-
GAAAGAGTATAAGTGCAAGGT
TAGCAATAAAGCATTGCCAGCACC-
TATAGAGAAGACAATTAGCAAAGCGAAGG
GACAGCCACGAGAGCCCCAAGTCTA-
CACGCTGCCTCCCAGCCGCGACGAGTTGA
CGAAGAATCAAGTGTCACTCA-
CATGTCTTGTCAAGGGATTCTATCCCTCAGA-
TAT TGCAGTAGAATGG-
GAGTCTAATGGACAACC
AGAGAACAACTATAAAACTACTCC
ACCGGTGCTTGA-
TAGTGACGGTAGTTTTTTCCTT-
TATAGTAAGCTGACTGTCGAT
AAGAGTCGCTGGCAACAGG-
GAAATGTTTTTTCTTGTAGTGTTATGCAT-
GAAGCAC TTCATAACCATTA-
CACACAAAAGTCTCTGTCAC
TTTCCCCTGGCAAATGA 238. 123-ATX1G5v2_Hs_IgG1_HC (SEQ ID NO: 238)

METDTLLLWVLLLWVPGSTGQVQLVQSG-
SEVKKPGSSVKVSCKASGGTFS
SYAISWVRQAPGQGLEWMGGIIP-
IFGTVTYAQKFQGRVTITA-
DESTNTVYMELSSLR SEDTAVYY-
CARDDFWTGDYWGQGTLVTVSSAST
KGPSVFPLAPSSKSTSGGTAALG CLVKDYF-
PEPVTVSWNSGALTSGVHTFPAVLQSSGLYS-
LSSVVTVPSSSLGTQTYICN
VNHKPSNTKVDKKVEPKSCDKTHTCPPCPA-
PELLGGPSVFLFPPKPKDTLMISRTPEV
TCVVVDVSHEDPE-
VKFNWYVDGVEVHNAKTKPREEQYN-
STYRVVSVLTVLHQDW LNGKEYKCKVSNKA-
LPAPIEKTISKAKGQPREPQV
YTLPPSRDELTKNQVSLTCLVK GFYPSDIA
VEWESNGQPENNYKTTPPVLDSDGSFFLYSK-
LTVDKSRWQQGNVFSCS VMHEALHN-
HYTQKSLSLSPGK

BOLD=signal peptide, underline=antibody variable region, regular font=antibody constant region 239. 123-ATX1G5v2_Hs_IgG4_HC (SEQ ID NO: 239)

ATGGAGACAGATACTTTGCTCCTTTGGGTA
CTCTTGCTGTGGGTTCCCGGT
AGCACCGGCCAGGTA-
CAGCTCGTTCAGTCAGGGAGTGAGGT-
CAAGAAACCGGGT TCCTCTGT-
CAAAGTTTCCTGCAAGGCCAGTG
GAGGCACCTTTAGTTCTTACGCAA
TTAGCTGGGTACGACAGGCACCCGGC-
CAAGGGCTGGAATGGATGGGAGGGATA
ATTCCCATTTTCGGTACAGTGACTTACGCC-
CAAAAGTTCCAAGGCCGCGTAACGA
TCACAGCAGACGAGTCTAC-
CAATACTGTGTACATGGAATTGAGTAGCCT-
TAGAA GCGAGGACACAGCAGTCTAT-
TACTGTGCGCGGGACGACT
TTTGGACTGGTGACT
ACTGGGGCCAGGGCACTCTGGTAAC
GGTGTCTAGCGCTAGCACCAAAGGACCCT
CCGTCTTTCCGCTCGCGCCGTGCTCTCGATC-
CACGAGCGAGTCTACGGCGGCCTT
GGGCTGTCTCGTGAAAGACTAT-
TTCCCAGAGCCAGTGACCGTTTCCTG-
GAACTCC GGAGCGCTCACATCAGGTGTG-
CATACCTTTCCAGCCGTACT
TCAATCTTCAGGGC
TGTATAGCTTGTCCTCTGTCGTGAC
CGTACCCTCCAGTTCTCTCGGGACAAAGAC
CTATACCTGTAACGTAGACCATAAGCCATC-
CAATACCAAAGTAGATAAGAGGGT
GGAATCTAAATATGGACCGCCTT
GTCCGCCGTGCCCGGCTCCT-
GAGTTCCTTGGA
GGGCCGTCCGTCTTTCTGTT
TCCCCCTAAACCTAAGGACACCCTGATGA-
TAAGTA GGACGCCG-
GAAGTAACCTGTGTCGTGGTTGATGTGT-
CACAGGAAGACCCGGAGG
TACAATTTAATTGGTACGTCGATG-
GAGTCGAGGTGCATAATGCGAAAACCAAGC
CACGAGAGGAGCAATTCAACAGCACC-
TACCGAGTAGTTTCAGTCTTGACTGTGC
TGCACCAAGACTGGCT-
GAATGGCAAGGAGTA-
CAAATGCAAGGTCAGTAATAAA GGAT-
TGCCGTCTTCAATAGAGAAG
ACTATCAGTAAGGCGAAGGGACAACCTCGC
GAGCCTCAGGTATACACTTTGCCGCCCAGC-
CAAGAAGAAATGACGAAGAACCAA
GTCTCTTTGACTTGCCTGGTCAAAGGCTTC-
TACCCCTCTGATATAGCAGTCGAAT
GGGAGTCCAACGGTCAACCGGAGAACAAT-
TATAAGACAACTCCACCTGTGCTTG ATTCA-
GACGGCTCTTTTTTCTTGTATAGCCGCCT-
TACCGTAGACAAGAGTCGATG
GCAGGAAGGTAATGTAT-
TTTCTTGTAGTGTAATGCACGAGGCACTT-
CATAATCAC TACACACAAAAGTCTCTGT-
CACTTTCCCTGGGCAAATGA 240. 123-ATX1G5v2_Hs_IgG4_HC (SEQ ID NO: 240)

METDTLLLWVLLLWVPGSTGQVQLVQSG-
SEVKKPGSSVKVSCKASGGTFS
SYAISWVRQAPGQGLEWMGGIIP-
IFGTVTYAQKFQGRVTITA-
DESTNTVYMELSSLR SEDTAVYY-
CARDDFWTGDYWGQGTLVTVSSASTKGPSVF-
PLAPCSRSTSESTAALG
CLVKDYFPEPVTVSWNSGALT-
SGVHTFPAVLQSSGLYS-
LSSVVTVPSSSLGTKTYTC
NVDHKPSNTKVDKRVESKYGPPCPPCPAPE-
FLGGPSVFLFPPKPKDTLMISRTPEVTC
VVVDVSQEDPE-
VQFNWYVDGVEVHNAKTKPREEQFN-
STYRVVSVLTVLHQDWLN
GKEYKCKVSNKGLPSSIEKTISKA
KGQPREPQVYTLPPSQEEMTKNQVSLT-
CLVKGF YPSDIAVEWESNGQPEN-
NYKTTPPVLDSDGSFFLY-
SRLTVDKSRWQEGNVFSCSVM
HEALHNHYTQKSLSLSLGK

BOLD=signal peptide, underline=antibody variable region, regular font=antibody constant region 241. Chi-10C4_Hs_IgG1_HC (SEQ ID NO: 241)
ATGGAGACCGACACACTGCTGCTGTGG GTGCTGCTGCTGTGGGTGCCAGG CTC-CACCGGACAGGTGCAGCT-GAAGAAGTCTGGACCTGGACTGGTGGCAC-CATC CCAGAACCTGTCTATCACCTGCACAGT-GAGCGGCTTCTCCCTGACCACATACGAC ATCAATTG-GATCAGGCAGCCCCCTGGCAAGGATCTG-GAGTGGCTGGGCGTGATC TGGACCGGAG-GAGGCACAAACTATAATAGCGC CTTCATGTCCCGCCTGTCTATC AGCAAGGACAACTC-CAAGTCTCAGGTGTTTCTGAAGAT-GAATAGCCTGCAGACC GACGATACAGC-CATGTACTATTGCGTGCGGGG CGACACCTACCACTATGCCCTG GAT-TTTTGGGGCCAGGGCACCTCTGTGACAGT-GAGCTCCGCTAGCACCAAAGGA CCCTCCGTCTTTCCGCTCGC GCCGAGCAGCAAGTC-CACGAGCGGGGGGACAGCC GCCCTTGGGTGTCTGGTCAAGGATTAT-TTTCCTGAGCCCGTTACTGTCTCCTGGA ATAGCGGTGCCTTGACTTCTGGGGTACAT-ACCTTCCCGGCGGTTTTGCAATCATC AGGACTGTATAGCCTCTCTAGCG TTGTAACGGTACCATCTTCAT-CACTTGGCACA CAAACATATAT-TTGTAATGTAAATCACAAACCTT-CAAATACTAAAGTTGACAAA AAAGTGGAGCCGAAGAGCTGTGA-TAAAACGCATACTTGCCCGCCTTGCCCCGCT CCAGAAT-TGCTGGGCGGGCCGTCTGTGTTCCTCTTCC-CACCGAAACCGAAGGAT ACGCTGATGA-TAAGTCGAACGCCCGAAGTAAC ATGCGTGGTTGTTGATGTAAGC CACGAA-GATCCGGAAGTAAAGTTCAACTGGTACGTA-GATGGAGTAGAAGTGCAT AACGCGAAAACTAAGCCCCGCGAG-GAGCAATATAATTCAACCTATCGGGTTGTT AGTGTGCTCACCGTTCTCCATCAGGAT-TGGCTTAACGGGAAAGAGTATAAGTGC AAGGTTAGCAATAAAGCATTGCCAGCACC-TATAGAGAAGACAATTAGCAAAGC GAAGGGACAGCCACGAGAGCCCCAAGTC-TACACGCTGCCTCCCAGCCGCGACGA GTTGACGAAGAATCAAGTGTCACTCA-CATGTCTTGTCAAGGGATTCTATCCCTCA GATATTGCAGTAGAATGG-GAGTCTAATGGACAACCAGAGAACAAC-TATAAAACT ACTCCACCGGTGCTTGA-TAGTGACGGTAGTTTTTTCCTT TATAGTAAGCTGACTG TCGA-TAAGAGTCGCTGGCAACAGG-GAAATGTTTTTTCTTGTAGTGTTATGCATGA AGCACTTCATAACCATTA-CACACAAAAGTCTCTGT-CACTTTCCCCTGGCAAATGA 242. Chi-10C4_Hs_IgG1_HC (SEQ ID NO: 242)
METDTLLLWVLLLWVPG-STGQVQLKKSGPGLVAPSQNL-SITCTVSGFSLTT YDINWIRQPPGKDLEW-LGVIWTGGGTNYNSAFMSRLSIS KDNSKSQVFLKMNSLQT DDTAMYYCVRGDTYHY-ALDFWGQGTSVTVSSASTKGPSVF-PLAPSSKSTSGGTAAL GCLVKDYF-PEPVTVSWNSGALTSGVHTFPAVLQ SSGLYSLSSVVTVPSSSLGTQTYIC NVNHKPSNTKVDKKVEPKSCDKTHTCPPCPA-PELLGGPSVFLFPPKPKDTLMISRTPE VTCVVVDVSHEDPE-VKFNWYVDGVEVHNAKTKPREEQYN-STYRVVSVLTVLHQD WLNGKEYKCKVSNKA-LPAPIEKTISKAKGQPREPQVYTLP PSRDELTKNQVSLTCLV KGFYPSDIA-VEWESNGQPENNYKTTPPVLDSDGSFFLYSK-LTVDKSRWQQGNVFSC SVMHEALHN-HYTQKSLSLSPGK BOLD=signal peptide, underline=antibody variable region, regular font=antibody constant region 243. Chi-10C4_Hs_IgG4_HC (SEQ ID NO: 243)
ATGGAGACCGACACACTGCTGCT GTGGGTGCTGCTGCTGTGGGTGCCAGG CTC-CACCGGACAGGTGCAGCT-GAAGAAGTCTGGACCTGGACTGGTGGCAC-CATC CCAGAACCTGTCTATCACCTGCACAGT-GAGCGGCTTCTCCCTGACCACATACGAC ATCAATTG-GATCAGGCAGCCCCCTGGCAAGGATCTG-GAGTGGCTGGGCGTGATC TGGACCGGAG-GAGGCACAAACTATAAT AGCGCCTTCATGTCCCGCCTGTCTATC AGCAAGGACAACTC-CAAGTCTCAGGTGTTTCTGAAGAT-GAATAGCCTGCAGACC GACGATACAGC-CATGTACTATTGCGTGCGG GGCGACACCTACCACTATGCCCTG GAT-TTTTGGGGCCAGGGCACCTCTGTGACAGT-GAGCTCCGCTAGCACCAAAGGA CCCTCCGTCTTTCCGCTCGCGCCGTGCTCTC-GATCCACGAGCGAGTCTACGGCGG CCTTGGGCTGTCTCGTGAAAGACTAT-TTCCCAGAGCCAGTGACCGTTTCCTGGAA CTCCGGAGCGCTCACATCAGGTGTGCAT-ACCTTTCCAGCCGTACTTCAATCTTCA GGGCTGTATAGCTTGTCCT CTGTCGTGACCGTACCCTCC AGTTCTCTCGGGACAA AGACC-TATACCTGTAACGTAGACCATAAGCCATC-CAATACCAAAGTAGATAAGA GGGTG-GAATCTAAATATGGACCGCCTT GTCCGCCGTGCCCGGCTCCTGAGTTCCT TGGAGGGCCGTCCGTCTTTCT GTTTCCCCCTAAACCTAAGGACACCCTGAT-GATA AGTAGGACGCCG-GAAGTAACCTGTGTCGTGGTTGATGTGT-CACAGGAAGACCCG GAGGTACAATTTAATTGGTACGTCGATG-GAGTCGAGGTGCATAATGCGAAAACC AAGCCACGAGAGGAGCAATT-CAACAGCACC-TACCGAGTAGTTTCAGTCTTGACT GTGCTGCACCAAGACTGGCT-GAATGGCAAGGAGTA-CAAATGCAAGGTCAGTAAT AAAGGAT-TGCCGTCTTCAATAGAGAAGAC TATCAGTAAGGCGAAGGGACAACCT CGCGAGCCTCAGGTATA-CACTTTGCCGCCCAGC- CAAGAAGAAATGACGAAGAAC CAAGTCTCTTTGACTTGCCTGGT-CAAAGGCTTCTACCCCTCTGA-TATAGCAGTCG AATGGGAGTCCAACGGT-CAACCGGAGAACAATTATAAGACAA CTCCACCTGTGC TTGATTCA-GACGGCTCTTTTTTCTTGTATAGCCGCCT-TACCGTAGACAAGAGTCG ATGGCAG-GAAGGTAATGTATTTTCTTGTAGT GTAATGCACGAGGCACTTCATAAT CACTA-CACACAAAAGTCTCTGT-CACTTTCCCTGGGCAAATGA 244. Chi-10C4_Hs_IgG1_HC (SEQ ID NO: 244)

METDTLLLWVLLLWVPG-STGQVOLKKSGPGLVAPSQNL-SITCTVSGFSLTT YDINWIRQPPGKDLEW-LGVIWTGGGTNYNSAFMSRLSIS KDNSKSQVFLKMNSLOT DDTAMYYCVRGDTYHY-ALDFWGQGTSVTVSSASTKGPSVF-PLAPCSRSTSESTAAL GCLVKDYF-PEPVTVSWNSGALTSGVHTFPAV LQSSGLYSLSSVVTVPSSSLGTKTYT CNVDHKPSNTKVDKRVESKYGPPCPPCPAPE-FLGGPSVFLFPPKPKDTLMISRTPEVT CVVVDVSQEDPE-VQFNWYVDGVEVHNAKTKPREEQFN-STYRVVSVLTVLHQDWL NGKEYKCKVSNKGLPSSIEK TISKAKGQPREPQVYTLPPSQEEMTKNQVSLT-CLVKG FYPSDIAVEWESNGQPEN-NYKTTPPVLDSDGSFFLY-SRLTVDKSRWQEGNVFSCSV MHEALHNHYTQKSLSLSLGK

BOLD=signal peptide, underline=antibody variable region, regular font=antibody constant region 245. Chi-10C4_Hs_IgK_LC (SEQ ID NO: 245)

atggagacagatactttgctcctttgggttttgttgctgtgggttccaggatc-cacgggggatattgtaatgagccagagtcct tcttcat-tggccgtttcagcaggtgaaaaggtcaccatgtcctgtaaatcaagt-caatctctcttgtcatcagggaccagaaagaattatct ggcttggtaccagcaaaaaccgggacaatcaccaaagcttttgatt-tactgggcctccacaagagaatctggcgtaccggatcgcttta ctggcagcggctccggtactgacttcactcttacgatt-agtagtgttcaggcggaggaccttgcggtctactactgtaaacagtctta-cat cctgttcactttcgggtcaggaacaaaattggagat-caagcgaactgttgcagctccaagtgttttcatattt ccgccgtcagatgaacaa ctgaaatcaggcacagcctcagtggtgtgtctgcttaataatttc-taccctcgagaggcaaaggtacagtggaaggtagacaacgccc tgcaaagcgggaatagtcaagaaagcgttacggaacaagatagcaaa-gattccacctactcactcagttctaccttgaccctcagcaa ggctgat-tacgagaagcataaagtgtatgcgtgcgaagtgacccat-caaggactctcctcacctgttacaaagtcctttaatcgcgggg agtgttaatga 246. Chi-10C4_Hs_IgK_LC (SEQ ID NO: 246)

METDTLLLWVLLLWVPGSTGDI-VMSQSPSSLAVSAGEKVTMSCKSSQSLLS SGTRKNYLAWYQQKPGQSPKLLIYWAST-RESGVPDRFTGSGSGTDFTLTISSVQAED LAVYYCKQSYIL-FTFGSGTKLEIKRTVAAPSVFIFPPSDEQLKSG-TASVVCLLNNFYPR EAKVQWKVD-NALQSGNSQESVTEQDSKDSTY SLSSTLTLSKADYEKHKVYACEVT HQGLSSPVTKSFNRGEC

BOLD=signal peptide, underline=antibody variable region, regular font=antibody constant region 247. HuV1-10C4_IgG1_HC (SEQ ID NO: 247)

ATGAGAGCCTGGATCTTCTTCCTGCTTTGTTTG GCAGGACGAGCGCTAGC CCAAGTGCAACTTCAG-GAATCCGGGCCGGGTCTCGTAAAGC CCAGCGAGACGCT TAGTCTCA-CATGCACAGTCAGTGGTTT CAGTTTGACGACGTACGATATAAACTGG ATCCGCCAACCCCCTGGCAAAGGGCTT-GAATGGATAGGCGTTATATGGACGGGC GGGGGCACTAATTACAACTCCGCTTT-CATGTCCCGAGTAACTATATCAGTAGACA CATCAAAGAACCAATTTCCCTGAAATT-GAGTAGTGTGACCGCAGCGGATACCG CAGTTTATTACTGTGCCAGAGCCGATACC-TATCACTACGCTCTTGATTTCTGGGG CCAAGGAACCTTGGTAACAGTGTC TTCAGCTAGCACCAAAGGACCCTCCGTCTTT CCGCTCGCGCCGAGCAGCAAGTC-CACGAGCGGGGGGACAGCCGCCC TTGGGTGT CTGGTCAAGGATTATTTCCT-GAGCCCGTTACTGTCTCCTG-GAATAGCGGTGCCT TGACTTCTGGGGTA-CATACCTTCCCGGCGGTTTTGCAATC ATCAGGACTGTATAG CCTCTCTAGCGTTGTAACGGTACCATCTT-CATCACTTGGCACACAAACATATATT TGTAATGTAAATCACAAACCTT-CAAATACTAAAGTTGACAAAAAAGTG-GAGCCG AAGAGCTGTGATAAAACGCAT-ACTTGCCCGCCTTGCCCCGCTCCA GAATTGCTG GGCGGGCCGTCTGTGTTCCTCTTCC-CACCGAAACCGAAGGATACGCTGATGATA AGTCGAACGCCCGAAGTAA-CATGCGTGGTTGTTGATGTAAGCCACGAA-GATCCG GAAGTAAAGTTCAACTGGTACGTA-GATGGAGTAGAAGTGCATAACGCGAAAACT AAGCCCCGCGAGGAGCAATATAATTCAACC-TATCGGGTTGTTAGTGTGCTCACC GTTCTC-CATCAGGATTGGCTTAACGG-GAAAGAGTATAAGTGCAAGGTTAGCAAT AAAGCATTGCCAGCACCTATAGAGAA-GACAATTAGCAAAGCGAAGGGACAGCC ACGAGAGCCCCAAGTCTA-CACGCTGCCTCCCAGCCGCGAC GAGTTGACGAAGAA TCAAGTGTCACTCA-CATGTCTTGTCAAGGGATTCTATCCCTCAGA-TATTGCAGTA GAATGG-GAGTCTAATGGACAACCAGAGA ACAACTATAAAACTACTCCACCGGTG CTT-GATAGTGACGGTAGTTTTTTCCTT-TATAGTAAGCTGACTGTCGATAAGAGTC GCTGGCAACAGG-GAAATGTTTTTTCTTGTAGTGTTATGCAT-GAAGCACTTCATAA CCATTA-CACACAAAAGTCTCTGTCA CTTTCCCCTGGCAAATGA

248. HuV1-10C4_IgG1_HC (SEQ ID NO: 248)

MRAWIFFLLCLAGRALAQVQLQESGPGLVKP-SETLSLTCTVSGFSLTTYDIN WIRQPPGK-GLEWIGVIWTGGGTNYN-SAFMSRVTISVDTSKNQFSLKLSSVTAADTAV YYCARADTYHYALDFWGQGTLVTVSSAS-TKGPSVFPLAPSSKSTSGGTAALGCLVK DYF-

PEPVTVSWNSGALTSGVHTFPAVLQSSGLYS-
LSSVVTVPSSSLGTQTYICNVNH
KPSNTKVDKKVEPKSCDKTHTCPPCPA-
PELLGGPSVFLFPPKPKDTLMISRTPEVTCV
VVDVSHEDPE-
VKFNWYVDGVEVHNAKTKPREEQYN-
STYRVVSVLTVLHQDWLNG KEYKCKVSNKA-
LPAPIEKTISKAKGQPREPQVY
TLPPSRDELTKNQVSLTCLVKGFY PSDIA
VEWESNGQPENNYKTTPPVLDSDGSFFLYSK-
LTVDKSRWQQGNVFSCSVMH EALHN-
HYTQKSLSLSPGK

BOLD=signal peptide, underline=antibody variable region, regular font=antibody constant region 249. HuV1-10C4_IgG4_HC (SEQ ID NO: 249)

ATGAGAGCCTG-
GATCTTCTTCCTGCTTTGTTTGG
CAGGACGAGCGCTAGC
CCAAGTGCAACTTCAG-
GAATCCGGGCCGGGTCTCGTA
AAGCCCAGCGAGACGCT TAGTCTCA-
CATGCACAGTCAGTGGTTTC
AGTTTGACGACGTACGATATAAACTGG
ATCCGCCAACCCCCTGGCAAAGGGCTT-
GAATGGATAGGCGTTATATGGACGGGC
GGGGGCACTAATTACAACTCCGCTTT-
CATGTCCCGAGTAACTATATCAGTAGACA
CATCAAAGAACCAATTTTCCCTGAAATT-
GAGTAGTGTGACCGCAGCGGATACCG
CAGTTTATTACTGTGCCAGAGCCGATACC-
TATCACTACGCTCTTGATTTCTGGGG
CCAAGGAACCTTGGTAACAGT
GTCTTCAGCTAGCAC-
CAAAGGACCCTCCGTCTTT
CCGCTCGCGCCGTGCTCTCGATC-
CACGAGCGAGTC-
TACGGCGGCCTTGGGCTGTC TCGTGAAA-
GACTATTTCCCAGA
GCCAGTGACCGTTTCCTGGAACTCCG-
GAGCGCT CACATCAGGTGTGCAT-
ACCTTTCCAGCCGTACTT-
CAATCTTCAGGGCTGTATAGC
TTGTCCTCTGTCGTGACCGTAC
CCTCCAGTTCTCTCGGGACAAAGACC-
TATACCT GTAACGTAGACCATAAGCCATC-
CAATACCAAAGTAGATAAGAGGGTG-
GAATCTA AATATGGACCGCCTTGTCCGCC
GTGCCCGGCTCCTGAGTTCCTTG-
GAGGGCCGTC
CGTCTTTCTGTTTCCCCCTAAACCT
AAGGACACCCTGATGATAAGTAGGACGCCG
GAAGTAACCTGTGTCGTGGTTGATGTGT-
CACAGGAAGACCCGGAGGTACAATTT AAT-
TGGTACGTCGATGGAGTCGAGGTGCAT-
AATGCGAAAACCAAGCCACGAGA
GGAGCAATTCAACAGCACC-
TACCGAGTAGTTTCAGTCTTGACT
GTGCTGCACCA AGACTGGCT-
GAATGGCAAGGAGTA-
CAAATGCAAGGTCAGTAATAAAGGATTGC
CGTCTTCAATAGAGAAGAC-
TATCAGTAAGGCGAAGGGACAAC
CTCGCGAGCCTC AGGTATA-
CACTTTGCCGCCCAGC-
CAAGAAGAAATGACGAAGAAC-
CAAGTCTCTT
TGACTTGCCTGGTCAAAGGCTTC-
TACCCCTCTGATATAGCAGTCGAATGG-
GAGTC CAACGGTCAACCGGAGAACAAT-
TATAAGACAACTCCACCTGTGCTTG
ATTCAGA
CGGCTCTTTTTTCTTGTATAGCCGCCT-
TACCGTAGACAAGAGTCGATGGCAGGAA
GGTAATGTAT-
TTTCTTGTAGTGTAATGCACGAGGCACTT-
CATAATCACTACACAC AAAAGTCTCTGT-
CACTTTCCCTGGGCAAATGA

250. HuV1-10C4_IgG4_HC (SEQ ID NO: 250)

MRAWIFFLLCLAGRALAQVQLQESGPGLVKP-
SETLSLTCTVSGFSLTTYDIN WIRQPPGK-
GLEWIGVIWTGGGTNYN-
SAFMSRVTISVDTSKNQFSLKLSSVTAADTAV
YYCARADTYHYALDFWGQGTLVTVSSAS-
TKGPSVFPLAPCSRSTSESTAALGCLVK DYF-
PEPVTVSWNSGALTSGVHTFPAVLQSSGLYS-
LSSVVTVPSSSLGTKTYTCNVDH
KPSNTKVDKRVESKYGPPCPPCPAPE-
FLGGPSVFLFPPKPKDTLMISRTPEVTCVVVD
VSQEDPEVQFNWYVDGVEVHNAKTKPRE-
EQFNSTYRVVSVLTVLHQDWLNGKEY
KCKVSNKGLPSSIEKTISKAKGQ
PREPQVYTLPPSQEEMTKNQVSLT-
CLVKGFYPSDI AVEWESNGQPEN-
NYKTTPPVLDSDGSFFLY-
SRLTVDKSRWQEGNVFSCSVMHEALH
NHYTQKSLSLSLGK

BOLD=signal peptide, underline=antibody variable region, regular font=antibody constant region 251. HuV1-10C4_IgK_LC (SEQ ID NO: 251)

ATGAGAGCCTGGATCTTCTTCCTGCTTTGTTTG
GCAGGACGAGCGCTAGC CGA-
CATCGTAATGACTCAATCTCCGGATT-
CACTTGCGGTCTCCTTGGGTGAACGA
GCAACTATAAATTGCAAATCAAGT-
CAATCCCTCCTCAGTAGCGGCACGAGGAAA
AACTACCTCGCATGGTAT-
CAACAAAAGCCAGGACAGCCGCC-
CAAACTGTTGATA TACTGGGCGTC-
CACCCGAGAGTCCGGGGTCC
CGGATCGATTTAGCGGTAGTGGA
TCTGGTACCGACTTCACTCTCACCAT-
TTCCTCTCTGCAAGCAGAAGACGTTGCAG
TATATTACTGCAAACAGAGTTACATCCTCTT-
TACTTTCGGTCAGGGAACTAAACT TGAAAT-
CAAGCGAACAGTGGCGGCACCGTCCGTATT-
TATTTTCCCTCCAAGTGAT
GAGCAGCTCAAAAGTGGCACAGCGAGC
GTTGTATGTCTCCTCAATAACTTTTACC
CCAGAGAGGCGAAAGTACAATGGAAGGTT-
GATAACGCACTCCAAAGCGGTAAC TCTCAG-
GAGAGTGTCACAGAACAGGATAGTAAA-
GACTCCACCTACTCCCTCAGT
TCTACCCTTACTCTTTCAAAAGCGGATTAT-
GAGAAACACAAGGTTTACGCCTGTG AAGT-
CACTCATCAGGGACTGAGTTCCCCGGT-
CACGAAGTCATTTAATCGCGGTG
AGTGCTGA

252. HuV1-10C4_IgK_LC (SEQ ID NO: 252)

MRAWIFFLLCLAGRALADIVMTQSPD-
SLAVSLGERATINCKSSQSLLSSGTR
KNYLAWYQQKPGQPPKLLIYWAST-
RESGVPDRFSGSGSGTDFTLTISSLQAEDVAVY
YCKQSYIL-
FTFGQGTKLEIKRTVAAPSVFIFPPSDEQLKSG-

TASVVCLLNNFYPREAK VQWKVD-
NALQSGNSQESVTEQDSKDSTY
SLSSTLTLSKADYEKHKVYACEVTHQG
LSSPVTKSFNRGEC

BOLD=signal peptide, underline=antibody variable region, regular font=antibody constant region 253. HuV2-10C4_IgG1_HC (SEQ ID NO: 253)

ATGAGAGCCTGGATCTTCTTCCTGCTTTGTTT
GGCAGGACGAGCGCTAGC CCAGGTA-
CAGTTGCAGGAGTCTGGCCCAGGCCTG
GTAAAGCCTAGCGAAACGCT
CAGTTTGACTTGCACCGTTT
CAGGCTTTTCCCTTACCACTTATGACTGGT-
CATGGA TACGACAACCACCTGG-
GAAAGGCCTGGAGTG-
GATCGGGTATATCTGGACCGGGG
GCGGTACGAACTATAACCCCTCCCT-
CAAATCTAGGGTTACTATTAGCGTAGATAC
TTCCAAGAACCAATTTTCTTTGAAATTGT-
CAAGCGTAACAGCAGCAGATACGGCT GTC-
TACTATTGCGTGAGGGGAGATACGTATCAT-
TATGCACTTGACTTTTGGGGAC
AAGGAACCTTGGTAACAGTGT
CTTCAGCTAGCAC-
CAAAGGACCCTCCGTCTTTCC
GCTCGCGCCGAGCAGCAAGTC-
CACGAGCGGGGGGACAGCCG
CCCTTGGGTGTCT GGTCAAGGATTAT-
TTTCCTGAGCCCGTTACTGTCTCCTG-
GAATAGCGGTGCCTTG ACTTCTGGGGTA-
CATACCTTCCCGGCGGTTTTGC
AATCATCAGGACTGTATAGCC
TCTCTAGCGTTGTAACGGTACCATCTTCAT-
CACTTGGCACACAAACATATATTTG
TAATGTAAATCACAAACCTT-
CAAATACTAAAGTTGACAAAAAAGTG-
GAGCCGAA GAGCTGTGATAAAACGCAT-
ACTTGCCCGCCTTGCCCCGCTCCA
GAATTGCTGGGC
GGGCCGTCTGTGTTCCTCTTCC-
CACCGAAACCGAAGGATACGCTGATGA-
TAAGTC GAACGCCCGAAGTAA-
CATGCGTGGTTGTTGATGTA
AGCCACGAAGATCCGGAAG TAAAGTT-
CAACTGGTACGTAGATGGAGTAGAAGTG-
CATAACGCGAAAACTAAGC CCCGCGAG-
GAGCAATATAATTCAACCTATC
GGGTTGTTAGTGTGCTCACCGTTCT
CCATCAGGATTGGCTTAACGG-
GAAAGAGTATAAGTGCAAGGT-
TAGCAATAAAGC ATTGCCAGCACC-
TATAGAGAAGACAATTAGCA
AAGCGAAGGGACAGCCACGAG AGCCC-
CAAGTCTACACGCTGCCTCCCAGCCGCG
ACGAGTTGACGAAGAATCAAG TGTCACT-
CACATGTCTTGTCAAGGGATTCTATCCCTCA-
GATATTGCAGTAGAATG
GGAGTCTAATGGACAACCAGAGAACAAC-
TATAAAACTACTCCACCGGTGCTTGA
TAGTGACGGTAGTTTTTTCCTT-
TATAGTAAGCTGACTGTCGA-
TAAGAGTCGCTGG CAACAGG-
GAAATGTTTTTTCTTGTAGTGT
TATGCATGAAGCACTTCATAACCATT
ACACACAAAAGTCTCTGT-
CACTTTCCCCTGGCAAATGA

254. HuV2-10C4_IgG1_HC (SEQ ID NO: 254)

MRAWIFFLLCLAGRALAQVQLQESGPGLVKP-
SETLSLTCTVSGFSLTTYDW SWIRQPPGK-
GLEWIGYIWTGGGTNYNPSLKSRVTI
SVDTSKNQFSLKLSSVTAADTA
VYYCVRGDTYHYALDFWGQGTLVTVSSAS-
TKGPSVFPLAPSSKSTSGGTAALGCLV KDYF-
PEPVTVSWNSGALTSGVHTFPAVLQSSGLYS-
LSSVVTVPSSSLGTQTYICNVN
HKPSNTKVDKKVEPKSCDKTHTCPPCPA-
PELLGGPSVFLFPPKPKDTLMISRTPEVTC
VVVDVSHEDPE-
VKFNWYVDGVEVHNAKTKPREEQYN-
STYRVVSVLTVLHQDWLN GKEYKCKVSNKA-
LPAPIEKTISKAKGQPREPQVYTLPPS
RDELTKNQVSLTCLVKGF YPSDIA-
VEWESNGQPENNYKTTPPVLDSDGSFFLYSK-
LTVDKSRWQQGNVFSCSVM HEALHN-
HYTQKSLSLSPGK

BOLD=signal peptide, underline=antibody variable region, regular font=antibody constant region 255. HuV2-10C4_IgG4_HC (SEQ ID NO: 255)

ATGAGAGCCTGGATCTTCTTCCTGCTTTG
TTTGGCAGGACGAGCGCTAGC CCAGGTA-
CAGTTGCAG-
GAGTCTGGCCCAGGCCTGGTAA
AGCCTAGCGAAACGCT
CAGTTTGACTTGCACCGTTTC
AGGCTTTTCCCTTACCACTTATGACTGGT-
CATGGA TACGACAACCACCTGG-
GAAAGGCCTGGAGTG-
GATCGGGTATATCTGGACCGGGG
GCGGTACGAACTATAACCCCTCCCT-
CAAATCTAGGGTTACTATTAGCGTAGATAC
TTCCAAGAACCAATTTTCTTTGAAATTGT-
CAAGCGTAACAGCAGCAGATACGGCT GTC-
TACTATTGCGTGAGGGGAGATACGTATCAT-
TATGCACTTGACTTTTGGGGAC
AAGGAACCTTGGTAACAGTGTC
TTCAGCTAGCAC-
CAAAGGACCCTCCGTCTTTCC
GCTCGCGCCGTGCTCTCGATC-
CACGAGCGAGTC-
TACGGCGGCCTTGGGCTGTCTC GTGAAA-
GACTATTTCCCAGAGCCAGT
GACCGTTTCCTGGAACTCCGGAGCGCTC
ACATCAGGTGTGCAT-
ACCTTTCCAGCCGTACTT-
CAATCTTCAGGGCTGTATAGCT
TGTCCTCTGTCGTGACCGT
ACCCTCCAGTTCTCTCGGGACAAAGACC-
TATACCTG TAACGTAGACCATAAGCCATC-
CAATACCAAAGTAGATAAGAGGGTG-
GAATCTAA ATATGGACCGCCTTGTCCGCCG
TGCCCGGCTCCTGAGTTCCTTG-
GAGGGCCGTCC
GTCTTTCTGTTTCCCCCTAAAC
CTAAGGACACCCTGATGA-
TAAGTAGGACGCCGG
AAGTAACCTGTGTCGTGGTTGATGTGT-
CACAGGAAGACCCGGAGGTACAATTTA
ATTGGTACGTCGATGGAGTCGAGGTGCAT-
AATGCGAAAACCAAGCCACGAGAG
GAGCAATTCAACAGCACC-
TACCGAGTAGTTTCAGTCTT
GACTGTGCTGCACCAA GACTGGCT-
GAATGGCAAGGAGTA-

CAAATGCAAGGTCAGTAATAAAGGATTGCC
GTCTTCAATAGAGAAGAC-
TATCAGTAAGGCGAAGGGACAA
CCTCGCGAGCCTCA GGTATA-
CACTTTGCCGCCCAGC-
CAAGAAGAAATGACGAAGAAC-
CAAGTCTCTTT
GACTTGCCTGGTCAAAGGCTTCTACCCCTCT-
GATATAGCAGTCGAATGGGAGTCC AACGGT-
CAACCGGAGAACAATTATAAGACAACTC-
CACCTGTGCTTGATTCAGAC
GGCTCTTTTTCTTGTATAGCCGCCT-
TACCGTAGACAAGAGTCGATGGCAGGAAG
GTAATGTAT-
TTTCTTGTAGTGTAATGCACGAGGCACTT-
CATAATCACTACACACA AAAGTCTCTGT-
CACTTTCCCTGGGCAAATGA

256. HuV2-10C4_IgG4_HC (SEQ ID NO: 256)
MRAWIFFLLCLAGRALAQVQLQESGPGLVKP-
SETLSLTCTVSGFSLTTYDW SWIRQPPGK-
GLEWIGYIWTGGGTNYNPSLKSRVTIS
VDTSKNQFSLKLSSVTAADTA VYYCVRGDTY-
HYALDFWGQGTLVTVSSASTKGPSVF-
PLAPCSRSTSESTAALGCLV KDYF-
PEPVTVSWNSGALTSGVHTFPAVL
QSSGLYSLSSVVTVPSSSLGTKTYTCNVD
HKPSNTKVDKRVESKYGPPCPPCPAPE-
FLGGPSVFLFPPKPKDTLMISRTPEVTCVVV
DVSQEDPEVQFNWYVDGVEVHNAKTKPRE-
EQFNSTYRVVSVLTVLHQDWLNGKE
YKCKVSNKGLPSSIEKTISKAK
GQPREPQVYTLPPSQEEMTKNQVSLT-
CLVKGFYPS DIAVEWESNGQPEN-
NYKTTPPVLDSDGSFFLY-
SRLTVDKSRWQEGNVFSCSVMHEA
LHNHYTQKSLSLSLGK*

BOLD=signal peptide, underline=antibody variable region, regular font=antibody constant region 257. HuV1-10C4_IgG1_siderocalin_HC humanized recombinant antibody heavy chain, siderocalin fusion, pairs with HuV1_10C4_IgK (SEQ ID NO: 257)
ATGAGAGCCTG-
GATCTTCTTCCTGCTTTGTTTGG
CAGGACGAGCGCTAGC
CCAAGTGCAACTTCAG-
GAATCCGGGCCGGGTCTCG
TAAAGCCCAGCGAGACGCT TAGTCTCA-
CATGCACAGTCAGTGGTTTCAGT
TTGACGACGTACGATATAAACTGG ATCCGC-
CAACCCCCTGGCAAAGGGCTTGAATGGA-
TAGGCGTTATATGGACGGGC
GGGGGCACTAATTACAACTCCGCTTT-
CATGTCCCGAGTAACTATATCAGTAGACA
CATCAAAGAACCAATTTTCCCTGAAATT-
GAGTAGTGTGACCGCAGCGGATACCG
CAGTTTATTACTGTGCCAGAGCCGATACC-
TATCACTACGCTCTTGATTTCTGGGG
CCAAGGAACCTTGGTAACAGTGT
CTTCAGCTAGCAC-
CAAAGGACCCTCCGTCTTT
CCGCTCGCGCCGAGCAGCAAGTC-
CACGAGCGGGGGGACAGC
CGCCCTTGGGTGT CTGGTCAAGGATTAT-
TTTCCTGAGCCCGTTACTGTCTCCTG-
GAATAGCGGTGCCT TGACTTCTGGGGTA-
CATACCTTCCCGGCGGTTTTGC
AATCATCAGGACTGTATAG
CCTCTCTAGCGTTGTAACGGTACCATCTT-
CATCACTTGGCACACAAACATATATT
TGTAATGTAAATCACAAACCTT-
CAAATACTAAAGTTGACAAAAAAGTG-
GAGCCG AAGAGCTGTGATAAAACGCAT-
ACTTGCCCGCCTTGCCCCGCTCCAG
AATTGCTG
GGCGGGCCGTCTGTGTTCCTCTTCC-
CACCGAAACCGAAGGATACGCTGATGATA
AGTCGAACGCCCGAAGTAA-
CATGCGTGGTTGTTGATGTAAGCCACGAA-
GATCCG GAAGTAAAGTTCAACTGGTACGTA-
GATGGAGTAGAAGTGCATAACGCGAAAACT
AAGCCCCGCGAGGAGCAATATAATTCAACC-
TATCGGGTTGTTAGTGTGCTCACC GTTCTC-
CATCAGGATTGGCTTAACGG-
GAAAGAGTATAAGTGCAAGGTTAGCAAT
AAAGCATTGCCAGCACCTATAGAGAA-
GACAATTAGCAAAGCGAAGGGACAGCC
ACGAGAGCCCCAAGTCTA-
CACGCTGCCTCCCAGCCGCGA
CGAGTTGACGAAGAA TCAAGTGTCACTCA-
CATGTCTTGTCAAGGGATTCTATCCCTCAGA-
TATTGCAGTA GAATGG-
GAGTCTAATGGACAACC
AGAGAACAACTATAAAACTACTC-
CACCGGTG CTTGA-
TAGTGACGGTAGTTTTTTCCTT-
TATAGTAAGCTGACTGTCGATAAGAGTC
GCTGGCAACAGG-
GAAATGTTTTTTCTTGTAGTGTTATGCAT-
GAAGCACTTCATAA CCATTA-
CACACAAAAGTCTCTGT
CACTTTCCCCTGGCAAACAGGACTC-
CACCTCA GACCTGATCCCAGCCCCACCTCT-
GAGCAAGGTCCCTCT
GCAGCAGAACTTCCAG GACAACCAAT-
TCCAGGG-
GAAGTGGTATGTGGTAGGCCTGGCAGG-
GAATGCAATT
CTCAGAGAAGACAAAGACCCGCAAAA-
GATGTAT
GCCACCATCTATGAGCTGAAA GAA-
GACAAGAGCTACAATGT-
CACCTCCGTCCTGTTTAG-
GAAAAAGAAGTGTGAC
TACTGGATCAGGACTTTTGTTC
CAGGTAGCCAGCCCGGCGAGTT-
CACGCTGGGC AACATTAA
GAGTTACCCTGGATTAACGAGT-
TACCTCGTCCGAGTGGTGAGCACC AACTA-
CAACCAGCATGCTAT
GGTGTTCTTCAAGAAAGTTTCT-
CAAAACAGGGAG TACTTCAAGATCACCCTC-
TACGGGA
GAACCAAGGAGCTGACTTCGGAACTAAAG
GAGAACTTCATCCGCTTCTC-
CAAATCTCTGGGCCTCCCTGAAAACCA-
CATCGTCT TCCCTGTCC-
CAATCGACCAGTGTATCGACGGCTGA 258. HuV1-10C4_IgG1_siderocalin_HC humanized recombinant antibody heavy chain, siderocalin fusion, pairs with HuV1_10C4_IgK (SEQ ID NO: 258)
MRAWIFFLLCLAGRALAQVQLQESGPGLVKP-
SETLSLTCTVSGFSLTTYDIN WIRQPPGK-
GLEWIGVIWTGGGTNYN-
SAFMSRVTISVDTSKNQFSLKLSSVTAADTAV
YYCARADTYHYALDFWGQGTLVTVSSAS-
TKGPSVFPLAPSSKSTSGGTAALGCLVKDY FPEPVTVSWNSGALTSGVHTFPAVLOSSGLYS-LSSVVTVPSSSLGTQTYICNVNHKPSNTKV DKKVEPKSCDKTHTCPPCPA-PELLGGPSVFLFPPKPKDTLMISRTPE-VTCVVVDVSHEDP EVKFNWYVDGVEVHNAKTKPREEQYN-STYRVVSVLTVLHQDWLNGKEYKCKVSNKA-LPA PIEKTISKAKGOPREPQVYTLPPSRDELT-KNQVSLTCLVKGFYPSDIAVEWESNGQPENNY KTTPPVLDSDGSFFLYSK-LTVDKSRWQQGNVFSCSVMHEALHN-HYTQKSLSLSPGKQDST SDLIPAPPL-SKVPLQQNFQDNQFQGKWYVVG LAGNAILREDKDPQKMYATIYELKE DKSYN-VTSVLFRKKKCDY-WIRTFVPGSQPGEFTLGNIKSYPGLTSYL-VRVVSTNYNQ HAMVFFKKVSQNREYFKITLYGRTKELT-SELKENFIRFSKSLGLPENHIVFPVPIDQCI DG BOLD=signal peptide, underline=antibody variable region, italics=antibody constant region, regular font=siderocalin 259. HuV1-10C4_linker1_minibody (SEQ ID NO: 259)

ATGAGAGCCTG-GATCTTCTTCCTGCTTTGTTTGGCA GGACGAGCGCTAGC CGACATCGTAATGACT-CAATCTCCGGATT-CACTTGCGGTCTCCTTGGGTGAACGA GCAACTATAAATTGCAAATCAAGT-CAATCCCTCCTCAGTAGCGGCACGAGGAAA AACTACCTCGCATGGTAT-CAACAAAAGCCAGGACAGCCGCC-CAAACTGTTGATA TACTGGGCGTC-CACCCGAGAGTCCGGGGTCC CGGATCGATTTAGCGGTAGTGGA TCTGGTACCGACTTCACTCTCACCAT-TTCCTCTCTGCAAGCAGAAGACGTTGCAG TATATTACTGCAAACAGAGTTACATCCTCTT-TACTTTCGGTCAGGGAACTAAACT TGAAAT-CAAGGGAGGCGGAGGATCCGGCG-GAGGGGGCTCTGGAGGAGGAGGAT CTCAAGTGCAACTTCAG-GAATCCGGGCCGGGTCTCG TAAAGCCCAGCGAGACGC TTAGTCTCA-CATGCACAGTCAGTGGTTTCAGT TTGACGACGTACGATATAAACTG GATCCGC-CAACCCCCTGGCAAAGGGCTTGAATGGA-TAGGCGTTATATGGACGGG CGGGGGCACTAATTACAACTCCGCTTT-CATGTCCCGAGTAACTATATCAGTAGAC ACATCAAAGAACCAATTTTCCCTGAAATT-GAGTAGTGTGACCGCAGCGGATACC GCAGTTTATTACTGTGCCAGAGCCGATACC-TATCACTACGCTCTTGATTTCTGGG GCCAAGGAACCTTGGTAACAGTGTCTT-CACGTACGGTGGCCGACAAAACTCATA CTTGTCCTCCGTGCCCCGCGCCTC CAGTCGCCGGTGGCCCGGGACAACCCCGAG AACCTCAGGTCTATACTCTCCCGCCAT-CAAGGGATGAATTGACTAAGAACCAAG TTAGTCTCACATGTCTCGTAAAGGGTTTC-TACCCGTCCGATATCGCCGTCGAATG GGAAT-CAAATGGACAGCCGGAGAATAACTA-CAAAACGACGCCACCAGTGCTCG ACTCCGATGGTTCTTTCTTTCTGTATT-CAAAGCTCACTGTAGACAAATCTAGGTG GCAGCAGGGCAACGTATTCTCATGTTCCGT-CATGCACGAAGCACTTCATAACCA CTA-CACACAGAAATCCCTGT-CACTTTCCCCTGGCAAATGA

260. HuV1-10C4_linker1_minibody-single-chain Fv (scFv) regions from HuV1 10C4_LC and HuV1_10C4_HC with a linker connecting scFv to human IgG1 CH3 domain (SEQ ID NO: 260) MRA-WIFFLLCLAGRALADIVMTQSPDSLAVSLGERAT-INCKSSQSLLSSGTRKNYL AWYQQKPGQPPKLLIYWAST-RESGVPDRFSGSGSGTDFTLTISSLQAEDVA-VYYCKQ SYILFTFGQGTKLEIKGGGGSGGGGS GGGGSQVQLQESGPGLVKPSETLSLTCTVSGF SLTTYDINWIRQPPGKGLEWIGVIWTGGGTNYN-SAFMSRVTISVDTSKNQFSLKLSS VTAAD-TAVYYCARADTYHYALDFWGQGTLVTVSSRT-VADKTHTCPPCPAPPVAG GPGQPREPQVYTLPPSRDELTKNQVSLT-CLVKGFYPSDIAVEWESNGQPENNYKTTP PVLDSDGSFFLYSK-LTVDKSRWQQGNVFSCSVMHEALHN-HYTQKSLSLSPGK BOLD=signal peptide, underline=HuV1_10C4_LC variable region, italics=(G4S)x3 linker, regular font=HuV1_10C4_HC variable region, BOLD underline=linker 1, BOLD italics=Human IgG1 CH3 domain.

261. HuV1-10C4_linker2_minibody (SEQ ID NO: 261)

ATGAGAGCCTGGATCTTCTTCCTGCTTTG TTTGGCAGGACGAGCGCTAGC CGA-CATCGTAATGACTCAATCTCCGGATT-CACTTGCGGTCTCCTTGGGTGAACGA GCAACTATAAATTGCAAATCAAGT-CAATCCCTCCTCAGTAGCGGCACGAGGAAA AACTACCTCGCATGGTAT-CAACAAAAGCCAGGACAGCCGCC-CAAACTGTTGATA TACTGGGCGTC-CACCCGAGAGTCCGGGGTCCCG GATCGATTTAGCGGTAGTGGA TCTGGTACCGACTTCACTCTCACCAT-TTCCTCTCTGCAAGCAGAAGACGTTGCAG TATATTACTGCAAACAGAGTTACATCCTCTT-TACTTTCGGTCAGGGAACTAAACT TGAAAT-CAAGGGAGGCGGAGGATCCGGCG-GAGGGGGCTCTGGAGGAGGAGGAT CTCAAGTGCAACTTCAG-GAATCCGGGCCGGGTCTCGTAA AGCCCAGCGAGACGC TTAGTCTCA-CATGCACAGTCAGTGGTTTCAGT TTGACGACGTACGATATAAACTG GATCCGC-CAACCCCCTGGCAAAGGGCTTGAATGGA-TAGGCGTTATATGGACGGG CGGGGGCACTAATTACAACTCCGCTTT-CATGTCCCGAGTAACTATATCAGTAGAC ACATCAAAGAACCAATTTTCCCTGAAATT-GAGTAGTGTGACCGCAGCGGATACC GCAGTTTATTACTGTGCCAGAGCCGATACC-TATCACTACGCTCTTGATTTCTGGG GCCAAGGAACCTTGGTAACAGTGTCTT-CACTCGAGCCAAAATCATGTGACAAAA CCCACACCTGCCCTCCCTGTG-GAGGGGGTAGCAGCGGAGGAGG-GAGCGGTGGA CAACCCCGAGAACCTCAGGTC-TATACTCTCCCGCCATCAAGGGATGAAT-TGACT AAGAACCAAGTTAGTCTCA-CATGTCTCGTAAAGGGTTTCT

ACCCGTCCGATATCG CCGTCGAATGGGAAT-
CAAATGGACAGCCGGAGAATAACTA-
CAAAACGACGCCA CCAGTGCTCGACTCC-
GATGGTTCTTTCTTTCTGTATT
CAAAGCTCACTGTAGACA
AATCTAGGTGGCAGCAGGGCAACGTATTCT-
CATGTTCCGTCATGCACGAAGCAC TTCAT-
AACCACTACACACAGAAATCCCTGT-
CACTTTCCCCTGGCAAATGA

262. HuV1-10C4_linker2_minibody (SEQ ID NO: 262)
MRAWIFFLLCLAGRALADIVMTQSPD-
SLAVSLGERATINCKSSQSLLSSGTR
KNYLAWYQQKPGQPPKLLIYWAST-
RESGVPDRFSGSGSGTDFTLTISSLQAEDVAVY
YCKQSYILFTFGQGTKLEIKGGGGSGGGGSG
GGGSQVQLQESGPGLVKPSETLSLTC
TVSGFSLTTYDINWIRQPPGK-
GLEWIGVIWTGGGTNYN-
SAFMSRVTISVDTSKNQFS LKLSSVTAAD-
TAVYYCARADTYHYALDFWGQGTLV
TVSSLEPKSCDKTHTCPPC
GGGSSGGGSGGQPREPQVYTLPPSRDELT-
KNQVSLTCLVKGFYPSDIAVEWESNGQ PEN-
NYKTTPPVLDSDGSFFLYSK-
LTVDKSRWQQGNVFSCSVMHEALHN
HYTQKSLS LSPGK BOLD=signal peptide, underline=HuV1_10C4_LC variable region, italics=(G4S)x3 linker, regular font=HuV1_10C4_HC variable region, BOLD underline=linker 1, BOLD italics=Human IgG1 CH3 domain 263. 10C4-Fc-C825 monomeric construct (SEQ ID NO: 263) ATGGATTTTCAAGTGCAGAT-
TTTCAGCTTCCTGCTAATCAGTGCTTCAGTCAT
AATGTCCAGAGGAGACATTGTGATGT-
CACAGTCTCCATCCTCCCTGGCTGTGT
CAGCAGGAGAGAAGGTCACTAT-
GAGCTGCAAATCCAGTCAGAGTCTGCTCAG
CAGTGGAACCCGAAAGAAC-
TACTTGGCTTGGTACCAGCAGAAACCAGGGCA
GTCTCCTAAACTGCTGATCTACTGGGCATC-
CACTAGGGAATCTGGGGTCCCTG ATCGCTT-
CACAGGCAGTGGATCTGGGACAGATTT-
CACTCTCACCATCAGCAG
TGTGCAGGCTGAAGACCTGGCAGTTTAT-
TACTGCAAGCAATCTTATATTCTAT
TCACGTTCGGCTCGGGGACAAAGTTG-
GAAATAAAGGGCGGTGGCTCGGGCG GTGGTG-
GATCTGGAGGAGGTGGGAGCGGGGGAGGAG-
GAAGCTCTCAGGTGC
AACT-
GAAGGAATCAGGACCTGGCCTGGTGGCGCCCT-
CACAGAACCTGTCCAT
TACCTGCACTGTCTCTGGGTTCTCATTAAC-
CACCTATGATATTAACTGGATTC GCCAGC-
CACCAGGAAAGGGTCTGGAGTGGCTTGGAGT-
GATATGGACTGGTG
GAGGCACAAATTATAATTCAGCTTT-
CATGTCCAGACTGAGCATCAGCAAGGA
CAACTCCAAGAGCCAAGTTTTCTTAAAAAT-
GAACAGTCTGCAAACTGATGAC ACAGC-
CATGTATTACTGTGTAAGAGGTGATACTTAC-
CATTATGCTTTGGACTT
CTGGGGTCAAGGAACCTCAGTCACCGTCTCCT-
CACTCGAGCCCAAATCTTCTG ACAAAACT-
CACACAAGCCCACCGTCCCCAGCACCT-
GAACTCCTGGGGGGACC
GTCAGTCTTCCTCTTCCCCCCAAAACC-
CAAGGACACCCTCATGATCTCCCGGA CCCCT-
GAGGTCACATGCGTGGTGGTGGACGTGAGC-
CACGAAGACCCTGAGGT
CAAGTTCAACTGGTACGTGGACGGCGTG-
GAGGTGCATAATGCCAAGACAAA GCCGCGG-
GAGGAGCAGTACAACAGCACGTACCGTGTGG
TCAGCGTCCTCACC
GTCCTGCACCAGGACTGGCT-
GAATGGCAAGGAGTA-
CAAGTGCAAGGTCTCCA
ACAAAGCCCTCCCAGCCCCCATCGAGAAAAC-
CATCTCCAAAGCCAAAGGGC
AGCCCCGAGAACCACAGGTGTA-
CACCCTGCCCCCATCCCGGGATGAGCTGAC
CAAGAACCAGGTCAGCCTGACCTGCCGGGT-
CAAAGGCTTCTATCCCAGCGAC ATCGCCGTG-
GAGTGGGAGAGCAATGGGCAGCCG-
GAGAACAACTACAAGACC
ACGCCTCCCGTGCTGGACTCCGACGGCTCCTTC-
CACCTGGAGAGCAAGCTCA
CCGTGGACAAGAGCAGGTGGCAGCAGGG-
GAACGTCTTCTCATGCTCCGTGAT GCAT-
GAGGGTCTGCACAACCACTA-
CACGCAGAAGAGCCTCTCTCTGTCTCCG
GGTAAAGTCGACGGTGCTAGCAGCCATGT-
GAATGTGAGCAGCCCTAGCGTGC AGGATATC-
CACGTTAAGTTGCAAGAATCTGGTC
CAGGTTTGGTTCAGCCATCT
CAATCTTTGTCTCT-
TACTTGTACTGTTTCTGGTTTCTCTTTGACT-
GATTATGGT GTTCATTGGGTTA-
GACAATCTCCAGGTAAAG
GTTTGGAATGGTTGGGTGTTAT
TTGGTCTGGTGGAGGTACTGCT-
TATAATACTGCTTTGATTTCTAGGTTGAATA
TTTATCGAGATAATTCTAAAAAT-
CAAGTTTTTCTTGAAATGAATTCTTTGCAA
GCTGAAGATACTGCTATGTATTAT-
TGTGCTAGAAGAGGTTCTTATCCATATAA TTAT-
TTTGATGCTTGGGGTTGTGGTACTACTGT-
TACTGTTTCTTCTGGAGGCGG
CGGATCTGGCGGTG-
GAGGTTCTGGCGGCGGCGGATCT-
CAAGCTGTTGTTATT CAAGAATCTGCTTTGAC-
TACTCCTCCAGGTGAAACCGTTACT
TTGACTTGTGG ATCTTCTACTGGTGCTGT-
TACTGCTTCTAATTATGCTAATTGGGTT-
CAAGAAA AACCAGATCATTGCTTTACTGGTTT-
GATTGGTGGTCATAATAATAGACCACCA
GGTGTTCCGGCTAGATTTTCTGGTTCTTTGAT-
TGGTGATAAAGCTGCTTTGAC TAT-
TGCTGGTACTCAAACTGAAGATGAAGCTATTT-
ATTTTTGTGCTTTGTGGT
ATTCTGATCATTGGGTTATTGGTGGTGGTACTA-
GATTGACTGTTTTGGGCTAA TAA 264. 10C4-Fc-C825 monomeric construct (SEQ ID NO: 264) MDFQVQIFSFLLISASVIMSRGDI-
VMSQSPSSLAVSAGEKVTMSCKSSQSLLSSG
TRKNYLAWYQQKPGOSPKLLIYWAST-
RESGVPDRFTGSGSGTDFTLTISSVQAED
LAVYYCKQSYIL-
FTFGSGTKLEIKGGGSGGGGSGGG
GSGGGGSSQVOLKESGPGL VAPSONL-
SITCTVSGFSLTTYDINWIRQPPGKGLEW-
LGVIWTGGGTNYNSAFMSRLSIS
KDNSKSQVFLKMNSLQTDDTAMYYCVRGDTY- HYALDFWGQGTSVTVSSLEPKSSDK THT-
SPPSPAPELLGGPSVFLFPPKPKDTLMISRTPE-
VTCVVVDVSHEDPEVKF
NWYVDGVEVHNAKTKPREEQYN-
STYRVVSVLTVLHQDWLNGKEYKCKVS NKAL-
PAPIEKTISKAKGQPREPQVYTLPPSRDELT-
KNQVSLTCRVKGFYPSDI
AVEWESNGQPENNYKTTPPVLDSDGSFHLESK-
LTVDKSRWQQGNVFSCSVM HEGLHN-
HYTQKSLSLSPGKVDGASSHVNVSSPSVQ-
DIHVKLOESGPGLVOPSQ
SLSLTCTVSGFSLTDYGVHWVROSPGKGLEW-
LGVIWSGGGTAYNTALISRLNIYR
DNSKNQVFLEMNSLQAEDTAMYYCARRGSY-
PYNYFDAWGCGTTVTVSSGGGGS
GGGGSGGGGSQAVVIQESALT-
TPPGETVTLTCGSSTGAVTASNYANWVQEKPD
HCFTGLIGGHNNRPPGVPARFSGSLIGDKAALTI-
AGTQTEDEAIYFCALWYSDHW
VIGGGTRLTVLG BOLD=signal peptide, underline=10C4 light chain variable region, regular font=linker 1, italics=10C4 heavy chain variable region, BOLD underline=hinge and human IgG1 Fc, BOLD italics=linker 2, BOLD italics underline=C825 heavy chain variable region, BOLD=linker 3, underline=C825 light chain variable region 265. 10C4-Fc-C825 dimeric construct (SEQ ID NO: 265)

ATGGATTTTCAAGTGCAGAT-
TTTCAGCTTCCTGCTAATCAGTGCTTCAGT-
CATAA TGTCCAGAGGAGACATTGTGATGT-
CACAGTCTCCATCCTCCCTGGCTGTGTCAGC
AGGAGAGAAGGTCACTAT-
GAGCTGCAAATCCAGTCAGAGTCTGC
TCAGCAGTGG AACCCGAAAGAAC-
TACTTGGCTTGGTACCAGCAGAAAC
CAGGGCAGTCTCCTAA ACTGCTGATC-
TACTGGGCATCCACTAGG-
GAATCTGGGGTCCCTGATCGCTTCACA
GGCAGTGGATCTGGGACAGATTTCACTCTCAC-
CATCAGCAGTGTGCAGGCTGAA
GACCTGGCAGTTTATTACTGCAAGCAATCTTAT-
ATTCTATTCACGTTCGGCTCGG
GGACAAAGTTG-
GAAATAAAGGGCGGTGGCTCGGGCGGTGGTG-
GATCTGGAGGA GGTGGGAGCGGGGGAGGAG-
GAAGCTCTCAGGTGCAACTGAAGG
AATCAGGACC TGGCCTGGTGGCGCCCT-
CACAGAACCTGTCCAT-
TACCTGCACTGTCTCTGGGTTC TCATTAAC-
CACCTATGATATTAACTGG
ATTCGCCAGCCACCAGGAAAGGGTCTG
GAGTGGCTTGGAGTGATATGGACTGGTG-
GAGGCACAAATTATAATTCAGCTTTC
ATGTCCAGACTGAG-
CATCAGCAAGGACAACTCCAAGAGC-
CAAGTTTTCTTAAAA
ATGAACAGTCTGCAAACTGATGACACAGC-
CATGTATTACTGTGTAAGAGGTGAT ACTTAC-
CATTATGCTTTGGACTTCTGGGGT-
CAAGGAACCTCAGTCACCGTCTCCT
CACTCGAGCCCAAATCTTCTGACAAAACT-
CACACATGTCCACCGTGCCCAGCAC
CTGAACTCCTGGGGGGAC
CGTCAGTCTTCCTCTTCCCCCCAAAACC-
CAAGGACAC CCTCATGATCTCCCGGACCCCT-
GAGGTCACATGCGTGGTGGTGGACGTGAGCCA
CGAAGACCCTGAGGTCAAGTT-
CAACTGGTACGTGGACGGCGTGGAGGTG-
CATAA TGCCAAGACAAAGCCGCGGGAG-
GAGCAGTACAACAGCACGTACCGTGTGGTCA
GCGTCCTCACCGTCCTGCACCAGGACTGGCT-
GAATGGCAAGGAGTACAAGTGCA AGGTCTC-
CAACAAAGCCCTCCCAGCCCC-
CATCGAGAAAACCATCTCCAAAGCCA
AAGGGCAGCCCCGAGAACCACAGGTGTA-
CACCCTGCCCCCATCCCGGGATGAGC TGAC-
CAAGAACCAGGTCAGCCTGACCTGCCTGGT-
CAAAGGCTTCTATCCCAGCG
ACATCGCCGTGGAGTGG-
GAGAGCAATGGGCAGCCGGAGAACAACTA-
CAAGACC
ACGCCTCCCGTGCTGGACTCCGACG
GCTCCTTCTTCCTCTACAGCAAGCTCACCG
TGGACAAGAGCAGGTGGCAGCAGGG-
GAACGTCTTCTCATGCTCCGTGATGCATG
AGGGTCTGCACAACCACTA-
CACGCAGAAGAGCCTCTCTCTGT
CTCCGGGTAAAG TCGACGGTGCTAGCAGC-
CATGTGAATGTGAGCAGCCCTAGCGTGCAG-
GATATCC ACGT-
TAAGTTGCAAGAATCTGGTCCAGGT
TTGGTTCAGCCATCTCAATCTTTGTC TCT-
TACTTGTACTGTTTCTGGTTTCTCTTTGACT-
GATTATGGTGTTCATTGGGTTA
GACAATCTCCAGGTAAAGGTTTG-
GAATGGTTGGGTGTTATTTGGTCTGGTGGAGG
TACTGCTTATAATACTGCTTTGATTTCTAGGTT-
GAATATTTATCGAGATAATTCTA AAAAT-
CAAGTTTTTCTTGAAATGAAT-
TCTTTGCAAGCTGAAGATACTGCTATGTA
TTATTGTGCTAGAAGAGGTTCTTATC-
CATATAATTATTTTGATGCTTGGGGTTGTG
GTACTACTGTTACTGTTTCTTCTG-
GAGGCGGCGGATCTGGCGGTGGAGGTTCTGG
CGGCGGCGGATCTCAAGCTGTTGTTATT-
CAAGAATCTGCTTTGACTACTCCTCCA GGT-
GAAACCGTTACTTTGACTTGTGGATCTTC-
TACTGGTGCTGTTACTGCTTCTAA
TTATGCTAATTGGGTTCAAGAAAAACCAGAT-
CATTGCTTTACTGGTTTGATTGGT GGTCAT-
AATAATAGACCACCAGGTGTTCCGGCTAGAT-
TTCTGGTTCTTTGATTG
GTGATAAAGCTGCTTTGACTATTGCTGGTACT-
CAAACTGAAGATGAAGCTATTTA
TTTTTGTGCTTTGTGGTATTCTGATCATTGGGT-
TATTGGTGGTGGTACTAGATTGA
CTGTTTTGGGCTAATAA 266. 10C4-Fc-C825 dimeric construct (SEQ ID NO: 266)

MDFQVQIFSFLLISASVIMSRGDI-
VMSQSPSSLAVSAGEKVTMSCKSSQSLLS
SGTRKNYLAWYQQKPGQSPKLLIYWAST-
RESGVPDRFTGSGSGTDFTLTISSVQAED
LAVYYCKQSYILFTFGSGTKLEIKGGGSGG
GGSGGGGSGGGGSSQVOLKESGPGLVA
PSQNLSITCTVSGFSLTTYDINWIRQPPGK-
GLEWLGVIWTGGGTNYNSAFMSRL-
SISKDNSK SQVFLKMNSLOTDD-
TAMYYCVRGDTYHYALDFWGQG
TSVTVSSLEPKSSDKTHTCPPC
PAPELLGGPSVFLFPPKPKDTLMISRTPE-
VTCVVVDVSHEDPEVKENWYVDGVE
VHNAKTKPREEQYNSTYRVVSVLTVL-
HODWLNGKEYKCKVSNKALPAPIEKTI

SKAKGQPREPQVYTLPPSRDELTKNOVSLT-CLVKGFYPSDIAVEWESNGQPENN YKTTPPVLDSDGSFFLYSK-LTVDKSRWQQGNVFSCSVMHEGLHNHY-TOKSLSL SPGKVDGASSHVNVSSPSVQ-DIHVKLQESGPGLVOPSQSLSLTCTVSG ESLTDYGVH WVROSPGKGLEW-LGVIWSGGGTAYNTALISRLNIYRDNS-KNOVFLEMNSLQAEDTA MYYCARRGSY-PYNYFDAWGCGTTVTVSSGGGGS GGGGSGGGGSQAVVIQESALTT PPGETVTLTCGSSTGAV-TASNYANWVQEKPDHCFTGLI GGHNNRPPGVPARFSGSLI GDKAALTIAGTQT-EDEAIYFCALWYSDHWVIGGGTRLTVLG

BOLD=signal peptide, underline=10C4 light chain variable region, regular font=linker 1, italics=10C4 heavy chain variable region, BOLD underline=hinge and human IgG1 Fc, BOLD italics=linker 2, BOLD italics underline=C825 heavy chain variable region, BOLD=linker 3, underline=C825 light chain variable region 267. 123-ATX1B7_Hs_IgG1_HC (SEQ ID NO: 267)

ATGGAGACAGATACTTTGCTCCTTTGGGTACT CTTGCTGTGGGTTCCCGGT AGCACCGGC-CAAGTA-CAACTCGTGCAGTCCGGGGCCGAAGT-GAAAAAACCCGG AGCGAGCGTCAAAGTTT-CATGCAAAGCCTCAGGTTATACTTT-CACCAGCTTTGGA CTTACGTGGGTGCGACAAGCTC CTGGACAAGGCTTGGAATG-GATGGGGTGGTTT AACGCTTAT-TCAGGCAAAACGTATTACGCTCCGACCCTT-CAAGATCGGGTAACC ATGACTACCGACCCATCCACATCAACGGCT-TATATGGAACTTATGTCTCTTACCT CTGAC-GATACTGCTATCTAT-TACTGCGCCCGCGACCTTGTCTTT GATTATTGGGG ACAAGGCACTCTGGTAACGGTGTCT AGCGCTAGCACCAAAGGACCCTCCGTCTT TCCGCTCGCGCCGAGCAGCAAGTC-CACGAGCGGGGGACAGCCGCCCTTGGGTG TCTGGTCAAGGATTATTTCCTGAGCCCGT-TACTGTCTCCTGGAATAGCGGTGCC TTGACTTCTGGGGTACAT-ACCTTCCCGGCGGTTTTGCAAT-CATCAGGACTGTATA GCCTCTCTAGCGTTGTAACGGTACCATCTT-CATCACTTGGCACACAAACATATAT TTGTAATGTAAATCACAAACCTT-CAAATACTAAAGTTGACAAAAAAGTG-GAGCC GAAGAGCTGTGATAAAACGCAT-ACTTGCCCGCCTTGCCCCGCTC CAGAATTGCT GGGCGGGCCGTCTGTGTTCCTCTTCC-CACCGAAACCGAAGGATACGCTGATGAT AAGTCGAACGCCCGAAGTAA-CATGCGTGGTTGTTGATGTAAGCCACGAA-GATCC GGAAGTAAAGTTCAACTGGTACGTA-GATGGAGTAGAAGTGCATAACGCGAAAA CTAAGCCCCGCGAGGAGCAATATAATT-CAACCTATCGGGTTGTTAGTGTGCTCAC CGTTCTCCATCAGGATTGGCTTAACGG-GAAAGAGTATAAGTGCAAGGTTAGCAA TAAAGCATTGCCAGCACCTATAGAGAA-GACAATTAGCAAAGCGAAGGGACAGC CACGAGAGCCCCAAGTCTA-CACGCTGCCTCCCAGCCGC GACGAGTTGACGAAGA ATCAAGTGTCACT-CACATGTCTTGTCAAGGGATTCTATCCCTCA-GATATTGCAGT AGAATGG-GAGTCTAATGGACAACCAGAGAA CAACTATAAAACTACTCCACCGGT GCTTGA-TAGTGACGGTAGTTTTTTCCTT-TATAGTAAGCTGACTGTCGATAAGAGT CGCTGGCAACAGG-GAAATGTTTTTTCTTGTAGTGTTATGCAT-GAAGCACTTCATA ACCATTA-CACACAAAAGTCTCTGTCA CTTTCCCCTGGCAAATGA 268. 123-ATX1B7_Hs_IgG1_HC (SEQ ID NO: 268)

METDTLLLWVLLLWVPGSTGQVOLVOS-GAEVKKPGASVKVSCKASGYTF TSFGLTWVRQAPGOGLEWMGWFNAY-SGKTYYAPTLQDRVTMTTDPSTSTAYMEL MSLTSDDTAIYYCARDLVFDYWGQGTLVTVS-SASTKGPSVFPLAPSSKSTSGGTAAL GCLVKDYFPEPVTVSWNSGALT-SGVHTFPAVLQSSGLYS-LSSVVTVPSSSLGTQTYIC NVNHKPSNTKVDKKVEPKSCDKTHTCPPCPA-PELLGGPSVFLFPPKPKDTLMISRTPE VTCVVVDVSHEDPE-VKFNWYVDGVEVHNAKTKPREEQYN-STYRVVSVLTVLHQD WLNGKEYKCKVSNKA-LPAPIEKTISKAKGQPREPQVYTL PPSRDELTKNQVSLTCLV KGFYPSDIA-VEWESNGQPENNYKTTPPVLDSDGSFFLYSK-LTVDKSRWQQGNVFSC SVMHEALHN-HYTQKSLSLSPGK

BOLD=signal peptide, underline=antibody variable region, regular font=antibody constant region 269. 123-ATX1B7_Hs_IgG4_HC ((SEQ ID NO: 269)

ATGGAGACAGA-TACTTTGCTCCTTTGGGTACTCT TGCTGTGGGTTCCCGGT AGCACCGGC-CAAGTA-CAACTCGTGCAGTCCGGGGCCGAAGT-GAAAAAACCCGG AGCGAGCGTCAAAGTTT-CATGCAAAGCCTCAGGTTATACTTT-CACCAGCTTTGGA CTTACGTGGGTGCGACAAGC TCCTGGACAAGGCTTGGAATG-GATGGGGTGGTTT AACGCTTAT-TCAGGCAAAACGTATTACGCTCCGACCCTT-CAAGATCGGGTAACC ATGACTACCGACCCATCCACATCAACGGCT-TATATGGAACTTATGTCTCTTACCT CTGAC-GATACTGCTATCTAT-TACTGCGCCCGCGACCTTGTCTTTG ATTATTGGGG ACAAGGCACTCTGGTAACGGTGTCT AGCGCTAGCACCAAAGGACCCTCCGTCTT TCCGCTCGCGCCGTGCTCTCGATC-CACGAGCGAGTC-TACGGCGGCCTTGGGCTGT CTCGTGAAA-GACTATTTCCCAGAGCCAGTGACC GTTTCCTGGAACTCCGGAGCG CTCA-CATCAGGTGTGCAT-ACCTTTCCAGCCGTACTT-CAATCTTCAGGGCTGTATA

GCTTGTCCTCTGTCGTGACCGTA
CCCTCCAGTTCTCTCGGGACAAAGACC-
TATAC CTGTAACGTAGACCATAAGCCATC-
CAATACCAAAGTAGATAAGAGGGTGGAATC
TAAATATGGACCGCCTTGTCCG
CCGTGCCCGGCTCCTGAGTTCCTTG-
GAGGGCCG TCCGTCTTTCTGTTTCCCCCTA
AACCTAAGGACACCCTGATGA-
TAAGTAGGACGC
CGGAAGTAACCTGTGTCGTGGTTGATGTGT-
CACAGGAAGACCCGGAGGTACAAT TTAAT-
TGGTACGTCGATGGAGTCGAGGTGCAT-
AATGCGAAAACCAAGCCACGAG
AGGAGCAATTCAACAGCACC-
TACCGAGTAGTTTCAGTCTTGACTG
TGCTGCACC AAGACTGGCT-
GAATGGCAAGGAGTA-
CAAATGCAAGGTCAGTAATAAAGGATTG
CCGTCTTCAATAGAGAAGAC-
TATCAGTAAGGCGAAGGGACAA
CCTCGCGAGCCT CAGGTATA-
CACTTTGCCGCCCAGC-
CAAGAAGAAATGACGAAGAACCAAGTCTCT
TTGACTTGCCTGGTCAAAGGCTTC-
TACCCCTCTGATATAGCAGTCGAATGGGAGT
CCAACGGTCAACCGGAGAACAATTATAA-
GACAACTCCACCTGTGCTTGATTCAG
ACGGCTCTTTTTTCTTGTATAGCCGCCT-
TACCGTAGACAAGAGTCGATGGCAGGA
AGGTAATGTAT-
TTTCTTGTAGTGTAATGCACGAGGCACTT-
CATAATCACTACACA CAAAAGTCTCTGT-
CACTTTCCCTGGGCAAATGA 270. 123-ATX1B7_Hs_IgG4_HC (SEQ ID NO: 270)
METDTLLLWVLLLWVPGSTGQVOLVOS-
GAEVKKPGASVKVSCKASGYTF
TSFGLTWVRQAPGQGLEWMGWFNAY-
SGKTYYAPTLQDRVTMTTDPSTSTAYMEL
MSLTSDDTAIYYCARDLVFDYWGQGTLVTVS-
SASTKGPSVFPLAPCSRSTSESTAAL
GCLVKDYFPEPVTVSWNSGALT-
SGVHTFPAVLQSSGLYS-
LSSVVTVPSSSLGTKTYT
CNVDHKPSNTKVDKRVESKYGPPCPPCPAPE-
FLGGPSVFLFPPKPKDTLMISRTPEVT
CVVVDVSQEDPE-
VQFNWYVDGVEVHNAKTKPREEQFN-
STYRVVSVLTVLHQDWL
NGKEYKCKVSNKGLPSSIEKT
ISKAKGQPREPQVYTLPPSQEEMTKNQVSLT-
CLVKG FYPSDIA VEWESNGQPEN-
NYKTTPPVLDSDGSFFLY-
SRLTVDKSRWQEGNVFSCSV
MHEALHNHYTQKSLSLSLGK

BOLD=signal peptide, underline=antibody variable region, regular font=antibody constant region 271. 123-ATX1B7_Hs_IgK_LC (SEQ ID NO: 271)
ATGAGAGCCTG-
GATCTTCTTCCTGCTTTGTTTGG
CAGGACGAGCGCTAGC
CGAAATCGTCCTGACCCAGTCACCAG-
GAACACTTTCCCTGAGTCCAGGTGAAAG
AGCAACACTTTCTTGCCGAGC
CTCTCAGAGCTTTTCCGACCGA-
TACTTGGCGTGG TACCAGCAAAAACCCGGT-
CAAGCACCTAGACTGCTCATC-
TACGGCACGAGCTCC
AGAGCCACCGGAATCCCAGACCGCTT-
TAGCGGAAGTGGTTCAGGCACCGATTTT
ACCCTGACCATCTCAAGGTTGGAATCCGAA-
GATTCAGCCGTGTATTACTGCCAAC
AGTATGGCAGATCCCCATT-
CACTTTCGGACCTGGGACAAAGGTTGATAT-
TAAGC GTACGGTAGCTGCGCCTAGCGTGTT-
TATTTTTCCGCCCTCTGACGAACAACTCAA
AAGTGGCACTGCCTCTGTAGTCTGTCTCCT-
GAACAATTTTTATCCAAGGGAAGCT
AAGGTACAGTGGAAAGTCGATAACGCGCTC-
CAAAGTGGCAACAGTCAAGAATCT
GTAACGGAGCAAGATAGTAAAGACAGCACT-
TACAGCTTGAGCAGCACACTCACA TTGTC-
CAAGGCCGACTACGAAAAACAT-
AAAGTGTACGCCTGTGAGGTAACACAC
CAGGGTCTGAGCAGCCCAGTGACGAAGT-
CATTTAATCGCGGTGAGTGCTGA 272. 123-ATX1B7_Hs_IgK_LC (SEQ ID NO: 272)
MRAWIFFLLCLAGRALAEIVLTQSPGTLSL-
SPGERATLSCRASQSFSDRYLA
WYQQKPGQAPRLLIYGTSSRAT-
GIPDRFSGSGSGTDFTLTISRLESED-
SAVYYCQQYG
RSPFTFGPGTKVDIKRTVAAPSVFIFPPSD-
EQLKSGTASVVCLLNNFYPREAKVQWK
VDNALQSGNSQESVTEQDSKDSTYSLSSTLTL-
SKADYEKHKVYACEVTHQGLSSPV
TKSFNRGEC BOLD=signal peptide, underline=antibody variable region, regular font=antibody constant region 273. Linker domain (SEQ ID NO: 273)
GGGGS 274. Linker domain (SEQ ID NO: 274)
GGGS While illustrative embodiments have been illustrated and described, it will be appreciated that various changes can be made therein without departing from the spirit and scope of the invention.

SEQUENCE LISTING

```
Sequence total quantity: 274
SEQ ID NO: 1            moltype = AA  length = 20
FEATURE                 Location/Qualifiers
source                  1..20
                        mol_type = protein
                        organism = Mus musculus
SEQUENCE: 1
METDTLLLWV LLLWVPGSTG                                                20

SEQ ID NO: 2            moltype = AA  length = 111
FEATURE                 Location/Qualifiers
```

```
source                  1..111
                        mol_type = protein
                        organism = Mus musculus
SEQUENCE: 2
DIVLTQSPAS LAVSLGQRAT ISCRASQSVS SSSYSFMHWY QKKPRQPPKL LIKYASTLEA  60
GVPARFSGSG SGTDFTLNIH PVEEEDTATY YCQHSWEIPY TFGGGTKLEI K           111

SEQ ID NO: 3            moltype = AA  length = 17
FEATURE                 Location/Qualifiers
source                  1..17
                        mol_type = protein
                        organism = Mus musculoides
SEQUENCE: 3
RASQSVSSSS YSFMHWY                                                 17

SEQ ID NO: 4            moltype = AA  length = 11
FEATURE                 Location/Qualifiers
source                  1..11
                        mol_type = protein
                        organism = Mus musculus
SEQUENCE: 4
LLIKYASTLE A                                                       11

SEQ ID NO: 5            moltype = AA  length = 9
FEATURE                 Location/Qualifiers
source                  1..9
                        mol_type = protein
                        organism = Mus musculus
SEQUENCE: 5
QHSWEIPYT                                                          9

SEQ ID NO: 6            moltype = AA  length = 19
FEATURE                 Location/Qualifiers
source                  1..19
                        mol_type = protein
                        organism = Mus musculus
SEQUENCE: 6
MYFRLSSVFL VLILKGVQC                                               19

SEQ ID NO: 7            moltype = AA  length = 119
FEATURE                 Location/Qualifiers
source                  1..119
                        mol_type = protein
                        organism = Mus musculus
SEQUENCE: 7
EVKLVESEGG LVQPGSSMKL SCTASGFTFS DYYMAWVRQV PEKGLEWVAN IDDEGSSTYY  60
LDSLKSRFII SRDNAKNILY LQMTSLKSED TATYYCARGT TQTSFFVHWG QGTLVTVSA   119

SEQ ID NO: 8            moltype = AA  length = 13
FEATURE                 Location/Qualifiers
source                  1..13
                        mol_type = protein
                        organism = Mus musculus
SEQUENCE: 8
TASGFTFSDY YMA                                                     13

SEQ ID NO: 9            moltype = AA  length = 20
FEATURE                 Location/Qualifiers
source                  1..20
                        mol_type = protein
                        organism = Mus musculus
SEQUENCE: 9
WVANIDDEGS STYYLDSLKS                                              20

SEQ ID NO: 10           moltype = AA  length = 12
FEATURE                 Location/Qualifiers
source                  1..12
                        mol_type = protein
                        organism = Mus musculus
SEQUENCE: 10
ARGTTQTSFF VH                                                      12

SEQ ID NO: 11           moltype = AA  length = 20
FEATURE                 Location/Qualifiers
source                  1..20
                        mol_type = protein
                        organism = Mus musculus
SEQUENCE: 11
MDSQAQVLML LLLWVSGTCG                                              20
```

```
SEQ ID NO: 12          moltype = AA  length = 113
FEATURE                Location/Qualifiers
source                 1..113
                       mol_type = protein
                       organism = Mus musculus
SEQUENCE: 12
DFVMSQSPSS LAVSVGEKIT INCKSSQSLF FGSTQKNYLA WYQQKPGQSP KLLIFWSSTR  60
ESGVPDRFTG SGSGTDFTLS INSVKAEDLA VYYCQQYYNY PWTFGGGTKL EIK         113

SEQ ID NO: 13          moltype = AA  length = 19
FEATURE                Location/Qualifiers
source                 1..19
                       mol_type = protein
                       organism = Mus musculus
SEQUENCE: 13
KSSQSLFFGS TQKNYLAWY                                               19

SEQ ID NO: 14          moltype = AA  length = 11
FEATURE                Location/Qualifiers
source                 1..11
                       mol_type = protein
                       organism = Mus musculus
SEQUENCE: 14
LLIFWSSTRE S                                                       11

SEQ ID NO: 15          moltype = AA  length = 9
FEATURE                Location/Qualifiers
source                 1..9
                       mol_type = protein
                       organism = Mus musculus
SEQUENCE: 15
QQYYNYPWT                                                          9

SEQ ID NO: 16          moltype = AA  length = 18
FEATURE                Location/Qualifiers
source                 1..18
                       mol_type = protein
                       organism = Mus musculus
SEQUENCE: 16
MKVLSLLYLL TAIPGILS                                                18

SEQ ID NO: 17          moltype = AA  length = 117
FEATURE                Location/Qualifiers
source                 1..117
                       mol_type = protein
                       organism = Mus musculus
SEQUENCE: 17
DVQLQESGPG LVKPSQSLSL TCSVTGYSIT SSYYWNWIRQ FPGNKLEWMG YISYDGSNNY  60
NPSLKNRISI TRDTSKTQFF LNLNSVTTED TATYYCARGD GYYFDYWGQG TTLTVSS     117

SEQ ID NO: 18          moltype = AA  length = 14
FEATURE                Location/Qualifiers
source                 1..14
                       mol_type = protein
                       organism = Mus musculus
SEQUENCE: 18
SVTGYSITSS YYWN                                                    14

SEQ ID NO: 19          moltype = AA  length = 19
FEATURE                Location/Qualifiers
source                 1..19
                       mol_type = protein
                       organism = Mus musculus
SEQUENCE: 19
WMGYISYDGS NNYNPSLKN                                               19

SEQ ID NO: 20          moltype = AA  length = 10
FEATURE                Location/Qualifiers
source                 1..10
                       mol_type = protein
                       organism = Mus musculus
SEQUENCE: 20
ARGDGYYFDY                                                         10

SEQ ID NO: 21          moltype = AA  length = 22
FEATURE                Location/Qualifiers
source                 1..22
                       mol_type = protein
```

```
                         organism = Mus musculus
SEQUENCE: 21
MDFQVQIFSF LLISASVIMS RG                                          22

SEQ ID NO: 22            moltype = AA  length = 108
FEATURE                  Location/Qualifiers
source                   1..108
                         mol_type = protein
                         organism = Mus musculus
SEQUENCE: 22
QIVLTQSPAI MSVSLGERVT MTCTASSSVT SSYFHWYQQK PGSSPKLWIY STSNLASGVP  60
ARFSGSGSGT SYSLTISSME AEDAATYYCH QYHRSPRTFG GGTKLEIK              108

SEQ ID NO: 23            moltype = AA  length = 14
FEATURE                  Location/Qualifiers
source                   1..14
                         mol_type = protein
                         organism = Mus musculus
SEQUENCE: 23
TASSSVTSSY FHWY                                                   14

SEQ ID NO: 24            moltype = AA  length = 11
FEATURE                  Location/Qualifiers
source                   1..11
                         mol_type = protein
                         organism = Mus musculus
SEQUENCE: 24
LWIYSTSNLA S                                                      11

SEQ ID NO: 25            moltype = AA  length = 9
FEATURE                  Location/Qualifiers
source                   1..9
                         mol_type = protein
                         organism = Mus musculus
SEQUENCE: 25
HQYHRSPRT                                                         9

SEQ ID NO: 26            moltype = AA  length = 9
FEATURE                  Location/Qualifiers
source                   1..9
                         mol_type = protein
                         organism = Mus musculus
SEQUENCE: 26
HQYHRSPRT                                                         9

SEQ ID NO: 27            moltype = AA  length = 113
FEATURE                  Location/Qualifiers
source                   1..113
                         mol_type = protein
                         organism = Mus musculus
SEQUENCE: 27
DVQLQESGPG LVKPSQSLSL TCTVTGYSIT SDYVWNWIRQ FPGNKLEWMA YISYSGTTSY  60
NPSLSSRISI TRDTSSNQFF LQLNSVTSED TATYYCARGL DYWGQGTSVT VSS         113

SEQ ID NO: 28            moltype = AA  length = 14
FEATURE                  Location/Qualifiers
source                   1..14
                         mol_type = protein
                         organism = Mus musculus
SEQUENCE: 28
TVTGYSITSD YVWN                                                   14

SEQ ID NO: 29            moltype = AA  length = 19
FEATURE                  Location/Qualifiers
source                   1..19
                         mol_type = protein
                         organism = Mus musculus
SEQUENCE: 29
WMAYISYSGT TSYNPSLSS                                              19

SEQ ID NO: 30            moltype = AA  length = 6
FEATURE                  Location/Qualifiers
source                   1..6
                         mol_type = protein
                         organism = Mus musculus
SEQUENCE: 30
ARGLDY                                                            6

SEQ ID NO: 31            moltype = AA  length = 20
```

```
FEATURE                Location/Qualifiers
source                 1..20
                       mol_type = protein
                       organism = Mus musculus
SEQUENCE: 31
MDSQAQVLIL LLLWVSGTCG                                          20

SEQ ID NO: 32          moltype = AA  length = 112
FEATURE                Location/Qualifiers
source                 1..112
                       mol_type = protein
                       organism = Mus musculus
SEQUENCE: 32
DIVMSQSPSS LAVSAGEKVT MSCKSSQSLL SSGTRKNYLA WYQQKPGQSP KLLIYWASTR  60
ESGVPDRFTG SGSGTDFTLT ISSVQAEDLA VYYCKQSYIL FTFGSGTKLE IK         112

SEQ ID NO: 33          moltype = AA  length = 17
FEATURE                Location/Qualifiers
source                 1..17
                       mol_type = protein
                       organism = Mus musculus
SEQUENCE: 33
KSSQSLLSSG TRKNYLA                                             17

SEQ ID NO: 34          moltype = AA  length = 11
FEATURE                Location/Qualifiers
source                 1..11
                       mol_type = protein
                       organism = Mus musculus
SEQUENCE: 34
LLIYWASTRE S                                                   11

SEQ ID NO: 35          moltype = AA  length = 8
FEATURE                Location/Qualifiers
source                 1..8
                       mol_type = protein
                       organism = Mus musculus
SEQUENCE: 35
KQSYILFT                                                       8

SEQ ID NO: 36          moltype = AA  length = 19
FEATURE                Location/Qualifiers
source                 1..19
                       mol_type = protein
                       organism = Mus musculus
SEQUENCE: 36
MAVLALLLCL VAFPSCTLS                                           19

SEQ ID NO: 37          moltype = AA  length = 118
FEATURE                Location/Qualifiers
source                 1..118
                       mol_type = protein
                       organism = Mus musculus
SEQUENCE: 37
QVQLKESGPG LVAPSQNLSI TCTVSGFSLT TYDINWIRQP PGKGLEWLGV IWTGGGTNYN  60
SAFMSRLSIS KDNSKSQVFL KMNSLQTDDT AMYYCVRGDT YHYALDFWGQ GTSVTVSS    118

SEQ ID NO: 38          moltype = AA  length = 13
FEATURE                Location/Qualifiers
source                 1..13
                       mol_type = protein
                       organism = Mus musculus
SEQUENCE: 38
TVSGFSLTTY DIN                                                 13

SEQ ID NO: 39          moltype = AA  length = 19
FEATURE                Location/Qualifiers
source                 1..19
                       mol_type = protein
                       organism = Mus musculus
SEQUENCE: 39
WLGVIWTGGG TNYNSAFMS                                           19

SEQ ID NO: 40          moltype = AA  length = 12
FEATURE                Location/Qualifiers
source                 1..12
                       mol_type = protein
                       organism = Mus musculus
SEQUENCE: 40
```

```
VRGDTYHYAL DF                                                    12

SEQ ID NO: 41          moltype = AA  length = 12
FEATURE                Location/Qualifiers
source                 1..12
                       mol_type = protein
                       organism = Mus musculus
SEQUENCE: 41
VRGDTYHYAL DF                                                    12

SEQ ID NO: 42          moltype = AA  length = 111
FEATURE                Location/Qualifiers
source                 1..111
                       mol_type = protein
                       organism = Mus musculus
SEQUENCE: 42
DIVLTQSPAS LAVSLGQRAT ISCRASESLD FYGNSFMHWY QQKSGQPPKL LISRASNLES  60
GIPPRFSGSG SRTDFTLTID PVEADDVATY YCQQSYEDPY TFGGGTKLEI K           111

SEQ ID NO: 43          moltype = AA  length = 17
FEATURE                Location/Qualifiers
source                 1..17
                       mol_type = protein
                       organism = Mus musculus
SEQUENCE: 43
RASESLDFYG NSFMHWY                                               17

SEQ ID NO: 44          moltype = AA  length = 11
FEATURE                Location/Qualifiers
source                 1..11
                       mol_type = protein
                       organism = Mus musculus
SEQUENCE: 44
LLISRASNLE S                                                     11

SEQ ID NO: 45          moltype = AA  length = 9
FEATURE                Location/Qualifiers
source                 1..9
                       mol_type = protein
                       organism = Mus musculus
SEQUENCE: 45
QQSYEDPYT                                                        9

SEQ ID NO: 46          moltype = AA  length = 19
FEATURE                Location/Qualifiers
source                 1..19
                       mol_type = protein
                       organism = Mus musculus
SEQUENCE: 46
MKLWLNWIFL VTLLNGIQC                                             19

SEQ ID NO: 47          moltype = AA  length = 126
FEATURE                Location/Qualifiers
source                 1..126
                       mol_type = protein
                       organism = Mus musculus
SEQUENCE: 47
EVTLVESGGG LEQPGGSLSL SCAASGFTFT DYYMSWVRQP PGKALEWLAL IRNKANGYTT  60
EYSASVKGRF TISRDNSQSI LYLQMNALRA EDSATYYCAR QVRNYYGYEE DALDYWGQGT  120
SVTVSS                                                           126

SEQ ID NO: 48          moltype = AA  length = 13
FEATURE                Location/Qualifiers
source                 1..13
                       mol_type = protein
                       organism = Mus musculus
SEQUENCE: 48
AASGFTFTDY YMS                                                   13

SEQ ID NO: 49          moltype = AA  length = 22
FEATURE                Location/Qualifiers
source                 1..22
                       mol_type = protein
                       organism = Mus musculus
SEQUENCE: 49
WLALIRNKAN GYTTEYSASV KG                                         22

SEQ ID NO: 50          moltype = AA  length = 17
FEATURE                Location/Qualifiers
```

```
source                  1..17
                        mol_type = protein
                        organism = Mus musculus
SEQUENCE: 50
ARQVRNYYGY EEDALDY                                          17

SEQ ID NO: 51           moltype = AA  length = 20
FEATURE                 Location/Qualifiers
source                  1..20
                        mol_type = protein
                        organism = Mus musculus
SEQUENCE: 51
MDSQAQVLML LLLWVSGTCG                                       20

SEQ ID NO: 52           moltype = AA  length = 113
FEATURE                 Location/Qualifiers
source                  1..113
                        mol_type = protein
                        organism = Mus musculus
SEQUENCE: 52
DIVMSQSPSS LAVSVGEKVT MSCKSSQSLL HSSNQKNYLA WYQQKPGQSP KLLIYWASTR  60
ESGVPDRFTG SGSGTDFTLT ISSVKAEDLA VYYCQQYYSF PRTFGGGTKL EIK        113

SEQ ID NO: 53           moltype = AA  length = 19
FEATURE                 Location/Qualifiers
source                  1..19
                        mol_type = protein
                        organism = Mus musculus
SEQUENCE: 53
KSSQSLLHSS NQKNYLAWY                                        19

SEQ ID NO: 54           moltype = AA  length = 11
FEATURE                 Location/Qualifiers
source                  1..11
                        mol_type = protein
                        organism = Mus musculus
SEQUENCE: 54
LLIYWASTRE S                                                11

SEQ ID NO: 55           moltype = AA  length = 9
FEATURE                 Location/Qualifiers
source                  1..9
                        mol_type = protein
                        organism = Mus musculus
SEQUENCE: 55
QQYYSFPRT                                                   9

SEQ ID NO: 56           moltype = AA  length = 19
FEATURE                 Location/Qualifiers
source                  1..19
                        mol_type = protein
                        organism = Mus musculus
SEQUENCE: 56
MGWSWIFLFL LSGTAGVLS                                        19

SEQ ID NO: 57           moltype = AA  length = 118
FEATURE                 Location/Qualifiers
source                  1..118
                        mol_type = protein
                        organism = Mus musculus
SEQUENCE: 57
EVQLQQSGPE LVKPGASVKI SCKTSGYTFT DYYMNWVKQS HGKSLEWIGD IIPNNGGTSY  60
HQKFKGKATL TVDKSSNTAY MELRSLTSED SAVYYCARYG SSWFFDVWGT GTTVTVSS    118

SEQ ID NO: 58           moltype = AA  length = 13
FEATURE                 Location/Qualifiers
source                  1..13
                        mol_type = protein
                        organism = Mus musculus
SEQUENCE: 58
KTSGYTFTDY YMN                                              13

SEQ ID NO: 59           moltype = AA  length = 20
FEATURE                 Location/Qualifiers
source                  1..20
                        mol_type = protein
                        organism = Mus musculus
SEQUENCE: 59
WIGDIIPNNG GTSYHQKFKG                                       20
```

```
SEQ ID NO: 60           moltype = AA  length = 11
FEATURE                 Location/Qualifiers
source                  1..11
                        mol_type = protein
                        organism = Mus musculus
SEQUENCE: 60
ARYGSSWFFD V                                                  11

SEQ ID NO: 61           moltype = AA  length = 20
FEATURE                 Location/Qualifiers
source                  1..20
                        mol_type = protein
                        organism = Mus musculus
SEQUENCE: 61
MESQTRVLMF LLLWVSGASA                                         20

SEQ ID NO: 62           moltype = AA  length = 113
FEATURE                 Location/Qualifiers
source                  1..113
                        mol_type = protein
                        organism = Mus musculus
SEQUENCE: 62
DIVLTQSPSS LAMSVGQKVT MSCKSSQSLL NSSNQKNYLA WYQQKPGQSP KLLVYFASTR  60
ESGVPDRFTG SGSGTDFTLT ISTVQAEDLA FYYCHQHYSI PRTFGGGTKL EIT         113

SEQ ID NO: 63           moltype = AA  length = 19
FEATURE                 Location/Qualifiers
source                  1..19
                        mol_type = protein
                        organism = Mus musculus
SEQUENCE: 63
KSSQSLLNSS NQKNYLAWY                                          19

SEQ ID NO: 64           moltype = AA  length = 11
FEATURE                 Location/Qualifiers
source                  1..11
                        mol_type = protein
                        organism = Mus musculus
SEQUENCE: 64
LLVYFASTRE S                                                  11

SEQ ID NO: 65           moltype = AA  length = 9
FEATURE                 Location/Qualifiers
source                  1..9
                        mol_type = protein
                        organism = Mus musculus
SEQUENCE: 65
HQHYSIPRT                                                     9

SEQ ID NO: 66           moltype = AA  length = 19
FEATURE                 Location/Qualifiers
source                  1..19
                        mol_type = protein
                        organism = Mus musculus
SEQUENCE: 66
MGWSWIFLFL LSGTAGVLS                                          19

SEQ ID NO: 67           moltype = AA  length = 118
FEATURE                 Location/Qualifiers
source                  1..118
                        mol_type = protein
                        organism = Mus musculus
SEQUENCE: 67
EVQLQQSGPE LVKPGASVKI SCKASGYTFT DHYMNWVKQS HGERLEWIGD IIPNNGGSTY  60
SQKFKGKATL TVDKSSSTAY MELRSLTSED SAVYYCARNG YYWYFDVWGT GTTVTVSS    118

SEQ ID NO: 68           moltype = AA  length = 13
FEATURE                 Location/Qualifiers
source                  1..13
                        mol_type = protein
                        organism = Mus musculus
SEQUENCE: 68
KASGYTFTDH YMN                                                13

SEQ ID NO: 69           moltype = AA  length = 20
FEATURE                 Location/Qualifiers
source                  1..20
                        mol_type = protein
```

```
                         organism = Mus musculus
SEQUENCE: 69
WIGDIIPNNG GSTYSQKFKG                                              20

SEQ ID NO: 70            moltype = AA  length = 11
FEATURE                  Location/Qualifiers
source                   1..11
                         mol_type = protein
                         organism = Mus musculus
SEQUENCE: 70
ARNGYYWYFD V                                                       11

SEQ ID NO: 71            moltype = AA  length = 20
FEATURE                  Location/Qualifiers
source                   1..20
                         mol_type = protein
                         organism = synthetic construct
SEQUENCE: 71
METPAQLLFL LLLWLPDTTG                                              20

SEQ ID NO: 72            moltype = AA  length = 107
FEATURE                  Location/Qualifiers
source                   1..107
                         mol_type = protein
                         organism = synthetic construct
SEQUENCE: 72
DIQMTQSPSS LSASVGDRVT ITCQASQDIT NYLNWYQQKP GKAPKLQIYD ASNLETGVPS  60
RFSGSGSGTD FTFTISSLQP EDIATYYCQQ HDDLPLTFGG GTKVEIK                107

SEQ ID NO: 73            moltype = AA  length = 13
FEATURE                  Location/Qualifiers
source                   1..13
                         mol_type = protein
                         organism = synthetic construct
SEQUENCE: 73
QASQDITNYL NWY                                                     13

SEQ ID NO: 74            moltype = AA  length = 11
FEATURE                  Location/Qualifiers
source                   1..11
                         mol_type = protein
                         organism = synthetic construct
SEQUENCE: 74
LQIYDASNLE T                                                       11

SEQ ID NO: 75            moltype = AA  length = 9
FEATURE                  Location/Qualifiers
source                   1..9
                         mol_type = protein
                         organism = synthetic construct
SEQUENCE: 75
QQHDDLPLT                                                          9

SEQ ID NO: 76            moltype = AA  length = 19
FEATURE                  Location/Qualifiers
source                   1..19
                         mol_type = protein
                         organism = synthetic construct
SEQUENCE: 76
MEFGLNWIFL AAILKGVQC                                               19

SEQ ID NO: 77            moltype = AA  length = 118
FEATURE                  Location/Qualifiers
source                   1..118
                         mol_type = protein
                         organism = synthetic construct
SEQUENCE: 77
QVQLVQSGAE VKKPGASVEV SCKASGYTFT GYYIHWVRQA PGQGLEWMGW INPNSGGTNY  60
AQKFQGRVTM TWDTSISTAF MELSRLRSDD TAVYSCARDR GGPYFDYWGQ GTLVIVSS    118

SEQ ID NO: 78            moltype = AA  length = 13
FEATURE                  Location/Qualifiers
source                   1..13
                         mol_type = protein
                         organism = synthetic construct
SEQUENCE: 78
KASGYTFTGY YIH                                                     13

SEQ ID NO: 79            moltype = AA  length = 20
```

```
FEATURE                Location/Qualifiers
source                 1..20
                       mol_type = protein
                       organism = synthetic construct
SEQUENCE: 79
WMGWINPNSG GTNYAQKFQG                                          20

SEQ ID NO: 80          moltype = AA  length = 11
FEATURE                Location/Qualifiers
source                 1..11
                       mol_type = protein
                       organism = synthetic construct
SEQUENCE: 80
ARDRGGPYFD Y                                                   11

SEQ ID NO: 81          moltype = AA  length = 22
FEATURE                Location/Qualifiers
source                 1..22
                       mol_type = protein
                       organism = synthetic construct
SEQUENCE: 81
MDMRVPAQLL GLLLLWLPGA KC                                       22

SEQ ID NO: 82          moltype = AA  length = 106
FEATURE                Location/Qualifiers
source                 1..106
                       mol_type = protein
                       organism = synthetic construct
SEQUENCE: 82
DIQMTQSPST LSASVGDRVT ITCRASQSIS SWLAWYQQKP GKAPKILIYK ASSLESGVPS  60
RFSGSGSGTE FTLTISSLQP DDFATYYCQQ YNSYWTFGQG TKVEIK             106

SEQ ID NO: 83          moltype = AA  length = 11
FEATURE                Location/Qualifiers
source                 1..11
                       mol_type = protein
                       organism = synthetic construct
SEQUENCE: 83
RASQSISSWL A                                                   11

SEQ ID NO: 84          moltype = AA  length = 11
FEATURE                Location/Qualifiers
source                 1..11
                       mol_type = protein
                       organism = synthetic construct
SEQUENCE: 84
ILIYKASSLE S                                                   11

SEQ ID NO: 85          moltype = AA  length = 8
FEATURE                Location/Qualifiers
source                 1..8
                       mol_type = protein
                       organism = synthetic construct
SEQUENCE: 85
QQYNSYWT                                                       8

SEQ ID NO: 86          moltype = AA  length = 19
FEATURE                Location/Qualifiers
source                 1..19
                       mol_type = protein
                       organism = synthetic construct
SEQUENCE: 86
MELGLSWVFL VAILEGVQC                                           19

SEQ ID NO: 87          moltype = AA  length = 121
FEATURE                Location/Qualifiers
source                 1..121
                       mol_type = protein
                       organism = synthetic construct
SEQUENCE: 87
EVQLVESGGG LVQPGGSLRL SCATSGFTFS NYDMHWVRQV TGKGLEWVSG IGIAGDTYYP  60
GSVKGRFTIS REDAKNSLYL QMNSLRAEDT AVYYCATERG SSSWYNYFDY WGQGTLVTVS  120
S                                                              121

SEQ ID NO: 88          moltype = AA  length = 13
FEATURE                Location/Qualifiers
source                 1..13
                       mol_type = protein
                       organism = synthetic construct
```

```
SEQUENCE: 88
ATSGFTFSNY DMH                                                   13

SEQ ID NO: 89          moltype = AA  length = 19
FEATURE                Location/Qualifiers
source                 1..19
                       mol_type = protein
                       organism = synthetic construct
SEQUENCE: 89
WVSGIGIAGD TYYPGSVKG                                             19

SEQ ID NO: 90          moltype = AA  length = 15
FEATURE                Location/Qualifiers
source                 1..15
                       mol_type = protein
                       organism = synthetic construct
SEQUENCE: 90
ATERGSSSWY NYFDY                                                 15

SEQ ID NO: 91          moltype = AA  length = 20
FEATURE                Location/Qualifiers
source                 1..20
                       mol_type = protein
                       organism = synthetic construct
SEQUENCE: 91
METPAQLLFL LLLWLPDTTG                                            20

SEQ ID NO: 92          moltype = AA  length = 108
FEATURE                Location/Qualifiers
source                 1..108
                       mol_type = protein
                       organism = synthetic construct
SEQUENCE: 92
EIVLTQSPGT LSLSPGERAT LSCRASQSFS DRYLAWYQQK PGQAPRLLIY GTSSRATGIP  60
DRFSGSGSGT DFTLTISRLE SEDSAVYYCQ QYGRSPFTFG PGTKVDIK               108

SEQ ID NO: 93          moltype = AA  length = 14
FEATURE                Location/Qualifiers
source                 1..14
                       mol_type = protein
                       organism = synthetic construct
SEQUENCE: 93
RASQSFSDRY LAWY                                                  14

SEQ ID NO: 94          moltype = AA  length = 11
FEATURE                Location/Qualifiers
source                 1..11
                       mol_type = protein
                       organism = synthetic construct
SEQUENCE: 94
LLIYGTSSRA T                                                     11

SEQ ID NO: 95          moltype = AA  length = 8
FEATURE                Location/Qualifiers
source                 1..8
                       mol_type = protein
                       organism = synthetic construct
SEQUENCE: 95
QQYGRSPF                                                         8

SEQ ID NO: 96          moltype = AA  length = 19
FEATURE                Location/Qualifiers
source                 1..19
                       mol_type = protein
                       organism = synthetic construct
SEQUENCE: 96
MEFGLSWVFL VAIIKGVHC                                             19

SEQ ID NO: 97          moltype = AA  length = 115
FEATURE                Location/Qualifiers
source                 1..115
                       mol_type = protein
                       organism = synthetic construct
SEQUENCE: 97
QVQLVQSGAE VKKPGASVKV SCKASGYTFT SFGLTWVRQA PGQGLEWMGW FNAYSGKTYY  60
APTLQDRVTM TTDPSTSTAY MELMSLTSDD TAIYYCARDL VFDYWGQGTL VTVSS       115

SEQ ID NO: 98          moltype = AA  length = 13
FEATURE                Location/Qualifiers
```

```
source                  1..13
                        mol_type = protein
                        organism = synthetic construct
SEQUENCE: 98
KASGYTFTSF GLT                                                  13

SEQ ID NO: 99           moltype = AA  length = 20
FEATURE                 Location/Qualifiers
source                  1..20
                        mol_type = protein
                        organism = synthetic construct
SEQUENCE: 99
WMGWFNAYSG KTYYAPTLQD                                           20

SEQ ID NO: 100          moltype = AA  length = 8
FEATURE                 Location/Qualifiers
source                  1..8
                        mol_type = protein
                        organism = synthetic construct
SEQUENCE: 100
ARDLVFDY                                                        8

SEQ ID NO: 101          moltype = AA  length = 19
FEATURE                 Location/Qualifiers
source                  1..19
                        mol_type = protein
                        organism = synthetic construct
SEQUENCE: 101
MAWALLLLTL LTQGTGSWA                                            19

SEQ ID NO: 102          moltype = AA  length = 110
FEATURE                 Location/Qualifiers
source                  1..110
                        mol_type = protein
                        organism = synthetic construct
SEQUENCE: 102
QSALTQPPSA SGSPGQSVTI SCTGTSSDVG GYNYVSWYQQ HPGKAPKIMI YEVNKRPAGV  60
PDRFSGSKSG NTASLTVSGL QAEDEAHYYC NSYTDSNNLI FGGGTKLTVL             110

SEQ ID NO: 103          moltype = AA  length = 16
FEATURE                 Location/Qualifiers
source                  1..16
                        mol_type = protein
                        organism = synthetic construct
SEQUENCE: 103
TGTSSDVGGY NYVSWY                                               16

SEQ ID NO: 104          moltype = AA  length = 11
FEATURE                 Location/Qualifiers
source                  1..11
                        mol_type = protein
                        organism = synthetic construct
SEQUENCE: 104
IMIYEVNKRP A                                                    11

SEQ ID NO: 105          moltype = AA  length = 10
FEATURE                 Location/Qualifiers
source                  1..10
                        mol_type = protein
                        organism = synthetic construct
SEQUENCE: 105
NSYTDSNNLI                                                      10

SEQ ID NO: 106          moltype = AA  length = 19
FEATURE                 Location/Qualifiers
source                  1..19
                        mol_type = protein
                        organism = synthetic construct
SEQUENCE: 106
MELGLSWIFL LAILKGVQC                                            19

SEQ ID NO: 107          moltype = AA  length = 122
FEATURE                 Location/Qualifiers
source                  1..122
                        mol_type = protein
                        organism = synthetic construct
SEQUENCE: 107
EVQLVESGGG LVQPGRSLRL SCAASGFTFG DYAMHWVRQA PGKGLEWVSG INWNNKNIGY  60
ADSVKGRFTI SKNNAKNSLY LQMNSLRVED TALYYCAKDR GYSYGYWYFD LWGRGTLVTV  120
```

```
SS                                                                  122

SEQ ID NO: 108          moltype = AA  length = 13
FEATURE                 Location/Qualifiers
source                  1..13
                        mol_type = protein
                        organism = synthetic construct
SEQUENCE: 108
AASGFTFGDY AMH                                                      13

SEQ ID NO: 109          moltype = AA  length = 20
FEATURE                 Location/Qualifiers
source                  1..20
                        mol_type = protein
                        organism = synthetic construct
SEQUENCE: 109
WVSGINWNNK NIGYADSVKG                                               20

SEQ ID NO: 110          moltype = AA  length = 15
FEATURE                 Location/Qualifiers
source                  1..15
                        mol_type = protein
                        organism = synthetic construct
SEQUENCE: 110
AKDRGYSYGY WYFDL                                                    15

SEQ ID NO: 111          moltype = AA  length = 20
FEATURE                 Location/Qualifiers
source                  1..20
                        mol_type = protein
                        organism = synthetic construct
SEQUENCE: 111
METPAQLLFL LLLWLPDATG                                               20

SEQ ID NO: 112          moltype = AA  length = 108
FEATURE                 Location/Qualifiers
source                  1..108
                        mol_type = protein
                        organism = synthetic construct
SEQUENCE: 112
EIVLMQSPGT LSLSPGERVT LSCRASQTFS SSYLAWYQQK PGQAPRLLIY GASSRATGIP  60
DRFSGSGSGT DFTLTINRLE PEDFAVYYCQ QYGRSPFTFG PGTKLDIK                108

SEQ ID NO: 113          moltype = AA  length = 12
FEATURE                 Location/Qualifiers
source                  1..12
                        mol_type = protein
                        organism = synthetic construct
SEQUENCE: 113
RASQTFSSSY LA                                                       12

SEQ ID NO: 114          moltype = AA  length = 11
FEATURE                 Location/Qualifiers
source                  1..11
                        mol_type = protein
                        organism = synthetic construct
SEQUENCE: 114
LLIYGASSRA T                                                        11

SEQ ID NO: 115          moltype = AA  length = 9
FEATURE                 Location/Qualifiers
source                  1..9
                        mol_type = protein
                        organism = synthetic construct
SEQUENCE: 115
QQYGRSPFT                                                           9

SEQ ID NO: 116          moltype = AA  length = 19
FEATURE                 Location/Qualifiers
source                  1..19
                        mol_type = protein
                        organism = synthetic construct
SEQUENCE: 116
MDWTWSILFL VAAATGAHS                                                19

SEQ ID NO: 117          moltype = AA  length = 115
FEATURE                 Location/Qualifiers
source                  1..115
                        mol_type = protein
```

```
                        organism = synthetic construct
SEQUENCE: 117
QVQLVQSGAE VKKPGASVKV SCKASGYTFN SYGISWVRQA PGQGLEWMGW FNAYSGITNY  60
AQKFQDRITM TTDTSTSTAY MELRSLRSDD TAVYYCARDL VFDFWGQGTL VTVSS       115

SEQ ID NO: 118          moltype = AA  length = 13
FEATURE                 Location/Qualifiers
source                  1..13
                        mol_type = protein
                        organism = synthetic construct
SEQUENCE: 118
KASGYTFNSY GIS                                                     13

SEQ ID NO: 119          moltype = AA  length = 20
FEATURE                 Location/Qualifiers
source                  1..20
                        mol_type = protein
                        organism = synthetic construct
SEQUENCE: 119
WMGWFNAYSG ITNYAQKFQD                                              20

SEQ ID NO: 120          moltype = AA  length = 8
FEATURE                 Location/Qualifiers
source                  1..8
                        mol_type = protein
                        organism = synthetic construct
SEQUENCE: 120
ARDLVFDF                                                           8

SEQ ID NO: 121          moltype = AA  length = 20
FEATURE                 Location/Qualifiers
source                  1..20
                        mol_type = protein
                        organism = synthetic construct
SEQUENCE: 121
MVLQTQVFIS LLLWISGAYG                                              20

SEQ ID NO: 122          moltype = AA  length = 108
FEATURE                 Location/Qualifiers
source                  1..108
                        mol_type = protein
                        organism = synthetic construct
SEQUENCE: 122
EIVLTQSPGT LSLSPGERAT LSCRASQSFS DRYLAWYQQK PGQAPRLLIY GTFSRATGIP  60
DRFSGSGSGT DFTLTISRLD SEDFAVYYCQ QYGSSPFTFG PGTKVDIK               108

SEQ ID NO: 123          moltype = AA  length = 14
FEATURE                 Location/Qualifiers
source                  1..14
                        mol_type = protein
                        organism = synthetic construct
SEQUENCE: 123
RASQSFSDRY LAWY                                                    14

SEQ ID NO: 124          moltype = AA  length = 11
FEATURE                 Location/Qualifiers
source                  1..11
                        mol_type = protein
                        organism = synthetic construct
SEQUENCE: 124
LLIYGTFSRA T                                                       11

SEQ ID NO: 125          moltype = AA  length = 8
FEATURE                 Location/Qualifiers
source                  1..8
                        mol_type = protein
                        organism = synthetic construct
SEQUENCE: 125
QQYGSSPF                                                           8

SEQ ID NO: 126          moltype = AA  length = 19
FEATURE                 Location/Qualifiers
source                  1..19
                        mol_type = protein
                        organism = synthetic construct
SEQUENCE: 126
MDWTWRILFL VAAATGAHS                                               19

SEQ ID NO: 127          moltype = AA  length = 115
```

```
FEATURE                Location/Qualifiers
source                 1..115
                       mol_type = protein
                       organism = synthetic construct
SEQUENCE: 127
QVQLVQSGAE VKKPGASVKV SCKASGYTFT SFGISWVRQA PGQGLEWMGW FNAYSGNTYY  60
APTLQDRVTM TTDTSTSTAY MELMSLRSDD TAIYYCARDL VFDYWGQGTL VTVSS       115

SEQ ID NO: 128         moltype = AA  length = 13
FEATURE                Location/Qualifiers
source                 1..13
                       mol_type = protein
                       organism = synthetic construct
SEQUENCE: 128
KASGYTFTSF GIS                                                     13

SEQ ID NO: 129         moltype = AA  length = 20
FEATURE                Location/Qualifiers
source                 1..20
                       mol_type = protein
                       organism = synthetic construct
SEQUENCE: 129
WMGWFNAYSG NTYYAPTLQD                                              20

SEQ ID NO: 130         moltype = AA  length = 8
FEATURE                Location/Qualifiers
source                 1..8
                       mol_type = protein
                       organism = synthetic construct
SEQUENCE: 130
ARDLVFDY                                                           8

SEQ ID NO: 131         moltype = AA  length = 20
FEATURE                Location/Qualifiers
source                 1..20
                       mol_type = protein
                       organism = synthetic construct
SEQUENCE: 131
MRVPAQLLGL LLLWFPGARC                                              20

SEQ ID NO: 132         moltype = AA  length = 107
FEATURE                Location/Qualifiers
source                 1..107
                       mol_type = protein
                       organism = synthetic construct
SEQUENCE: 132
DIQMTQSPSS LSASVGDRVT ITCRASQGIR NDLGWYQQRP GKAPKRLIYA ASSLQSGVPS  60
RFSGSGSGTE FTLAISSLQP EDFATYSCLQ HNSYPWTFGQ GTKVEIK                107

SEQ ID NO: 133         moltype = AA  length = 13
FEATURE                Location/Qualifiers
source                 1..13
                       mol_type = protein
                       organism = synthetic construct
SEQUENCE: 133
RASQGIRNDL GWY                                                     13

SEQ ID NO: 134         moltype = AA  length = 11
FEATURE                Location/Qualifiers
source                 1..11
                       mol_type = protein
                       organism = synthetic construct
SEQUENCE: 134
RLIYAASSLQ S                                                       11

SEQ ID NO: 135         moltype = AA  length = 9
FEATURE                Location/Qualifiers
source                 1..9
                       mol_type = protein
                       organism = synthetic construct
SEQUENCE: 135
LQHNSYPWT                                                          9

SEQ ID NO: 136         moltype = AA  length = 19
FEATURE                Location/Qualifiers
source                 1..19
                       mol_type = protein
                       organism = synthetic construct
SEQUENCE: 136
```

```
MDCTWRILFL VAAATGTHA                                                19

SEQ ID NO: 137         moltype = AA  length = 122
FEATURE                Location/Qualifiers
source                 1..122
                       mol_type = protein
                       organism = synthetic construct
SEQUENCE: 137
QVQLVQSGAE VKKPGASVKV SCKVSGYTLT EFSMHWVRQA PGKGLEWMGV FDPEHGATIY  60
AQKFQGRVTM TEDTSTDTAY MDLSYLRSED TAVYYCATYF DFWSGYSHFD FWGQGTLVTV  120
SS                                                                  122

SEQ ID NO: 138         moltype = AA  length = 13
FEATURE                Location/Qualifiers
source                 1..13
                       mol_type = protein
                       organism = synthetic construct
SEQUENCE: 138
KVSGYTLTEF SMH                                                      13

SEQ ID NO: 139         moltype = AA  length = 20
FEATURE                Location/Qualifiers
source                 1..20
                       mol_type = protein
                       organism = synthetic construct
SEQUENCE: 139
WMGVFDPEHG ATIYAQKFQG                                               20

SEQ ID NO: 140         moltype = AA  length = 15
FEATURE                Location/Qualifiers
source                 1..15
                       mol_type = protein
                       organism = synthetic construct
SEQUENCE: 140
ATYFDFWSGY SHFDF                                                    15

SEQ ID NO: 141         moltype = AA  length = 22
FEATURE                Location/Qualifiers
source                 1..22
                       mol_type = protein
                       organism = synthetic construct
SEQUENCE: 141
MDMRVLAQLL GLLLLCFPGA RC                                            22

SEQ ID NO: 142         moltype = AA  length = 107
FEATURE                Location/Qualifiers
source                 1..107
                       mol_type = protein
                       organism = synthetic construct
SEQUENCE: 142
DIQMTQSPSS LSASVGDRVT ITCRASQGIS NYLAWFQQKP GKAPKSLIYA ASSLQSGVPS  60
KFSGSGSGTD FTLTISSLQP EDLATYYCQQ YNSYPYTFGQ GTKLEIK                 107

SEQ ID NO: 143         moltype = AA  length = 11
FEATURE                Location/Qualifiers
source                 1..11
                       mol_type = protein
                       organism = synthetic construct
SEQUENCE: 143
RASQGISNYL A                                                        11

SEQ ID NO: 144         moltype = AA  length = 11
FEATURE                Location/Qualifiers
source                 1..11
                       mol_type = protein
                       organism = synthetic construct
SEQUENCE: 144
SLIYAASSLQ S                                                        11

SEQ ID NO: 145         moltype = AA  length = 9
FEATURE                Location/Qualifiers
source                 1..9
                       mol_type = protein
                       organism = synthetic construct
SEQUENCE: 145
QQYNSYPYT                                                           9

SEQ ID NO: 146         moltype = AA  length = 19
FEATURE                Location/Qualifiers
```

```
source                  1..19
                        mol_type = protein
                        organism = synthetic construct
SEQUENCE: 146
MDWTWRFLFV VAAATGVQS                                        19

SEQ ID NO: 147          moltype = AA  length = 117
FEATURE                 Location/Qualifiers
source                  1..117
                        mol_type = protein
                        organism = synthetic construct
SEQUENCE: 147
QVQLVQSGSE VKKPGSSVKV SCKASGGTFS SYAISWVRQA PGQGLEWMGG IIPIFGTVTY  60
AQKFQGRVTI TADESTNTVY MELSSLRSED TAVYYCARDD FWTGDYWGQG TLVTVSS     117

SEQ ID NO: 148          moltype = AA  length = 13
FEATURE                 Location/Qualifiers
source                  1..13
                        mol_type = protein
                        organism = synthetic construct
SEQUENCE: 148
KASGGTFSSY AIS                                              13

SEQ ID NO: 149          moltype = AA  length = 20
FEATURE                 Location/Qualifiers
source                  1..20
                        mol_type = protein
                        organism = synthetic construct
SEQUENCE: 149
WMGGIIPIFG TVTYAQKFQG                                       20

SEQ ID NO: 150          moltype = AA  length = 10
FEATURE                 Location/Qualifiers
source                  1..10
                        mol_type = protein
                        organism = synthetic construct
SEQUENCE: 150
ARDDFWTGDY                                                  10

SEQ ID NO: 151          moltype = AA  length = 117
FEATURE                 Location/Qualifiers
source                  1..117
                        mol_type = protein
                        organism = synthetic construct
SEQUENCE: 151
QVQLVQSGSE VKKPGSSVKV SCKASGGTFS SYAISWVRQA PGQGLEWMGG IIPIFGTVTY  60
AQKFQGGVTI TADESTNTVY MELSSLRSED TAVYYCARDD FWTGDYWGQG TLVTVSS     117

SEQ ID NO: 152          moltype = AA  length = 244
FEATURE                 Location/Qualifiers
source                  1..244
                        mol_type = protein
                        organism = synthetic construct
SEQUENCE: 152
QVKLQESGPG LVQPSQSLSI TCTVSGFSLT DYGVHWVRQS PGKGLEWLGV IWSGGGTATY  60
AAFISRLNIY KDNSKNQVFF EMNSLQANDT AMYYCARRGS YPYNYFDVWG QGTTVTVSSG  120
GGGSGGGGSG GGGSQAVVTQ ESALTTSPGE TVTLTCRSST GAVTTSNYAN WVQEKPDHLF  180
TGLIGGNNNR PPGVPARFSG SLIGDKAALT IAGTQTEADA IYFCALWYSN HWVFGGGFRG  240
RVLG                                                        244

SEQ ID NO: 153          moltype = AA  length = 244
FEATURE                 Location/Qualifiers
source                  1..244
                        mol_type = protein
                        organism = synthetic construct
SEQUENCE: 153
QVKLQESGPG LVQPSQSLSI TCTVSGFSLT DYGVHWVRQS PGKGLEWLGV IWSGGGTAYN  60
TALISRLNIY RDNSKNQVFL EMNSLQADDT AMYYCARRGS YPYNYFDAWG RGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLG                                                        244

SEQ ID NO: 154          moltype = AA  length = 229
FEATURE                 Location/Qualifiers
source                  1..229
                        mol_type = protein
                        organism = synthetic construct
SEQUENCE: 154
LVKLQESGPG LVQPSQSLSI TCTVSGFSLT DYGVHWVRQS PGKGLEWLGV IWSGGGTAYN  60
```

```
TALISRLNIY RDNSKNQVFL EMNSLQAEDT AMYYCARRGS YPYNYFDAWG RGTTVTVSSE  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFLCFVVF             229

SEQ ID NO: 155         moltype = AA  length = 244
FEATURE                Location/Qualifiers
source                 1..244
                       mol_type = protein
                       organism = synthetic construct
SEQUENCE: 155
QAKLQESGPG LVQPSQSLSI TCTVSGFSLT DYGVHWVRQS PGKGLEWLGV IWSGGGTAYN  60
TALISRLNIY RDNSKNQVFL EMNSLQAEDT AMYYCARRGS YPYNYFDAWG CGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLG                                                              244

SEQ ID NO: 156         moltype = AA  length = 244
FEATURE                Location/Qualifiers
source                 1..244
                       mol_type = protein
                       organism = synthetic construct
SEQUENCE: 156
QVKLQESGPG LVQPSQSLSI TCTVSGFSLT DYGVHWVRQS PGKGLEWLGV IWSGGGTAYN  60
TALISRLNIY RDNSKNQVFL EMNSLQADDT AMYYCARRGS YPYNYFDAWG CGTTVTVSSG  120
GGGPGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLS                                                              244

SEQ ID NO: 157         moltype = AA  length = 244
FEATURE                Location/Qualifiers
source                 1..244
                       mol_type = protein
                       organism = synthetic construct
SEQUENCE: 157
HVKLQESGPG LVQPSQSLSL TCTVSGFSLT DYGVHWVRQS PGKGLEWLGV IWSGGGTAYN  60
TALISRLNIY RDNSKNQVFL EMNSLQAEDT AMYYCARRGS YPYNYFDAWG CGTTVTVSSG  120
GGGSGGGGSG GGGSQAVVIQ ESALTTPPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLG                                                              244

SEQ ID NO: 158         moltype = AA  length = 244
FEATURE                Location/Qualifiers
source                 1..244
                       mol_type = protein
                       organism = synthetic construct
SEQUENCE: 158
QVKLQESGPG LVRPSQPLSI TCTVSGFSLT DYGVHWVRQS PGKGLEWLGV IWSGGGTAYN  60
TALISRLNIY RDNSKNQVFL EMNSLQADDT AMYYCARRGS YPYNYFDAWG CGTTVTVSSG  120
GGGSGGGGSG GGGSQAVVIQ ESALTTSPGE TVTLTCGSST GAVTAFNYAN WVQEKPDHCF  180
TGLIGGHNNR PPGVPARFSG SLIGGKAALT IAGTQTEDEA IYFCALWYSD HWVIGGGTRL  240
TVLG                                                              244

SEQ ID NO: 159         moltype = AA  length = 244
FEATURE                Location/Qualifiers
source                 1..244
                       mol_type = protein
                       organism = synthetic construct
SEQUENCE: 159
QVKLQESGPG LVQPSQSLSI TCTVSGFSLT DYGVHWVRQS PGKGLEWLGV IWSGGGTAYN  60
TALISRLNIY RDNSKNQVFF EMNSLQADDT AMYYCARRGS YPYNYFDAWG CGTTVTVSSG  120
GGGSGGGGSG GGGSQAVVIQ ESALITSPGE TVTLTCGSST GAVTASNYAN WVQEKPDHCF  180
TGLIGGHNNR PPGVPARFSG SLIGDKAALT IAGTQTGDEA IYFCALWYSD HWVIGGGTRL  240
TVLG                                                              244

SEQ ID NO: 160         moltype = AA  length = 244
FEATURE                Location/Qualifiers
source                 1..244
                       mol_type = protein
                       organism = synthetic construct
SEQUENCE: 160
QVKLQESGPG LVQPSQSLSI TCTVSGFSLT DYGVHWVRQS PGKGLEWLGV IWSGGGTAYN  60
TALISRLNIY RDNSKNQVFL EMNSLQADDT AMYYCARRGS YPYNYFDAWG CGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLG                                                              244

SEQ ID NO: 161         moltype = AA  length = 244
FEATURE                Location/Qualifiers
source                 1..244
```

```
                        mol_type = protein
                        organism = synthetic construct
SEQUENCE: 161
QVKLQESGPG LVQPSQSLSI TCTVSGFSLT DYGVHWVRQS PGKGLEWLGV IWSGGGTAYN  60
TALISRLNIY RDNSKNQVFL EMNSLQADDT AMYYCARRGS YPYNYFDAWG CGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLG                                                              244

SEQ ID NO: 162          moltype = AA  length = 244
FEATURE                 Location/Qualifiers
source                  1..244
                        mol_type = protein
                        organism = synthetic construct
SEQUENCE: 162
QVKLQESGPG LVQPSQSLSI TCTVSGFSLT DYGVHWVRQS PGKGLEWLGV IWSGGGTAYN  60
TALISRLNIY RDNSKNQVFF EMNSLQADDT AMYYCARRGS YPYNYFDAWG CGTTVTVSSG  120
GGGSGSGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLG                                                              244

SEQ ID NO: 163          moltype = AA  length = 244
FEATURE                 Location/Qualifiers
source                  1..244
                        mol_type = protein
                        organism = synthetic construct
SEQUENCE: 163
QVKLQESGPG LVQPPQSLSI TCTVSGFSLT DYGVHWVRQS PGKGLEWLGV IWSGGGTAYN  60
TALISRLNIY RDNSKNQVFF EMNSLQADDT AMYYCARRGS YPYNYFDAWG CGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKATLT IAGTQTEDEA IYFCALWYSD HWVIGGGTRL  240
TVLG                                                              244

SEQ ID NO: 164          moltype = AA  length = 244
FEATURE                 Location/Qualifiers
source                  1..244
                        mol_type = protein
                        organism = synthetic construct
SEQUENCE: 164
QVKLQESGPG LVQPSQSLSI TCTVSGFSLT DYGVHWVRQS PGKGLEWLGV IWSGGGTAYN  60
TALISRLNIY RDNSKNQVFF EMNSLQAEDT AMYYCARRGS YPYNYFDAWG CGTTVTVSSG  120
GGGPGGGGSG GGGSQAVVIQ ESALTTSPGE TVTLTCGSST GAITTSNYAN WVQEKPDHCF  180
TGLIGGHNNR PPGVPARFSG SLIGDKAALT IAGTQTEDEA IYFCALWYSD HWVIGGGTRL  240
TVLG                                                              244

SEQ ID NO: 165          moltype = AA  length = 244
FEATURE                 Location/Qualifiers
source                  1..244
                        mol_type = protein
                        organism = synthetic construct
SEQUENCE: 165
QVKLQESGPG LVQPSQSLSI TCTVSGFSLT DYGVHWVRQS PGKGLEWLGV IWSGGGTAYN  60
TALISRLNIY RDNSKNQVFL EMNSLQAEDT AMYYCARRGS YPYNYFDAWG CGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IVGTQTEDEA IYFCALWYSD HWVIGGGTRL  240
TVLG                                                              244

SEQ ID NO: 166          moltype = AA  length = 244
FEATURE                 Location/Qualifiers
source                  1..244
                        mol_type = protein
                        organism = synthetic construct
SEQUENCE: 166
QVKLQESGPG LVQPSQSLSI TCTVSGFSLT DYGVHWVRQS PGKGLEWLGV IWSGGGTAYN  60
TALISRLNIY RDNSKNQVFF EMNSLQADDT AMYYCARRGR YPYNYFDAWG CGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGGGTRL  240
TVLG                                                              244

SEQ ID NO: 167          moltype = AA  length = 244
FEATURE                 Location/Qualifiers
source                  1..244
                        mol_type = protein
                        organism = synthetic construct
SEQUENCE: 167
QVKLQESGPG LVQPSQSLSI TCTVSGFSLT DYGVHWVRQS PGKSLEWLGV IWSGGGTAYN  60
TALISRLNIY KDNSKNQVFF EMNSLQAEDT AMYYCARRGS YPYNYFDAWG CGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYYCALWYSD HWVIGGGTRL  240
```

```
TVLG                                                          244

SEQ ID NO: 168         moltype = AA  length = 238
FEATURE                Location/Qualifiers
source                 1..238
                       mol_type = protein
                       organism = synthetic construct
SEQUENCE: 168
QVKLQESGPG LVQPSQSLSI TCTVSGFSLT DYGVHWVRQS PGKGLEWLGV IWSGGGTAYN  60
TALISRLNIY RDNSKNQVFL EMNSLQADDT AMYYCARRGS YPYNYFDAWG RGTTVTVSSG  120
GGGSGGGGSG GGGSQAVVIQ ESALTTSPGE TVTLTCGSST GAVTASNYAN WVQEKPDHCF  180
TGLIGGHNNR PPGVPARFSG SLIGDKAALT IAGTQTEDEA IYFCALWYSD HWVIGWWY    238

SEQ ID NO: 169         moltype = AA  length = 745
FEATURE                Location/Qualifiers
source                 1..745
                       mol_type = protein
                       organism = synthetic construct
SEQUENCE: 169
DIVMSQSPSS LAVSAGEKVT MSCKSSQSLL SSGTRKNYLA WYQQKPGQSP KLLIYWASTR  60
ESGVPDRFTG SGSGTDFTLT ISSVQAEDLA VYYCKQSYIL FTFGSGTKLE IKGGGSGGGG  120
SGGGGSGGGG SSQVQLKESG PGLVAPSQNL SITCTVSGFS LTTYDINWIR QPPGKGLEWL  180
GVIWTGGGTN YNSAFMSRLS ISKDNSKSQV FLKMNSLQTD DTAMYYCVRG DTYHYALDFW  240
GQGTSVTVSS LEPKSSDKTH TCPPCPAPEL LGGPSVFLFP PKPKDTLMIS RTPEVTCVVV  300
DVSHEDPEVK FNWYVDGVEV HNAKTKPREE QYNSTYRVVS VLTVLHQDWL NGKEYKCKVS  360
NKALPAPIEK TISKAKGQPR EPQVYTLPPS RDELTKNQVS LTCLVKGFYP SDIAVEWESN  420
GQPENNYKTT PPVLDSDGSF FLYSKLTVDK SRWQQGNVFS CSVMHEGLHN HYTQKSLSLS  480
PGKVDGASSH VNVSSPSVQD IHVKLQESGP GLVQPSQSLS LTCTVSGFSL TDYGVHWVRQ  540
SPGKGLEWLG VIWSGGGTAY NTALISRLNI YRDNSKNQVF LEMNSLQAED TAMYYCARRG  600
SYPYNYFDAW GCGTTVTVSS GGGGSGGGGS GGGGSQAVVI QESALTTPPG ETVTLTCGSS  660
TGAVTASNYA NWVQEKPDHC FTGLIGGHNN RPPGVPARFS GSLIGDKAAL TIAGTQTEDE  720
AIYFCALWYS DHWVIGGGTR LTVLG                                   745

SEQ ID NO: 170         moltype = AA  length = 745
FEATURE                Location/Qualifiers
source                 1..745
                       mol_type = protein
                       organism = synthetic construct
SEQUENCE: 170
DIVMSQSPSS LAVSAGEKVT MSCKSSQSLL SSGTRKNYLA WYQQKPGQSP KLLIYWASTR  60
ESGVPDRFTG SGSGTDFTLT ISSVQAEDLA VYYCKQSYIL FTFGSGTKLE IKGGGSGGGG  120
SGGGGSGGGG SSQVQLKESG PGLVAPSQNL SITCTVSGFS LTTYDINWIR QPPGKGLEWL  180
GVIWTGGGTN YNSAFMSRLS ISKDNSKSQV FLKMNSLQTD DTAMYYCVRG DTYHYALDFW  240
GQGTSVTVSS LEPKSSDKTH TSPPSPAPEL LGGPSVFLFP PKPKDTLMIS RTPEVTCVVV  300
DVSHEDPEVK FNWYVDGVEV HNAKTKPREE QYNSTYRVVS VLTVLHQDWL NGKEYKCKVS  360
NKALPAPIEK TISKAKGQPR EPQVYTLPPS RDELTKNQVS LTCRVKGFYP SDIAVEWESN  420
GQPENNYKTT PPVLDSDGSF HLESKLTVDK SRWQQGNVFS CSVMHEGLHN HYTQKSLSLS  480
PGKVDGASSH VNVSSPSVQD IHVKLQESGP GLVQPSQSLS LTCTVSGFSL TDYGVHWVRQ  540
SPGKGLEWLG VIWSGGGTAY NTALISRLNI YRDNSKNQVF LEMNSLQAED TAMYYCARRG  600
SYPYNYFDAW GCGTTVTVSS GGGGSGGGGS GGGGSQAVVI QESALTTPPG ETVTLTCGSS  660
TGAVTASNYA NWVQEKPDHC FTGLIGGHNN RPPGVPARFS GSLIGDKAAL TIAGTQTEDE  720
AIYFCALWYS DHWVIGGGTR LTVLG                                   745

SEQ ID NO: 171         moltype = AA  length = 112
FEATURE                Location/Qualifiers
source                 1..112
                       mol_type = protein
                       organism = synthetic construct
SEQUENCE: 171
DIVMTQSPDS LAVSLGERAT INCKSSQSLL SSGTRKNYLA WYQQKPGQPP KLLIYWASTR  60
ESGVPDRFSG SGSGTDFTLT ISSLQAEDVA VYYCKQSYIL FTFGQGTKLE IK         112

SEQ ID NO: 172         moltype = AA  length = 19
FEATURE                Location/Qualifiers
source                 1..19
                       mol_type = protein
                       organism = synthetic construct
SEQUENCE: 172
KSSQSLLSSG TRKNYLAWY                                          19

SEQ ID NO: 173         moltype = AA  length = 11
FEATURE                Location/Qualifiers
source                 1..11
                       mol_type = protein
                       organism = synthetic construct
SEQUENCE: 173
LLIYWASTRE S                                                  11

SEQ ID NO: 174         moltype = AA  length = 7
```

```
FEATURE                Location/Qualifiers
source                 1..7
                       mol_type = protein
                       organism = synthetic construct
SEQUENCE: 174
KQSYILF                                                            7

SEQ ID NO: 175         moltype = AA  length = 118
FEATURE                Location/Qualifiers
source                 1..118
                       mol_type = protein
                       organism = synthetic construct
SEQUENCE: 175
QVQLQESGPG LVKPSETLSL TCTVSGFSLT TYDINWIRQP PGKGLEWIGV IWTGGGTNYN  60
SAFMSRVTIS VDTSKNQFSL KLSSVTAADT AVYYCARADT YHYALDFWGQ GTLVTVSS    118

SEQ ID NO: 176         moltype = AA  length = 13
FEATURE                Location/Qualifiers
source                 1..13
                       mol_type = protein
                       organism = synthetic construct
SEQUENCE: 176
TVSGFSLTTY DIN                                                     13

SEQ ID NO: 177         moltype = AA  length = 19
FEATURE                Location/Qualifiers
source                 1..19
                       mol_type = protein
                       organism = synthetic construct
SEQUENCE: 177
WIGVIWTGGG TNYNSAFMS                                               19

SEQ ID NO: 178         moltype = AA  length = 12
FEATURE                Location/Qualifiers
source                 1..12
                       mol_type = protein
                       organism = synthetic construct
SEQUENCE: 178
ARADTYHYAL DF                                                      12

SEQ ID NO: 179         moltype = AA  length = 112
FEATURE                Location/Qualifiers
source                 1..112
                       mol_type = protein
                       organism = synthetic construct
SEQUENCE: 179
DIVMTQSPDS LAVSLGERAT INCKSSQSLL SSGTRKNYLA WYQQKPGQPP KLLIYWASTR  60
ESGVPDRFSG SGSGTDFTLT ISSLQAEDVA VYYCKQSYIL FTFGQGTKLE IK          112

SEQ ID NO: 180         moltype = AA  length = 19
FEATURE                Location/Qualifiers
source                 1..19
                       mol_type = protein
                       organism = synthetic construct
SEQUENCE: 180
KSSQSLLSSG TRKNYLAWY                                               19

SEQ ID NO: 181         moltype = AA  length = 11
FEATURE                Location/Qualifiers
source                 1..11
                       mol_type = protein
                       organism = synthetic construct
SEQUENCE: 181
LLIYWASTRE S                                                       11

SEQ ID NO: 182         moltype = AA  length = 8
FEATURE                Location/Qualifiers
source                 1..8
                       mol_type = protein
                       organism = synthetic construct
SEQUENCE: 182
KQSYILFT                                                           8

SEQ ID NO: 183         moltype = AA  length = 118
FEATURE                Location/Qualifiers
source                 1..118
                       mol_type = protein
                       organism = synthetic construct
SEQUENCE: 183
```

```
QVQLQESGPG LVKPSETLSL TCTVSGFSLT TYDWSWIRQP PGKGLEWIGY IWTGGGTNYN  60
PSLKSRVTIS VDTSKNQFSL KLSSVTAADT AVYYCVRGDT YHYALDFWGQ GTLVTVSS    118

SEQ ID NO: 184          moltype = AA  length = 15
FEATURE                 Location/Qualifiers
source                  1..15
                        mol_type = protein
                        organism = synthetic construct
SEQUENCE: 184
TVSGFSLTTY DWSWY                                                   15

SEQ ID NO: 185          moltype = AA  length = 19
FEATURE                 Location/Qualifiers
source                  1..19
                        mol_type = protein
                        organism = synthetic construct
SEQUENCE: 185
WIGYIWTGGG TNYNPSLKS                                               19

SEQ ID NO: 186          moltype = AA  length = 12
FEATURE                 Location/Qualifiers
source                  1..12
                        mol_type = protein
                        organism = synthetic construct
SEQUENCE: 186
VRGDTYHYAL DF                                                      12

SEQ ID NO: 187          moltype = AA  length = 529
FEATURE                 Location/Qualifiers
source                  1..529
                        mol_type = protein
                        organism = Homo sapiens
SEQUENCE: 187
MVLLWLTLLL IALPCLLQTK EDPNPPITNL RMKAKAQQLT WDLNRNVTDI ECVKDADYSM  60
PAVNNSYCQF GAISLCEVTN YTVRVANPPF STWILFPENS GKPWAGAENL TCWIHDVDFL  120
SCSWAVGPGA PADVQYDLYL NVANRRQQYE CLHYKTDAQG TRIGCRFDDI SRLSSGSQSS  180
HILVRGRSAA FGIPCTDKFV VFSQIEILTP PNMTAKCNKT HSFMHWKMRS HFNRKFRYEL  240
QIQKRMQPVI TEQVRDRTSF QLLNPGTYTV QIRARERVYE FLSAWSTPQR FECDQEEGAN  300
TRAGGGSGCK PCICTVPEVS SVFIFPPKPK DVLTITLTPK VTCVVVDISK DDPEVQFSWF  360
VDDVEVHTAQ TQPREEQFNS TFRSVSELPI MHQDWLNGKE FKCRVNSAAF PAPIEKTISK  420
TKGRPKAPQV YTIPPPKEQM AKDKVSLTCM ITDFFPEDIT VEWQWNGQPA ENYKNTQPIM  480
NTNGSYFVYS KLNVQKSNWE AGNTFTCSVL HEGLHNHHTE KSLSHSPGK              529

SEQ ID NO: 188          moltype = AA  length = 529
FEATURE                 Location/Qualifiers
source                  1..529
                        mol_type = protein
                        organism = Macaca fascicularis
SEQUENCE: 188
MTLLWLTLLL VATPCLLRTK EDPNAPIRNL RMKEKAQQLM WDLNRNVTDV ECIKGTDYSM  60
PAMNNSYCQF GAISLCEVTN YTVRVASPPF STWILFPENS GTPRAGAENL TCWVHDVDFL  120
SCSWVVGPAA PADVQYDLYL NNPNSHEQYR CLHYKTDARG TQIGCRFDDI APLSRGSQSS  180
HILVRGRSAA VSIPCTDKFV FFSQIERLTP PNMTGECNET HSFMHWKMKS HFNRKFRYEL  240
RIQKRMQPVR TEQVRDTTSF QLPNPGTYTV QIRARETVYE FLSAWSTPQR FECDQEEGAS  300
SRAGGGSGCK PCICTVPEVS SVFIFPPKPK DVLTITLTPK VTCVVVDISK DDPEVQFSWF  360
VDDVEVHTAQ TQPREEQFNS TFRSVSELPI MHQDWLNGKE FKCRVNSAAF PAPIEKTISK  420
TKGRPKAPQV YTIPPPKEQM AKDKVSLTCM ITDFFPEDIT VEWQWNGQPA ENYKNTQPIM  480
NTNGSYFVYS KLNVQKSNWE AGNTFTCSVL HEGLHNHHTE KSLSHSPGK              529

SEQ ID NO: 189          moltype = DNA  length = 1137
FEATURE                 Location/Qualifiers
source                  1..1137
                        mol_type = other DNA
                        organism = Homo sapiens
SEQUENCE: 189
atggtcctcc tttggctcac gctgctcctg atcgccctgc cctgtctcct gcaaacgaag  60
gaagatccaa acccaccaat cacgaaccta aggatgaaag caaaggctca gcagttgacc  120
tgggacctta acagaaatgt gaccgatatc gagtgtgtta aagacgccga ctattctatg  180
ccggcagtga acaatagcta ttgccagttt ggagcaattt ccttatgtga agtgaccaac  240
tacaccgtcc gagtggccaa cccaccattc tccacgtgga tcctcttccc tgagaacagt  300
gggaagcctt gggcaggtgc ggagaatctg acctgctgga ttcatgacgt ggatttcttg  360
agctgcagct gggcggtagg cccgggggcc cccgcggacg tccagtacga cctgtacttg  420
aacgttgcca acaggcgtca acagtacgag tgtcttcact acaaaacgga tgctcaggga  480
acacgtatcg ggtgtcgttt cgatgacatc tctcgactct ccagcggttc tcaaagttcc  540
cacatcctgg tgcggggcag gagcgcagcc ttcggtatcc cctgcacaga taagtttgtc  600
gtcttttcac agattgagat attaactcca cccaacatga ctgcaaagtg taataagaca  660
cattccttta tgcactggaa aatgagaagt catttcaatc gcaaatttcg ctatgagctt  720
cagatacaaa agagaatgca gcctgtaatc acagaacagg tcagagacag aacctccttc  780
cagctactca atcctggaac gtacacagta caaataagag cccgggaaag agtgtatgaa  840
```

```
ttcttgagcg cctggagcac cccccagcgc ttcgagtgcg accaggagga gggcgcaaac  900
acacgtgcct ggcggacgtc gctgctgatc gcgctgggga cgctgctggc cctggtctgt  960
gtcttcgtga tctgcagaag gtatctggtg atgcagagac tctttccccg catccctcac  1020
atgaaagacc ccatcggtga cagcttccaa aacgacaagc tggtggtctg ggaggcgggc  1080
aaagccggcc tggaggagtg tctggtgact gaagtacagg tcgtgcagaa aacttga     1137

SEQ ID NO: 190         moltype = AA  length = 378
FEATURE                Location/Qualifiers
source                 1..378
                       mol_type = protein
                       organism = Homo sapiens
SEQUENCE: 190
MVLLWLTLLL IALPCLLQTK EDPNPPITNL RMKAKAQQLT WDLNRNVTDI ECVKDADYSM  60
PAVNNSYCQF GAISLCEVTN YTVRVANPPF STWILFPENS GKPWAGAENL TCWIHDVDFL  120
SCSWAVGPGA PADVQYDLYL NVANRRQQYE CLHYKTDAQG TRIGCRFDDI SRLSSGSQSS  180
HILVRGRSAA FGIPCTDKFV VFSQIEILTP PNMTAKCNKT HSFMHWKMRS HFNRKFRYEL  240
QIQKRMQPVI TEQVRDRTSF QLLNPGTYTV QIRARERVYE FLSAWSTPQR FECDQEEGAN  300
TRAWRTSLLI ALGTLLALVC VFVICRRYLV MQRLFPRIPH MKDPIGDSFQ NDKLVVWEAG  360
KAGLEECLVT EVQVVQKT                                                378

SEQ ID NO: 191         moltype = DNA  length = 1020
FEATURE                Location/Qualifiers
source                 1..1020
                       mol_type = other DNA
                       organism = synthetic construct
SEQUENCE: 191
atgctctggc cgctgcccct ctttctcctc tgcgcgggga gtctcgccca ggaccttgaa  60
tttcagcttg tagcgcctga gtccgtaacg gtagaagagg gtctctgtgt tcacgtaccg  120
tgctcagtgt tttacccaag tattaagctc acattggggc ccgtgaccgg atcctggctt  180
cgcaagggtg tttcattgca tgaagacagt cctgtcgcta cctccgaccc gagacaactc  240
gttcaaaaag ctacacaggg tagatttcag ctgctcggag acccccagaa acatgactgc  300
agtctgttta ttagagacgc tcaaaaaaat gacacaggaa tgtacttttt ccgggtggtt  360
cgagaaccgt tcgtacgata ctcctataag aagtcccagt tgtccctcca tgtcacagga  420
ggtggaggat caggcggtgg tgggagtgga ggtggagggt ctccttgcac agataaattc  480
gtggtatttt cacaaataga gatactcacg ccaccgaaca tgacggcaaa gtgcaataaa  540
acccactctt tcatgcattg gaaaatgcga agccacttta acaggaaatt tcggtacgag  600
ttgcaaatcc agaaaagaat gcaaccagta atcaccgagc aagtgcgcga cagaacttca  660
ttccaacttt tgaatccagg cacgtacacg gtacaaatac gggctagaga gcgggtttac  720
gaatttcttt ccgcatggag caccccccag cgcttcgagt gcgaccagga ggagggcgca  780
aacacacgtg cctggcggac gtcgctgctg atcgcgctgg ggacgctgct ggccctggtc  840
tgtgtcttcg tgatctgcag aaggtatctg gtgatgcaga gactctttcc ccgcatccct  900
cacatgaaag accccatcgg tgacagcttc caaaacgaca agctggtggt ctgggaggcg  960
ggcaaagccg gcctggagga gtgtctggtg actgaagtac aggtcgtgca gaaaacttga  1020

SEQ ID NO: 192         moltype = AA  length = 339
FEATURE                Location/Qualifiers
source                 1..339
                       mol_type = protein
                       organism = synthetic construct
SEQUENCE: 192
MLWPLPLFLL CAGSLAQDLE FQLVAPESVT VEEGLCVHVP CSVFYPSIKL TLGPVTGSWL  60
RKGVSLHEDS PVATSDPRQL VQKATQGRFQ LLGDPQKHDC SLFIRDAQKN DTGMYFFRVV  120
REPFVRYSYK KSQLSLHVTG GGGSGGGGSG GGGSPCTDKF VVFSQIEILT PPNMTAKCNK  180
THSFMHWKMR SHFNRKFRYE LQIQKRMQPV ITEQVRDRTS FQLLNPGTYT VQIRARERVY  240
EFLSAWSTPQ RFECDQEEGA NTRAWRTSLL IALGTLLALV CVFVICRRYL VMQRLFPRIP  300
HMKDPIGDSF QNDKLVVWEA GKAGLEECLV TEVQVVQKT                         339

SEQ ID NO: 193         moltype = AA  length = 328
FEATURE                Location/Qualifiers
source                 1..328
                       mol_type = protein
                       organism = synthetic construct
SEQUENCE: 193
MVLLWLTLLL IALPCLLQTK EDPNPPITNL RMKAKAQQLT WDLNRNVTDI ECVKDADYSM  60
PAVNNSYCQF GAISLCEVTN YTVRVANPPF STWILFPENS GKPWAGAENL TCWIHDVDFL  120
SCSWAVGPGA PADVQYDLYL NVANRRQQYE CLHYKTDAQG TRIGCRFDDI SRLSSGSQSS  180
HILVRGRSAA FGIPCTDKFV VFSQIEILTP PNMTAKCNKT HSFMHWKMRS HFNRKFRYEL  240
QIQKRMQPVI TEQVRDRTSF QLLNPGTYTV QIRARERVYE FLSAWSTPQR FECDQEEGAN  300
TRAGSHHHHH HGSGLNDIFE AQKIEWHE                                     328

SEQ ID NO: 194         moltype = AA  length = 328
FEATURE                Location/Qualifiers
source                 1..328
                       mol_type = protein
                       organism = synthetic construct
SEQUENCE: 194
MTLLWLTLLL VATPCLLRTK EDPNAPIRNL RMKEKAQQLM WDLNRNVTDV ECIKGTDYSM  60
PAMNNSYCQF GAISLCEVTN YTVRVASPPF STWILFPENS GTPRAGAENL TCWVHDVDFL  120
SCSWVVGPAA PADVQYDLYL NNPNSHEQYR CLHYKTDARG TQIGCRFDDI APLSRGSQSS  180
```

```
HILVRGRSAA VSIPCTDKFV FFSQIERLTP PNMTGECNET HSFMHWKMKS HFNRKFRYEL  240
RIQKRMQPVR TEQVRDTTSF QLPNPGTYTV QIRARETVYE FLSAWSTPQR FECDQEEGAS  300
SRAGSHHHHH HGSGLNDIFE AQKIEWHE                                    328

SEQ ID NO: 195         moltype = DNA  length = 1407
FEATURE                Location/Qualifiers
source                 1..1407
                       mol_type = other DNA
                       organism = synthetic construct
SEQUENCE: 195
atggagacag atactttgct cctttgggta ctcttgctgt gggttcccgg tagcaccggc  60
caggtacaac tggtgcaatc tggggccgaa gtcaagaagc ccggtgcgtc cgtcgaagta  120
tcatgtaaag cctcaggata cacgttcacc ggatattaca tccattgggt cagacaagca  180
cctggacaag gacttgaatg gatgggctgg ataaacccaa attccggcgg tacaaactat  240
gctcaaaagt tccaagggag agtgactatg acttgggaca cgtctatttc cacagctttt  300
atggagttgt ctaggttgcg aagcgatgat actgcggttt actcctgtgc gcgggatagg  360
gggggaccat atttcgatta ttggggacag ggtacacttg taatcgtctc ctccgctagc  420
accaaaggac cctccgtctt tccgctcgcg ccgagcagca agtccacgag cgggggggaca  480
gccgcccttg ggtgtctggt caaggattat tttcctgagc ccgttactgt ctcctggaat  540
agcggtgcct tgacttctgg ggtacatacc ttcccggcgg ttttgcaatc atcaggactg  600
tatagcctct ctagcgttgt aacggtacca tcttcatcac ttggcacaca aacatatatt  660
tgtaatgtaa atcacaaacc ttcaaatact aaagttgaca aaaaagtgga gccgaagagc  720
tgtgataaaa cgcatacttg cccgccttgc cccgctccag aattgctggg cgggccgtct  780
gtgttcctct tcccaccgaa accgaaggat acgctgatga taagtcgaac gcccgaagta  840
acatgcgtgg ttgttgatgt aagccacgaa gatccggaag taaagttcaa ctggtacgta  900
gatggagtag aagtgcataa cgcgaaaact aagccccgcg aggagcaata taattcaacc  960
tatcgggttg ttagtgtgct caccgttctc catcaggatt ggcttaacgg gaaagagtat  1020
aagtgcaagg ttagcaataa agcattgcca gcacctatag agaagacaat tagcaaagcg  1080
aagggacagc cacgagagcc ccaagtctac acgctgcctc ccagccgcga cgagttgacg  1140
aagaatcaag tgtcactcac atgtcttgtc aagggattct atccctcaga tattgcagta  1200
gaatgggagt ctaatggaca accagagaac aactataaaa ctactccacc ggtgcttgat  1260
agtgacggta gttttttcct ttatagtaag ctgactgtcg ataagagtcg ctggcaacag  1320
ggaaatgttt tttcttgtag tgttatgcat gaagcacttc ataaccatta cacacaaaag  1380
tctctgtcac tttcccctgg caaatga                                     1407

SEQ ID NO: 196         moltype = AA  length = 468
FEATURE                Location/Qualifiers
source                 1..468
                       mol_type = protein
                       organism = synthetic construct
SEQUENCE: 196
METDTLLLWV LLLWVPGSTG QVQLVQSGAE VKKPGASVEV SCKASGYTFT GYYIHWVRQA  60
PGQGLEWMGW INPNSGGTNY AQKFQGRVTM TWDTSISTAF MELSRLRSDD TAVYSCARDR  120
GGPYFDYWGQ GTLVIVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
CDKTHTCPPC PAPELLGGPS VFLFPPKPKD TLMISRTPEV TCVVVDVSHE DPEVKFNWYV  300
DGVEVHNAKT KPREEQYNST YRVVSVLTVL HQDWLNGKEY KCKVSNKALP APIEKTISKA  360
KGQPREPQVY TLPPSRDELT KNQVSLTCLV KGFYPSDIAV EWESNGQPEN NYKTTPPVLD  420
SDGSFFLYSK LTVDKSRWQQ GNVFSCSVMH EALHNHYTQK SLSLSPGK                468

SEQ ID NO: 197         moltype = DNA  length = 1398
FEATURE                Location/Qualifiers
source                 1..1398
                       mol_type = other DNA
                       organism = synthetic construct
SEQUENCE: 197
atggagacag atactttgct cctttgggta ctcttgctgt gggttcccgg tagcaccggc  60
caggtacaac tggtgcaatc tggggccgaa gtcaagaagc ccggtgcgtc cgtcgaagta  120
tcatgtaaag cctcaggata cacgttcacc ggatattaca tccattgggt cagacaagca  180
cctggacaag gacttgaatg gatgggctgg ataaacccaa attccggcgg tacaaactat  240
gctcaaaagt tccaagggag agtgactatg acttgggaca cgtctatttc cacagctttt  300
atggagttgt ctaggttgcg aagcgatgat actgcggttt actcctgtgc gcgggatagg  360
gggggaccat atttcgatta ttggggacag ggtacacttg taatcgtctc ctccgctagc  420
accaaaggac cctccgtctt tccgctcgcg ccgtgctctc gatccacgag cgagtctacg  480
gcggccttgg gctgtctcgt gaaagactat ttcccagagc cagtgaccgt ttcctggaac  540
tccggagcgc tcacatcagg tgtgcatacc tttccagccg tacttcaatc ttcagggctg  600
tatagcttgt cctctgtcgt gaccgtaccc tccagttctc tcgggacaaa gacctatacc  660
tgtaacgtag accataagcc atccaatacc aaagtagata agagggtgga atctaaatat  720
ggaccgcctt gtccgccgtg cccggctcct gagttccttg gagggccgtc cgtctttctg  780
tttccccccta aacctaagga caccctgatg ataagtagga cgccggaagt aacctgtgtc  840
gtggttgatg tgtcacagga agacccggag gtacaattta attggtacgt cgatggagtc  900
gaggtgcata atgcgaaaac caagccacga gaggagcaat tcaacagcac ctaccgagta  960
gtttcagtct tgactgtgct gcaccaagac tggctgaatg gcaaggagta caaatgcaag  1020
gtcagtaata aaggattgcc gtcttcaata gagaagacta tcagtaaggc gaagggacaa  1080
cctcgcgagc ctcaggtata cactttgccg cccagccaag aagaaatgac gaagaaccaa  1140
gtctctttga cttgcctggt caaaggcttc taccccctctg atatagcagt cgaatgggag  1200
tccaacggtc aaccggagaa caattataag acaactccac ctgtgcttga ttcagacggc  1260
tctttttct tgtatagccg ccttaccgta gacaagagtc gatggcagga aggtaatgta  1320
ttttcttgta gtgtaatgca cgaggcactt cataatcact acacacaaaa gtctctgtca  1380
```

```
ctttccctgg gcaaatga                                          1398

SEQ ID NO: 198         moltype = AA  length = 465
FEATURE                Location/Qualifiers
source                 1..465
                       mol_type = protein
                       organism = synthetic construct
SEQUENCE: 198
METDTLLLWV LLLWVPGSTG QVQLVQSGAE VKKPGASVEV SCKASGYTFT GYYIHWVRQA  60
PGQGLEWMGW INPNSGGTNY AQKFQGRVTM TWDTSISTAF MELSRLRSDD TAVYSCARDR  120
GGPYFDYWGQ GTLVIVSSAS TKGPSVFPLA PCSRSTSEST AALGCLVKDY FPEPVTVSWN  180
SGALTSGVHT FPAVLQSSGL YSLSSVVTVP SSSLGTKTYT CNVDHKPSNT KVDKRVESKY  240
GPPCPPCPAP EFLGGPSVFL FPPKPKDTLM ISRTPEVTCV VVDVSQEDPE VQFNWYVDGV  300
EVHNAKTKPR EEQFNSTYRV VSVLTVLHQD WLNGKEYKCK VSNKGLPSSI EKTISKAKGQ  360
PREPQVYTLP PSQEEMTKNQ VSLTCLVKGF YPSDIAVEWE SNGQPENNYK TTPPVLDSDG  420
SFFLYSRLTV DKSRWQEGNV FSCSVMHEAL HNHYTQKSLS LSLGK                465

SEQ ID NO: 199         moltype = DNA  length = 696
FEATURE                Location/Qualifiers
source                 1..696
                       mol_type = other DNA
                       organism = synthetic construct
SEQUENCE: 199
atgagagcct ggatcttctt cctgctttgt ttggcaggac gagcgctagc cgatatacag  60
atgacgcaat ccccttctag cttgtcagct agtgttggcg accgagtaac aatcacgtgt  120
caagcgagtc aagacataac caactacctg aactggtatc aacaaaaacc tggaaaggca  180
cccaaacttc aaatttacga tgcgagcaat ctcgagacgg gcgttcccag cagattttca  240
ggatcaggct caggcaccga ctttactttc actatcagtt ccttgcaacc cgaggacatc  300
gccacatact attgtcaaca acacgatgac ttgcccctca ctttcggagg tggcacgaag  360
gtcgagatca aacgtacggt agctgcgcct agcgtgttta tttttccgcc ctctgacgaa  420
caactcaaaa gtggcactgc ctctgtagtc tgtctcctga acaattttta tccaagggaa  480
gctaaggtac agtggaaagt cgataacgcg ctccaaagtg gcaacagtca agaatctgta  540
acggagcaag atagtaaaga cagcacttac agcttgagca gcacactcac attgtccaag  600
gccgactacg aaaaacataa agtgtacgcc tgtgaggtaa cacaccaggg tctgagcagc  660
ccagtgacga agtcatttaa tcgcggtgag tgctga                          696

SEQ ID NO: 200         moltype = AA  length = 231
FEATURE                Location/Qualifiers
source                 1..231
                       mol_type = protein
                       organism = synthetic construct
SEQUENCE: 200
MRAWIFFLLC LAGRALADIQ MTQSPSSLSA SVGDRVTITC QASQDITNYL NWYQQKPGKA  60
PKLQIYDASN LETGVPSRFS GSGSGTDFTF TISSLQPEDI ATYYCQQHDD LPLTFGGGTK  120
VEIKRTVAAP SVFIFPPSDE QLKSGTASVV CLLNNFYPRE AKVQWKVDNA LQSGNSQESV  180
TEQDSKDSTY SLSSTLTLSK ADYEKHKVYA CEVTHQGLSS PVTKSFNRGE C          231

SEQ ID NO: 201         moltype = DNA  length = 1416
FEATURE                Location/Qualifiers
source                 1..1416
                       mol_type = other DNA
                       organism = synthetic construct
SEQUENCE: 201
atggagacag atactttgct cctttgggtt ttgttgctgt gggttccagg atccacgggg  60
gaagtacagc tggttgagtc tggaggcgga ttggttcagc ctggggggtc cctccgcctt  120
tcctgtgcta ccagcggatt tacattttct aactacgata tgcattgggt ccgacaagtg  180
actggcaagg gccttgaatg ggtctcaggc attggcatag ctggtgacac atactaccct  240
ggctccgtaa aggaaggtt tactatttca agagaggacg caaagaactc tctctacctc  300
caaatgaatt ctctgcgagc agaggatact gctgtgtatt attgtgctac agagcgcggg  360
agtagcagtt ggtataatta tttcgactat tggggccagg gcactctggt aacggtgtct  420
agcgctagca ccaaaggacc ctccgtcttt ccgctcgcgc cgagcagcaa gtccacgagc  480
ggggggacag ccgcccttgg gtgtctggtc aaggattatt ttcctgagcc cgttactgtc  540
tcctggaata gcggtgcctt gacttctggg gtacatacct tcccggcggt tttgcaatca  600
tcaggactgt atagcctctc tagcgttgta acggtaccat cttcatcact tggcacacaa  660
acatatattt gtaatgtaaa tcacaaacct tcaaatacta aagttgacaa aaaagtggag  720
ccgaagagct gtgataaaac gcatacttgc ccgccttgcc ccgctccaga attgctgggc  780
gggccgtctg tgttcctctt cccaccgaaa ccgaaggata cgctgatgat aagtcgaacg  840
cccgaagtaa catgcgtggt tgttgatgta agccacgaag atccggaagt aaagttcaac  900
tggtacgtag atggagtaga agtgcataac gcgaaaacta agccccgcga ggagcaatat  960
aattcaacct atcgggttgt tagtgtgctc accgttctcc atcaggattg gcttaacggg  1020
aaagagtata agtgcaaggt tagcaataaa gcattgccag cacctataga gaagacaatt  1080
agcaaagcga agggacagcc acgagagccc caagtctaca cgctgcctcc cagccgcgac  1140
gagttgacga agaatcaagt gtcactcaca tgtcttgtca agggattcta tccctcagat  1200
attgcagtag aatgggagtc taatggacaa ccagagaaca actataaaac tactccaccg  1260
gtgcttgata gtgacggtag ttttttcctt tatagtaagc tgactgtcga taagagtcgc  1320
tggcaacagg gaaatgtttt ttcttgtagt gttatgcatg aagcacttca taaccattac  1380
acacaaaagt ctctgtcact ttcccctggc aaatga                          1416

SEQ ID NO: 202         moltype = AA  length = 471
```

```
FEATURE                Location/Qualifiers
source                 1..471
                       mol_type = protein
                       organism = synthetic construct
SEQUENCE: 202
METDTLLLWV LLLWVPGSTG EVQLVESGGG LVQPGGSLRL SCATSGFTFS NYDMHWVRQV  60
TGKGLEWVSG IGIAGDTYYP GSVKGRFTIS REDAKNSLYL QMNSLRAEDT AVYYCATERG  120
SSSWYNYFDY WGQGTLVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKKVE  240
PKSCDKTHTC PPCPAPELLG GPSVFLFPPK PKDTLMISRT PEVTCVVVDV SHEDPEVKFN  300
WYVDGVEVHN AKTKPREEQY NSTYRVVSVL TVLHQDWLNG KEYKCKVSNK ALPAPIEKTI  360
SKAKGQPREP QVYTLPPSRD ELTKNQVSLT CLVKGFYPSD IAVEWESNGQ PENNYKTTPP  420
VLDSDGSFFL YSKLTVDKSR WQQGNVFSCS VMHEALHNHY TQKSLSLSPG K           471

SEQ ID NO: 203         moltype = DNA  length = 1407
FEATURE                Location/Qualifiers
source                 1..1407
                       mol_type = other DNA
                       organism = synthetic construct
SEQUENCE: 203
atggagacag atactttgct cctttgggtt ttgttgctgt gggttccagg atccacgggg  60
gaagtacagc tggttgagtc tggaggcgga ttggttcagc ctggggggtc cctccgcctt  120
tcctgtgcta ccagcggatt tacattttct aactacgata tgcattgggt ccgacaagtg  180
actggcaagg gccttgaatg ggtctcaggc attggcatag ctggtgacac atactaccct  240
ggctccgtaa aaggaaggtt tactatttca agagaggacg caaagaactc tctctacctc  300
caaatgaatt ctctgcgagc agaggatact gctgtgtatt attgtgctac agagcgcggg  360
agtagcagtt ggtataatta tttcgactat tggggccagg gcactctggt aacggtgtct  420
agcgctagca ccaaaggacc ctccgtcttt ccgctcgcgc cgtgctctcg atccacgagc  480
gagtctacgg cggccttggg ctgtctcgtg aaagactatt tcccagagcc agtgaccgtt  540
tcctggaact ccggagcgct cacatcaggt gtgcatacct ttccagccgt acttcaatct  600
tcagggctgt atagcttgtc ctctgtcgtg accgtaccct ccagttctct cgggacaaag  660
acctatacct gtaacgtaga ccataagcca tccaatacca aagtagataa gagggtggaa  720
tctaaatatg gaccgccttg tccgccgtgc ccggctcctg agttccttgg agggccgtcc  780
gtctttctgt ttccccctaa acctaaggac accctgatga taagtaggac gccggaagta  840
acctgtgtcg tggttgatgt gtcacaggaa gacccggagg tacaatttaa ttggtacgtc  900
gatggagtcg aggtgcataa tgcgaaaacc aagccacgag aggagcaatt caacagcacc  960
taccgagtag tttcagtctt gactgtgctg caccaagact ggctgaatgg caaggagtac  1020
aaatgcaagg tcagtaataa aggattgccg tcttcaatag agaagactat cagtaaggcg  1080
aagggacaac ctcgcgagcc tcaggtatac actttgccgc ccagccaaga agaaatgacg  1140
aagaaccaag tctctttgac ttgcctggtc aaaggcttct acccctctga tatagcagtc  1200
gaatgggagt ccaacggtca accggagaac aattataaga caactccacc tgtgcttgat  1260
tcagacggct ctttttcttt gtatagccgc cttaccgtag acaagagtcg atggcaggaa  1320
ggtaatgtat ttcttgtag tgtaatgcac gaggcacttc ataatcacta cacacaaaag  1380
tctctgtcac tttccctggg caaatga                                     1407

SEQ ID NO: 204         moltype = AA  length = 468
FEATURE                Location/Qualifiers
source                 1..468
                       mol_type = protein
                       organism = synthetic construct
SEQUENCE: 204
METDTLLLWV LLLWVPGSTG EVQLVESGGG LVQPGGSLRL SCATSGFTFS NYDMHWVRQV  60
TGKGLEWVSG IGIAGDTYYP GSVKGRFTIS REDAKNSLYL QMNSLRAEDT AVYYCATERG  120
SSSWYNYFDY WGQGTLVTVS SASTKGPSVF PLAPCSRSTS ESTAALGCLV KDYFPEPVTV  180
SWNSGALTSG VHTFPAVLQS SGLYSLSSVV TVPSSSLGTK TYTCNVDHKP SNTKVDKRVE  240
SKYGPPCPPC PAPEFLGGPS VFLFPPKPKD TLMISRTPEV TCVVVDVSQE DPEVQFNWYV  300
DGVEVHNAKT KPREEQFNST YRVVSVLTVL HQDWLNGKEY KCKVSNKGLP SSIEKTISKA  360
KGQPREPQVY TLPPSQEEMT KNQVSLTCLV KGFYPSDIAV EWESNGQPEN NYKTTPPVLD  420
SDGSFFLYSR LTVDKSRWQE GNVFSCSVMH EALHNHYTQK SLSLSLGK               468

SEQ ID NO: 205         moltype = DNA  length = 693
FEATURE                Location/Qualifiers
source                 1..693
                       mol_type = other DNA
                       organism = synthetic construct
SEQUENCE: 205
atgagagcct ggatcttctt cctgctttgt ttggcaggac gagcgctagc cgacatccaa  60
atgactcaat caccgtctac cttgtcagca agcgtggggg accgcgttac gataacttgc  120
agagccagtc agagcataag cagttggctg gcatggtatc agcagaagcc cggaaaagca  180
cccaagatcc tgatttacaa agcctcaagc ctcgaatctg gtgtcccaag tcggtttagt  240
ggaagcggtt ctggtacaga gtttaccctc acaattagta gtcttcaacc cgatgatttt  300
gctacctact attgtcagca gtataattct tattggactt tcggacaggg aacaaaggtc  360
gaaatcaaac gtacggtagc tgcgcctagc gtgtttattt ttccgccctc tgacgaacaa  420
ctcaaaagtg gcactgcctc tgtagtctgt ctcctgaaca atttttatcc aagggaagct  480
aaggtacagt ggaaagtcga taacgcgctc caaagtggca acagtcaaga atctgtaacg  540
gagcaagata gtaaagacag cacttacagc ttgagcagca cactcacatt gtccaaggcc  600
gactacgaaa aacataaagt gtacgcctgt gaggtaacac accagggtct gagcagccca  660
gtgacgaagt catttaatcg cggtgagtgc tga                              693
```

-continued

```
SEQ ID NO: 206          moltype = AA  length = 230
FEATURE                 Location/Qualifiers
source                  1..230
                        mol_type = protein
                        organism = synthetic construct
SEQUENCE: 206
MRAWIFFLLC LAGRALADIQ MTQSPSTLSA SVGDRVTITC RASQSISSWL AWYQQKPGKA  60
PKILIYKASS LESGVPSRFS GSGSGTEFTL TISSLQPDDF ATYYCQQYNS YWTFGQGTKV  120
EIKRTVAAPS VFIFPPSDEQ LKSGTASVVC LLNNFYPREA KVQWKVDNAL QSGNSQESVT  180
EQDSKDSTYS LSSTLTLSKA DYEKHKVYAC EVTHQGLSSP VTKSFNRGEC             230

SEQ ID NO: 207          moltype = DNA  length = 1419
FEATURE                 Location/Qualifiers
source                  1..1419
                        mol_type = other DNA
                        organism = synthetic construct
SEQUENCE: 207
atggagacag atactttgct cctttgggtt ttgttgctgt gggttccagg atccacgggg  60
gaggtacaac tggttgaatc aggtggcgga cttgtccagc cggggaggtc tcttcgattg  120
tcttgcgcgg cgagcggctt tacgttcggt gactacgcta tgcactgggt tcgacaagct  180
ccaggcaagg gtcttgaatg ggtgtcaggc attaactgga ataacaaaaa tataggctat  240
gccgattctg tgaaggggag attcacgatt tcaaaaaaca acgcgaagaa tagcctttat  300
ctgcaaatga actctcttag ggttgaagac acagcattgt actactgtgc aaaggatagg  360
gggtattctt acggatattg gtattttgac ctttggggtc ggggaacatt ggtcactgtc  420
agctctgcta gcaccaaagg accctccgtc tttccgctcg cgccgagcag caagtccacg  480
agcgggggga cagccgccct tgggtgtctg gtcaaggatt attttcctga gcccgttact  540
gtctcctgga atagcggtgc cttgacttct ggggtacata ccttcccggc ggttttgcaa  600
tcatcaggac tgtatagcct ctctagcgtt gtaacggtac catcttcatc acttggcaca  660
caaacatata tttgtaatgt aaatcacaaa ccttcaaata ctaaagttga caaaaaagtg  720
gagccgaaga gctgtgataa aacgcatact tgcccgcctt gccccgctcc agaattgctg  780
ggcgggccgt ctgtgttcct cttcccaccg aaaccgaagg atacgctgat gataagtcga  840
acgcccgaag taacatgcgt ggttgttgat gtaagccacg aagatccgga agtaaagttc  900
aactggtacg tagatggagt agaagtgcat aacgcgaaaa ctaagccccg cgaggagcaa  960
tataattcaa cctatcgggt tgttagtgtg ctcaccgttc tccatcagga ttggcttaac  1020
gggaaagagt ataagtgcaa ggttagcaat aaagcattgc cagcacctat agagaagaca  1080
attagcaaag cgaagggaca gccacgagag ccccaagtct acacgctgcc tcccagccgc  1140
gacgagttga cgaagaatca agtgtcactc acatgtcttg tcaagggatt ctatccctca  1200
gatattgcag tagaatggga gtctaatgga caaccagaga acaactataa aactactcca  1260
ccggtgcttg atagtgacgg tagtttttc ctttatagta agctgactgt cgataagagt  1320
cgctggcaac agggaaatgt tttttcttgt agtgttatgc atgaagcact tcataaccat  1380
tacacacaaa agtctctgtc actttcccct ggcaaatga                         1419

SEQ ID NO: 208          moltype = AA  length = 472
FEATURE                 Location/Qualifiers
source                  1..472
                        mol_type = protein
                        organism = synthetic construct
SEQUENCE: 208
METDTLLLWV LLLWVPGSTG EVQLVESGGG LVQPGRSLRL SCAASGFTFG DYAMHWVRQA  60
PGKGLEWVSG INWNNKNIGY ADSVKGRFTI SKNNAKNSLY LQMNSLRVED TALYYCAKDR  120
GYSYGYWYFD LWGRGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 209          moltype = DNA  length = 1410
FEATURE                 Location/Qualifiers
source                  1..1410
                        mol_type = other DNA
                        organism = synthetic construct
SEQUENCE: 209
atggagacag atactttgct cctttgggtt ttgttgctgt gggttccagg atccacgggg  60
gaggtacaac tggttgaatc aggtggcgga cttgtccagc cggggaggtc tcttcgattg  120
tcttgcgcgg cgagcggctt tacgttcggt gactacgcta tgcactgggt tcgacaagct  180
ccaggcaagg gtcttgaatg ggtgtcaggc attaactgga ataacaaaaa tataggctat  240
gccgattctg tgaaggggag attcacgatt tcaaaaaaca acgcgaagaa tagcctttat  300
ctgcaaatga actctcttag ggttgaagac acagcattgt actactgtgc aaaggatagg  360
gggtattctt acggatattg gtattttgac ctttggggtc ggggaacatt ggtcactgtc  420
agctctgcta gcaccaaagg accctccgtc tttccgctcg cgccgtgctc tcgatccacg  480
agcgagtcta cggcggcctt gggctgtctc gtgaaagact atttcccaga gccagtgacc  540
gtttcctgga actccggagc gctcacatca ggtgtgcata cctttccagc cgtacttcaa  600
tcttcagggc tgtatagctt gtcctctgtc gtgaccgtac cctccagttc tctcgggaca  660
aagacctata cctgtaacgt agaccataag ccatccaata ccaaagtaga taagagggtg  720
gaatctaaat atggaccgcc ttgtccgccg tgcccggctc ctgagttcct tggagggccg  780
tccgtctttc tgtttccccc taaacctaag gacaccctga tgataagtag gacgccggaa  840
gtaacctgtg tcgtggttga tgtgtcacag gaagacccgg aggtacaatt taattggtac  900
gtcgatggag tcgaggtgca taatgcgaaa accaagccac gagaggagca attcaacagc  960
```

```
acctaccgag tagtttcagt cttgactgtg ctgcaccaag actggctgaa tggcaaggag  1020
tacaaatgca aggtcagtaa taaaggattg ccgtcttcaa tagagaagac tatcagtaag  1080
gcgaagggac aacctcgcga gcctcaggta tacactttgc cgcccagcca agaagaaatg  1140
acgaagaacc aagtctcttt gacttgcctg gtcaaaggct tctacccctc tgatatagca  1200
gtcgaatggg agtccaacgg tcaaccggag aacaattata agacaactcc acctgtgctt  1260
gattcagacg gctctttttt cttgtatagc cgccttaccg tagacaagag tcgatggcag  1320
gaaggtaatg tattttcttg tagtgtaatg cacgaggcac ttcataatca ctacacacaa  1380
aagtctctgt cactttccct gggcaaatga                                   1410

SEQ ID NO: 210         moltype = AA  length = 469
FEATURE                Location/Qualifiers
source                 1..469
                       mol_type = protein
                       organism = synthetic construct
SEQUENCE: 210
METDTLLLWV LLLWVPGSTG EVQLVESGGG LVQPGRSLRL SCAASGFTFG DYAMHWVRQA  60
PGKGLEWVSG INWNNKNIGY ADSVKGRFTI SKNNAKNSLY LQMNSLRVED TALYYCAKDR  120
GYSYGYWYFD LWGRGTLVTV SSASTKGPSV FPLAPCSRST SESTAALGCL VKDYFPEPVT  180
VSWNSGALTS GVHTFPAVLQ SSGLYSLSSV VTVPSSSLGT KTYTCNVDHK PSNTKVDKRV  240
ESKYGPPCPP CPAPEFLGGP SVFLFPPKPK DTLMISRTPE VTCVVVDVSQ EDPEVQFNWY  300
VDGVEVHNAK TKPREEQFNS TYRVVSVLTV LHQDWLNGKE YKCKVSNKGL PSSIEKTISK  360
AKGQPREPQV YTLPPSQEEM TKNQVSLTCL VKGFYPSDIA VEWESNGQPE NNYKTTPPVL  420
DSDGSFFLYS RLTVDKSRWQ EGNVFSCSVM HEALHNHYTQ KSLSLSLGK              469

SEQ ID NO: 211         moltype = DNA  length = 705
FEATURE                Location/Qualifiers
source                 1..705
                       mol_type = other DNA
                       organism = synthetic construct
SEQUENCE: 211
atgagagcct ggatcttctt cctgctttgt ttggcaggac gagcgctagc ccagtcagcg  60
ctcacacagc ccccatcagc cagcgggtcc ccagggcagt ccgtaactat tagctgcacg  120
gggacctcca gcgacgtggg gggttacaat tatgtttctt ggtaccagca acatcctgga  180
aaagcaccaa agattatgat atatgaagtt aataaaaggc cggctggcgt gcctgatcgg  240
ttctccggtt ctaagagcgg caacaccgca tccttgactg tatccggtct ccaggcagaa  300
gacgaagccc attactactg caattcttat accgacagta ataacctcat attcggggga  360
ggcacaaaac ttacagtgct gggacagcct aaagcaaatc caaccgtaac cttgtttcca  420
ccgtccagcg aagagcttca ggctaacaaa gctacactcg tatgcctgat cagtgacttc  480
tatcctgggg ccgtaacagt agcgtggaaa gcagatgggt cacccgtcaa agcaggggtg  540
gagacgacca aaccctccaa gcagtccaac aataagtacg cagcctcaag ttatttgtca  600
cttactcctg aacaatggaa atcacatcga tcctattcct gtcaagttac ccatgagggg  660
agcactgttg aaaaaactgt cgccccaact gaatgtagtt aatga                  705

SEQ ID NO: 212         moltype = AA  length = 233
FEATURE                Location/Qualifiers
source                 1..233
                       mol_type = protein
                       organism = synthetic construct
SEQUENCE: 212
MRAWIFFLLC LAGRALAQSA LTQPPSASGS PGQSVTISCT GTSSDVGGYN YVSWYQQHPG  60
KAPKIMIYEV NKRPAGVPDR FSGSKSGNTA SLTVSGLQAE DEAHYYCNSY TDSNNLIFGG  120
GTKLTVLGQP KANPTVTLFP PSSEELQANK ATLVCLISDF YPGAVTVAWK ADGSPVKAGV  180
ETTKPSKQSN NKYAASSYLS LTPEQWKSHR SYSCQVTHEG STVEKTVAPT ECS          233

SEQ ID NO: 213         moltype = DNA  length = 1398
FEATURE                Location/Qualifiers
source                 1..1398
                       mol_type = other DNA
                       organism = synthetic construct
SEQUENCE: 213
atggagacag atactttgct cctttgggta ctcttgctgt gggttcccgg tagcaccggc  60
caggtacaac ttgtgcagtc cggggctgaa gttaaaaagc ccggcgcgtc cgtaaaggtc  120
agttgtaagg ctagtgggta cacgtttaac agttatggaa tctcatgggt taggcaagcc  180
cccggacaag ggcttgagtg gatgggatgg tttaacgcgt atagcgggat aactaactat  240
gcccagaagt tccaagacag gataacaatg accaccgaca catccacaag tacagcatac  300
atggaattgc gaagtcttcg ctcagacgac acagccgtgt attattgtgc tcgcgatctt  360
gtgttcgatt tttgggggca aggcactctg gtaacggtgt ctagcgctag caccaaagga  420
ccctccgtct ttccgctcgc gccgagcagc aagtccacga gcgggggac agccgccctt  480
gggtgtctgg tcaaggatta ttttcctgag cccgttactg tctcctggaa tagcggtgcc  540
ttgacttctg gggtacatac cttcccggcg gttttgcaat catcaggact gtatagcctc  600
tctagcgttg taacggtacc atcttcatca cttggcacac aaacatatat ttgtaatgta  660
aatcacaaac cttcaaatac taaagttgac aaaaaagtgg agccgaagag ctgtgataaa  720
acgcatactt gcccgccttg ccccgctcca gaattgctgg gcgggccgtc tgtgttcctc  780
ttcccaccga aaccgaagga tacgctgatg ataagtcgaa cgcccgaagt aacatgcgtg  840
gttgttgatg taagccacga agatccggaa gtaaagttca actggtacgt agatggagta  900
gaagtgcata acgcgaaaac taagccccgc gaggagcaat ataattcaac ctatcgggtt  960
gttagtgtgc tcaccgttct ccatcaggat tggcttaacg ggaaagagta taagtgcaag  1020
gttagcaata aagcattgcc agcacctata gagaagacaa ttagcaaagc gaagggacag  1080
ccacgagagc cccaagtcta cacgctgcct cccagccgcg acgagttgac gaagaatcaa  1140
```

```
gtgtcactca catgtcttgt caagggattc tatccctcag atattgcagt agaatgggag  1200
tctaatggac aaccagagaa caactataaa actactccac cggtgcttga tagtgacggt  1260
agttttttcc tttatagtaa gctgactgtc gataagagtc gctggcaaca gggaaatgtt  1320
ttttcttgta gtgttatgca tgaagcactt cataaccatt acacacaaaa gtctctgtca  1380
ctttcccctg gcaaatga                                                1398

SEQ ID NO: 214         moltype = AA  length = 465
FEATURE                Location/Qualifiers
source                 1..465
                       mol_type = protein
                       organism = synthetic construct
SEQUENCE: 214
METDTLLLWV LLLWVPGSTG QVQLVQSGAE VKKPGASVKV SCKASGYTFN SYGISWVRQA  60
PGQGLEWMGW FNAYSGITNY AQKFQDRITM TTDTSTSTAY MELRSLRSDD TAVYYCARDL  120
VFDFWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSRDELTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                  465

SEQ ID NO: 215         moltype = DNA  length = 1389
FEATURE                Location/Qualifiers
source                 1..1389
                       mol_type = other DNA
                       organism = synthetic construct
SEQUENCE: 215
atggagacag atactttgct cctttgggta ctcttgctgt gggttcccgg tagcaccggc  60
caggtacaac ttgtgcagtc cggggctgaa gttaaaaagc ccggcgcgtc cgtaaaggtc  120
agttgtaagg ctagtgggta cacgtttaac agttatggaa tctcatgggt taggcaagcc  180
cccggacaag ggcttgagtg gatgggatgg tttaacgcgt atagcgggat aactaactat  240
gcccagaagt tccaagacag gataacaatg accaccgaca catccacaag tacagcatac  300
atggaattgc gaagtcttcg ctcagacgac acagccgtgt attattgtgc tcgcgatctt  360
gtgttcgatt tttgggggca aggcactctg gtaacggtgt ctagcgctag caccaaagga  420
ccctccgtct ttccgctcgc gccgtgctct cgatccacga gcgagtctac ggcggccttg  480
ggctgtctcg tgaaagacta tttcccagag ccagtgaccg tttcctggaa ctccggagcg  540
ctcacatcag gtgtgcatac ctttccagcc gtacttcaat cttcagggct gtatagcttg  600
tcctctgtcg tgaccgtacc ctccagttct ctcgggacaa agacctatac ctgtaacgta  660
gaccataagc catccaatac caaagtagat aagagggtgg aatctaaata tggaccgcct  720
tgtccgccgt gcccggctcc tgagttcctt ggagggccgt ccgtctttct gtttccccct  780
aaacctaagg acaccctgat gataagtagg acgccggaag taacctgtgt cgtggttgat  840
gtgtcacagg aagacccgga ggtacaattt aattggtacg tcgatggagt cgaggtgcat  900
aatgcgaaaa ccaagccacg agaggagcaa ttcaacagca cctaccgagt agtttcagtc  960
ttgactgtgc tgcaccaaga ctggctgaat ggcaaggagt acaaatgcaa ggtcagtaat  1020
aaaggattgc cgtcttcaat agagaagact atcagtaagg cgaagggaca acctcgcgag  1080
cctcaggtat acactttgcc gcccagccaa gaagaaatga cgaagaacca agtctctttg  1140
acttgcctgg tcaaaggctt ctacccctct gatatagcag tcgaatggga gtccaacggt  1200
caaccggaga acaattataa gacaactcca cctgtgcttg attcagacgg ctcttttttc  1260
ttgtatagcc gccttaccgt agacaagagt cgatggcagg aaggtaatgt attttcttgt  1320
agtgtaatgc acgaggcact tcataatcac tacacacaaa agtctctgtc actttccctg  1380
ggcaaatga                                                          1389

SEQ ID NO: 216         moltype = AA  length = 462
FEATURE                Location/Qualifiers
source                 1..462
                       mol_type = protein
                       organism = synthetic construct
SEQUENCE: 216
METDTLLLWV LLLWVPGSTG QVQLVQSGAE VKKPGASVKV SCKASGYTFN SYGISWVRQA  60
PGQGLEWMGW FNAYSGITNY AQKFQDRITM TTDTSTSTAY MELRSLRSDD TAVYYCARDL  120
VFDFWGQGTL VTVSSASTKG PSVFPLAPCS RSTSESTAAL GCLVKDYFPE PVTVSWNSGA  180
LTSGVHTFPA VLQSSGLYSL SSVVTVPSSS LGTKTYTCNV DHKPSNTKVD KRVESKYGPP  240
CPPCPAPEFL GGPSVFLFPP KPKDTLMISR TPEVTCVVVD VSQEDPEVQF NWYVDGVEVH  300
NAKTKPREEQ FNSTYRVVSV LTVLHQDWLN GKEYKCKVSN KGLPSSIEKT ISKAKGQPRE  360
PQVYTLPPSQ EEMTKNQVSL TCLVKGFYPS DIAVEWESNG QPENNYKTTP PVLDSDGSFF  420
LYSRLTVDKS RWQEGNVFSC SVMHEALHNH YTQKSLSLSL GK                     462

SEQ ID NO: 217         moltype = DNA  length = 699
FEATURE                Location/Qualifiers
source                 1..699
                       mol_type = other DNA
                       organism = synthetic construct
SEQUENCE: 217
atgagagcct ggatcttctt cctgctttgt ttggcaggac gagcgctagc cgaaatcgta  60
ttgatgcaaa gtcccggcac actctcattg agccctgggg agagagtcac gctctcttgt  120
agagccagtc aaacattctc tagcagctat ctcgcctggt accaacagaa acctggacag  180
gcgcctagac tcctgatata tggcgcaagc agtcgggcca caggtattcc agatcggttt  240
tcaggatctg gctctggcac tgacttcacc cttactatca accgattgga accagaggac  300
tttgctgtct attattgtca acagtatggc aggtcaccct ttacttttgg ccccggtacc  360
```

```
aagctcgata ttaagcgtac ggtagctgcg cctagcgtgt ttatttttcc gccctctgac  420
gaacaactca aaagtggcac tgcctctgta gtctgtctcc tgaacaattt ttatccaagg  480
gaagctaagg tacagtggaa agtcgataac gcgctccaaa gtggcaacag tcaagaatct  540
gtaacggagc aagatagtaa agacagcact tacagcttga gcagcacact cacattgtcc  600
aaggccgact acgaaaaaca taaagtgtac gcctgtgagg taacacacca gggtctgagc  660
agcccagtga cgaagtcatt taatcgcggt gagtgctga                         699

SEQ ID NO: 218         moltype = AA  length = 232
FEATURE                Location/Qualifiers
source                 1..232
                       mol_type = protein
                       organism = synthetic construct
SEQUENCE: 218
MRAWIFFLLC LAGRALAEIV LMQSPGTLSL SPGERVTLSC RASQTFSSSY LAWYQQKPGQ  60
APRLLIYGAS SRATGIPDRF SGSGSGTDFT LTINRLEPED FAVYYCQQYG RSPFTFGPGT  120
KLDIKRTVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG EC           232

SEQ ID NO: 219         moltype = DNA  length = 1398
FEATURE                Location/Qualifiers
source                 1..1398
                       mol_type = other DNA
                       organism = synthetic construct
SEQUENCE: 219
atggagacag atactttgct cctttgggta ctcttgctgt gggttcccgg tagcaccggc  60
caggtccaac ttgttcagtc aggcgcagaa gtaaaaaaac cgggtgcctc agtgaaagta  120
agctgtaaag caagtgggta cacgttcacg agttttggga ttagctgggt tagacaagct  180
ccgggtcagg ggcttgaatg gatgggatgg tttaacgcat actctggaaa tacctactat  240
gcaccgaccc ttcaggacag agtgacgatg actactgaca ccagcacatc tacggcgtac  300
atggaattga tgtccttgcg atcagacgat actgcaatct actattgcgc acgggatttg  360
gttttcgatt attggggcca gggcactctg gtaacggtgt ctagcgctag caccaaagga  420
ccctccgtct ttccgctcgc gccgagcagc aagtccacga gcggggggac agccgccctt  480
gggtgtctgg tcaaggatta ttttcctgag cccgttactg tctcctggaa tagcggtgcc  540
ttgacttctg gggtacatac cttcccggcg gttttgcaat catcaggact gtatagcctc  600
tctagcgttg taacggtacc atcttcatca cttggcacac aaacatatat ttgtaatgta  660
aatcacaaac cttcaaatac taaagttgac aaaaaagtgg agccgaagag ctgtgataaa  720
acgcatactt gcccgccttg ccccgctcca gaattgctgg gcgggccgtc tgtgttcctc  780
ttcccaccga aaccgaagga tacgctgatg ataagtcgaa cgcccgaagt aacatgcgtg  840
gttgttgatg taagccacga agatccggaa gtaaagttca actggtacgt agatggagta  900
gaagtgcata acgcgaaaac taagccccgc gaggagcaat ataattcaac ctatcgggtt  960
gttagtgtgc tcaccgttct ccatcaggat tggcttaacg ggaaagagta taagtgcaag  1020
gttagcaata aagcattgcc agcacctata gagaagacaa ttagcaaagc gaagggacag  1080
ccacgagagc cccaagtcta cacgctgcct cccagccgcg acgagttgac gaagaatcaa  1140
gtgtcactca catgtcttgt caagggattc tatccctcag atattgcagt agaatgggag  1200
tctaatggac aaccagagaa caactataaa actactccac cggtgcttga tagtgacggt  1260
agtttttttcc tttatagtaa gctgactgtc gataagagtc gctggcaaca gggaaatgtt  1320
ttttcttgta gtgttatgca tgaagcactt cataaccatt acacacaaaa gtctctgtca  1380
ctttcccctg gcaaatga                                                 1398

SEQ ID NO: 220         moltype = AA  length = 465
FEATURE                Location/Qualifiers
source                 1..465
                       mol_type = protein
                       organism = synthetic construct
SEQUENCE: 220
METDTLLLWV LLLWVPGSTG QVQLVQSGAE VKKPGASVKV SCKASGYTFT SFGISWVRQA  60
PGQGLEWMGW FNAYSGNTYY APTLQDRVTM TTDTSTSTAY MELMSLRSDD TAIYYCARDL  120
VFDYWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSRDELTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                   465

SEQ ID NO: 221         moltype = DNA  length = 1389
FEATURE                Location/Qualifiers
source                 1..1389
                       mol_type = other DNA
                       organism = synthetic construct
SEQUENCE: 221
atggagacag atactttgct cctttgggta ctcttgctgt gggttcccgg tagcaccggc  60
caggtccaac ttgttcagtc aggcgcagaa gtaaaaaaac cgggtgcctc agtgaaagta  120
agctgtaaag caagtgggta cacgttcacg agttttggga ttagctgggt tagacaagct  180
ccgggtcagg ggcttgaatg gatgggatgg tttaacgcat actctggaaa tacctactat  240
gcaccgaccc ttcaggacag agtgacgatg actactgaca ccagcacatc tacggcgtac  300
atggaattga tgtccttgcg atcagacgat actgcaatct actattgcgc acgggatttg  360
gttttcgatt attggggcca gggcactctg gtaacggtgt ctagcgctag caccaaagga  420
ccctccgtct ttccgctcgc gccgtgctct cgatccacga gcgagtctac ggcggccttg  480
ggctgtctcg tgaaagacta tttcccagag ccagtgaccg tttcctggaa ctccggagcg  540
```

-continued

```
ctcacatcag gtgtgcatac ctttccagcc gtacttcaat cttcagggct gtatagcttg  600
tcctctgtcg tgaccgtacc ctccagttct ctcgggacaa agacctatac ctgtaacgta  660
gaccataagc catccaatac caaagtagat aagagggtgg aatctaaata tggaccgcct  720
tgtccgccgt gcccggctcc tgagttcctt ggagggccgt ccgtctttct gtttccccct  780
aaacctaagg acaccctgat gataagtagg acgccggaag taacctgtgt cgtggttgat  840
gtgtcacagg aagacccgga ggtacaattt aattggtacg tcgatggagt cgaggtgcat  900
aatgcgaaaa ccaagccacg agaggagcaa ttcaacagca cctaccgagt agtttcagtc  960
ttgactgtgc tgcaccaaga ctggctgaat ggcaaggagt acaaatgcaa ggtcagtaat  1020
aaaggattgc cgtcttcaat agagaagact atcagtaagg cgaagggaca acctcgcgag  1080
cctcaggtat acactttgcc gcccagccaa gaagaaatga cgaagaacca agtctctttg  1140
acttgcctgg tcaaaggctt ctacccctct gatatagcag tcgaatggga gtccaacggt  1200
caaccggaga acaattataa gacaactcca cctgtgcttg attcagacgg ctctttttc  1260
ttgtatagcc gccttaccgt agacaagagt cgatggcagg aaggtaatgt attttcttgt  1320
agtgtaatgc acgaggcact tcataatcac tacacacaaa agtctctgtc actttccctg  1380
ggcaaatga                                                          1389

SEQ ID NO: 222          moltype = AA  length = 462
FEATURE                 Location/Qualifiers
source                  1..462
                        mol_type = protein
                        organism = synthetic construct
SEQUENCE: 222
METDTLLLWV LLLWVPGSTG QVQLVQSGAE VKKPGASVKV SCKASGYTFT SFGISWVRQA  60
PGQGLEWMGW FNAYSGNTYY APTLQDRVTM TTDTSTSTAY MELMSLRSDD TAIYYCARDL  120
VFDYWGQGTL VTVSSASTKG PSVFPLAPCS RSTSESTAAL GCLVKDYFPE PVTVSWNSGA  180
LTSGVHTFPA VLQSSGLYSL SSVVTVPSSS LGTKTYTCNV DHKPSNTKVD KRVESKYGPP  240
CPPCPAPEFL GGPSVFLFPP KPKDTLMISR TPEVTCVVVD VSQEDPEVQF NWYVDGVEVH  300
NAKTKPREEQ FNSTYRVVSV LTVLHQDWLN GKEYKCKVSN KGLPSSIEKT ISKAKGQPRE  360
PQVYTLPPSQ EEMTKNQVSL TCLVKGFYPS DIAVEWESNG QPENNYKTTP PVLDSDGSFF  420
LYSRLTVDKS RWQEGNVFSC SVMHEALHNH YTQKSLSLSL GK                    462

SEQ ID NO: 223          moltype = DNA  length = 699
FEATURE                 Location/Qualifiers
source                  1..699
                        mol_type = other DNA
                        organism = synthetic construct
SEQUENCE: 223
atgagagcct ggatcttctt cctgctttgt ttggcaggac gagcgctagc cgagatcgtg  60
cttacccaaa gccctggcac tctttccctc agccccggtg aaagagcgac cctttcctgt  120
cgcgcctcac agagttttc agacaggtac ttggcatggt atcaacaaaa accgggacaa  180
gcacctaggc tgctcatata cggcactttc agccgcgcga ctggaatacc tgacaggttt  240
tctgggtctg gttcaggaac ggacttcact cttacaattt ctcgactcga ttctgaagac  300
ttcgctgtct actactgtca acaatacggt agctctccat tcacatttgg tccgggcact  360
aaggtcgata taaagcgtac ggtagctgcg cctagcgtgt ttatttttcc gccctctgac  420
gaacaactca aaagtggcac tgcctctgta gtctgtctcc tgaacaattt ttatccaagg  480
gaagctaagg tacagtggaa agtcgataac gcgctccaaa gtggcaacag tcaagaatct  540
gtaacggagc aagatagtaa agacagcact tacagcttga gcagcacact cacattgtcc  600
aaggccgact acgaaaaaca taaagtgtac gcctgtgagg taacacacca gggtctgagc  660
agcccagtga cgaagtcatt taatcgcggt gagtgctga                        699

SEQ ID NO: 224          moltype = AA  length = 232
FEATURE                 Location/Qualifiers
source                  1..232
                        mol_type = protein
                        organism = synthetic construct
SEQUENCE: 224
MRAWIFFLLC LAGRALAEIV LTQSPGTLSL SPGERATLSC RASQSFSDRY LAWYQQKPGQ  60
APRLLIYGTF SRATGIPDRF SGSGSGTDFT LTISRLDSED FAVYYCQQYG SSPFTFGPGT  120
KVDIKRTVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG EC          232

SEQ ID NO: 225          moltype = DNA  length = 1419
FEATURE                 Location/Qualifiers
source                  1..1419
                        mol_type = other DNA
                        organism = synthetic construct
SEQUENCE: 225
atggagacag atactttgct cctttgggta ctcttgctgt gggttcccgg tagcaccggc  60
caggttcagc ttgtccaaag tggtgcagag gttaaaaagc ctggtgcctc tgtgaaagtc  120
agttgtaagg tcagcggcta tacattgact gagtttagca tgcactgggt acgccaagcc  180
cccggtaagg gactggaatg gatgggcgtc tttgacccag aacacggggc tacgatatac  240
gctcaaaagt tccaggggcg ggtaacgatg acagaagaca ctagcacgga caccgcctac  300
atggacctct cctatctgag gtccgaggat acagcggttt attattgtgc aacgtacttt  360
gacttctggt caggttacag ccattttgat ttctggggtc agggcactct ggtaacggtg  420
tctagcgcta gcaccaaagg accctccgtc tttccgctcg cgccgagcag caagtccacg  480
agcgggggga cagccgccct tgggtgtctg gtcaaggatt attttcctga gcccgttact  540
gtctcctgga atagcggtgc cttgacttct ggggtacata ccttcccggc ggttttgcaa  600
tcatcaggac tgtatagcct ctctagcgtt gtaacggtac catcttcatc acttggcaca  660
caaacatata tttgtaatgt aaatcacaaa ccttcaaata ctaaagttga caaaaaagtg  720
```

```
gagccgaaga gctgtgataa aacgcatact tgcccgcctt gccccgctcc agaattgctg  780
ggcgggccgt ctgtgttcct cttcccaccg aaaccgaagg atacgctgat gataagtcga  840
acgcccgaag taacatgcgt ggttgttgat gtaagccacg aagatccgga agtaaagttc  900
aactggtacg tagatggagt agaagtgcat aacgcgaaaa ctaagccccg cgaggagcaa  960
tataattcaa cctatcgggt tgttagtgtg ctcaccgttc tccatcagga ttggcttaac  1020
gggaaagagt ataagtgcaa ggttagcaat aaagcattgc cagcacctat agagaagaca  1080
attagcaaag cgaagggaca gccacgagag ccccaagtct acacgctgcc tcccagccgc  1140
gacgagttga cgaagaatca agtgtcactc acatgtcttg tcaagggatt ctatccctca  1200
gatattgcag tagaatggga gtctaatgga caaccagaga acaactataa aactactcca  1260
ccggtgcttg atagtgacgg tagttttttc ctttatagta agctgactgt cgataagagt  1320
cgctggcaac agggaaatgt tttttcttgt agtgttatgc atgaagcact tcataaccat  1380
tacacacaaa agtctctgtc actttcccct ggcaaatga                        1419

SEQ ID NO: 226          moltype = AA  length = 472
FEATURE                 Location/Qualifiers
source                  1..472
                        mol_type = protein
                        organism = synthetic construct
SEQUENCE: 226
METDTLLLWV LLLWVPGSTG QVQLVQSGAE VKKPGASVKV SCKVSGYTLT EFSMHWVRQA  60
PGKGLEWMGV FDPEHGATIY AQKFQGRVTM TEDTSTDTAY MDLSYLRSED TAVYYCATYF  120
DFWSGYSHFD FWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPELL GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GK          472

SEQ ID NO: 227          moltype = DNA  length = 1410
FEATURE                 Location/Qualifiers
source                  1..1410
                        mol_type = other DNA
                        organism = synthetic construct
SEQUENCE: 227
atggagacag atactttgct cctttgggta ctcttgctgt gggttcccgg tagcaccggc  60
caggttcagc ttgtccaaag tggtgcagag gttaaaaagc ctggtgcctc tgtgaaagtc  120
agttgtaagg tcagcggcta tacattgact gagtttagca tgcactgggt acgccaagcc  180
cccggtaagg gactggaatg gatgggcgtc tttgacccag aacacggggc tacgatatac  240
gctcaaaagt tccaggggcg ggtaacgatg acagaagaca ctagcacgga caccgcctac  300
atggacctct cctatctgag gtccgaggat acagcggttt attattgtgc aacgtacttt  360
gacttctggt caggttacag ccattttgat ttctggggtc agggcactct ggtaacggtg  420
tctagcgcta gcaccaaagg accctccgtc tttccgctcg cgccgtgctc tcgatccacg  480
agcgagtcta cggcggcctt gggctgtctc gtgaaagact atttcccaga gccagtgacc  540
gtttcctgga actccggagc gctcacatca ggtgtgcata cctttccagc cgtacttcaa  600
tcttcagggc tgtatagctt gtcctctgtc gtgaccgtac cctccagttc tctcgggaca  660
aagacctata cctgtaacgt agaccataag ccatccaata ccaaagtaga taagagggtg  720
gaatctaaat atggaccgcc ttgtccgccg tgcccggctc ctgagttcct tggagggccg  780
tccgtctttc tgtttccccc taaacctaag gacaccctga tgataagtag gacgccggaa  840
gtaacctgtg tcgtggttga tgtgtcacag gaagacccgg aggtacaatt taattggtac  900
gtcgatggag tcgaggtgca taatgcgaaa accaagccac gagaggagca attcaacagc  960
acctaccgag tagtttcagt cttgactgtg ctgcaccaag actggctgaa tggcaaggag  1020
tacaaatgca aggtcagtaa taaaggattg ccgtcttcaa tagagaagac tatcagtaag  1080
gcgaagggac aacctcgcga gcctcaggta tacactttgc cgcccagcca agaagaaatg  1140
acgaagaacc aagtctcttt gacttgcctg gtcaaaggct tctacccctc tgatatagca  1200
gtcgaatggg agtccaacgg tcaaccggag aacaattata agacaactcc acctgtgctt  1260
gattcagacg gctctttttt cttgtatagc cgccttaccg tagacaagag tcgatggcag  1320
gaaggtaatg tatttttcttg tagtgtaatg cacgaggcac ttcataatca ctacacacaa  1380
aagtctctgt cactttccct gggcaaatga                                  1410

SEQ ID NO: 228          moltype = AA  length = 469
FEATURE                 Location/Qualifiers
source                  1..469
                        mol_type = protein
                        organism = synthetic construct
SEQUENCE: 228
METDTLLLWV LLLWVPGSTG QVQLVQSGAE VKKPGASVKV SCKVSGYTLT EFSMHWVRQA  60
PGKGLEWMGV FDPEHGATIY AQKFQGRVTM TEDTSTDTAY MDLSYLRSED TAVYYCATYF  120
DFWSGYSHFD FWGQGTLVTV SSASTKGPSV FPLAPCSRST SESTAALGCL VKDYFPEPVT  180
VSWNSGALTS GVHTFPAVLQ SSGLYSLSSV VTVPSSSLGT KTYTCNVDHK PSNTKVDKRV  240
ESKYGPPCPP CPAPEFLGGP SVFLFPPKPK DTLMISRTPE VTCVVVDVSQ EDPEVQFNWY  300
VDGVEVHNAK TKPREEQFNS TYRVVSVLTV LHQDWLNGKE YKCKVSNKGL PSSIEKTISK  360
AKGQPREPQV YTLPPSQEEM TKNQVSLTCL VKGFYPSDIA VEWESNGQPE NNYKTTPPVL  420
DSDGSFFLYS RLTVDKSRWQ EGNVFSCSVM HEALHNHYTQ KSLSLSLGK             469

SEQ ID NO: 229          moltype = DNA  length = 696
FEATURE                 Location/Qualifiers
source                  1..696
                        mol_type = other DNA
                        organism = synthetic construct
```

```
SEQUENCE: 229
atgagagcct ggatcttctt cctgctttgt ttggcaggac gagcgctagc cgacatccaa  60
atgactcaaa gtccgtcaag tcttagtgcg agtgtgggtg accgagttac gattacctgc  120
cgagctagtc agggcatccg caacgacctt ggctggtatc aacagagacc tggaaaagcg  180
cctaagcgac tcatctatgc ggcgtcctca cttcaaagcg gcgtaccttc aaggttttct  240
ggttctggga gtgggaccga gttcaccctt gccattagtt ccttgcaacc tgaagacttc  300
gctacttact cttgtctcca acataatagt tacccctgga cctttggaca gggaacaaag  360
gtcgaaatca aacgtacggt agctgcgcct agcgtgttta tttttccgcc ctctgacgaa  420
caactcaaaa gtggcactgc ctctgtagtc tgtctcctga acaattttta tccaagggaa  480
gctaaggtac agtggaaagt cgataacgcg ctccaaagtg gcaacagtca agaatctgta  540
acggagcaag atagtaaaga cagcacttac agcttgagca gcacactcac attgtccaag  600
gccgactacg aaaaacataa agtgtacgcc tgtgaggtaa cacaccaggg tctgagcagc  660
ccagtgacga agtcatttaa tcgcggtgag tgctga                            696

SEQ ID NO: 230         moltype = AA  length = 231
FEATURE                Location/Qualifiers
source                 1..231
                       mol_type = protein
                       organism = synthetic construct
SEQUENCE: 230
MRAWIFFLLC LAGRALADIQ MTQSPSSLSA SVGDRVTITC RASQGIRNDL GWYQQRPGKA  60
PKRLIYAASS LQSGVPSRFS GSGSGTEFTL AISSLQPEDF ATYSCLQHNS YPWTFGQGTK  120
VEIKRTVAAP SVFIFPPSDE QLKSGTASVV CLLNNFYPRE AKVQWKVDNA LQSGNSQESV  180
TEQDSKDSTY SLSSTLTLSK ADYEKHKVYA CEVTHQGLSS PVTKSFNRGE C           231

SEQ ID NO: 231         moltype = DNA  length = 1404
FEATURE                Location/Qualifiers
source                 1..1404
                       mol_type = other DNA
                       organism = synthetic construct
SEQUENCE: 231
atggagacag atactttgct cctttgggta ctcttgctgt gggttcccgg tagcaccggc  60
caggtacagc tcgttcagtc agggagtgag gtcaagaaac cgggttcctc tgtcaaagtt  120
tcctgcaagg ccagtggagg caccttttagt tcttacgcaa ttagctgggt acgacaggca  180
cccggccaag ggctggaatg gatgggaggg ataattccca ttttcggtac agtgacttac  240
gcccaaaagt tccaaggcgg cgtaacgatc acagcagacg agtctaccaa tactgtgtac  300
atggaattga gtagccttag aagcgaggac acagcagtct attactgtgc gcgggacgac  360
ttttggactg gtgactactg gggccagggc actctggtaa cggtgtctag cgctagcacc  420
aaaggaccct ccgtctttcc gctcgcgccg agcagcaagt ccacgagcgg ggggacagcc  480
gcccttgggt gtctggtcaa ggattatttt cctgagcccg ttactgtctc ctggaatagc  540
ggtgccttga cttctggggt acatacccttc ccggcggttt tgcaatcatc aggactgtat  600
agcctctcta gcgttgtaac ggtaccatct tcatcacttg gcacacaaac atatatttgt  660
aatgtaaatc acaaaccttc aaatactaaa gttgacaaaa aagtggagcc gaagagctgt  720
gataaaacgc atacttgccc gccttgcccc gctccagaat tgctgggcgg gccgtctgtg  780
ttcctcttcc caccgaaacc gaaggatacg ctgatgataa gtcgaacgcc cgaagtaaca  840
tgcgtggttg ttgatgtaag ccacgaagat ccggaagtaa agttcaactg gtacgtagat  900
ggagtagaag tgcataacgc gaaaactaag ccccgcgagg agcaatataa ttcaacctat  960
cgggttgtta gtgtgctcac cgttctccat caggattggc ttaacgggaa agagtataag  1020
tgcaaggtta gcaataaagc attgccagca cctatagaga agacaattag caaagcgaag  1080
ggacagccac gagagcccca agtctacacg ctgcctccca gccgcgacga gttgacgaag  1140
aatcaagtgt cactcacatg tcttgtcaag ggattctatc cctcagatat tgcagtagaa  1200
tgggagtcta atggacaacc agagaacaac tataaaacta ctccaccggt gcttgatagt  1260
gacggtagtt ttttccttta tagtaagctg actgtcgata agagtcgctg gcaacaggga  1320
aatgtttttt cttgtagtgt tatgcatgaa gcacttcata accattacac acaaaagtct  1380
ctgtcacttt cccctggcaa atga                                         1404

SEQ ID NO: 232         moltype = AA  length = 467
FEATURE                Location/Qualifiers
source                 1..467
                       mol_type = protein
                       organism = synthetic construct
SEQUENCE: 232
METDTLLLWV LLLWVPGSTG QVQLVQSGSE VKKPGSSVKV SCKASGGTFS SYAISWVRQA  60
PGQGLEWMGG IIPIFGTVTY AQKFQGGVTI TADESTNTVY MELSSLRSED TAVYYCARDD  120
FWTGDYWGQG TLVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK                467

SEQ ID NO: 233         moltype = DNA  length = 1395
FEATURE                Location/Qualifiers
source                 1..1395
                       mol_type = other DNA
                       organism = synthetic construct
SEQUENCE: 233
atggagacag atactttgct cctttgggta ctcttgctgt gggttcccgg tagcaccggc  60
caggtacagc tcgttcagtc agggagtgag gtcaagaaac cgggttcctc tgtcaaagtt  120
```

-continued

```
tcctgcaagg ccagtggagg cacctttagt tcttacgcaa ttagctgggt acgacaggca  180
cccggccaag ggctggaatg gatgggaggg ataattccca ttttcggtac agtgacttac  240
gcccaaaagt tccaaggcgg cgtaacgatc acagcagacg agtctaccaa tactgtgtac  300
atggaattga gtagccttag aagcgaggac acagcagtct attactgtgc gcgggacgac  360
ttttggactg gtgactactg gggccagggc actctggtaa cggtgtctag cgctagcacc  420
aaaggaccct ccgtctttcc gctcgcgccg tgctctcgat ccacgagcga gtctacggcg  480
gccttgggct gtctcgtgaa agactatttc ccagagccag tgaccgtttc ctggaactcc  540
ggagcgctca catcaggtgt gcatacctttt ccagccgtac ttcaatcttc agggctgtat  600
agcttgtcct ctgtcgtgac cgtaccctcc agttctctcg ggacaaagac ctatacctgt  660
aacgtagacc ataagccatc caataccaaa gtagataaga gggtggaatc taaatatgga  720
ccgccttgtc cgccgtgccc ggctcctgag ttccttggag ggccgtccgt ctttctgttt  780
ccccctaaac ctaaggacac cctgatgata agtaggacgc cggaagtaac ctgtgtcgtg  840
gttgatgtgt cacaggaaga cccggaggta caatttaatt ggtacgtcga tggagtcgag  900
gtgcataatg cgaaaaccaa gccacgagag gagcaattca acagcaccta ccgagtagtt  960
tcagtcttga ctgtgctgca ccaagactgg ctgaatggca aggagtacaa atgcaaggtc  1020
agtaataaag gattgccgtc ttcaatagag aagactatca gtaaggcgaa gggacaacct  1080
cgcgagcctc aggtatacac tttgccgccc agccaagaag aaatgacgaa gaaccaagtc  1140
tctttgactt gcctggtcaa aggcttctac ccctctgata tagcagtcga atgggagtcc  1200
aacggtcaac cggagaacaa ttataagaca actccacctg tgcttgattc agacggctct  1260
tttttcttgt atagccgcct taccgtagac aagagtcgat ggcaggaagg taatgtattt  1320
tcttgtagtg taatgcacga ggcacttcat aatcactaca cacaaaagtc tctgtcactt  1380
tccctgggca aatga                                                  1395

SEQ ID NO: 234         moltype = AA  length = 464
FEATURE                Location/Qualifiers
source                 1..464
                       mol_type = protein
                       organism = synthetic construct
SEQUENCE: 234
METDTLLLWV LLLWVPGSTG QVQLVQSGSE VKKPGSSVKV SCKASGGTFS SYAISWVRQA  60
PGQGLEWMGG IIPIFGTVTY AQKFQGGVTI TADESTNTVY MELSSLRSED TAVYYCARDD  120
FWTGDYWGQG TLVTVSSAST KGPSVFPLAP CSRSTSESTA ALGCLVKDYF PEPVTVSWNS  180
GALTSGVHTF PAVLQSSGLY SLSSVVTVPS SSLGTKTYTC NVDHKPSNTK VDKRVESKYG  240
PPCPPCPAPE FLGGPSVFLF PPKPKDTLMI SRTPEVTCVV VDVSQEDPEV QFNWYVDGVE  300
VHNAKTKPRE EQFNSTYRVV SVLTVLHQDW LNGKEYKCKV SNKGLPSSIE KTISKAKGQP  360
REPQVYTLPP SQEEMTKNQV SLTCLVKGFY PSDIAVEWES NGQPENNYKT TPPVLDSDGS  420
FFLYSRLTVD KSRWQEGNVF SCSVMHEALH NHYTQKSLSL SLGK                  464

SEQ ID NO: 235         moltype = DNA  length = 696
FEATURE                Location/Qualifiers
source                 1..696
                       mol_type = other DNA
                       organism = synthetic construct
SEQUENCE: 235
atgagagcct ggatcttctt cctgctttgt ttggcaggac gagcgctagc cgatattcag  60
atgacgcagt ctccaagtag cctttccgcc tctgtaggcg acagggtgac aattacctgc  120
cgggcgagcc aaggcatctc caattatctc gcgtggtttc agcagaaacc aggaaaagct  180
ccgaagtccc ttatctatgc agcttctagt cttcaaagtg gagtcccttc aaagttctcc  240
gggtccggca gcggcacgga cttcaccctc acaatatcat cactccagcc agaggatttg  300
gcaacgtact attgccagca atacaatagt tacccttaca cttttgggca aggcactaag  360
ctcgaaatta agcgtacggt agctgcgcct agcgtgttta tttttccgcc ctctgacgaa  420
caactcaaaa gtggcactgc ctctgtagtc tgtctcctga acaattttta tccaagggaa  480
gctaaggtac agtggaaagt cgataacgcg ctccaaagtg gcaacagtca agaatctgta  540
acggagcaag atagtaaaga cagcacttac agcttgagca gcacactcac attgtccaag  600
gccgactacg aaaaacataa agtgtacgcc tgtgaggtaa cacaccaggg tctgagcagc  660
ccagtgacga agtcatttaa tcgcggtgag tgctga                            696

SEQ ID NO: 236         moltype = AA  length = 231
FEATURE                Location/Qualifiers
source                 1..231
                       mol_type = protein
                       organism = synthetic construct
SEQUENCE: 236
MRAWIFFLLC LAGRALADIQ MTQSPSSLSA SVGDRVTITC RASQGISNYL AWFQQKPGKA  60
PKSLIYAASS LQSGVPSKFS GSGSGTDFTL TISSLQPEDL ATYYCQQYNS YPYTFGQGTK  120
LEIKRTVAAP SVFIFPPSDE QLKSGTASVV CLLNNFYPRE AKVQWKVDNA LQSGNSQESV  180
TEQDSKDSTY SLSSTLTLSK ADYEKHKVYA CEVTHQGLSS PVTKSFNRGE C           231

SEQ ID NO: 237         moltype = DNA  length = 1404
FEATURE                Location/Qualifiers
source                 1..1404
                       mol_type = other DNA
                       organism = synthetic construct
SEQUENCE: 237
atggagacag atactttgct cctttgggta ctcttgctgt gggttcccgg tagcaccggc  60
caggtacagc tcgttcagtc agggagtgag gtcaagaaac cgggttcctc tgtcaaagtt  120
tcctgcaagg ccagtggagg cacctttagt tcttacgcaa ttagctgggt acgacaggca  180
cccggccaag ggctggaatg gatgggaggg ataattccca ttttcggtac agtgacttac  240
gcccaaaagt tccaaggccg cgtaacgatc acagcagacg agtctaccaa tactgtgtac  300
```

-continued

```
atggaattga gtagccttag aagcgaggac acagcagtct attactgtgc gcgggacgac  360
ttttggactg gtgactactg gggccagggc actctggtaa cggtgtctag cgctagcacc  420
aaaggaccct ccgtctttcc gctcgcgccg agcagcaagt ccacgagcgg ggggacagcc  480
gcccttgggt gtctggtcaa ggattatttt cctgagcccg ttactgtctc ctggaatagc  540
ggtgccttga cttctggggt acatacettc ccggcggttt tgcaatcatc aggactgtat  600
agcctctcta gcgttgtaac ggtaccatct tcatcacttg gcacacaaac atatatttgt  660
aatgtaaatc acaaaccttc aaatactaaa gttgacaaaa aagtggagcc gaagagctgt  720
gataaaacgc atacttgccc gccttgcccc gctccagaat tgctgggcgg gccgtctgtg  780
ttcctcttcc caccgaaacc gaaggatacg ctgatgataa gtcgaacgcc cgaagtaaca  840
tgcgtggttg ttgatgtaag ccacgaagat ccggaagtaa agttcaactg gtacgtagat  900
ggagtagaag tgcataacgc gaaaactaag ccccgcgagg agcaatataa ttcaacctat  960
cgggttgtta gtgtgctcac cgttctccat caggattggc ttaacgggaa agagtataag  1020
tgcaaggtta gcaataaagc attgccagca cctatagaga agacaattag caaagcgaag  1080
ggacagccac gagagcccca agtctacacg ctgcctccca gccgcgacga gttgacgaag  1140
aatcaagtgt cactcacatg tcttgtcaag ggattctatc cctcagatat tgcagtagaa  1200
tgggagtcta atggacaacc agagaacaac tataaaacta ctccaccggt gcttgatagt  1260
gacggtagtt ttttccttta tagtaagctg actgtcgata agagtcgctg gcaacaggga  1320
aatgtttttt cttgtagtgt tatgcatgaa gcacttcata accattacac acaaaagtct  1380
ctgtcacttt cccctggcaa atga                                         1404
```

```
SEQ ID NO: 238          moltype = AA  length = 467
FEATURE                 Location/Qualifiers
source                  1..467
                        mol_type = protein
                        organism = synthetic construct
SEQUENCE: 238
METDTLLLWV LLLWVPGSTG QVQLVQSGSE VKKPGSSVKV SCKASGGTFS SYAISWVRQA  60
PGQGLEWMGG IIPIFGTVTY AQKFQGRVTI TADESTNTVY MELSSLRSED TAVYYCARDD  120
FWTGDYWGQG TLVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSRDELTK NQVSLTCLVK GFYPSDIAVE WESNGQPENN YKTTPPVLDS  420
DGSFFLYSKL TVDKSRWQQG NVFSCSVMHE ALHNHYTQKS LSLSPGK             467
```

```
SEQ ID NO: 239          moltype = DNA  length = 1395
FEATURE                 Location/Qualifiers
source                  1..1395
                        mol_type = other DNA
                        organism = synthetic construct
SEQUENCE: 239
atggagacag atactttgct cctttgggta ctcttgctgt gggttcccgg tagcaccggc  60
caggtacagc tcgttcagtc agggagtgag gtcaagaaac cgggttcctc tgtcaaagtt  120
tcctgcaagg ccagtggagg cacctttagt tcttacgcaa ttagctgggt acgacaggca  180
cccggccaag ggctggaatg gatgggaggg ataattccca ttttcggtac agtgacttac  240
gcccaaaagt tccaaggccg cgtaacgatc acagcagacg agtctaccaa tactgtgtac  300
atggaattga gtagccttag aagcgaggac acagcagtct attactgtgc gcgggacgac  360
ttttggactg gtgactactg gggccagggc actctggtaa cggtgtctag cgctagcacc  420
aaaggaccct ccgtctttcc gctcgcgccg tgctctcgat ccacgagcga gtctacggcg  480
gccttgggct gtctcgtgaa agactatttc ccagagccag tgaccgtttc ctggaactcc  540
ggagcgctca catcaggtgt gcatacettt ccagccgtac ttcaatcttc agggctgtat  600
agcttgtcct ctgtcgtgac cgtaccctcc agttctctcg ggacaaagac ctatacctgt  660
aacgtagacc ataagccatc caataccaaa gtagataaga gggtggaatc taaatatgga  720
ccgccttgtc cgccgtgccc ggctcctgag ttccttggag ggccgtccgt ctttctgttt  780
ccccctaaac ctaaggacac cctgatgata agtaggacgc cggaagtaac ctgtgtcgtg  840
gttgatgtgt cacaggaaga cccggaggta caatttaatt ggtacgtcga tggagtcgag  900
gtgcataatg cgaaaaccaa gccacgagag gagcaattca acagcaccta ccgagtagtt  960
tcagtcttga ctgtgctgca ccaagactgg ctgaatggca aggagtacaa atgcaaggtc  1020
agtaataaag gattgccgtc ttcaatagag aagactatca gtaaggcgaa gggacaacct  1080
cgcgagcctc aggtatacac tttgccgccc agccaagaag aaatgacgaa gaaccaagtc  1140
tctttgactt gcctggtcaa aggcttctac ccctctgata tagcagtcga atgggagtcc  1200
aacggtcaac cggagaacaa ttataagaca actccacctg tgcttgattc agacggctct  1260
tttttcttgt atagccgcct taccgtagac aagagtcgat ggcaggaagg taatgtattt  1320
tcttgtagtg taatgcacga ggcacttcat aatcactaca cacaaaagtc tctgtcactt  1380
tccctgggca aatga                                                   1395
```

```
SEQ ID NO: 240          moltype = AA  length = 464
FEATURE                 Location/Qualifiers
source                  1..464
                        mol_type = protein
                        organism = synthetic construct
SEQUENCE: 240
METDTLLLWV LLLWVPGSTG QVQLVQSGSE VKKPGSSVKV SCKASGGTFS SYAISWVRQA  60
PGQGLEWMGG IIPIFGTVTY AQKFQGRVTI TADESTNTVY MELSSLRSED TAVYYCARDD  120
FWTGDYWGQG TLVTVSSAST KGPSVFPLAP CSRSTSESTA ALGCLVKDYF PEPVTVSWNS  180
GALTSGVHTF PAVLQSSGLY SLSSVVTVPS SSLGTKTYTC NVDHKPSNTK VDKRVESKYG  240
PPCPPCPAPE FLGGPSVFLF PPKPKDTLMI SRTPEVTCVV VDVSQEDPEV QFNWYVDGVE  300
VHNAKTKPRE EQFNSTYRVV SVLTVLHQDW LNGKEYKCKV SNKGLPSSIE KTISKAKGQP  360
REPQVYTLPP SQEEMTKNQV SLTCLVKGFY PSDIAVEWES NGQPENNYKT TPPVLDSDGS  420
```

```
FFLYSRLTVD KSRWQEGNVF SCSVMHEALH NHYTQKSLSL SLGK                 464

SEQ ID NO: 241          moltype = DNA  length = 1407
FEATURE                 Location/Qualifiers
source                  1..1407
                        mol_type = other DNA
                        organism = synthetic construct
SEQUENCE: 241
atggagaccg acacactgct gctgtgggtg ctgctgctgt gggtgccagg ctccaccgga  60
caggtgcagc tgaagaagtc tggacctgga ctggtggcac catcccagaa cctgtctatc  120
acctgcacag tgagcggctt ctccctgacc acatacgaca tcaattggat caggcagccc  180
cctggcaagg atctggagtg gctgggcgtg atctggaccg gaggaggcac aaactataat  240
agcgccttca tgtcccgcct gtctatcagc aaggacaact ccaagtctca ggtgtttctg  300
aagatgaata gcctgcagac cgacgataca gccatgtact attgcgtgcg gggcgacacc  360
taccactatg ccctggattt ttggggccag ggcacctctg tgacagtgag ctccgctagc  420
accaaaggac cctccgtctt tccgctcgcg ccgagcagca agtccacgag cggggggaca  480
gccgcccttg ggtgtctggt caaggattat ttcctgagc ccgttactgt ctcctggaat  540
agcggtgcct tgacttctgg ggtacatacc ttcccggcgg ttttgcaatc atcaggactg  600
tatagcctct ctagcgttgt aacggtacca tcttcatcac ttggcacaca aacatatatt  660
tgtaatgtaa atcacaaacc ttcaaatact aaagttgaca aaaaagtgga gccgaagagc  720
tgtgataaaa cgcatacttg cccgccttgc cccgctccag aattgctggg cgggccgtct  780
gtgttcctct tcccaccgaa accgaaggat acgctgatga taagtcgaac gcccgaagta  840
acatgcgtgg ttgttgatgt aagccacgaa gatccggaag taaagttcaa ctggtacgta  900
gatggagtag aagtgcataa cgcgaaaact aagccccgcg aggagcaata taattcaacc  960
tatcgggttg ttagtgtgct caccgttctc catcaggatt ggcttaacgg gaaagagtat  1020
aagtgcaagg ttagcaataa agcattgcca gcacctatag agaagacaat tagcaaagcg  1080
aagggacagc cacgagagcc ccaagtctac acgctgcctc ccagccgcga cgagttgacg  1140
aagaatcaag tgtcactcac atgtcttgtc aagggattct atccctcaga tattgcagta  1200
gaatgggagt ctaatggaca accagagaac aactataaaa ctactccacc ggtgcttgat  1260
agtgacggta gtttttttcct ttatagtaag ctgactgtcg ataagagtcg ctggcaacag  1320
ggaaatgttt tttcttgtag tgttatgcat gaagcacttc ataaccatta cacacaaaag  1380
tctctgtcac tttcccctgg caaatga                                    1407

SEQ ID NO: 242          moltype = AA  length = 468
FEATURE                 Location/Qualifiers
source                  1..468
                        mol_type = protein
                        organism = synthetic construct
SEQUENCE: 242
METDTLLLWV LLLWVPGSTG QVQLKKSGPG LVAPSQNLSI TCTVSGFSLT TYDINWIRQP  60
PGKDLEWLGV IWTGGGTNYN SAFMSRLSIS KDNSKSQVFL KMNSLQTDDT AMYYCVRGDT  120
YHYALDFWGQ GTSVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
CDKTHTCPPC PAPELLGGPS VFLFPPKPKD TLMISRTPEV TCVVVDVSHE DPEVKFNWYV  300
DGVEVHNAKT KPREEQYNST YRVVSVLTVL HQDWLNGKEY KCKVSNKALP APIEKTISKA  360
KGQPREPQVY TLPPSRDELT KNQVSLTCLV KGFYPSDIAV EWESNGQPEN NYKTTPPVLD  420
SDGSFFLYSK LTVDKSRWQQ GNVFSCSVMH EALHNHYTQK SLSLSPGK             468

SEQ ID NO: 243          moltype = DNA  length = 1398
FEATURE                 Location/Qualifiers
source                  1..1398
                        mol_type = other DNA
                        organism = synthetic construct
SEQUENCE: 243
atggagaccg acacactgct gctgtgggtg ctgctgctgt gggtgccagg ctccaccgga  60
caggtgcagc tgaagaagtc tggacctgga ctggtggcac catcccagaa cctgtctatc  120
acctgcacag tgagcggctt ctccctgacc acatacgaca tcaattggat caggcagccc  180
cctggcaagg atctggagtg gctgggcgtg atctggaccg gaggaggcac aaactataat  240
agcgccttca tgtcccgcct gtctatcagc aaggacaact ccaagtctca ggtgtttctg  300
aagatgaata gcctgcagac cgacgataca gccatgtact attgcgtgcg gggcgacacc  360
taccactatg ccctggattt ttggggccag ggcacctctg tgacagtgag ctccgctagc  420
accaaaggac cctccgtctt tccgctcgcg ccgtgctctc gatccacgag cgagtctacg  480
gcggccttgg gctgtctcgt gaaagactat ttcccagagc cagtgaccgt ttcctggaac  540
tccggagcgc tcacatcagg tgtgcatacc tttccagccg tacttcaatc ttcagggctg  600
tatagcttgt cctctgtcgt gaccgtaccc tccagttctc tcgggacaaa gacctatacc  660
tgtaacgtag accataagcc atccaatacc aaagtagata agagggtgga atctaaatat  720
ggaccgcctt gtccgccgtg cccggctcct gagttccttg gagggccgtc cgtctttctg  780
tttcccccta aacctaagga caccctgatg ataagtagga cgccggaagt aacctgtgtc  840
gtggttgatg tgtcacagga agacccggag gtacaattta attggtacgt cgatggagtc  900
gaggtgcata atgcgaaaac caagccacga gaggagcaat tcaacagcac ctaccgagta  960
gtttcagtct tgactgtgct gcaccaagac tggctgaatg gcaaggagta caaatgcaag  1020
gtcagtaata aaggattgcc gtcttcaata gagaagacta tcagtaaggc gaagggacaa  1080
cctcgcgagc ctcaggtata cactttgccg cccagccaag aagaaatgac gaagaaccaa  1140
gtctctttga cttgcctggt caaaggcttc taccccctctg atatagcagt cgaatgggag  1200
tccaacggtc aaccggagaa caattataag acaactccac ctgtgcttga ttcagacggc  1260
tcttttttct tgtatagccg ccttaccgta gacaagagtc gatggcagga aggtaatgta  1320
ttttcttgta gtgtaatgca cgaggcactt cataatcact acacacaaaa gtctctgtca  1380
ctttccctgg gcaaatga                                              1398
```

```
SEQ ID NO: 244          moltype = AA  length = 465
FEATURE                 Location/Qualifiers
source                  1..465
                        mol_type = protein
                        organism = synthetic construct
SEQUENCE: 244
METDTLLLWV LLLWVPGSTG QVQLKKSGPG LVAPSQNLSI TCTVSGFSLT TYDINWIRQP  60
PGKDLEWLGV IWTGGGTNYN SAFMSRLSIS KDNSKSQVFL KMNSLQTDDT AMYYCVRGDT  120
YHYALDFWGQ GTSVTVSSAS TKGPSVFPLA PCSRSTSEST AALGCLVKDY FPEPVTVSWN  180
SGALTSGVHT FPAVLQSSGL YSLSSVVTVP SSSLGTKTYT CNVDHKPSNT KVDKRVESKY  240
GPPCPPCPAP EFLGGPSVFL FPPKPKDTLM ISRTPEVTCV VVDVSQEDPE VQFNWYVDGV  300
EVHNAKTKPR EEQFNSTYRV VSVLTVLHQD WLNGKEYKCK VSNKGLPSSI EKTISKAKGQ  360
PREPQVYTLP PSQEEMTKNQ VSLTCLVKGF YPSDIAVEWE SNGQPENNYK TTPPVLDSDG  420
SFFLYSRLTV DKSRWQEGNV FSCSVMHEAL HNHYTQKSLS LSLGK                465

SEQ ID NO: 245          moltype = DNA  length = 723
FEATURE                 Location/Qualifiers
source                  1..723
                        mol_type = other DNA
                        organism = synthetic construct
SEQUENCE: 245
atggagacag atactttgct cctttgggtt ttgttgctgt gggttccagg atccacgggg  60
gatattgtaa tgagccagag tccttcttca ttggccgttt cagcaggtga aaaggtcacc  120
atgtcctgta aatcaagtca atctctcttg tcatcaggga ccagaaagaa ttatctggct  180
tggtaccagc aaaaaccggg acaatcacca aagcttttga tttactgggc ctccacaaga  240
gaatctggcg taccggatcg ctttactggc agcggctccg gtactgactt cactcttacg  300
attagtagtg ttcaggcgga ggaccttgcg gtctactact gtaaacagtc ttacatcctg  360
ttcactttcg ggtcaggaac aaaattggag atcaagcgaa ctgttgcagc tccaagtgtt  420
ttcatatttc cgccgtcaga tgaacaactg aaatcaggca cagcctcagt ggtgtgtctg  480
cttaataatt tctaccctcg agaggcaaag gtacagtgga aggtagacaa cgccctgcaa  540
agcgggaata gtcaagaaag cgttacggaa caagatagca aagattccac ctactcactc  600
agttctacct tgaccctcag caaggctgat tacgagaagc ataaagtgta tgcgtgcgaa  660
gtgacccatc aaggactctc ctcacctgtt acaaagtcct ttaatcgcgg ggagtgttaa  720
tga                                                                723

SEQ ID NO: 246          moltype = AA  length = 239
FEATURE                 Location/Qualifiers
source                  1..239
                        mol_type = protein
                        organism = synthetic construct
SEQUENCE: 246
METDTLLLWV LLLWVPGSTG DIVMSQSPSS LAVSAGEKVT MSCKSSQSLL SSGTRKNYLA  60
WYQQKPGQSP KLLIYWASTR ESGVPDRFTG SGSGTDFTLT ISSVQAEDLA VYYCKQSYIL  120
FTFGSGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 247          moltype = DNA  length = 1398
FEATURE                 Location/Qualifiers
source                  1..1398
                        mol_type = other DNA
                        organism = synthetic construct
SEQUENCE: 247
atgagagcct ggatcttctt cctgctttgt ttggcaggac gagcgctagc ccaagtgcaa  60
cttcaggaat ccgggccggg tctcgtaaag cccagcgaga cgcttagtct cacatgcaca  120
gtcagtggtt tcagtttgac gacgtacgat ataaactgga tccgccaacc ccctggcaaa  180
gggcttgaat ggataggcgt tatatggacg ggcgggggca ctaattacaa ctccgctttc  240
atgtcccgag taactatatc agtagacaca tcaaagaacc aattttccct gaaattgagt  300
agtgtgaccg cagcggatac cgcagtttat tactgtgcca gagccgatac ctatcactac  360
gctcttgatt tctggggcca aggaaccttg gtaacagtgt cttcagctag caccaaagga  420
ccctccgtct ttccgctcgc gccgagcagc aagtccacga gcgggggac agccgccctt  480
gggtgtctgg tcaaggatta ttttcctgag cccgttactg tctcctggaa tagcggtgcc  540
ttgacttctg gggtacatac cttcccggcg gttttgcaat catcaggact gtatagcctc  600
tctagcgttg taacggtacc atcttcatca cttggcacac aaacatatat ttgtaatgta  660
aatcacaaac cttcaaatac taaagttgac aaaaaagtgg agccgaagag ctgtgataaa  720
acgcatactt gcccgccttg ccccgctcca gaattgctgg gcgggccgtc tgtgttcctc  780
ttcccaccga aaccgaagga tacgctgatg ataagtcgaa cgcccgaagt aacatgcgtg  840
gttgttgatg taagccacga agatccggaa gtaaagttca actggtacgt agatggagta  900
gaagtgcata acgcgaaaac taagccccgc gaggagcaat ataattcaac ctatcgggtt  960
gttagtgtgc tcaccgttct ccatcaggat tggcttaacg ggaaagagta taagtgcaag  1020
gttagcaata aagcattgcc agcacctata gagaagacaa ttagcaaagc gaagggacag  1080
ccacgagagc cccaagtcta cacgctgcct cccagccgcg acgagttgac gaagaatcaa  1140
gtgtcactca catgtcttgt caagggattc tatccctcag atattgcagt agaatgggag  1200
tctaatggac aaccagagaa caactataaa actactccac cggtgcttga tagtgacggt  1260
agttttttcc tttatagtaa gctgactgtc gataagagtc gctggcaaca gggaaatgtt  1320
ttttcttgta gtgttatgca tgaagcactt cataaccatt acacacaaaa gtctctgtca  1380
ctttcccctg gcaaatga                                                1398

SEQ ID NO: 248          moltype = AA  length = 465
FEATURE                 Location/Qualifiers
```

```
source                  1..465
                        mol_type = protein
                        organism = synthetic construct
SEQUENCE: 248
MRAWIFFLLC LAGRALAQVQ LQESGPGLVK PSETLSLTCT VSGFSLTTYD INWIRQPPGK  60
GLEWIGVIWT GGGTNYNSAF MSRVTISVDT SKNQFSLKLS SVTAADTAVY YCARADTYHY  120
ALDFWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSRDELTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                465

SEQ ID NO: 249          moltype = DNA  length = 1389
FEATURE                 Location/Qualifiers
source                  1..1389
                        mol_type = other DNA
                        organism = synthetic construct
SEQUENCE: 249
atgagagcct ggatcttctt cctgctttgt ttggcaggac gagcgctagc ccaagtgcaa  60
cttcaggaat ccgggccggg tctcgtaaag cccagcgaga cgcttagtct cacatgcaca  120
gtcagtggtt tcagtttgac gacgtacgat ataaactgga tccgccaacc ccctggcaaa  180
gggcttgaat ggataggcgt tatatggacg ggcgggggca ctaattacaa ctccgctttc  240
atgtcccgag taactatatc agtagacaca tcaaagaacc aatttccct gaaattgagt  300
agtgtgaccg cagcggatac cgcagtttat tactgtgcca gagccgatac ctatcactac  360
gctcttgatt tctggggcca aggaaccttg gtaacagtgt cttcagctag caccaaagga  420
ccctccgtct ttccgctcgc gccgtgctct cgatccacga gcgagtctac ggcggccttg  480
ggctgtctcg tgaaagacta tttcccagag ccagtgaccg tttcctggaa ctccggagcg  540
ctcacatcag gtgtgcatac ctttccagcc gtacttcaat cttcagggct gtatagcttg  600
tcctctgtcg tgaccgtacc ctccagttct ctcgggacaa agacctatac ctgtaacgta  660
gaccataagc catccaatac caaagtagat aagagggtgg aatctaaata tggaccgcct  720
tgtccgccgt gcccggctcc tgagttcctt ggagggccgt ccgtctttct gtttccccct  780
aaacctaagg acaccctgat gataagtagg acgccggaag taacctgtgt cgtggttgat  840
gtgtcacagg aagacccgga ggtacaattt aattggtacg tcgatggagt cgaggtgcat  900
aatgcgaaaa ccaagccacg agaggagcaa ttcaacagca cctaccgagt agtttcagtc  960
ttgactgtgc tgcaccaaga ctggctgaat ggcaaggagt acaaatgcaa ggtcagtaat  1020
aaaggattgc cgtcttcaat agagaagact atcagtaagg cgaagggaca acctcgcgag  1080
cctcaggtat acactttgcc gcccagccaa gaagaaatga cgaagaacca agtctctttg  1140
acttgcctgg tcaaaggctt ctacccctct gatatagcag tcgaatggga gtccaacggt  1200
caaccggaga acaattataa gacaactcca cctgtgcttg attcagacgg ctcttttttc  1260
ttgtatagcc gccttaccgt agacaagagt cgatggcagg aaggtaatgt attttcttgt  1320
agtgtaatgc acgaggcact tcataatcac tacacacaaa agtctctgtc actttccctg  1380
ggcaaatga                                                        1389

SEQ ID NO: 250          moltype = AA  length = 462
FEATURE                 Location/Qualifiers
source                  1..462
                        mol_type = protein
                        organism = synthetic construct
SEQUENCE: 250
MRAWIFFLLC LAGRALAQVQ LQESGPGLVK PSETLSLTCT VSGFSLTTYD INWIRQPPGK  60
GLEWIGVIWT GGGTNYNSAF MSRVTISVDT SKNQFSLKLS SVTAADTAVY YCARADTYHY  120
ALDFWGQGTL VTVSSASTKG PSVFPLAPCS RSTSESTAAL GCLVKDYFPE PVTVSWNSGA  180
LTSGVHTFPA VLQSSGLYSL SSVVTVPSSS LGTKTYTCNV DHKPSNTKVD KRVESKYGPP  240
CPPCPAPEFL GGPSVFLFPP KPKDTLMISR TPEVTCVVVD VSQEDPEVQF NWYVDGVEVH  300
NAKTKPREEQ FNSTYRVVSV LTVLHQDWLN GKEYKCKVSN KGLPSSIEKT ISKAKGQPRE  360
PQVYTLPPSQ EEMTKNQVSL TCLVKGFYPS DIAVEWESNG QPENNYKTTP PVLDSDGSFF  420
LYSRLTVDKS RWQEGNVFSC SVMHEALHNH YTQKSLSLSL GK                   462

SEQ ID NO: 251          moltype = DNA  length = 711
FEATURE                 Location/Qualifiers
source                  1..711
                        mol_type = other DNA
                        organism = synthetic construct
SEQUENCE: 251
atgagagcct ggatcttctt cctgctttgt ttggcaggac gagcgctagc cgacatcgta  60
atgactcaat ctccggattc acttgcggtc tccttgggtg aacgagcaac tataaattgc  120
aaatcaagtc aatccctcct cagtagcggc acgaggaaaa actacctcgc atggtatcaa  180
caaaagccag gacagccgcc caaactgttg atatactggg cgtccacccg agagtccggg  240
gtcccggatc gatttagcgg tagtggatct ggtaccgact tcactctcac catttcctct  300
ctgcaagcag aagacgttgc agtatattac tgcaaacaga gttacatcct ctttactttc  360
ggtcagggaa ctaaacttga aatcaagcga acagtggcgg caccgtccgt atttattttc  420
cctccaagtg atgagcagct caaaagtggc acagcgagcg ttgtatgtct cctcaataac  480
ttttacccca gagaggcgaa agtacaatgg aaggttgata acgcactcca aagcggtaac  540
tctcaggaga gtgtcacaga acaggatagt aaagactcca cctactccct cagttctacc  600
cttactcttt caaaagcgga ttatgagaaa cacaaggttt acgcctgtga agtcactcat  660
cagggactga gttccccggt cacgaagtca tttaatcgcg gtgagtgctg a          711

SEQ ID NO: 252          moltype = AA  length = 236
```

```
FEATURE                 Location/Qualifiers
source                  1..236
                        mol_type = protein
                        organism = synthetic construct
SEQUENCE: 252
MRAWIFFLLC LAGRALADIV MTQSPDSLAV SLGERATINC KSSQSLLSSG TRKNYLAWYQ  60
QKPGQPPKLL IYWASTRESG VPDRFSGSGS GTDFTLTISS LQAEDVAVYY CKQSYILFTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 253          moltype = DNA  length = 1398
FEATURE                 Location/Qualifiers
source                  1..1398
                        mol_type = other DNA
                        organism = synthetic construct
SEQUENCE: 253
atgagagcct ggatcttctt cctgctttgt ttggcaggac gagcgctagc ccaggtacag  60
ttgcaggagt ctggcccagg cctggtaaag cctagcgaaa cgctcagttt gacttgcacc  120
gtttcaggct tttcccttac cacttatgac tggtcatgga tacgacaacc acctgggaaa  180
ggcctggagt ggatcgggta tatctggacc gggggcggta cgaactataa cccctccctc  240
aaatctaggg ttactattag cgtagatact tccaagaacc aattttcttt gaaattgtca  300
agcgtaacag cagcagatac ggctgtctac tattgcgtga ggggagatac gtatcattat  360
gcacttgact tttggggaca aggaaccttg gtaacagtgt cttcagctag caccaaagga  420
ccctccgtct ttccgctcgc gccgagcagc aagtccacga gcggggggac agccgccctt  480
gggtgtctgg tcaaggatta ttttcctgag cccgttactg tctcctggaa tagcggtgcc  540
ttgacttctg gggtacatac cttcccggcg gttttgcaat catcaggact gtatagcctc  600
tctagcgttg taacggtacc atcttcatca cttggcacac aaacatatat ttgtaatgta  660
aatcacaaac cttcaaatac taaagttgac aaaaaagtgg agccgaagag ctgtgataaa  720
acgcatactt gcccgccttg ccccgctcca gaattgctgg gcgggccgtc tgtgttcctc  780
ttcccaccga aaccgaagga tacgctgatg ataagtcgaa cgcccgaagt aacatgcgtg  840
gttgttgatg taagccacga agatccggaa gtaaagttca actggtacgt agatggagta  900
gaagtgcata acgcgaaaac taagccccgc gaggagcaat ataattcaac ctatcgggtt  960
gttagtgtgc tcaccgttct ccatcaggat tggcttaacg ggaaagagta taagtgcaag  1020
gttagcaata aagcattgcc agcacctata gagaagacaa ttagcaaagc gaagggacag  1080
ccacgagagc cccaagtcta cacgctgcct cccagccgcg acgagttgac gaagaatcaa  1140
gtgtcactca catgtcttgt caagggattc tatccctcag atattgcagt agaatgggag  1200
tctaatggac aaccagagaa caactataaa actactccac cggtgcttga tagtgacggt  1260
agtttttcc  tttatagtaa gctgactgtc gataagagtc gctggcaaca gggaaatgtt  1320
ttttcttgta gtgttatgca tgaagcactt cataaccatt acacacaaaa gtctctgtca  1380
ctttcccctg gcaaatga                                                1398

SEQ ID NO: 254          moltype = AA  length = 465
FEATURE                 Location/Qualifiers
source                  1..465
                        mol_type = protein
                        organism = synthetic construct
SEQUENCE: 254
MRAWIFFLLC LAGRALAQVQ LQESGPGLVK PSETLSLTCT VSGFSLTTYD WSWIRQPPGK  60
GLEWIGYIWT GGGTNYNPSL KSRVTISVDT SKNQFSLKLS SVTAADTAVY YCVRGDTYHY  120
ALDFWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSRDELTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                  465

SEQ ID NO: 255          moltype = DNA  length = 1389
FEATURE                 Location/Qualifiers
source                  1..1389
                        mol_type = other DNA
                        organism = synthetic construct
SEQUENCE: 255
atgagagcct ggatcttctt cctgctttgt ttggcaggac gagcgctagc ccaggtacag  60
ttgcaggagt ctggcccagg cctggtaaag cctagcgaaa cgctcagttt gacttgcacc  120
gtttcaggct tttcccttac cacttatgac tggtcatgga tacgacaacc acctgggaaa  180
ggcctggagt ggatcgggta tatctggacc gggggcggta cgaactataa cccctccctc  240
aaatctaggg ttactattag cgtagatact tccaagaacc aattttcttt gaaattgtca  300
agcgtaacag cagcagatac ggctgtctac tattgcgtga ggggagatac gtatcattat  360
gcacttgact tttggggaca aggaaccttg gtaacagtgt cttcagctag caccaaagga  420
ccctccgtct ttccgctcgc gccgtgctct cgatccacga gcgagtctac ggcggccttg  480
ggctgtctcg tgaaagacta tttcccagag ccagtgaccg tttcctggaa ctccggagcg  540
ctcacatcag gtgtgcatac ctttccagcc gtacttcaat cttcagggct gtatagcttg  600
tcctctgtcg tgaccgtacc ctccagttct ctcgggacaa agacctatac ctgtaacgta  660
gaccataagc catccaatac caaagtagat aagagggtgg aatctaaata tggaccgcct  720
tgtccgccgt gcccggctcc tgagttcctt ggagggccgt ccgtctttct gtttccccct  780
aaacctaagg acaccctgat gataagtagg acgccggaag taacctgtgt cgtggttgat  840
gtgtcacagg aagacccgga ggtacaattt aattggtacg tcgatggagt cgaggtgcat  900
aatgcgaaaa ccaagccacg agaggagcaa ttcaacagca cctaccgagt agtttcagtc  960
ttgactgtgc tgcaccaaga ctggctgaat ggcaaggagt acaaatgcaa ggtcagtaat  1020
```

```
aaaggattgc cgtcttcaat agagaagact atcagtaagg cgaagggaca acctcgcgag  1080
cctcaggtat acactttgcc gcccagccaa gaagaaatga cgaagaacca agtctctttg  1140
acttgcctgg tcaaaggctt ctacccctct gatatagcag tcgaatggga gtccaacggt  1200
caaccggaga acaattataa gacaactcca cctgtgcttg attcagacgg ctcttttttc  1260
ttgtatagcc gccttaccgt agacaagagt cgatggcagg aaggtaatgt attttcttgt  1320
agtgtaatgc acgaggcact tcataatcac tacacacaaa agtctctgtc actttccctg  1380
ggcaaatga                                                          1389

SEQ ID NO: 256         moltype = AA  length = 462
FEATURE                Location/Qualifiers
source                 1..462
                       mol_type = protein
                       organism = synthetic construct
SEQUENCE: 256
MRAWIFFLLC LAGRALAQVQ LQESGPGLVK PSETLSLTCT VSGFSLTTYD WSWIRQPPGK  60
GLEWIGYIWT GGGTNYNPSL KSRVTISVDT SKNQFSLKLS SVTAADTAVY YCVRGDTYHY  120
ALDFWGQGTL VTVSSASTKG PSVFPLAPCS RSTSESTAAL GCLVKDYFPE PVTVSWNSGA  180
LTSGVHTFPA VLQSSGLYSL SSVVTVPSSS LGTKTYTCNV DHKPSNTKVD KRVESKYGPP  240
CPPCPAPEFL GGPSVFLFPP KPKDTLMISR TPEVTCVVVD VSQEDPEVQF NWYVDGVEVH  300
NAKTKPREEQ FNSTYRVVSV LTVLHQDWLN GKEYKCKVSN KGLPSSIEKT ISKAKGQPRE  360
PQVYTLPPSQ EEMTKNQVSL TCLVKGFYPS DIAVEWESNG QPENNYKTTP PVLDSDGSFF  420
LYSRLTVDKS RWQEGNVFSC SVMHEALHNH YTQKSLSLSL GK                      462

SEQ ID NO: 257         moltype = DNA  length = 1932
FEATURE                Location/Qualifiers
source                 1..1932
                       mol_type = other DNA
                       organism = synthetic construct
SEQUENCE: 257
atgagagcct ggatcttctt cctgctttgt ttggcaggac gagcgctagc ccaagtgcaa  60
cttcaggaat ccgggccggg tctcgtaaag cccagcgaga cgcttagtct cacatgcaca  120
gtcagtggtt tcagtttgac gacgtacgat ataaactgga tccgccaacc ccctggcaaa  180
gggcttgaat ggataggcgt tatatggacg ggcgggggca ctaattacaa ctccgctttc  240
atgtcccgag taactatatc agtagacaca tcaaagaacc aattttccct gaaattgagt  300
agtgtgaccg cagcggatac cgcagtttat tactgtgcca gagccgatac ctatcactac  360
gctcttgatt tctggggcca aggaaccttg gtaacagtgt cttcagctag caccaaagga  420
ccctccgtct ttccgctcgc gccgagcagc aagtccacga gcggggggac agccgccctt  480
gggtgtctgg tcaaggatta ttttcctgag cccgttactg tctcctggaa tagcggtgcc  540
ttgacttctg gggtacatac cttcccggcg gttttgcaat catcaggact gtatagcctc  600
tctagcgttg taacggtacc atcttcatca cttggcacac aaacatatat ttgtaatgta  660
aatcacaaac cttcaaatac taaagttgac aaaaaagtgg agccgaagag ctgtgataaa  720
acgcatactt gcccgccttg ccccgctcca gaattgctgg gcgggccgtc tgtgttcctc  780
ttcccaccga aaccgaagga tacgctgatg ataagtcgaa cgcccgaagt aacatgcgtg  840
gttgttgatg taagccacga agatccggaa gtaaagttca actggtacgt agatggagta  900
gaagtgcata acgcgaaaac taagccccgc gaggagcaat ataattcaac ctatcgggtt  960
gttagtgtgc tcaccgttct ccatcaggat tggcttaacg ggaaagagta taagtgcaag  1020
gttagcaata aagcattgcc agcacctata gagaagacaa ttagcaaagc gaagggacag  1080
ccacgagagc cccaagtcta cacgctgcct cccagccgcg acgagttgac gaagaatcaa  1140
gtgtcactca catgtcttgt caagggattc tatccctcag atattgcagt agaatgggag  1200
tctaatggac aaccagagaa caactataaa actactccac cggtgcttga tagtgacggt  1260
agtttttttcc tttatagtaa gctgactgtc gataagagtc gctggcaaca gggaaatgtt  1320
ttttcttgta gtgttatgca tgaagcactt cataaccatt acacacaaaa gtctctgtca  1380
ctttcccctg gcaaacagga ctccacctca gacctgatcc cagcccccacc tctgagcaag  1440
gtccctctgc agcagaactt ccaggacaac caattccagg ggaagtggta tgtggtaggc  1500
ctggcaggga atgcaattct cagagaagac aaagacccgc aaaagatgta tgccaccatc  1560
tatgagctga aagaagacaa gagctacaat gtcacctccg tcctgtttag gaaaaagaag  1620
tgtgactact ggatcaggac ttttgttcca ggtagccagc ccggcgagtt cacgctgggc  1680
aacattaaga gttaccctgg attaacgagt tacctcgtcc gagtggtgag caccaactac  1740
aaccagcatg ctatggtgtt cttcaagaaa gtttctcaaa acagggagta cttcaagatc  1800
accctctacg ggagaaccaa ggagctgact tcggaactaa aggagaactt catccgcttc  1860
tccaaatctc tgggcctccc tgaaaaccac atcgtcttcc ctgtcccaat cgaccagtgt  1920
atcgacggct ga                                                      1932

SEQ ID NO: 258         moltype = AA  length = 643
FEATURE                Location/Qualifiers
source                 1..643
                       mol_type = protein
                       organism = synthetic construct
SEQUENCE: 258
MRAWIFFLLC LAGRALAQVQ LQESGPGLVK PSETLSLTCT VSGFSLTTYD INWIRQPPGK  60
GLEWIGVIWT GGGTNYNSAF MSRVTISVDT SKNQFSLKLS SVTAADTAVY YCARADTYHY  120
ALDFWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSRDELTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGKQDSTS DLIPAPPLSK  480
VPLQQNFQDN QFQGKWYVVG LAGNAILRED KDPQKMYATI YELKEDKSYN VTSVLFRKKK  540
CDYWIRTFVP GSQPGEFTLG NIKSYPGLTS YLVRVVSTNY NQHAMVFFKK VSQNREYFKI  600
```

```
TLYGRTKELT SELKENFIRF SKSLGLPENH IVFPVPIDQC IDG                643

SEQ ID NO: 259         moltype = DNA  length = 1176
FEATURE                Location/Qualifiers
source                 1..1176
                       mol_type = other DNA
                       organism = synthetic construct
SEQUENCE: 259
atgagagcct ggatcttctt cctgctttgt ttggcaggac gagcgctagc cgacatcgta  60
atgactcaat ctccggattc acttgcggtc tccttgggtg aacgagcaac tataaattgc  120
aaatcaagtc aatccctcct cagtagcggc acgaggaaaa actacctcgc atggtatcaa  180
caaaagccag gacagccgcc caaactgttg atatactggg cgtccacccg agagtccggg  240
gtcccggatc gatttagcgg tagtggatct ggtaccgact tcactctcac catttcctct  300
ctgcaagcag aagacgttgc agtatattac tgcaaacaga gttacatcct ctttactttc  360
ggtcagggaa ctaaacttga aatcaaggga ggcggaggat ccggcggagg gggctctgga  420
ggaggaggat ctcaagtgca acttcaggaa tccgggccgg gtctcgtaaa gcccagcgag  480
acgcttagtc tcacatgcac agtcagtggt ttcagtttga cgacgtacga tataaactgg  540
atccgccaac cccctggcaa agggcttgaa tggataggcg ttatatggac gggcgggggc  600
actaattaca actccgcttt catgtcccga gtaactatat cagtagacac atcaaagaac  660
caattttccc tgaaattgag tagtgtgacc gcagcggata ccgcagttta ttactgtgcc  720
agagccgata cctatcacta cgctcttgat ttctggggcc aaggaacctt ggtaacagtg  780
tcttcacgta cggtggccga caaaactcat acttgtcctc cgtgccccgc gcctccagtc  840
gccggtggcc cgggacaacc ccgagaacct caggtctata ctctcccgcc atcaagggat  900
gaattgacta agaaccaagt tagtctcaca tgtctcgtaa agggtttcta cccgtccgat  960
atcgccgtcg aatgggaatc aaatggacag ccggagaata actacaaaac gacgccacca  1020
gtgctcgact ccgatggttc tttctttctg tattcaaagc tcactgtaga caaatctagg  1080
tggcagcagg gcaacgtatt ctcatgttcc gtcatgcacg aagcacttca taaccactac  1140
acacagaaat ccctgtcact ttcccctggc aaatga                        1176

SEQ ID NO: 260         moltype = AA  length = 391
FEATURE                Location/Qualifiers
source                 1..391
                       mol_type = protein
                       organism = synthetic construct
SEQUENCE: 260
MRAWIFFLLC LAGRALADIV MTQSPDSLAV SLGERATINC KSSQSLLSSG TRKNYLAWYQ  60
QKPGQPPKLL IYWASTRESG VPDRFSGSGS GTDFTLTISS LQAEDVAVYY CKQSYILFTF  120
GQGTKLEIKG GGGSGGGGSG GGGSQVQLQE SGPGLVKPSE TLSLTCTVSG FSLTTYDINW  180
IRQPPGKGLE WIGVIWTGGG TNYNSAFMSR VTISVDTSKN QFSLKLSSVT AADTAVYYCA  240
RADTYHYALD FWGQGTLVTV SSRTVADKTH TCPPCPAPPV AGGPGQPREP QVYTLPPSRD  300
ELTKNQVSLT CLVKGFYPSD IAVEWESNGQ PENNYKTTPP VLDSDGSFFL YSKLTVDKSR  360
WQQGNVFSCS VMHEALHNHY TQKSLSLSPG K                             391

SEQ ID NO: 261         moltype = DNA  length = 1185
FEATURE                Location/Qualifiers
source                 1..1185
                       mol_type = other DNA
                       organism = synthetic construct
SEQUENCE: 261
atgagagcct ggatcttctt cctgctttgt ttggcaggac gagcgctagc cgacatcgta  60
atgactcaat ctccggattc acttgcggtc tccttgggtg aacgagcaac tataaattgc  120
aaatcaagtc aatccctcct cagtagcggc acgaggaaaa actacctcgc atggtatcaa  180
caaaagccag gacagccgcc caaactgttg atatactggg cgtccacccg agagtccggg  240
gtcccggatc gatttagcgg tagtggatct ggtaccgact tcactctcac catttcctct  300
ctgcaagcag aagacgttgc agtatattac tgcaaacaga gttacatcct ctttactttc  360
ggtcagggaa ctaaacttga aatcaaggga ggcggaggat ccggcggagg gggctctgga  420
ggaggaggat ctcaagtgca acttcaggaa tccgggccgg gtctcgtaaa gcccagcgag  480
acgcttagtc tcacatgcac agtcagtggt ttcagtttga cgacgtacga tataaactgg  540
atccgccaac cccctggcaa agggcttgaa tggataggcg ttatatggac gggcgggggc  600
actaattaca actccgcttt catgtcccga gtaactatat cagtagacac atcaaagaac  660
caattttccc tgaaattgag tagtgtgacc gcagcggata ccgcagttta ttactgtgcc  720
agagccgata cctatcacta cgctcttgat ttctggggcc aaggaacctt ggtaacagtg  780
tcttcactcg agccaaaatc atgtgacaaa acccacacct gccctccctg tggagggggt  840
agcagcggag gagggagcgg tggacaaccc cgagaacctc aggtctatac tctcccgcca  900
tcaagggatg aattgactaa gaaccaagtt agtctcacat gtctcgtaaa gggtttctac  960
ccgtccgata tcgccgtcga atgggaatca aatggacagc cggagaataa ctacaaaacg  1020
acgccaccag tgctcgactc cgatggttct ttctttctgt attcaaagct cactgtagac  1080
aaatctaggt ggcagcaggg caacgtattc tcatgttccg tcatgcacga agcacttcat  1140
aaccactaca cacagaaatc cctgtcactt tcccctggca aatga              1185

SEQ ID NO: 262         moltype = AA  length = 394
FEATURE                Location/Qualifiers
source                 1..394
                       mol_type = protein
                       organism = synthetic construct
SEQUENCE: 262
MRAWIFFLLC LAGRALADIV MTQSPDSLAV SLGERATINC KSSQSLLSSG TRKNYLAWYQ  60
QKPGQPPKLL IYWASTRESG VPDRFSGSGS GTDFTLTISS LQAEDVAVYY CKQSYILFTF  120
GQGTKLEIKG GGGSGGGGSG GGGSQVQLQE SGPGLVKPSE TLSLTCTVSG FSLTTYDINW  180
```

```
IRQPPGKGLE WIGVIWTGGG TNYNSAFMSR VTISVDTSKN QFSLKLSSVT AADTAVYYCA  240
RADTYHYALD FWGQGTLVTV SSLEPKSCDK THTCPPCGGG SSGGGSGGQP REPQVYTLPP  300
SRDELTKNQV SLTCLVKGFY PSDIAVEWES NGQPENNYKT TPPVLDSDGS FFLYSKLTVD  360
KSRWQQGNVF SCSVMHEALH NHYTQKSLSL SPGK                             394

SEQ ID NO: 263          moltype = DNA  length = 2307
FEATURE                 Location/Qualifiers
source                  1..2307
                        mol_type = other DNA
                        organism = synthetic construct
SEQUENCE: 263
atggattttc aagtgcagat tttcagcttc ctgctaatca gtgcttcagt cataatgtcc  60
agaggagaca ttgtgatgtc acagtctcca tcctccctgg ctgtgtcagc aggagagaag  120
gtcactatga gctgcaaatc cagtcagagt ctgctcagca gtggaacccg aaagaactac  180
ttggcttggt accagcagaa accagggcag tctcctaaac tgctgatcta ctgggcatcc  240
actagggaat ctggggtccc tgatcgcttc acaggcagtg gatctgggac agatttcact  300
ctcaccatca gcagtgtgca ggctgaagac ctggcagttt attactgcaa gcaatcttat  360
attctattca cgttcggctc ggggacaaag ttggaaataa agggcggtgg ctcgggcggt  420
ggtggatctg gaggaggtgg gagcggggga ggaggaagct ctcaggtgca actgaaggaa  480
tcaggacctg gcctggtggc gccctcacag aacctgtcca ttacctgcac tgtctctggg  540
ttctcattaa ccacctatga tattaactgg attcgccagc caccaggaaa gggtctggag  600
tggcttggag tgatatggac tggtggaggc acaaattata attcagcttt catgtccaga  660
ctgagcatca gcaaggacaa ctccaagagc caagttttct taaaaatgaa cagtctgcaa  720
actgatgaca cagccatgta ttactgtgta agaggtgata cttaccatta tgctttggac  780
ttctggggtc aaggaacctc agtcaccgtc tcctcactcg agcccaaatc ttctgacaaa  840
actcacacaa gcccaccgtc cccagcacct gaactcctgg ggggaccgtc agtcttcctc  900
ttccccccaa aacccaagga caccctcatg atctcccgga cccctgaggt cacatgcgtg  960
gtggtggacg tgagccacga agaccctgag gtcaagttca actggtacgt ggacggcgtg  1020
gaggtgcata atgccaagac aaagccgcgg gaggagcagt acaacagcac gtaccgtgtg  1080
gtcagcgtcc tcaccgtcct gcaccaggac tggctgaatg gcaaggagta caagtgcaag  1140
gtctccaaca aagccctccc agcccccatc gagaaaacca tctccaaagc caaagggcag  1200
ccccgagaac cacaggtgta caccctgccc ccatcccggg atgagctgac caagaaccag  1260
gtcagcctga cctgccgggt caaaggcttc tatcccagcg acatcgccgt ggagtgggag  1320
agcaatgggc agccggagaa caactacaag accacgcctc ccgtgctgga ctccgacggc  1380
tccttccacc tggagagcaa gctcaccgtg gacaagagca ggtggcagca ggggaacgtc  1440
ttctcatgct ccgtgatgca tgagggtctg cacaaccact acacgcagaa gagcctctct  1500
ctgtctccgg gtaaagtcga cggtgctagc agccatgtga atgtgagcag ccctagcgtg  1560
caggatatcc acgttaagtt gcaagaatct ggtccaggtt tggttcagcc atctcaatct  1620
ttgtctctta cttgtactgt ttctggtttc tctttgactg attatggtgt tcattgggtt  1680
agacaatctc caggtaaagg tttggaatgg ttgggtgtta tttggtctgg tggaggtact  1740
gcttataata ctgctttgat ttctaggttg aatatttatc gagataattc taaaaatcaa  1800
gtttttcttg aaatgaattc tttgcaagct gaagatactg ctatgtatta ttgtgctaga  1860
agaggttctt atccatataa ttattttgat gcttggggtt gtggtactac tgttactgtt  1920
tcttctggag gcggcggatc tggcggtgga ggttctggcg gcggcggatc tcaagctgtt  1980
gttattcaag aatctgcttt gactactcct ccaggtgaaa ccgttacttt gacttgtgga  2040
tcttctactg gtgctgttac tgcttctaat tatgctaatt gggttcaaga aaaaccagat  2100
cattgcttta ctggtttgat tggtggtcat aataatagac caccaggtgt tccggctaga  2160
ttttctggtt ctttgattgg tgataaagct gctttgacta ttgctggtac tcaaactgaa  2220
gatgaagcta tttatttttg tgctttgtgg tattctgatc attgggttat tggtggtggt  2280
actagattga ctgttttggg ctaataa                                     2307

SEQ ID NO: 264          moltype = AA  length = 767
FEATURE                 Location/Qualifiers
source                  1..767
                        mol_type = protein
                        organism = synthetic construct
SEQUENCE: 264
MDFQVQIFSF LLISASVIMS RGDIVMSQSP SSLAVSAGEK VTMSCKSSQS LLSSGTRKNY  60
LAWYQQKPGQ SPKLLIYWAS TRESGVPDRF TGSGSGTDFT LTISSVQAED LAVYYCKQSY  120
ILFTFGSGTK LEIKGGGSGG GGSGGGGSGG GGSSQVQLKE SGPGLVAPSQ NLSITCTVSG  180
FSLTTYDINW IRQPPGKGLE WLGVIWTGGG TNYNSAFMSR LSISKDNSKS QVFLKMNSLQ  240
TDDTAMYYCV RGDTYHYALD FWGQGTSVTV SSLEPKSSDK THTSPPSPAP ELLGGPSVFL  300
FPPKPKDTLM ISRTPEVTCV VVDVSHEDPE VKFNWYVDGV EVHNAKTKPR EEQYNSTYRV  360
VSVLTVLHQD WLNGKEYKCK VSNKALPAPI EKTISKAKGQ PREPQVYTLP PSRDELTKNQ  420
VSLTCRVKGF YPSDIAVEWE SNGQPENNYK TTPPVLDSDG SFHLESKLTV DKSRWQQGNV  480
FSCSVMHEGL HNHYTQKSLS LSPGKVDGAS SHVNVSSPSV QDIHVKLQES GPGLVQPSQS  540
LSLTCTVSGF SLTDYGVHWV RQSPGKGLEW LGVIWSGGGT AYNTALISRL NIYRDNSKNQ  600
VFLEMNSLQA EDTAMYYCAR RGSYPYNYFD AWGCGTTVTV SSGGGGSGGG GSGGGGSQAV  660
VIQESALTTP PGETVTLTCG SSTGAVTASN YANWVQEKPD HCFTGLIGGH NNRPPGVPAR  720
FSGSLIGDKA ALTIAGTQTE DEAIYFCALW YSDHWVIGGG TRLTVLG               767

SEQ ID NO: 265          moltype = DNA  length = 2307
FEATURE                 Location/Qualifiers
source                  1..2307
                        mol_type = other DNA
                        organism = synthetic construct
SEQUENCE: 265
atggattttc aagtgcagat tttcagcttc ctgctaatca gtgcttcagt cataatgtcc  60
agaggagaca ttgtgatgtc acagtctcca tcctccctgg ctgtgtcagc aggagagaag  120
```

```
gtcactatga gctgcaaatc cagtcagagt ctgctcagca gtggaacccg aaagaactac  180
ttggcttggt accagcagaa accagggcag tctcctaaac tgctgatcta ctgggcatcc  240
actagggaat ctggggtccc tgatcgcttc acaggcagtg gatctgggac agatttcact  300
ctcaccatca gcagtgtgca ggctgaagac ctggcagttt attactgcaa gcaatcttat  360
attctattca cgttcggctc ggggacaaag ttggaaataa agggcggtgg ctcgggcggt  420
ggtggatctg gaggaggtgg gagcggggga ggaggaagct ctcaggtgca actgaaggaa  480
tcaggacctg gcctggtggc gccctcacag aacctgtcca ttacctgcac tgtctctggg  540
ttctcattaa ccacctatga tattaactgg attcgccagc caccaggaaa gggtctggag  600
tggcttggag tgatatggac tggtggaggc acaaattata attcagcttt catgtccaga  660
ctgagcatca gcaaggacaa ctccaagagc caagttttct taaaaatgaa cagtctgcaa  720
actgatgaca cagccatgta ttactgtgta agaggtgata cttaccatta tgctttggac  780
ttctggggtc aaggaacctc agtcaccgtc tcctcactcg agcccaaatc ttctgacaaa  840
actcacacat gtccaccgtg cccagcacct gaactcctgg ggggaccgtc agtcttcctc  900
ttccccccaa aacccaagga caccctcatg atctcccgga cccctgaggt cacatgcgtg  960
gtggtggacg tgagccacga agaccctgag gtcaagttca actggtacgt ggacggcgtg  1020
gaggtgcata atgccaagac aaagccgcgg gaggagcagt acaacagcac gtaccgtgtg  1080
gtcagcgtcc tcaccgtcct gcaccaggac tggctgaatg gcaaggagta caagtgcaag  1140
gtctccaaca aagccctccc agcccccatc gagaaaacca tctccaaagc caaagggcag  1200
ccccgagaac cacaggtgta caccctgccc ccatcccggg atgagctgac caagaaccag  1260
gtcagcctga cctgcctggt caaaggcttc tatcccagcg acatcgccgt ggagtgggag  1320
agcaatgggc agccggagaa caactacaag accacgcctc ccgtgctgga ctccgacggc  1380
tccttcttcc tctacagcaa gctcaccgtg gacaagagca ggtggcagca ggggaacgtc  1440
ttctcatgct ccgtgatgca tgagggtctg cacaaccact acacgcagaa gagcctctct  1500
ctgtctccgg gtaaagtcga cggtgctagc agccatgtga atgtgagcag ccctagcgtg  1560
caggatatcc acgttaagtt gcaagaatct ggtccaggtt tggttcagcc atctcaatct  1620
ttgtctctta cttgtactgt ttctggtttc tctttgactg attatggtgt tcattgggtt  1680
agacaatctc caggtaaagg tttggaatgg ttgggtgtta tttggtctgg tggaggtact  1740
gcttataata ctgctttgat ttctaggttg aatatttatc gagataattc taaaaatcaa  1800
gtttttcttg aaatgaattc tttgcaagct gaagatactg ctatgtatta ttgtgctaga  1860
agaggttctt atccatataa ttattttgat gcttggggtt gtggtactac tgttactgtt  1920
tcttctggag gcggcggatc tggcggtgga ggttctggcg gcggcggatc tcaagctgtt  1980
gttattcaag aatctgcttt gactactcct ccaggtgaaa ccgttacttt gacttgtgga  2040
tcttctactg gtgctgttac tgcttctaat tatgctaatt gggttcaaga aaaaccagat  2100
cattgcttta ctggtttgat tggtggtcat aataatagac caccaggtgt tccggctaga  2160
ttttctggtt ctttgattgg tgataaagct gctttgacta ttgctggtac tcaaactgaa  2220
gatgaagcta tttatttttg tgctttgtgg tattctgatc attgggttat tggtggtggt  2280
actagattga ctgttttggg ctaataa                                      2307
```

```
SEQ ID NO: 266         moltype = AA  length = 767
FEATURE                Location/Qualifiers
source                 1..767
                       mol_type = protein
                       organism = synthetic construct
SEQUENCE: 266
MDFQVQIFSF LLISASVIMS RGDIVMSQSP SSLAVSAGEK VTMSCKSSQS LLSSGTRKNY  60
LAWYQQKPGQ SPKLLIYWAS TRESGVPDRF TGSGSGTDFT LTISSVQAED LAVYYCKQSY  120
ILFTFGSGTK LEIKGGGSGG GGSGGGGSGG GGSSQVQLKE SGPGLVAPSQ NLSITCTVSG  180
FSLTTYDINW IRQPPGKGLE WLGVIWTGGG TNYNSAFMSR LSISKDNSKS QVFLKMNSLQ  240
TDDTAMYYCV RGDTYHYALD FWGQGTSVTV SSLEPKSSDK THTCPPCPAP ELLGGPSVFL  300
FPPKPKDTLM ISRTPEVTCV VVDVSHEDPE VKFNWYVDGV EVHNAKTKPR EEQYNSTYRV  360
VSVLTVLHQD WLNGKEYKCK VSNKALPAPI EKTISKAKGQ PREPQVYTLP PSRDELTKNQ  420
VSLTCLVKGF YPSDIAVEWE SNGQPENNYK TTPPVLDSDG SFFLYSKLTV DKSRWQQGNV  480
FSCSVMHEGL HNHYTQKSLS LSPGKVDGAS SHVNVSSPSV QDIHVKLQES GPGLVQPSQS  540
LSLTCTVSGF SLTDYGVHWV RQSPGKGLEW LGVIWSGGGT AYNTALISRL NIYRDNSKNQ  600
VFLEMNSLQA EDTAMYYCAR RGSYPYNYFD AWGCGTTVTV SSGGGGSGGG GSGGGGSQAV  660
VIQESALTTP PGETVTLTCG SSTGAVTASN YANWVQEKPD HCFTGLIGGH NNRPPGVPAR  720
FSGSLIGDKA ALTIAGTQTE DEAIYFCALW YSDHWVIGGG TRLTVLG                767
```

```
SEQ ID NO: 267         moltype = DNA  length = 1398
FEATURE                Location/Qualifiers
source                 1..1398
                       mol_type = other DNA
                       organism = synthetic construct
SEQUENCE: 267
atggagacag atactttgct cctttgggta ctcttgctgt gggttcccgg tagcaccggc  60
caagtacaac tcgtgcagtc cggggccgaa gtgaaaaaac ccggagcgag cgtcaaagtt  120
tcatgcaaag cctcaggtta tactttcacc agctttggac ttacgtgggt gcgacaagct  180
cctggacaag gcttggaatg gatggggtgg tttaacgctt attcaggcaa aacgtattac  240
gctccgaccc ttcaagatcg ggtaaccatg actaccgacc catccacatc aacggcttat  300
atggaactta tgtctcttac ctctgacgat actgctatct attactgcgc ccgcgacctt  360
gtctttgatt attggggaca aggcactctg gtaacggtgt ctagcgctag caccaaagga  420
ccctccgtct ttccgctcgc gccgagcagc aagtccacga gcgggggggac agccgccctt  480
gggtgtctgg tcaaggatta ttttcctgag cccgttactg tctcctggaa tagcggtgcc  540
ttgacttctg gggtacatac cttcccggcg gttttgcaat catcaggact gtatagcctc  600
tctagcgttg taacggtacc atcttcatca cttggcacac aaacatatat ttgtaatgta  660
aatcacaaac cttcaaatac taaagttgac aaaaaagtgg agccgaagag ctgtgataaa  720
acgcatactt gcccgccttg ccccgctcca gaattgctgg gcgggccgtc tgtgttcctc  780
ttcccaccga aaccgaagga tacgctgatg ataagtcgaa cgcccgaagt aacatgcgtg  840
gttgttgatg taagccacga agatccggaa gtaaagttca actggtacgt agatggagta  900
```

```
gaagtgcata acgcgaaaac taagccccgc gaggagcaat ataattcaac ctatcgggtt  960
gttagtgtgc tcaccgttct ccatcaggat tggcttaacg ggaaagagta taagtgcaag  1020
gttagcaata aagcattgcc agcacctata gagaagacaa ttagcaaagc gaagggacag  1080
ccacgagagc cccaagtcta cacgctgcct cccagccgcg acgagttgac gaagaatcaa  1140
gtgtcactca catgtcttgt caagggattc tatccctcag atattgcagt agaatgggag  1200
tctaatggac aaccagagaa caactataaa actactccac cggtgcttga tagtgacggt  1260
agttttttcc tttatagtaa gctgactgtc gataagagtc gctggcaaca gggaaatgtt  1320
ttttcttgta gtgttatgca tgaagcactt cataaccatt acacacaaaa gtctctgtca  1380
ctttcccctg gcaaatga                                                1398

SEQ ID NO: 268         moltype = AA  length = 465
FEATURE                Location/Qualifiers
source                 1..465
                       mol_type = protein
                       organism = synthetic construct
SEQUENCE: 268
METDTLLLWV LLLWVPGSTG QVQLVQSGAE VKKPGASVKV SCKASGYTFT SFGLTWVRQA  60
PGQGLEWMGW FNAYSGKTYY APTLQDRVTM TTDPSTSTAY MELMSLTSDD TAIYYCARDL  120
VFDYWGQGTL VTVSSASTKG PSVFPLAPSS KSTSGGTAAL GCLVKDYFPE PVTVSWNSGA  180
LTSGVHTFPA VLQSSGLYSL SSVVTVPSSS LGTQTYICNV NHKPSNTKVD KKVEPKSCDK  240
THTCPPCPAP ELLGGPSVFL FPPKPKDTLM ISRTPEVTCV VVDVSHEDPE VKFNWYVDGV  300
EVHNAKTKPR EEQYNSTYRV VSVLTVLHQD WLNGKEYKCK VSNKALPAPI EKTISKAKGQ  360
PREPQVYTLP PSRDELTKNQ VSLTCLVKGF YPSDIAVEWE SNGQPENNYK TTPPVLDSDG  420
SFFLYSKLTV DKSRWQQGNV FSCSVMHEAL HNHYTQKSLS LSPGK                  465

SEQ ID NO: 269         moltype = DNA  length = 1389
FEATURE                Location/Qualifiers
source                 1..1389
                       mol_type = other DNA
                       organism = synthetic construct
SEQUENCE: 269
atggagacag atactttgct cctttgggta ctcttgctgt gggttcccgg tagcaccggc  60
caagtacaac tcgtgcagtc cggggccgaa gtgaaaaaac ccggagcgag cgtcaaagtt  120
tcatgcaaag cctcaggtta tactttcacc agctttggac ttacgtgggt gcgacaagct  180
cctggacaag gcttggaatg gatggggtgg tttaacgctt attcaggcaa aacgtattac  240
gctccgaccc ttcaagatcg ggtaaccatg actaccgacc catccacatc aacggcttat  300
atggaactta tgtctcttac ctctgacgat actgctatct attactgcgc ccgcgacctt  360
gtctttgatt attggggaca aggcactctg gtaacggtgt ctagcgctag caccaaagga  420
ccctccgtct ttccgctcgc gccgtgctct cgatccacga gcgagtctac ggcggccttg  480
ggctgtctcg tgaaagacta tttcccagag ccagtgaccg tttcctggaa ctccggagcg  540
ctcacatcag gtgtgcatac ctttccagcc gtacttcaat cttcagggct gtatagcttg  600
tcctctgtcg tgaccgtacc ctccagttct ctcgggacaa agacctatac ctgtaacgta  660
gaccataagc catccaatac caaagtagat aagagggtgg aatctaaata tggaccgcct  720
tgtccgccgt gcccggctcc tgagttcctt ggagggccgt ccgtctttct gtttccccct  780
aaacctaagg acaccctgat gataagtagg acgccggaag taacctgtgt cgtggttgat  840
gtgtcacagg aagacccgga ggtacaattt aattggtacg tcgatggagt cgaggtgcat  900
aatgcgaaaa ccaagccacg agaggagcaa ttcaacagca cctaccgagt agtttcagtc  960
ttgactgtgc tgcaccaaga ctggctgaat ggcaaggagt acaaatgcaa ggtcagtaat  1020
aaaggattgc cgtcttcaat agagaagact atcagtaagg cgaagggaca acctcgcgag  1080
cctcaggtat acactttgcc gcccagccaa gaagaaatga cgaagaacca agtctctttg  1140
acttgcctgg tcaaaggctt ctacccctct gatatagcag tcgaatggga gtccaacggt  1200
caaccggaga acaattataa gacaactcca cctgtgcttg attcagacgg ctctttttc  1260
ttgtatagcc gccttaccgt agacaagagt cgatggcagg aaggtaatgt attttcttgt  1320
agtgtaatgc acgaggcact tcataatcac tacacacaaa agtctctgtc actttccctg  1380
ggcaaatga                                                          1389

SEQ ID NO: 270         moltype = AA  length = 462
FEATURE                Location/Qualifiers
source                 1..462
                       mol_type = protein
                       organism = synthetic construct
SEQUENCE: 270
METDTLLLWV LLLWVPGSTG QVQLVQSGAE VKKPGASVKV SCKASGYTFT SFGLTWVRQA  60
PGQGLEWMGW FNAYSGKTYY APTLQDRVTM TTDPSTSTAY MELMSLTSDD TAIYYCARDL  120
VFDYWGQGTL VTVSSASTKG PSVFPLAPCS RSTSESTAAL GCLVKDYFPE PVTVSWNSGA  180
LTSGVHTFPA VLQSSGLYSL SSVVTVPSSS LGTKTYTCNV DHKPSNTKVD KRVESKYGPP  240
CPPCPAPEFL GGPSVFLFPP KPKDTLMISR TPEVTCVVVD VSQEDPEVQF NWYVDGVEVH  300
NAKTKPREEQ FNSTYRVVSV LTVLHQDWLN GKEYKCKVSN KGLPSSIEKT ISKAKGQPRE  360
PQVYTLPPSQ EEMTKNQVSL TCLVKGFYPS DIAVEWESNG QPENNYKTTP PVLDSDGSFF  420
LYSRLTVDKS RWQEGNVFSC SVMHEALHNH YTQKSLSLSL GK                     462

SEQ ID NO: 271         moltype = DNA  length = 699
FEATURE                Location/Qualifiers
source                 1..699
                       mol_type = other DNA
                       organism = synthetic construct
SEQUENCE: 271
atgagagcct ggatcttctt cctgctttgt ttggcaggac gagcgctagc cgaaatcgtc  60
ctgacccagt caccaggaac actttccctg agtccaggtg aaagagcaac actttcttgc  120
```

-continued

```
cgagcctctc agagcttttc cgaccgatac ttggcgtggt accagcaaaa acccggtcaa  180
gcacctagac tgctcatcta cggcacgagc tccagagcca ccggaatccc agaccgcttt  240
agcggaagtg gttcaggcac cgattttacc ctgaccatct caaggttgga atccgaagat  300
tcagccgtgt attactgcca acagtatggc agatccccat tcactttcgg acctgggaca  360
aaggttgata ttaagcgtac ggtagctgcg cctagcgtgt ttatttttcc gccctctgac  420
gaacaactca aaagtggcac tgcctctgta gtctgtctcc tgaacaattt ttatccaagg  480
gaagctaagg tacagtggaa agtcgataac gcgctccaaa gtggcaacag tcaagaatct  540
gtaacggagc aagatagtaa agacagcact tacagcttga gcagcacact cacattgtcc  600
aaggccgact acgaaaaaca taaagtgtac gcctgtgagg taacacacca gggtctgagc  660
agcccagtga cgaagtcatt taatcgcggt gagtgctga                        699

SEQ ID NO: 272         moltype = AA  length = 232
FEATURE                Location/Qualifiers
source                 1..232
                       mol_type = protein
                       organism = synthetic construct
SEQUENCE: 272
MRAWIFFLLC LAGRALAEIV LTQSPGTLSL SPGERATLSC RASQSFSDRY LAWYQQKPGQ  60
APRLLIYGTS SRATGIPDRF SGSGSGTDFT LTISRLESED SAVYYCQQYG RSPFTFGPGT  120
KVDIKRTVAA PSVFIFPPSD EQLKSGTASV VCLLNNFYPR EAKVQWKVDN ALQSGNSQES  180
VTEQDSKDST YSLSSTLTLS KADYEKHKVY ACEVTHQGLS SPVTKSFNRG EC          232

SEQ ID NO: 273         moltype = AA  length = 5
FEATURE                Location/Qualifiers
source                 1..5
                       mol_type = protein
                       organism = synthetic construct
SEQUENCE: 273
GGGGS                                                              5

SEQ ID NO: 274         moltype = AA  length = 4
FEATURE                Location/Qualifiers
source                 1..4
                       mol_type = protein
                       organism = synthetic construct
SEQUENCE: 274
GGGS                                                               4
```

The embodiments of the invention in which an exclusive property or privilege is claimed are defined as follows:

1. An antibody or antigen binding derivative thereof that binds to an extracellular domain of interleukin-3 (IL-3) receptor α-chain (CD123), and comprises a light chain variable ($V_L$) domain and a heavy chain variable ($V_H$) domain, wherein:

a) the $V_L$ domain comprises a VL-CDR1 of SEQ ID NO: 3, a VL-CDR2 of SEQ ID NO: 4, and a VL-CDR3 of SEQ ID NO: 5; and the $V_H$ domain comprises a VH-CDR1 of SEQ ID NO: 8, a VH-CDR2 of SEQ ID NO: 9, and a VH-CDR3 of SEQ ID NO: 10;

b) the $V_L$ domain comprises a VL-CDR1 of SEQ ID NO: 13, a VL-CDR2 of SEQ ID NO: 14, and a VL-CDR3 of SEQ ID NO: 15; and the $V_H$ domain comprises a VH-CDR1 of SEQ ID NO: 18, a VH-CDR2 of SEQ ID NO: 19, and a VH-CDR3 of SEQ ID NO: 20;

c) the $V_L$ domain comprises a VL-CDR1 of SEQ ID NO: 23, a $V_L$-CDR2 of SEQ ID NO: 24, and a VL-CDR3 of SEQ ID NO: 25; and the $V_H$ domain comprises a VH-CDR1 of SEQ ID NO: 28, a VH-CDR2 of SEQ ID NO: 29, and a VH-CDR3 of SEQ ID NO: 30;

d) the $V_L$ domain comprises a VL-CDR1 of SEQ ID NO: 33, a VL-CDR2 of SEQ ID NO: 34, and a VL-CDR3 of SEQ ID NO: 35; and the $V_H$ domain comprises a VH-CDR1 of SEQ ID NO: 38, a VH-CDR2 of SEQ ID NO: 39, and a VH-CDR3 of SEQ ID NO: 40;

e) the VL domain comprises a $V_L$-CDR1 of SEQ ID NO: 43, a VL-CDR2 of SEQ ID NO: 44, and a VL-CDR3 of SEQ ID NO: 45; and the $V_H$ domain comprises a VH-CDR1 of SEQ ID NO: 48, a VH-CDR2 of SEQ ID NO: 49, and a VH-CDR3 of SEQ ID NO: 50;

f) the $V_L$ domain comprises a VL-CDR1 of SEQ ID NO: 53, a VL-CDR2 of SEQ ID NO: 54, and a VL-CDR3 of SEQ ID NO: 55; and the $V_H$ domain comprises a VH-CDR1 of SEQ ID NO: 58, a VH-CDR2 of SEQ ID NO: 59, and a VH-CDR3 of SEQ ID NO: 60;

g) the $V_L$ domain comprises a VL-CDR1 of SEQ ID NO: 63, a VL-CDR2 of SEQ ID NO: 64, and a VL-CDR3 of SEQ ID NO: 65; and the $V_H$ domain comprises a VH-CDR1 of SEQ ID NO: 68, a VH-CDR2 of SEQ ID NO: 69, and a VH-CDR3 of SEQ ID NO: 70;

h) the $V_L$ domain comprises a VL-CDR1 of SEQ ID NO: 73, a VL-CDR2 of SEQ ID NO: 74, and a VL-CDR3 of SEQ ID NO: 75; and the $V_H$ domain comprises a VH-CDR1 of SEQ ID NO: 78, a VH-CDR2 of SEQ ID NO: 79, and a VH-CDR3 of SEQ ID NO: 80;

i) the $V_L$ domain comprises a VL-CDR1 of SEQ ID NO: 83, a VL-CDR2 of SEQ ID NO: 84, and a VL-CDR3 of SEQ ID NO: 85; and the $V_H$ domain comprises a VH-CDR1 of SEQ ID NO: 88, a VH-CDR2 of SEQ ID NO: 89, and a VH-CDR3 of SEQ ID NO: 90;

j) the $V_L$ domain comprises a VL-CDR1 of SEQ ID NO: 93, a VL-CDR2 of SEQ ID NO: 94, and a VL-CDR3 of SEQ ID NO: 95; and the $V_H$ domain comprises a VH-CDR1 of SEQ ID NO: 98, a VH-CDR2 of SEQ ID NO: 99, and a VH-CDR3 of SEQ ID NO: 100;

k) the $V_L$ domain comprises a VL-CDR1 of SEQ ID NO: 103, a VL-CDR2 of SEQ ID NO: 104, and a VL-CDR3 of SEQ ID NO: 105; and the $V_H$ domain comprises a VH-CDR1 of SEQ ID NO: 108, a VH-CDR2 of SEQ ID NO: 109, and a VH-CDR3 of SEQ ID NO: 110;

l) The $V_L$ domain comprises a VL-CDR1 of SEQ ID NO: 113, a VL-CDR2 of SEQ ID NO: 114, and a VL-CDR3 of SEQ ID NO: 115; and the $V_H$ domain comprises a VH-CDR1 of SEQ ID NO: 118, a VH-CDR2 of SEQ ID NO: 119, and a VH-CDR3 of SEQ ID NO: 120;

m) the $V_L$ domain comprises a VL-CDR1 of SEQ ID NO: 123, a VL-CDR2 of SEQ ID NO: 124, and a VL-CDR3 of SEQ ID NO: 125; and the $V_H$ domain comprises a VH-CDR1 of SEQ ID NO: 128, a VH-CDR2 of SEQ ID NO: 129, and a VH-CDR3 of SEQ ID NO: 130;

n) the $V_L$ domain comprises a VL-CDR1 of SEQ ID NO: 133, a VL-CDR2 of SEQ ID NO: 134, and a VL-CDR3 of SEQ ID NO: 135; and the $V_H$ domain comprises a VH-CDR1 of SEQ ID NO: 138, a VH-CDR2 of SEQ ID NO: 139, and a VH-CDR3 of SEQ ID NO: 140;

o) the $V_L$ domain comprises a VL-CDR1 of SEQ ID NO: 143, a VL-CDR2 of SEQ ID NO: 144, and a VL-CDR3 of SEQ ID NO: 145; and the $V_H$ domain comprises a VH-CDR1 of SEQ ID NO: 148, a VH-CDR2 of SEQ ID NO: 149, and a VH-CDR3 of SEQ ID NO: 150;

p) the $V_L$ domain comprises a VL-CDR1 of SEQ ID NO: 172, a VL-CDR2 of SEQ ID NO: 173, and a VL-CDR3 of SEQ ID NO: 174; and the $V_H$ domain comprises a VH-CDR1 of SEQ ID NO: 176, a VH-CDR2 of SEQ ID NO: 177, and a VH-CDR3 of SEQ ID NO: 178; or q) the $V_L$ domain comprises a VL-CDR1 of SEQ ID NO: 176, a VL-CDR2 of SEQ ID NO: 177, and a VL-CDR3 of SEQ ID NO: 178; and the $V_H$ domain comprises a VH-CDR1 of SEQ ID NO: 184, a VH-CDR2 of SEQ ID NO: 185, and a VH-CDR3 of SEQ ID NO: 186.

2. The antibody or antigen binding derivative thereof of claim 1, comprising:

(i) a $V_L$ domain comprising an amino acid sequence with at least about 95% identity to the sequence of selected from SEQ ID NOS: 2, 12, 22, 32, 42, 52, 62, 72, 82, 92, 102, 112, 122, 132, 142, 171, and 179; and (ii) a $V_H$ domain comprising an amino acid sequence with at least about 95% identity to the sequence of selected from SEQ ID NOS: 7, 17, 27, 37, 47, 57, 67, 77, 87, 97, 107, 117, 127, 137, 147, 175, and 183.

3. The antibody or antigen binding derivative thereof of claim 1, wherein the antibody is a monoclonal antibody, and wherein the monoclonal antibody is a chimeric antibody, a humanized antibody, or a human antibody.

4. The antibody or antigen binding derivative thereof of claim 1, wherein the antigen binding derivative comprises an antigen binding antibody fragment, a single-chain antibody, a minibody, a diabody, a triabody, scTCR, or an scFv-Fc construct.

5. The antibody or antigen binding derivative thereof of claim 1, further comprising a therapeutic payload.

* * * * *